(12) United States Patent
Meckenzie et al.

(10) Patent No.: US 12,290,721 B2
(45) Date of Patent: May 6, 2025

(54) SYSTEMS AND METHODS FOR WORKOUT SCORING USING IMAGE AND EXERTION DATA

(71) Applicant: Ores Technology Services LTD, Tel Aviv (IL)

(72) Inventors: Shalom Meckenzie, Savyon (IL); Rebecca Shultz, San Carlos, CA (US); Amir Levanon, Sunnyvale, CA (US); Eitan Gebler, San Jose, CA (US)

(73) Assignee: AMP FIT ISRAEL LTD, Tel Aviv (IL)

( * ) Notice: Subject to any disclaimer, the term of this patent is extended or adjusted under 35 U.S.C. 154(b) by 0 days.

(21) Appl. No.: 18/764,691

(22) Filed: Jul. 5, 2024

(65) Prior Publication Data
US 2024/0359059 A1  Oct. 31, 2024

Related U.S. Application Data

(63) Continuation of application No. PCT/US2024/025060, filed on Apr. 17, 2024.
(Continued)

(51) Int. Cl.
A63B 24/00 (2006.01)
A63B 21/005 (2006.01)
(Continued)

(52) U.S. Cl.
CPC ...... *A63B 24/0075* (2013.01); *A63B 21/0058* (2013.01); *A63B 21/072* (2013.01);
(Continued)

(58) Field of Classification Search
CPC ........ A63B 24/0075; A63B 2024/0068; A63B 2024/0071; A63B 2220/05;
(Continued)

(56) References Cited

U.S. PATENT DOCUMENTS 4,624,457 A  11/1986  Silberman et al.
5,385,525 A  1/1995  Davis
(Continued)

FOREIGN PATENT DOCUMENTS

CN  108176032 A  * 6/2018 ......... A63B 24/0062
CN  113616976 A  11/2021
(Continued)

OTHER PUBLICATIONS

Anghel, Ionut et. al. "Smart Environments and Social Robots for Age-Friendly Integrated Care Services." International Journal of Environmental Research and Public Health 17.11: NA. MDPI AG. (Jun. 1, 2020) (Year: 2020).*
(Continued)

*Primary Examiner* — Linh Giang Le
(74) *Attorney, Agent, or Firm* — FINNEGAN, HENDERSON, FARABOW, GARRETT & DUNNER, LLP

(57) ABSTRACT

Systems, methods, and computer readable medium are disclosed for performance of exercise scoring operations. Performance of exercise scoring operations includes storing an exercise goal for a particular individual; receiving from a sensor on a piece of electronic exercise equipment, exertion data; receiving, from at least one image sensor monitoring use of the piece of electronic exercise equipment, image data reflecting form and posture of the particular individual during an exercise set; generating a score for the exercise set by performing an aggregate analysis of the exercise goal, the exertion data, and the image data reflecting the form and posture; and outputting the score.

19 Claims, 42 Drawing Sheets

Related U.S. Application Data

(60) Provisional application No. 63/496,605, filed on Apr. 17, 2023.

(51) Int. Cl.
- *A63B 21/072* (2006.01)
- *A63B 71/06* (2006.01)
- *G06T 13/40* (2011.01)
- *G16H 20/30* (2018.01)

(52) U.S. Cl.
CPC ...... *A63B 24/0062* (2013.01); *A63B 71/0622* (2013.01); *G06T 13/40* (2013.01); *G16H 20/30* (2018.01); *A63B 2024/0065* (2013.01); *A63B 2024/0068* (2013.01); *A63B 2024/0071* (2013.01); *A63B 2071/0638* (2013.01); *A63B 2220/05* (2013.01); *A63B 2220/17* (2013.01); *A63B 2220/806* (2013.01); *A63B 2220/833* (2013.01); *A63B 2225/20* (2013.01); *A63B 2225/50* (2013.01); *A63B 2230/62* (2013.01)

(58) Field of Classification Search
CPC .......... A63B 2220/17; A63B 2220/806; A63B 2230/62; G16H 20/30
See application file for complete search history.

(56) References Cited

U.S. PATENT DOCUMENTS

| | | |
|---|---|---|
| 5,626,546 A | 5/1997 | Little |
| 5,820,629 A | 10/1998 | Cox |
| 6,152,856 A | 11/2000 | Studor |
| 7,549,947 B2 | 6/2009 | Hickman |
| 8,485,950 B2 | 7/2013 | Adams |
| 9,132,330 B2 | 9/2015 | Brendle |
| 9,661,355 B2 | 5/2017 | Ho |
| 9,708,164 B2 | 7/2017 | Jakob et al. |
| 9,782,625 B1 | 10/2017 | Blum et al. |
| 9,832,491 B2 | 11/2017 | Ho |
| 10,022,590 B2 | 7/2018 | Foley et al. |
| 10,052,026 B1 | 8/2018 | Tran |
| 10,161,488 B1 | 12/2018 | Meyer |
| 10,179,265 B2 | 1/2019 | Carr |
| 10,322,315 B2 | 6/2019 | Foley et al. |
| 10,486,026 B2 | 11/2019 | Foley et al. |
| D873,935 S | 1/2020 | Van Den Berg |
| 10,617,903 B2 | 4/2020 | Orady et al. |
| 10,639,521 B2 | 5/2020 | Foley et al. |
| 10,737,134 B2 | 8/2020 | Anderson et al. |
| 10,758,780 B2 | 9/2020 | Putnam |
| 10,814,172 B1 | 10/2020 | Ilfrey et al. |
| 10,828,551 B2 | 11/2020 | Putnam |
| 10,864,406 B2 | 12/2020 | Foley et al. |
| 10,905,916 B1 | 2/2021 | Malik |
| 10,946,238 B1 | 3/2021 | Rogus |
| 10,974,094 B2 | 4/2021 | Consiglio et al. |
| 10,981,047 B2 | 4/2021 | Putnam |
| 10,987,565 B2 | 4/2021 | Orady et al. |
| D921,132 S | 6/2021 | Orady et al. |
| 11,045,709 B2 | 6/2021 | Putnam |
| 11,065,527 B2 | 7/2021 | Putnam |
| 11,090,547 B2 | 8/2021 | Putnam |
| 11,097,148 B2 | 8/2021 | Kennington |
| 11,110,336 B2 | 9/2021 | Putnam |
| 11,117,038 B2 | 9/2021 | Putnam |
| 11,117,039 B2 | 9/2021 | Putnam |
| 11,123,626 B1 | 9/2021 | Putnam |
| 11,135,503 B2 | 10/2021 | Putnam |
| 11,135,504 B1 | 10/2021 | Putnam |
| 11,135,505 B2 | 10/2021 | Putnam |
| 11,139,061 B2 | 10/2021 | Foley et al. |
| 11,145,398 B2 | 10/2021 | Foley et al. |
| 11,145,399 B2 | 10/2021 | Foley et al. |
| 11,167,172 B1 | 11/2021 | Putnam et al. |
| 11,170,886 B2 | 11/2021 | Foley et al. |
| 11,173,377 B1 | 11/2021 | Putnam |
| 11,173,378 B2 | 11/2021 | Putnam |
| 11,179,620 B2 | 11/2021 | Putnam |
| 11,183,288 B2 | 11/2021 | Foley et al. |
| 11,191,996 B2 | 12/2021 | Fung |
| 11,202,951 B1 | 12/2021 | Augustin et al. |
| 11,207,564 B2 | 12/2021 | Ward et al. |
| 11,219,799 B2 | 1/2022 | Poure et al. |
| 11,219,816 B2 | 1/2022 | Putnam |
| 11,220,412 B2 | 1/2022 | Peuker et al. |
| 11,253,770 B2 | 2/2022 | Putnam |
| 11,273,343 B2 | 3/2022 | Augustin et al. |
| 11,285,355 B1 | 3/2022 | Nicholson et al. |
| 11,289,185 B2 | 3/2022 | Foley et al. |
| 11,295,849 B2 | 4/2022 | Foley et al. |
| 11,295,850 B2 | 4/2022 | Foley et al. |
| 11,298,591 B2 | 4/2022 | Evancha et al. |
| 11,298,606 B2 | 4/2022 | Putnam |
| 11,311,778 B2 | 4/2022 | Ward et al. |
| 11,311,791 B2 | 4/2022 | Dion et al. |
| 11,324,983 B2 | 5/2022 | Orady et al. |
| 11,331,538 B2 | 5/2022 | Ward et al. |
| 11,331,557 B2 | 5/2022 | Summit |
| 11,389,687 B2 * | 7/2022 | Orady ..................... G01L 5/04 |
| 11,517,785 B1 | 12/2022 | Nolan |
| 11,593,056 B2 | 2/2023 | Chiang |
| 11,623,126 B1 | 4/2023 | Lagree et al. |
| 11,642,560 B1 | 5/2023 | Hewlett |
| 11,642,569 B2 | 5/2023 | Zhang |
| 11,779,793 B2 | 10/2023 | Peal et al. |
| 11,806,580 B1 | 11/2023 | Nolan |
| 11,931,616 B2 | 3/2024 | Orady et al. |
| 2002/0045519 A1 | 4/2002 | Watterson |
| 2002/0055419 A1 | 4/2002 | Hinnebusch |
| 2002/0091043 A1 | 7/2002 | Rexach |
| 2003/0015414 A1 | 1/2003 | Kajiura et al. |
| 2004/0103146 A1 | 5/2004 | Park |
| 2004/0127272 A1 | 7/2004 | Park |
| 2004/0229730 A1 | 11/2004 | Ainsworth et al. |
| 2006/0040793 A1 | 2/2006 | Martens |
| 2008/0207401 A1 | 8/2008 | Harding |
| 2009/0023554 A1 | 1/2009 | Shim |
| 2009/0098980 A1 | 4/2009 | Walters |
| 2009/0170675 A1 | 7/2009 | Giannelli et al. |
| 2010/0004097 A1 | 1/2010 | D'Eredita |
| 2010/0035726 A1 | 2/2010 | Fisher |
| 2010/0125026 A1 | 5/2010 | Zavadsky et al. |
| 2011/0082010 A1 | 4/2011 | Dyer et al. |
| 2011/0105278 A1 | 5/2011 | Fabbri et al. |
| 2012/0237911 A1 | 9/2012 | Watterson |
| 2013/0102439 A1 | 4/2013 | Napolitano |
| 2013/0123071 A1 | 5/2013 | Rhea |
| 2013/0204410 A1 | 8/2013 | Napolitano |
| 2013/0345883 A1 | 12/2013 | Sloo et al. |
| 2014/0038777 A1 | 2/2014 | Bird |
| 2014/0038781 A1 | 2/2014 | Foley et al. |
| 2014/0121072 A1 | 5/2014 | Ercanbrack |
| 2014/0135181 A1 | 5/2014 | Smith |
| 2014/0244008 A1 | 8/2014 | Kennett |
| 2015/0044648 A1 | 2/2015 | White |
| 2015/0087486 A1 | 3/2015 | Franks |
| 2015/0182773 A1 | 7/2015 | Olson et al. |
| 2016/0250519 A1 | 9/2016 | Watterson |
| 2016/0300390 A1 | 10/2016 | Malafeew |
| 2017/0007886 A1 | 1/2017 | Alessandri |
| 2017/0177295 A1 | 6/2017 | Bowen |
| 2017/0216667 A1 | 8/2017 | Garvey |
| 2017/0274268 A1 | 9/2017 | Renduchintala |
| 2017/0312564 A1 | 11/2017 | Perez Gomez |
| 2017/0319941 A1 | 11/2017 | Smith et al. |
| 2017/0333755 A1 | 11/2017 | Rider |
| 2018/0005615 A1 | 1/2018 | Macpherson |
| 2018/0048196 A1 | 2/2018 | Kuo et al. |
| 2018/0096621 A1 | 4/2018 | Zavoyskikh |
| 2018/0159618 A1 | 6/2018 | Winata |
| 2018/0174347 A1 | 6/2018 | Chaney |
| 2018/0253840 A1 | 9/2018 | Tran |
| 2019/0005373 A1 | 1/2019 | Nims |

(56) References Cited

U.S. PATENT DOCUMENTS

| | | |
|---|---|---|
| 2019/0099632 A1 | 4/2019 | Orady et al. |
| 2019/0099633 A1 | 4/2019 | Orady et al. |
| 2019/0126099 A1 | 5/2019 | Hoang |
| 2019/0143194 A1 | 5/2019 | Evancha et al. |
| 2019/0184234 A1 | 6/2019 | Packles et al. |
| 2019/0209891 A1 | 7/2019 | Fung |
| 2019/0259292 A1 | 8/2019 | Williams |
| 2019/0290964 A1 | 9/2019 | Oren |
| 2019/0299043 A1 | 10/2019 | Gisin et al. |
| 2019/0336827 A1 | 11/2019 | Intonato et al. |
| 2019/0371114 A1 | 12/2019 | Diefenbach |
| 2020/0009444 A1 | 1/2020 | Putnam |
| 2020/0014967 A1 | 1/2020 | Putnam |
| 2020/0047027 A1 | 2/2020 | Ward et al. |
| 2020/0047030 A1 | 2/2020 | Ward et al. |
| 2020/0047031 A1 | 2/2020 | Orady et al. |
| 2020/0047053 A1 | 2/2020 | Ward et al. |
| 2020/0047055 A1 | 2/2020 | Ward et al. |
| 2020/0054922 A1 | 2/2020 | Azaria et al. |
| 2020/0070032 A1 | 3/2020 | Orady et al. |
| 2020/0114194 A1 | 4/2020 | McGhee |
| 2020/0139194 A1 | 5/2020 | Min |
| 2020/0254311 A1 | 8/2020 | Watterson et al. |
| 2020/0272311 A1 | 8/2020 | Rotta |
| 2020/0276465 A1 | 9/2020 | Orady et al. |
| 2020/0297269 A1 | 9/2020 | Vieri |
| 2020/0376339 A1 | 12/2020 | Chu |
| 2020/0376368 A1 | 12/2020 | Galasso |
| 2021/0001205 A1 | 1/2021 | Kim |
| 2021/0004981 A1 | 1/2021 | Song et al. |
| 2021/0060423 A1 | 3/2021 | Kitahara |
| 2021/0086030 A1 | 3/2021 | Kashyap |
| 2021/0093921 A1 | 4/2021 | Foley et al. |
| 2021/0106875 A1 | 4/2021 | Hansen |
| 2021/0128978 A1 | 5/2021 | Gilstrom et al. |
| 2021/0170222 A1 | 6/2021 | Consiglio et al. |
| 2021/0170224 A1 | 6/2021 | Rogus |
| 2021/0205688 A1 | 7/2021 | Liao et al. |
| 2021/0236874 A1 | 8/2021 | Ward et al. |
| 2021/0291015 A1 | 9/2021 | Consiglio et al. |
| 2021/0299520 A1 | 9/2021 | Evancha et al. |
| 2021/0308528 A1 | 10/2021 | Soifer |
| 2021/0335145 A1 | 10/2021 | Denn |
| 2021/0339110 A1 | 11/2021 | Putnam et al. |
| 2021/0342952 A1 | 11/2021 | Putnam et al. |
| 2021/0362030 A1 | 11/2021 | Putnam |
| 2021/0362031 A1 | 11/2021 | Putnam |
| 2021/0370154 A1 | 12/2021 | Putnam |
| 2021/0379447 A1 | 12/2021 | Lee |
| 2021/0379469 A1 | 12/2021 | Mann |
| 2021/0379471 A1 | 12/2021 | Putnam |
| 2021/0379472 A1 | 12/2021 | Putnam |
| 2021/0379473 A1 | 12/2021 | Putnam |
| 2021/0387038 A1 | 12/2021 | Premachandra et al. |
| 2021/0404826 A1 | 12/2021 | Yu |
| 2022/0023738 A1 | 1/2022 | Putnam |
| 2022/0032115 A1 | 2/2022 | Mallard et al. |
| 2022/0032162 A1 | 2/2022 | Putnam |
| 2022/0032163 A1 | 2/2022 | Putnam |
| 2022/0040535 A1 | 2/2022 | Warren |
| 2022/0050655 A1 | 2/2022 | Chiang et al. |
| 2022/0054891 A1 | 2/2022 | Owusu |
| 2022/0054925 A1 | 2/2022 | Chiang et al. |
| 2022/0062680 A1 | 3/2022 | Orady et al. |
| 2022/0071415 A1 | 3/2022 | Putnam et al. |
| 2022/0072375 A1 | 3/2022 | Putnam et al. |
| 2022/0072376 A1 | 3/2022 | Putnam et al. |
| 2022/0072379 A1 | 3/2022 | Putnam et al. |
| 2022/0072380 A1 | 3/2022 | Trehan |
| 2022/0078503 A1 | 3/2022 | Putnam et al. |
| 2022/0080284 A1 | 3/2022 | Churchman |
| 2022/0105417 A1 | 4/2022 | Putnam |
| 2022/0118301 A1 | 4/2022 | Valente et al. |
| 2022/0118304 A1 | 4/2022 | McNally et al. |
| 2022/0118338 A1 | 4/2022 | Putnam |
| 2022/0118339 A1 | 4/2022 | Putnam |
| 2022/0118340 A1 | 4/2022 | Putnam |
| 2022/0212055 A1 | 7/2022 | Valente et al. |
| 2022/0225769 A1 | 7/2022 | Brown et al. |
| 2022/0266084 A1 | 8/2022 | Hoover |
| 2022/0296966 A1* | 9/2022 | Asikainen ............... G16H 20/30 |
| 2022/0370854 A1 | 11/2022 | Zhang |
| 2022/0386260 A1 | 12/2022 | Lee et al. |
| 2023/0089962 A1 | 3/2023 | Shavit |
| 2023/0123415 A1 | 4/2023 | Walter |
| 2023/0128118 A1 | 4/2023 | Kadav |
| 2023/0128721 A1 | 4/2023 | Plummer |
| 2023/0211208 A1 | 7/2023 | Warren |
| 2023/0226413 A1 | 7/2023 | Nehaus |
| 2023/0264062 A1 | 8/2023 | Parker et al. |
| 2023/0277890 A1 | 9/2023 | Peal et al. |
| 2023/0285806 A1 | 9/2023 | Webster |
| 2023/0338770 A1 | 10/2023 | Chen |
| 2024/0033571 A1 | 2/2024 | James et al. |
| 2024/0042266 A1 | 2/2024 | Chevalier |
| 2024/0135479 A1 | 4/2024 | Rezajoo |
| 2024/0226661 A1 | 7/2024 | Schloss et al. |
| 2024/0233462 A1 | 7/2024 | Rezajoo |
| 2024/0316343 A1 | 9/2024 | Zandona Freitas |

FOREIGN PATENT DOCUMENTS

| | | | |
|---|---|---|---|
| CN | 217724440 U | 11/2022 | |
| CN | 116139456 A | 5/2023 | |
| GB | 2414078 A | 11/2005 | |
| GB | 2531038 A | 4/2016 | |
| WO | WO-2014190013 A1 * | 11/2014 | ......... A63B 69/0026 |
| WO | 2018044721 A1 | 3/2018 | |
| WO | 2019063960 A1 | 4/2019 | |
| WO | 2019143488 A1 | 7/2019 | |
| WO | 2019231982 A1 | 12/2019 | |
| WO | 2020033508 A1 | 2/2020 | |
| WO | 2020033530 A1 | 2/2020 | |
| WO | 2020033544 A1 | 2/2020 | |
| WO | 2020033548 A2 | 2/2020 | |
| WO | 2020123756 A1 | 6/2020 | |
| WO | 2021021447 A1 | 2/2021 | |
| WO | 2021118859 A1 | 6/2021 | |
| WO | 2021154298 A1 | 8/2021 | |
| WO | 2021222497 A1 | 11/2021 | |
| WO | 2022011448 A1 | 1/2022 | |
| WO | 2022026486 A1 | 2/2022 | |
| WO | 2022051474 A2 | 3/2022 | |
| WO | 2022132814 A1 | 6/2022 | |

OTHER PUBLICATIONS

Intentional Search Report and Written Opinion, dated Aug. 8, 2024, issued in International Patent Application No. PCT/US24/25060. (16 pages).

* cited by examiner

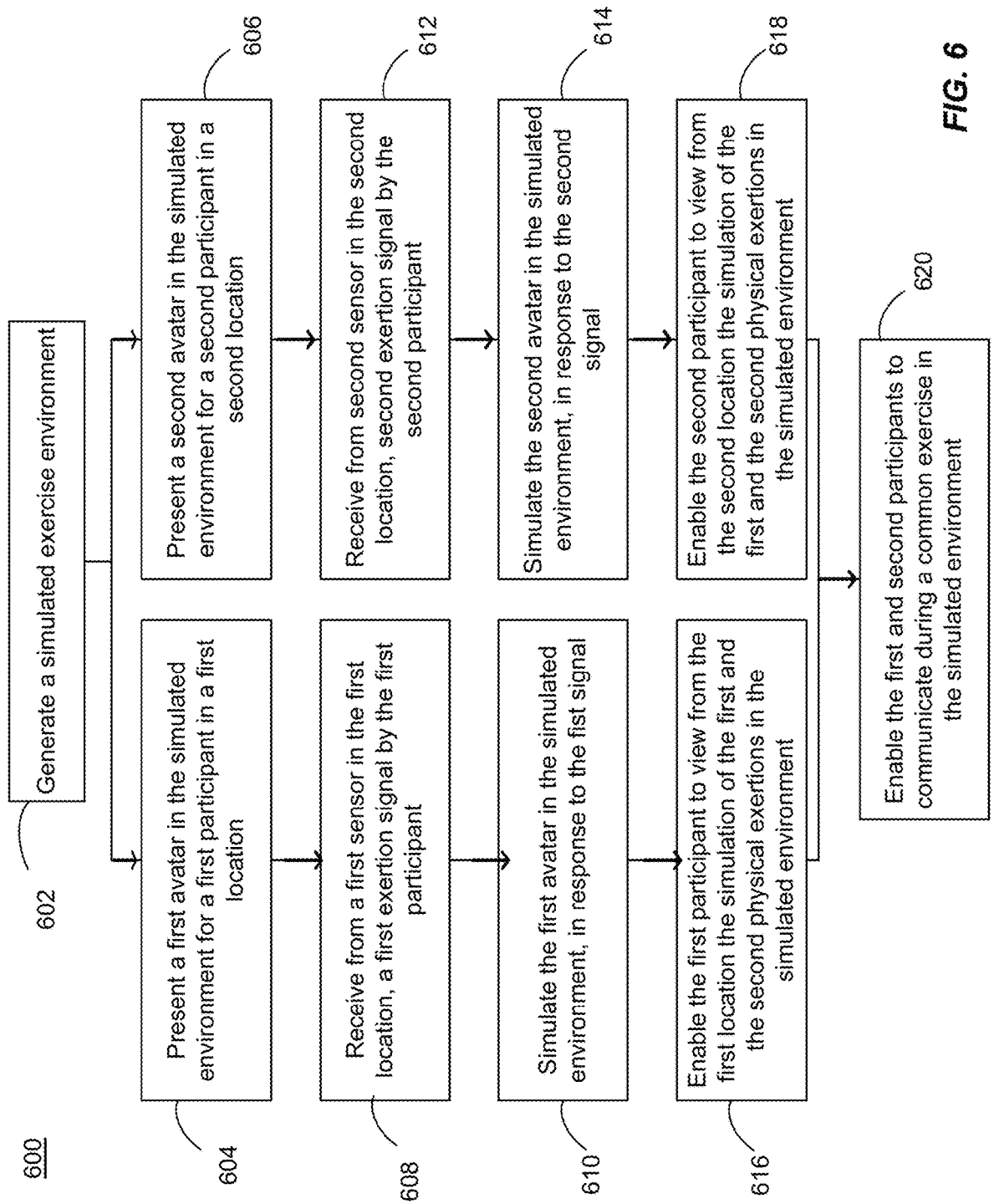

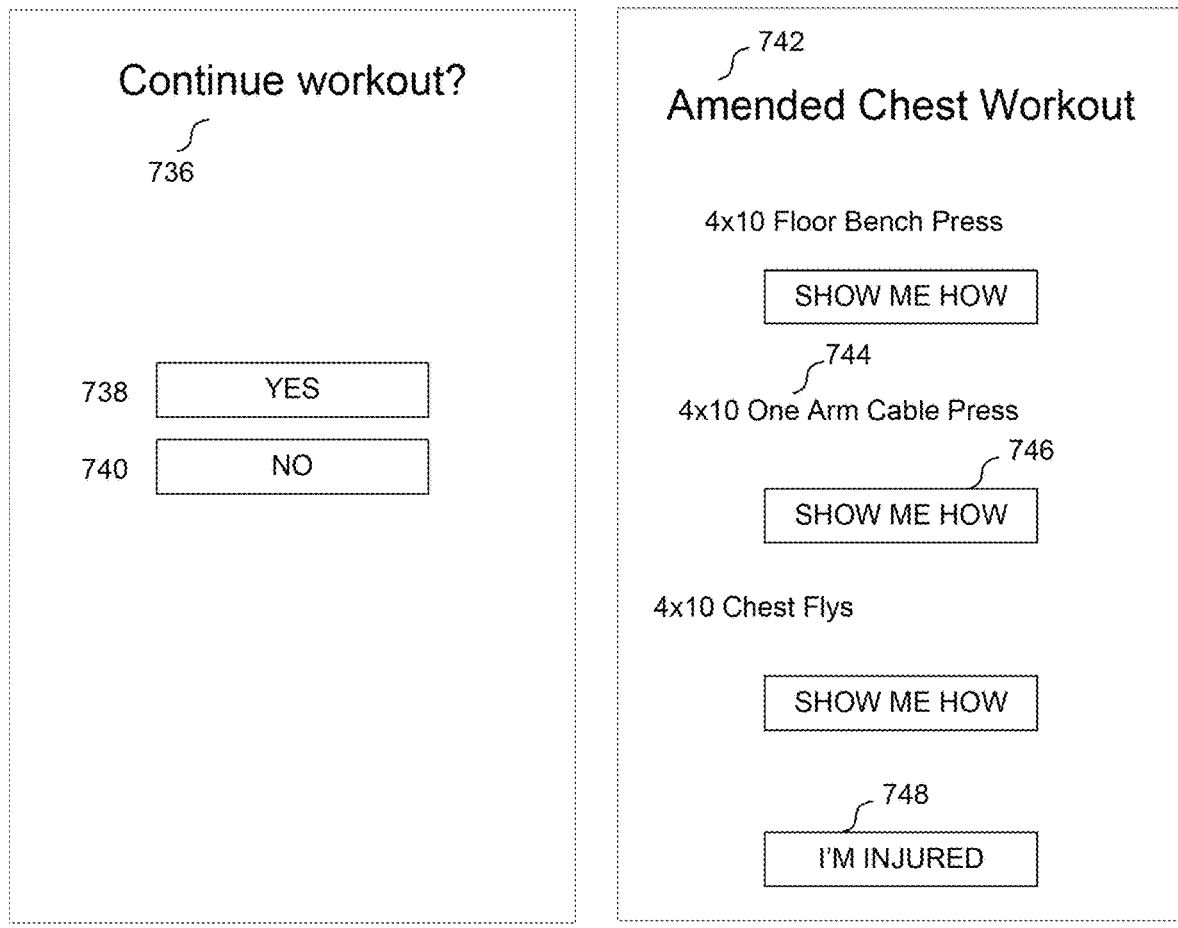
*FIG. 7E*  *FIG. 7F*

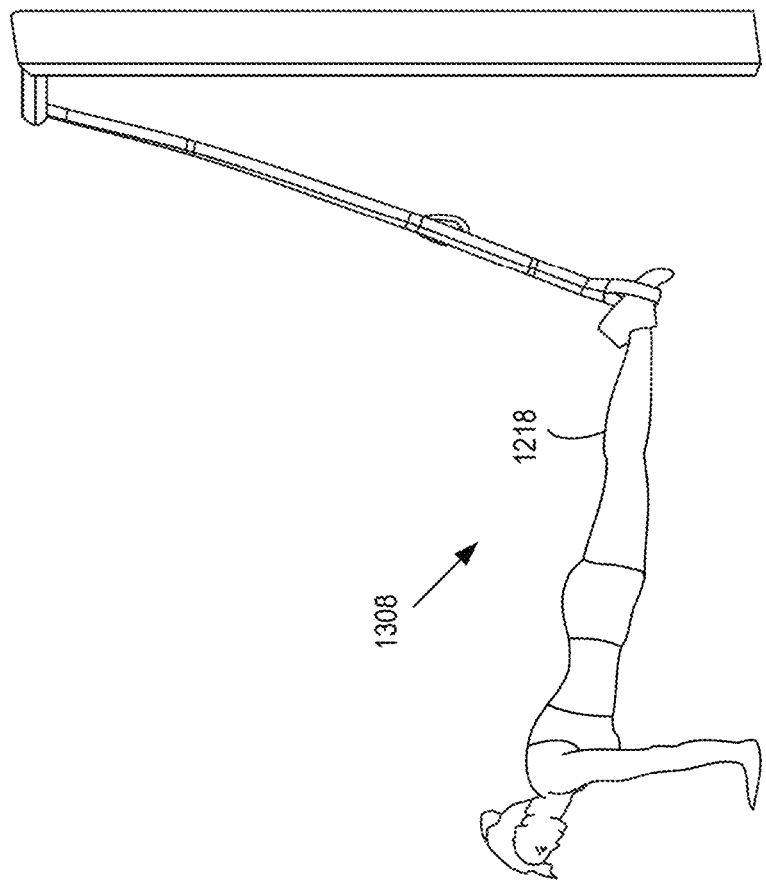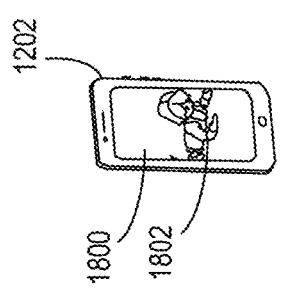
FIG. 18

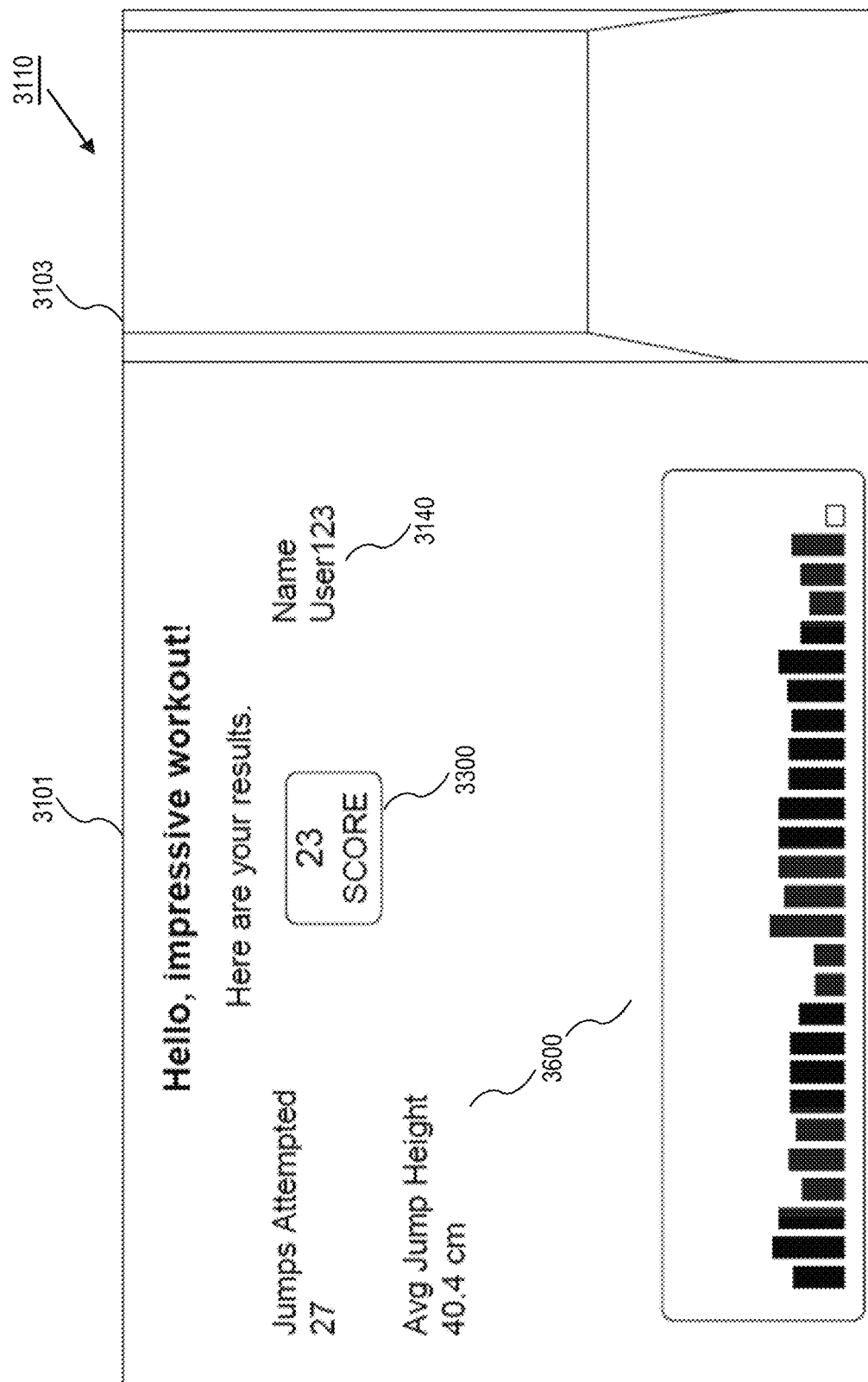

SYSTEMS AND METHODS FOR WORKOUT SCORING USING IMAGE AND EXERTION DATA

CROSS REFERENCE TO RELATED APPLICATIONS

This application is a continuation of PCT International Application No. PCT/US2024/25060, filed Apr. 17, 2024, which claims the benefit of priority of U.S. Provisional Patent Application No. 63/496,605, filed on Apr. 17, 2023, which is incorporated herein by reference in its entirety.

TECHNICAL FIELD

This disclosure relates to systems, methods, and computer readable media associated with operating computerized electronic exercise equipment.

BACKGROUND

Resistance training promotes the building and strengthening of muscles and bone tissue, and burns fat. While electronic exercise equipment may facilitate resistance training, most machines tend to be bulky. Wall mounted machines tend to require an amount of wall space that limits the locations where the machines can be mounted from both physical and esthetic perspectives. Moreover, electronic exercise equipment may have controls and adjustment mechanisms that are more cumbersome to use than necessary. Therefore, there is a need for unconventional innovative technologies that take up less space, have a smaller wall "footprint," and that provide for more streamlined use.

Many traditional exercise machines have mechanical and/or electrical controls that require two-handed adjustment. Electronic exercise systems can be rigid, limiting alteration of routines after they are initially set, and many, to varying degrees, fail to sufficiently motivate. Various aspects of this disclosure address the forgoing issues and others.

SUMMARY

Embodiments consistent with the present disclosure provide systems, methods, and devices for operating electronic exercise equipment. Disclosed systems and methods may involve one or more processors in communication with a memory that stores instructions. The one or more processors may execute the stored instructions to perform operations disclosed herein.

Some embodiments involve communicating with a plurality of remote sensors associated with dispersed exercise equipment and to simulate a virtual training experience. Disclosed operations may include generating a simulated exercise environment, presenting a first avatar in the simulated exercise environment, wherein the first avatar is associated with a first participant located in a first physical location, presenting a second avatar in the simulated exercise environment, wherein the second avatar is associated with a second participant located in a second physical location remote from the first physical location, receiving, from at least one first sensor associated with a first piece of exercise equipment in the first physical location, first signals representing first physical exertions by the first participant, in response to the first signals, causing the first avatar to simulate, in the simulated exercise environment, the first physical exertions, receiving, from at least one second sensor associated with a second piece of exercise equipment in the second physical location, second signals representing second physical exertions by the second participant. Based on the second signals, at least one processor may cause the second avatar to simulate, in the simulated exercise environment, the second physical exertions, enable the first participant to view, from the first physical location, the simulations of the first physical exertions and the second physical exertions in the simulated exercise environment, enable the second participant to view, from the second physical location, the simulations of the first physical exertions and the second physical exertions in the simulated exercise environment, and enable the first participant and the second participant to communicate with each other during a common exercise session in the simulated exercise environment.

Some embodiments involve performing dynamic injury-related adjustments during exercise. Disclosed operations may include initiating an exercise routine including a series of varied electronically controlled exercises on exercise equipment, wherein differing exercises work differing groups of muscles, instructing a user to engage in one of the series of varied electronically controlled exercises using the exercise equipment, receiving from the user an electronic indication of injury, wherein the electronic indication of injury includes an indication of at least one injured muscle, and in response to the received electronic indication of injury, changing the series of varied electronically controlled exercises to limit use of the injured muscle.

Some embodiments involve performing operations for dynamically modifying automated electronic exercise equipment usage instructions, the operations including receiving a selection of a fitness a goal associated with a user of electronic exercise equipment configured for implementing an automated exercise program, wherein the fitness goal is typically associated with a series of exercises in the automated exercise program, electronically prompting the user to identify disliked movements, identifying alternative movements to the disliked movements, wherein the alternative movements are chosen from a group consisting of movements that work muscles typically worked by the disliked movements, building an alternative automated exercise program including the alternative movements, wherein the alternative automated exercise program omits the disliked movements while enabling attainment of the fitness goal, and sequentially outputting for presentation on a display prompts for performing the alternative automated exercise program, obtaining feedback on performance of the alternative automated exercise program from at least one sensor monitoring the electronic exercise equipment.

Some embodiments involve performing operations for coordinating multi-space exertion routines, involving operations including receiving from a mobile communications device during a first time period an indication of a first space in which the mobile communications device is located, receiving from the mobile communications device first data reflective of a first exercise routine during the first time period, wherein the first exercise routine is associated with a fitness goal, receiving from the mobile communications device at a second time different from the first time, an indication of a second space in which the mobile communications device is located, outputting to the mobile communications device, instructions for performing a second exercise routine associated with at least one of the fitness goal and the first exercise routine, and receiving from the mobile communications device second data reflective of the second exercise routine, wherein at least the first or the second exercise routine is preformed using at least one exercise equipment.

Some embodiments involve performing overlapping individualized data transfer operations, including establishing a first communications channel between a trainer application and a first piece of electronic exercise equipment associated with a first client, the first communications channel being configured to convey a first dialogue data stream and to convey a first exertion data stream from at least one first sensor associated with the first piece of electronic exercise equipment, establishing a second communications channel between the trainer application and a second piece of electronic exercise equipment associated with a second client, the second communications channel being configured to convey a second dialogue data stream and to convey a second exertion data stream from at least a second sensor associated with the second piece of electronic exercise equipment, enabling a first selection, via the trainer application, of the first communications channel, wherein in response to the first selection, the first dialogue data stream and the first exertion data stream are open between the first client and the trainer thereby enabling the first trainer to view first exertion data while simultaneously conducting a dialogue with the first client, and wherein while the first dialogue data stream is open, at least a return path of second dialogue data stream from the trainer application to the second client is blocked, preventing dialogue from the trainer application to the second client, and enabling a second selection, via the trainer application, of the second communications channel, wherein in response to the second selection, the second dialogue data stream and the second exertion data stream are open between the first client and the trainer thereby enabling the first trainer to view first exertion data while simultaneously conducting a dialogue with the first client, and wherein while the second dialogue data stream is open, at least a return path of the first dialogue data stream from the trainer application to the first client is blocked, preventing communication from the trainer application to the first client.

Some embodiments involve exercise scoring operations including storing an exercise goal for a particular individual, receiving from a sensor on a piece of electronic exercise equipment, exertion data, receiving, from at least one image sensor monitoring use of the piece of electronic exercise equipment, image data reflecting form and posture of the particular individual during an exercise set, generating a score for the exercise set by performing an aggregate analysis of the exercise goal, the exertion data, and the image data reflecting the form and posture, and outputting the score.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

BRIEF DESCRIPTION OF FIGURES

FIG. 6 is a flowchart of an example process for communicating with a plurality of remote sensors associated with dispersed exercise equipment and simulating a virtual training experience, consistent with embodiments of the present disclosure.

FIG. 7E illustrates an exemplary graphical user interface for adjusting an exercise based on a user's injury, consistent with some disclosed embodiments.

FIG. 7F illustrates an exemplary graphical user interface for performing dynamic injury-related adjustments during exercise, consistent with some disclosed embodiments.

FIG. 18 illustrates an exemplary user interface displayed on mobile communication device for simulating an avatar performing an exercise routine, consistent with some embodiments of the present disclosure.

FIGS. 31A-31D are exemplary user interface screens associated with an implementation of exercise scoring operations, consistent with disclosed embodiments.

DETAILED DESCRIPTION

Figure 1A:
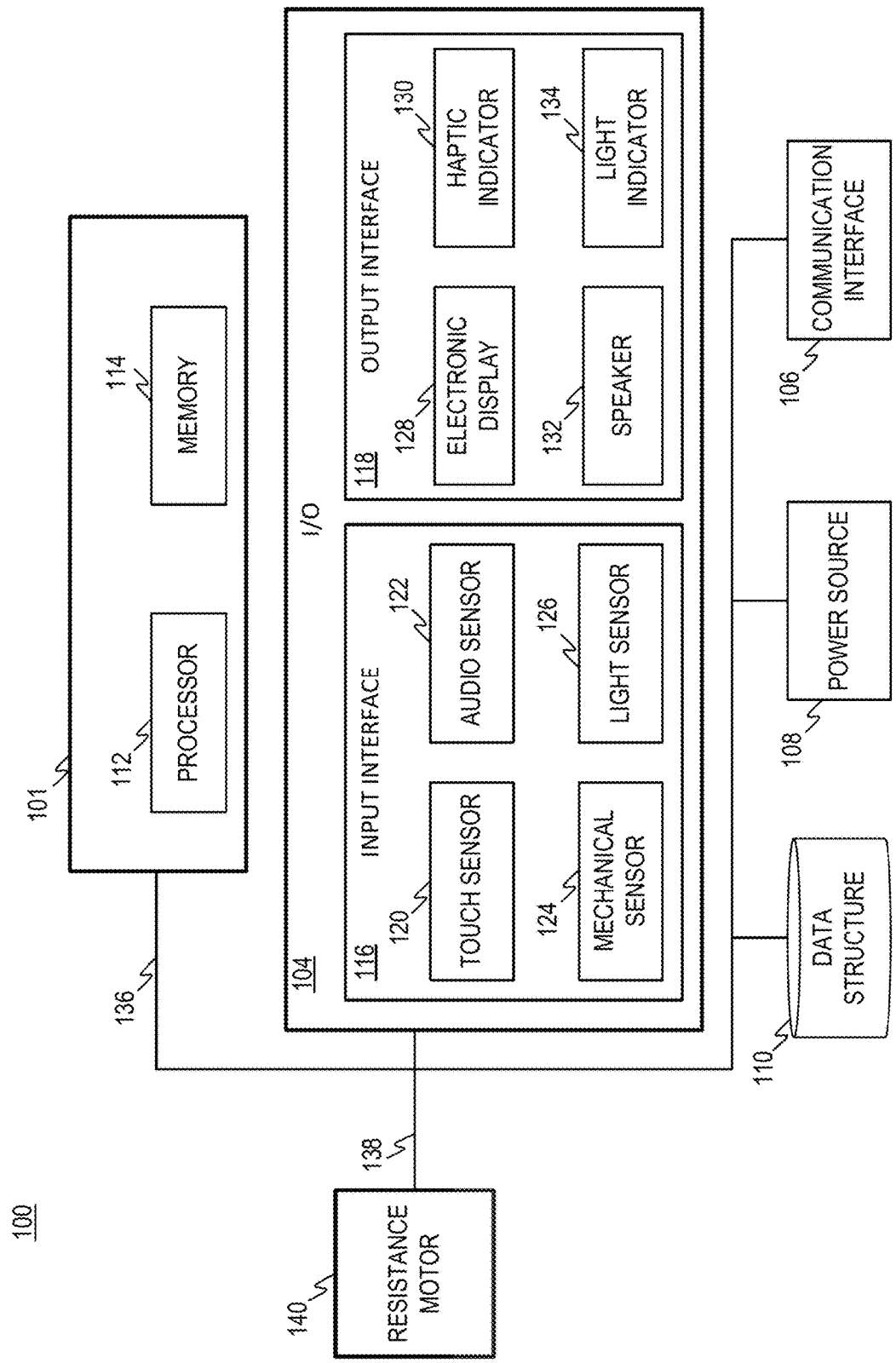
FIG. 1A is a schematic diagram of system architecture for an electronic exercise equipment including an electronic exercise machine, consistent with some embodiments of the present disclosure.

Disclosed herein are systems, methods, and non-transitory computer readable media relating to performance and adaptation of exercise routines, optionally using electronic exercise equipment such as electronic exercise machines. Some disclosed embodiments relate to software applications for using an electronic exercise machine. Some embodiments relate to operation of a modular electronic exercise machine, allowing integration of a plurality of individual electronic exercise machines. Some disclosed embodiments relate to performance of exercise routines. Some disclosed embodiments related to control of and interaction with exercise equipment using a mobile communications device such as a smartphone, tablet, smartwatch, or other type of computing device. Some disclosed embodiments relate to one or more combinations software applications, and/or operation of modular electronic exercise machines with associated mechanical, electrical, or electromechanical features.

Various terms used in this detailed description and in the claims may be defined or summarized differently when discussed in connection with differing examples. It is to be understood that the definitions, summaries, and explanations of terminology in each instance apply to all instances, even when not repeated, unless the transitive definition, explanation or summary would result in inoperability of an embodiment.

Throughout, this disclosure mentions "disclosed embodiments," which refer to examples of inventive ideas, concepts, and/or manifestations described herein. Many related and unrelated embodiments and examples are described throughout this disclosure. The fact that some "disclosed embodiments" are described as exhibiting a feature or characteristic does not mean that other disclosed embodiments necessarily lack that feature or characteristic.

This disclosure employs open-ended permissive language, indicating for example, that some embodiments "may" employ, involve, or include specific features. The use of the term "may" and other open-ended terminology is intended to indicate that although not every embodiment may employ the specific disclosed feature, at least one embodiment employs the specific disclosed feature.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the specific embodiments and examples but is inclusive of general principles described herein and illustrated in the figures in addition to the general principles encompassed by the appended claims.

Some embodiments described herein involve an exercise machine or electronic exercise equipment. An exercise machine may refer to a mechanical device that may be used to perform physical exercise. Electronic exercise equipment refers to fitness equipment such as exercise machines that incorporate electronic components and/or features to enhance the workout experience. Examples of exercise machines may include wall-mountable resistance devices, free standing resistance devices, treadmills, stationary bicycles, elliptical machines, weight machines, other resistance machines, and/or any other machine designed to engage a user in physical exercise. Examples of electronic exercise equipment includes treadmills (electronics may control one or more of speed, incline, and tracking of workout progress), stationary bikes, elliptical trainers (with electronically controlled resistance), rowing machines, stair climbers, punching bags with sensor technology, smart dumbbells, balance boards with interactive games, smart jump ropes, interactive fitness mirrors, and smart home gyms, any of the forgoing of which include electronically controlled programmable workouts, pre-programmed workouts, physical adjustments and/or adjustable resistance. An electronic exercise machine may refer to an exercise machine including a resistance motor associated with electronics for controlling the resistance. As a non-limiting example, electronic exercise equipment may include electronic exercise machine 200 shown in FIGS. 2A and 3. The electronics may control an amount of resistance applied during a weightlifting exercise by regulating, for example, a level, a frequency, a duration, a speed, a duty cycle, a range of motion, an exercise type, an operational mode, and/or any other attribute associated with resistance applied by a resistance motor. In some embodiments, electronics, including for example, at least one processor, may control force applied by a resistance motor in response to one or more user inputs.

Some embodiments provide exercise equipment associated with a user interface. The user interface may allow a user to adjust one or more aspects of a workout, such as adjusting a time duration of a suggested/planned workout (e.g., to lengthen or shorten a workout) without changing the goal of the workout. The user may adjust the time duration before the workout starts, during the workout, or both. Some disclosed embodiments allow a user to shorten a workout while adapting the workout to meet the original goal via a software application that may adjust a remainder of a workout while meeting the goal.

A user interface may include one or more of an electronic display, a touch-sensitive screen, a microphone, a speaker, a haptic interface, a light emitting diode (LED), one or more adjustable dials, knobs, buttons, switches, and/or levers and/or any other type of manipulatable control enabling user inputs and/or information display. For example, a user may provide one or more inputs via a user interface associated with an electronic exercise machine to initiate, select, modify, share, and/or terminate an exercise routine. Such an interface may initiate signals to at least one processor associated with an electronic exercise machine. In a similar manner, the at least one processor may transmit one or more signals to convey information via a user interface to a user of an electronic exercise machine.

Some disclosed embodiments involve an electromagnet. An electromagnet may refer to a temporary magnet created by intermittent electrical currents. For example, an electromagnet may be formed by passing an electrical current through an electrically conductive wire wrapped around a piece of magnetic metal to produce an electromagnetic field. Some examples of electrically conductive wires may include copper, steel, and/or aluminum wires. Some examples of magnetic metal may include cast iron, wrought iron, galvanized steel, ferritic and martensitic stainless steel. The strength of an electromagnetic field produced by an electromagnet may be increased, decreased, or terminated by controlling a level of electrical current through the wire. Electromagnetic fields produced by one or more electromagnets may be used to introduce resistance to mechanical motion. Overcoming such resistance may require an application of a mechanical force.

Some disclosed embodiments involve a motor (e.g., a resistance motor). Such a motor may include a one or more electromagnets configured to apply a variable electromagnetic field as resistance. For example, a level of resistance produced by a resistance motor may correspond to an amount of weight (e.g., "digital weight") needed to be overcome by muscles during performance of a weight-bearing exercise. A resistance motor may be associated with at least one processor configured to control a level of electrical current flowing therethrough, allowing the at least one processor to control attributes associated with resistance or digital weight produced by the resistance motor. In some embodiments, a resistance motor may be associated with a lower bracket configured to connect a bottom end of a vertical wall-mountable beam to a wall. For example, a resistance motor may be located inside a housing configured as a lower bracket for connecting a vertical wall-mountable beam to a wall. A lower bracket may be made of durable metal, such as stainless or galvanized steel, or aluminum.

Some disclosed embodiments involve an electronic wall-mountable exercise machine. An electronic wall-mountable exercise machine may refer to an electronic exercise machine including a frame (e.g., a vertically wall-mountable beam) for attachment to a wall via a plurality of supporting brackets. The frame and brackets may be made of durable metal (e.g., steel and/or aluminum) for sturdiness and may support a pulley system, allowing a first end of a cable to be connected to a resistance motor and a second end of the cable to be connected to exercise equipment. In some embodiments, an electronic wall-mountable exercise machine may include a user interface (e.g., including one or more adjustable dials, knobs, buttons, switches, and/or levers) allowing interaction with a controller of the wall-mountable exercise machine, e.g., to receive feedback and/or customize a workout to meet a fitness level and/or goal. For example, a dial may allow adjusting a resistance of a resistance motor, and a button may allow changing a direction and/or mode for exerting a force on a cable.

Some disclosed embodiments may involve a cable. A cable may include a rope, cord, chain, belt, and/or any other band or cordage having a tensile strength for withstanding repeated applications of tension. A cable may include a plurality of fibers (e.g., stainless and/or galvanized steel) that may be combined and twisted to form an elongated structure, and may optionally include a coating such as nylon and/or PVC to reduce friction and wear. In some embodiments, a cable may have a tensile strength suitable for withstanding a resistance force associated with a resistance motor of an electronic exercise machine. For instance, a first end of a cable may connect to a resistive motor and a second end of the cable may connect to a moveable arm of an electronic exercise machine, allowing for a mechanical force applied to move the arm to be at least partially resisted by the resistive motor.

Some disclosed embodiments include at least one processor. "At least one processor" may involve any physical device or group of devices having electric circuitry that performs a logic operation on an input or inputs. For example, the at least one processor may include one or more integrated circuits (IC), including an application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact At least one processor may include a single processor or multiple processors communicatively linked to each other and capable of performing computations in a cooperative manner, such as to collectively perform a single task by dividing the task into subtasks and distributing the subtasks among the multiple processors, e.g., using a load balancer. In some embodiments, at least one processor may include multiple processors communicatively linked over a communications network (e.g., a local and/or remote communications network including wired and/or wireless communications links). The multiple linked processors may be configured to collectively perform computations in a distributed manner (e.g., as known in the art of distributed computing).

Some disclosed embodiments involve a non-transitory computer-readable medium or a memory. Such terms may refer to any type of physical memory on which information or data readable by at least one processor can be stored. Examples include Random Access Memory (RAM), Read-Only Memory (ROM), volatile memory, nonvolatile memory, hard drives, CD ROMs, DVDs, flash drives, disks, any other optical data storage medium, any physical medium with patterns of holes, markers, or other readable elements, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within a wearable device or at a remote location. Additionally, one or more computer-readable storage mediums can be utilized in implementing a computer-implemented method. Accordingly, the term computer-readable storage medium should be understood to include tangible items and exclude carrier waves and transient signals.

Some disclosed embodiments involve one or more sensors. A sensor refers to a device which detects or measures something. A sensor may also be a detector or sensing element. In some embodiments, a sensor may measure or detect a property and record, indicate, or otherwise respond to it.

Some disclosed embodiments involve a touch sensor. A touch sensor may include any type of equipment that cap- tures and records physical touch or contact. Touch sensors, for example, may be capacitive and/or may include one or more of complementary metal-oxide semiconductor (CMOS) integrated circuit (IC) chips, an application-specific integrated circuit (ASIC) controller and a digital signal processor (DSP) for sensing pressure, temperature, humidity, and/or any other indicator of touch. A touch sensor may convert an indication of touch to an electronic signal, which may be transmitted to at least one processor.

Some disclosed embodiments involve an audio sensor. An audio sensor may include any device that detects sound waves and coverts the sound waves into at least one electrical signal. An audio sensor may include, for example, one or more microphones. Some examples of such microphones include, unidirectional microphones, bidirectional microphones, cardioid microphones, omnidirectional microphones, onboard microphones, wired microphones, wireless microphones, or any combination of the above. The electronic signals from an audio sensor may be transmitted to at least one processor.

Some disclosed embodiments involve a mechanical sensor. A mechanical sensor includes any device that detects some sort of mechanical deformation or movement and translates that detection into an electrical signal. A mechanical sensor may be associated with a mechanical interface (e.g., a button, key, ball, switch, lever, touch pad, or dial) such that applying a mechanical force on the mechanical interface may cause the mechanical sensor to transmit a signal to at least one processor. In some embodiments, a mechanical sensor may measure a level of tension on a portion of an electronic exercise equipment, such as tension on a cable. As an example, an electronic exercise machine 200 (shown in FIG. 2A) may include a mechanical sensor 124 (shown in FIG. 1A) that measures a tension level on cable 206 of electronic exercise machine 200.

Some disclosed embodiments involve a light sensor. A light sensor may be included any device or be capable of detecting and converting optical signals in the near-infrared, infrared, visible, and ultraviolet spectrums into electrical signals. Examples of light sensors include photodetectors, photosensors, digital cameras, semiconductor charge-coupled devices (CCDs), active pixel sensors in complementary metal-oxide semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct one or more 3D images, a sequence of 3D images, 3D videos, or a virtual 3D representation. A light sensor may convert an optic signal to an electronic signal, which may be transmitted to at least one processor.

Some disclosed embodiments involve an electronic display. An electronic display includes any device or element capable of generating a visible image from electrical signals. For example, an electronic display may include a screen (e.g., LCD or dot-matrix screen), an electroluminescent (EL) display, a liquid crystal display (LCD), light-emitting diode (LED)-backlit Liquid crystal display (LCD), a light-emitting diode (LED) display, an organic light-emitting diode (OLED) display, an active matrix organic light-emitting diode (AMOLED) display, a plasma (P) display, a quantum dot (QD) display, and/or any other type of technology for rendering information visually. At least one processor may transmit signals to an electronic display to cause information to be displayed visually.

Some disclosed embodiments involve a haptic indicator. A haptic indicator may include any element or device that outputs vibrations or forces detectable to a human when in contact with a portion of the human body, such as a finger or hand. A haptic indicator may include, for example, a vibrating motor, linear actuator, vibrational transducer, or any other force feedback device that provide tactile or haptic cues or that is capable of converting an electrical signal into corresponding vibrations or force applications. At least one processor may transmit signals to a haptic indicator to cause information to be rendered haptically.

Some disclosed embodiments involve a speaker. A speaker may include any element or device capable of outputting sound. For example, a speaker may include one or more transducers for converting electromagnetic waves into sound waves. At least one processor may transmit signals to a speaker to cause information to be rendered as sound.

Some disclosed embodiments involve a light indicator. A light indicator may include any element or device that emits light in order to convey information. (e.g., indicating that a machine is powered on, indicating a mode of operation, indicating proper or improper usage, or indicating any other information. A light indicator may include a single light source (e.g., an LED), an array of light sources, (e.g., an LED array associated with different colors). At least one processor may transmit signals to a light indicator to cause information to be rendered visually.

Some disclosed embodiments involve a data structure. A data structure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures. A data structure may also include any hardware, software, firmware, or combination thereof for storing and facilitating the retrieval of information in the data structure.

Some disclosed embodiments involve a mobile communications device. A mobile communications device is a portable electronic instrument designed to facilitate information transmission to other devices or networks. Mobile communications devices may, for example, use cellular or other wireless and/or wired networks to transmit information such as voice and/or other data. For example, such transmissions may be in the form of voice calls, text messages, internet access, and application usage.

Mobile communications devices come in various forms, such as smartphones, tablets, laptop computers, IoT devices, wearable electronics (such as smart watches, smart rings, fitness trackers, smart glasses, smart clothing, smart jewelry, smart headphones, wearable digital assistants), and portable wireless hotspots. Depending on configuration and intended use, they may include features such as a touchscreen interface, a built-in camera, Wi-Fi, NFC, and/or Bluetooth connectivity, and GPS navigation.

Some disclosed embodiments involve a power source. A power source may include any element, device, or system for providing electrical energy to an electrical load or a circuit. Examples of power sources include one or more batteries (e.g., a lead-acid battery, a lithium-ion battery, a nickel-metal hydride battery, a nickel-cadmium battery), fuel cells, generators, capacitors, power converters, or connections (e.g., an electrical wall outlet) to an external source of electrical energy (e.g., an electric grid or other mechanism for supplying electricity). A power source may further include combinations of any of the foregoing.

Some disclosed embodiments involve a communications network. Illustrated examples of a communication network include communication link 226 or network 306. A communications network may include any type of physical or wireless infrastructure used to exchange data. For example, a communications network may be the Internet, a private data network, a virtual private network using a public network, a Wi-Fi network, a LAN or WAN network, a combination of one or more of the forgoing, and/or other suitable connections that may enable information exchange among or between various system components. In some embodiments, a communications network may include one or more physical links used to exchange data, such as Ethernet, coaxial cables, twisted pair cables, fiber optics, or any other suitable physical medium for exchanging data. A communications network may also include a public switched telephone network ("PSTN") and/or a wireless cellular network. A communications network may be secured or unsecured network. In other embodiments, one or more system components may communicate directly through a dedicated communications network. Direct communications may use any suitable technologies, including, for example, BLUETOOTH™, BLUETOOTH LET™ (BLE), Wi-Fi, near field communications (NFC), or other suitable communication methods that provide a medium for exchanging data and/or information between separate entities.

A communications network may include a plurality of nodes interconnected via network infrastructure allowing encoded information to flow therebetween. Such network infrastructure may include, for example, one or more routers, switches, boosters, cables (e.g., Ethernet, coaxial cables, twisted pair cables, fiber optics, wires, buses), antennae, and/or any other wired and/or wireless computer networking technology configured for exchanging data.

Some disclosed embodiments involve a network interface. A network interface may include electronic circuitry and/or software code enabling at least one processor to communicate with another processor or processors via a network according to a communications protocol (e.g., Transmission Control Protocol/Internet Protocol or TCP/IP). Such circuitry may include, for example, at least one processor, a memory, one or more antennae configured to send and/or receive wireless signals from other devices, one or more wires and/or cables configured to send and/or receive wired signals from other devices, a plurality of physical and/or virtual ports, one or more software interface layers for implementing one or more communications protocols (e.g., lower layer protocols such as TCP, User Datagram Protocol (UDP), IP, and Internet Control Message Protocol (ICMP), and application layer protocols, such as Hypertext Transfer Protocol (HTTP), Secure Socket Shell (SSH), Transport Layer Security (TLS), and Secure Sockets Layer (SSL), and/or any other component required to enable networked communication between a plurality of computing devices.

Some disclosed embodiments involve a cloud service. A cloud service is a product that enables access to computing resources, such as servers, storage, and applications, over a network such as the internet. Cloud services are typically provided by third-party vendors who manage and maintain the underlying infrastructure allowing users to access and use the services via the internet. Non-limiting examples of types of cloud services, include Infrastructure as a Service (IaaS), Platform as a Service (PaaS), and Software as a Service (SaaS). In some embodiments, a cloud service may execute program code instructions to implement one or more virtual machines.

Some disclosed embodiments may involve a cloud service configured to communicate with an electronic device and/or with an electronic exercise machine, e.g., allowing a user to participate in one or more pre-programmed exercise routines, and/or change one or more exercise routines. For example, a software application associated with a cloud service may be installed on a mobile communications device of a user. The software application may permit the cloud service to receive data from the user, and/or to provide recording, monitoring, tracking, and/or feedback services related to performances of exercise routines. In addition, the cloud service may communicate with a controller of an electronic exercise machine, allowing the cloud service to receive data from the electronic exercise machine. The cloud server may analyze data received from the mobile communications device and/or the electronic exercise machine, provide feedback, e.g., to modify one or more aspects of an exercise routine. Such modifications may include, for example, changing a timing, a frequency, a speed, an intensity, and/or a mode of one or more exercise routine (e.g., by making corresponding changes to a resistance of a resistance motor of the exercise machine), changing a height and/or angle of an arm of the exercise machine, switching an accessory connected to the arm, recommending a change of posture or position of the user, and/or make any other change to an exercise routine. In some embodiments, a cloud service may collect and analyze data unrelated to an exercise machine and associated with a user and/or user training aspects. In some applications, a cloud service may use data unrelated to an exercise machine and associated with a user and/or user training aspect to operate an electronic exercise machine.

While a number of the foregoing examples are described in connection with a cloud service, similar functionality may be achieved with disclosed embodiments by incorporating the various functions into the exercise equipment itself, into software paired with the exercise equipment, or through networking with another device or server that aids in providing the associated functionality.

In some embodiments, a communications network may be associated with a client-server model, allowing a cloud service to provide data storage and/or computational services to one or more client devices via the communications network. For example, a cloud service may store data and software associated with one or more electronic exercise machines and/or mobile communications devices (e.g., client devices) and/or execute program code instructions associated with using one or more electronic exercise machines. For example, a cloud server may store data and/or execute program code instructions for implementing a plurality of operational modes for an electronic exercise machine (e.g., in association with one or more exercise routines), creating an interface between a mobile communications device and one or more electronic exercise machines, and/or pairing two or more modular electronic exercise machines.

As another example, a cloud server may store data and execute program code instructions associated with performances of exercise routines (e.g., with or without an electronic exercise machine). For example, a cloud server may store results or achievements and/or provide feedback associated with performances of exercise routines (e.g., by a single or by multiple users), provide instructions for using an electronic exercise machine and/or for implementing differing modes of operation of an electronic exercise machine, facilitate interactions between remote users performing exercise routines (e.g., with or without an electronic exercise machine), and/or provide any other service associated with performances of exercise routines.

Some disclosed embodiments may involve signals. Signals may refer to an electrical or electromagnetic wave that carries information such as voice, video, or data. Signals can take various forms, including analog signals and digital signals. Other signal examples include radio signals, optical signals, microwave signals, infrared signals, ultrasonic signals, or any other wave or other conveyance that carries information. Non-limiting examples of signals include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium.

Some disclosed embodiments involve an indication. An indication may include a measurement, sign, and/or a signal conveying information about a state and/or level of a physical phenomenon. For example, an indication may signal the presence, occurrence, or status of something. An indication may be provided in a form that can be detected by a person or a system. For example, computers or other electronics may detect indications through signals, and humans may detect indications through light, audio, haptics, odor, or taste. In some instances, electronic sensors can also detect indications through light, audio, haptics, and odor, as well as through substance or image sensing.

FIG. 1A is a block diagram of exemplary system architecture of an electronic exercise machine, consistent with some embodiments of the present disclosure. It is to be noted that FIG. 1A is a representation of just one embodiment, and it is to be understood that some illustrated elements might be omitted, and others added within the scope of this disclosure. For example, some elements of FIG. 1A may be grouped and/or housed separately. In some embodiments, circuitry associated with a resistance motor of an electronic exercise machine may be housed and/or positioned separately from at least one processor configured to control settings for operating the electronic exercise machine (e.g., a control unit may be located in proximity to a resistance motor and at least one processor may be located elsewhere, and may be in electronic communication with the control unit). While housed and/or located separately, the control unit and the at least one processor may be in communication via wired and/or wireless means. For example, a user may set a desired resistance weight via a software application installed on a mobile communications device. The mobile communications device may transmit an indication of the desired resistance weight to at least one processor. Based on the indication, the at least one processor may transmit a control signal to the control unit to cause the resistance motor to apply the desired resistance weight.

System architecture 100 may include a control circuit 101, an I/O (input-output) unit 104, a communication interface 106, a power source 108, and a data storage 110. Control circuit 101 may include at least one processor 112 and a memory 114. I/O unit 104 may include an input interface 116 and an output interface 118. Input interface 116 may include one or more of a touch sensor 120, an audio sensor 122, a mechanical sensor 124, and a light sensor 126, and/or any other type of sensor configured to receive an input. Output interface 118 may include one or more of an electronic display 128, a haptic indicator 130, a speaker 132, one or more light indicators 134, and/or any other type of output interface. Control circuit 101, I/O unit 104, communication interface 106, power source 108, and data storage 110 may be interconnected via bus system 136. Control circuit 101 may be connected to a resistance motor 140 via one or more wires and/or cables 138. In some embodiments, one or more components of control circuit 101 may be located inside a housing encasing resistance motor 140, however this is not required.

For example, upon receiving a selection of an exercise routine to be performed using an electronic exercise machine via input interface 116, at least one processor 112 may retrieve data from memory 114 associated with the selected exercise routine. Such data may include, for instance, settings, preferences, a history of prior performances of the selected exercise routine, and/or any other data associated with the selected exercise routine. The at least one processor 112 may apply the retrieved data to control a current supplied to resistance motor 140, to thereby control the resistance applied by resistance motor 140 during performance of the selected exercise routine.

Figure 1B:
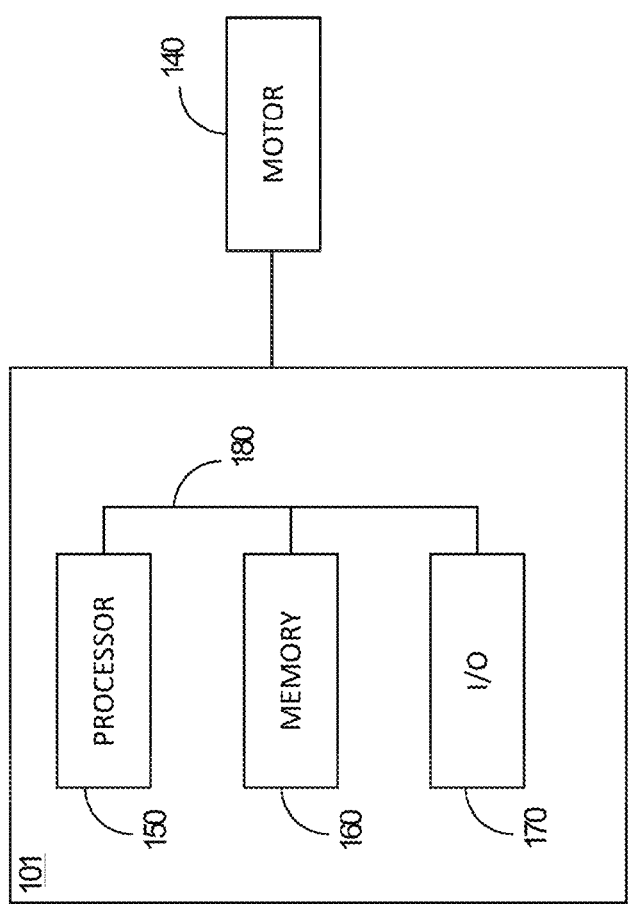
FIG. 1B is a block diagram of a controller for controlling an electronic exercise machine, consistent with some embodiments of the present disclosure.

FIG. 1B is a block diagram of a controller for controlling an electronic exercise machine, consistent with some embodiments of the present disclosure. Components of FIG. 1B may be similar in description to the corresponding components of FIG. 1A. A control circuit 101 of electronic exercise equipment 200 may include at least one processor 150, at least one memory 160, and an input output (I/O) 170 connected via a bus system 180. I/O 170 may include wired and/or wireless (e.g., one or more antennas) communications means enabling electronic communication between at least one processor 150 and another processor and/or device via a communications network. For instance, at least one processor 150 may communicate with mobile communications device 224 and/or another at least one processor 150 configured with another instance of electronic exercise equipment 200 (e.g., see FIG. 2B showing paired electronic exercise equipment 200A and 200B) via a pairing interface such as I/O 170. In some embodiments, at least one processor 150 may communicate with a wearable extended reality appliance via I/O 170. Some or all of control circuit 101 may be located within a motor housing 140, while some elements such as at least one processor 150, at least one memory 160, input output (I/O) 170, a bus system 180 may be encased within other portions of the equipment.

In some embodiments, a microphone may detect voice input from a user. The microphone may be embedded in the exercise equipment, or may be in another device that is in communication with the processor. For example, the microphone may be in a nearby device such as a smartphone or wearable device that is in communication with the processor. In some embodiments, the received input may occur via a control on the exercise equipment. In such embodiments, inputs may be received via one or more input devices on the exercise equipment, such as a touchscreen, touchpad, button press, or other tactile input mechanism. In some embodiments, the received input may occur via a mobile communication device paired with the exercise equipment. In addition to the microphone example provided above, an input interface of a mobile communication device may receive an input associated with adjusting an exercise session, such as using a mobile application associated with the exercise equipment.

In some embodiments, some or all of the input, output, and/or control functions described herein may be provided using an app of a mobile communications device such as smartphone 224. In such embodiments, the electronic exercise equipment may be operated by a user without the user directly interacting with the hardware of the electronic exercise equipment.

Figure 2A:
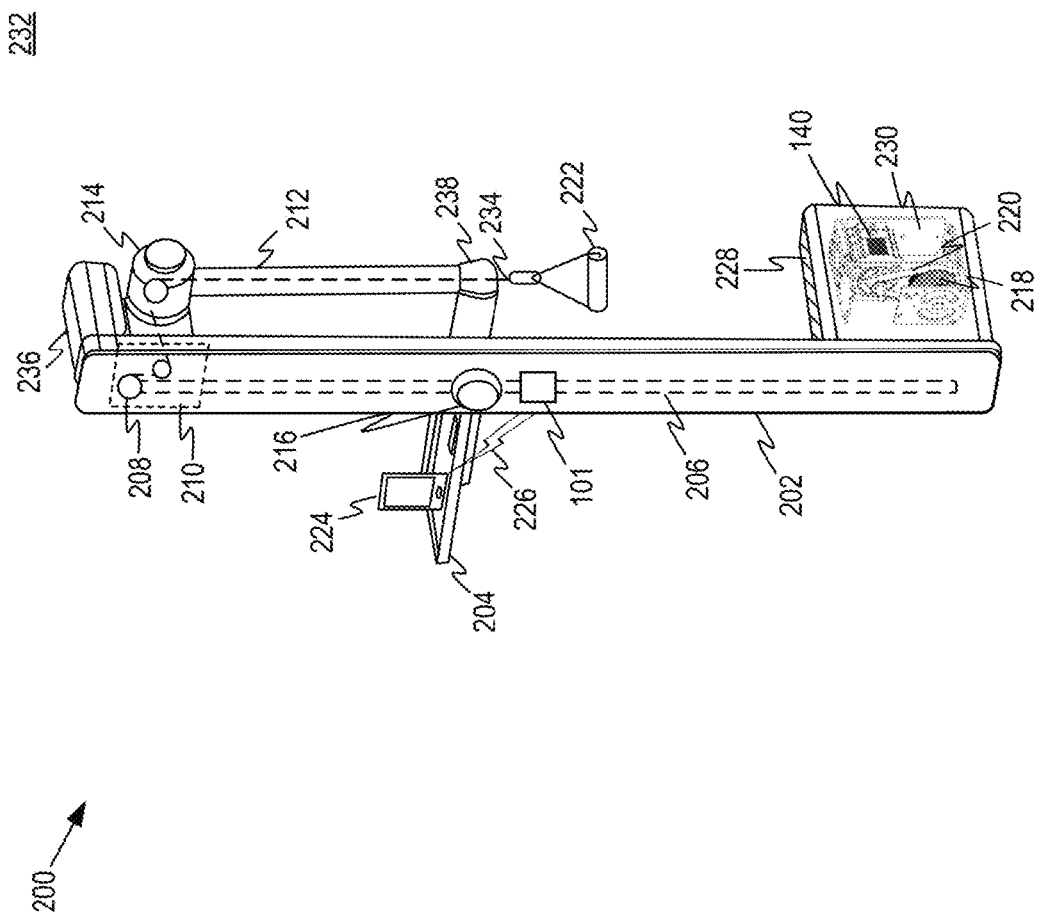
FIG. 2A is a perspective view of an exemplary wall-mountable electronic exercise machine, consistent with some embodiments of the present disclosure.
Figure 2B:
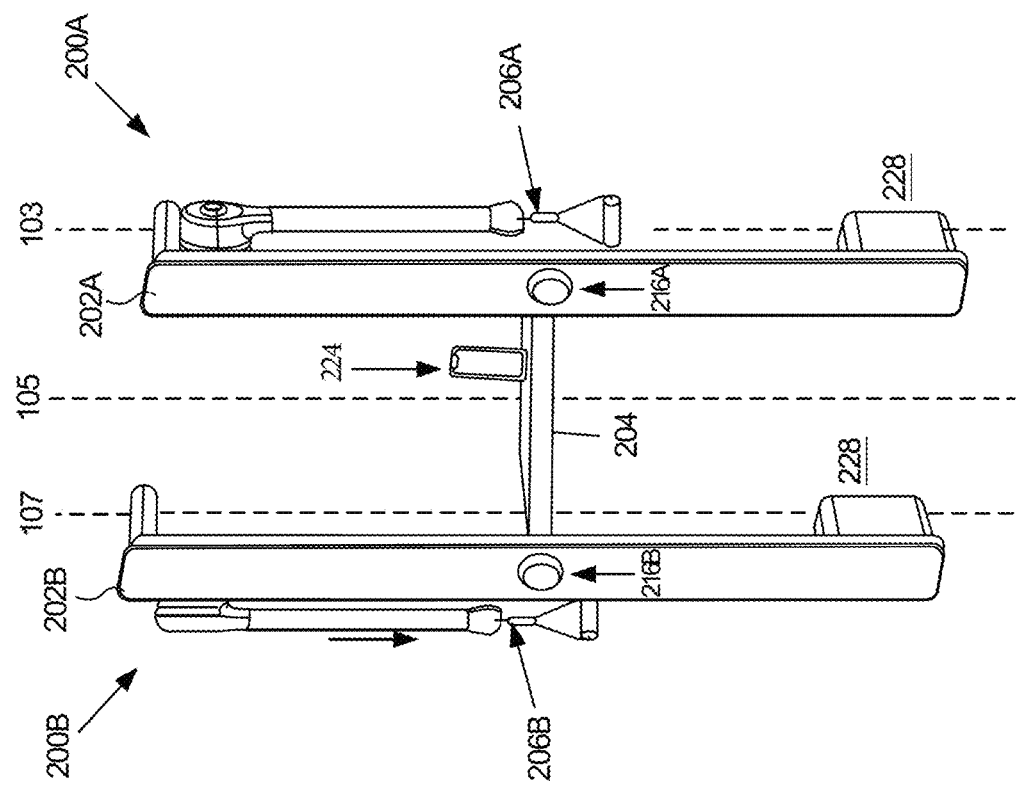
FIG. 2B is a perspective view of electronic exercise equipment illustrating positioning relative to wall studs, consistent with some embodiments of the present disclosure.

FIG. 2A is a perspective view of an exemplary wall-mountable electronic exercise machine 200, consistent with some embodiments of the present disclosure. Wall-mountable electronic exercise machine 200 may include a vertically wall-mountable beam 202 connected to a T-bar 204, resistance motor 140, control circuit 101 (e.g., see FIG. 1B) or a control circuit 101, a cable 206, a pulley system 208, a trolley 210, an arm 212, a rotatable shoulder 214, and a control knob or dial 216. Resistance motor 140 may be located towards a base of vertically wall-mountable beam 202, however this is not required. Resistance motor 140 may be housed inside a housing 228 including a bracket 230 (e.g., a lower bracket) for attaching to a lower section of wall 232. Vertically wall-mountable beam 202 may include an upper bracket 236 for attaching to an upper section of wall 232.

In some embodiments, T-bar 204 may include a bracket and a shelf. The bracket may be configured to attach to the wall and to vertically wall-mountable beam 202 and the shelf may be configured to cover the bracket and support one or more accessories (e.g., a cellular phone, a water bottle, and/or any other accessory.) As an example, a width of vertically wall-mountable beam 202 may be approximately 130 mm, a distance from a base of vertically wall-mountable beam 202 and T-bar 204 may be approximately 806 mm, and a length of T-bar 204 may be approximately 322 mm.

Pulley system 208 may be located towards a top of vertically wall-mountable beam 202. Resistance motor 140 may be connected to a spool 218 via a belt 220. Cable 206 may extend from spool 218, running substantially along the length of vertically wall-mountable beam 202, through pulley system 208, to trolley 210 and rotatable shoulder 214 through arm 212, exiting from a wrist 238 to connect to an exercise accessory 222 connected thereto at a second end 234, such that a pulling force applied to exercise accessory 222 may be at least partially resisted by resistance motor 140 via cable 206. Trolley 210 may be configured to move along the length of vertically wall-mountable beam 202 and lock at differing heights, allowing to adjust a height of arm 212, as described in greater detail herein. Rotatable shoulder 214 may allow adjusting an angle of arm 212 relative to vertically wall-mountable beam 202, as described in greater detail herein. At least one processor 112 of control circuit 101 may transmit one or more signals to control a level of current flowing through resistance motor 140, thereby controlling a level of resistance applied by resistance motor 140 onto cable 206.

A control knob such as dial 216 may provide a user interface allowing a user to engage in electronic communication with wall-mountable electronic exercise machine 200. Dial 216 may be associated with I/O unit 104. For example, a user may use dial 216 to adjust one or more operational parameters and/or attributes associated with a resistance applied by resistance motor 140 onto cable 206. At least one processor 112 of control circuit 101 may receive an indication of an attribute selection via dial 216 from I/O 104 and may transmit a signal causing an adjustment to a current or a voltage flowing to resistance motor 140, to thereby cause resistance motor 140 to apply resistance characterized by the selected attributes to cable 206.

In some embodiments, control circuit 101 may pair to a mobile communications device 224 via communication interface 106 (e.g., see FIG. 1A) to establish a (e.g., wireless) communications channel 226. A communications channel 226 may be any type of networked or peer-to-peer communication link consistent with the communication types and device operations disclosed herein. Mobile communications device 224 may be configured with a user interface associated with wall-mountable electronic exercise machine 200, allowing a user to engage in electronic communication with at least one processor 112 of wall-mountable electronic exercise machine 200 via communications channel 226. For example, a user may use mobile communications device 224 to adjust a resistance and/or receive an indication of resistance applied by resistance motor 140 onto cable 206, change a mode of operation wall-mountable electronic exercise machine 200, receive updates and/or a report associated with an exercise routine performed using wall-mountable electronic exercise machine 200, as described in greater detail herein.

In some embodiments, an electronic exercise machine and/or a paired mobile communications device may communicate with an associated cloud service via a communications network. For example, the cloud service may include a server and a data structure configured to provide data and/or processing services associated with operating an electronic exercise machine, and/or for with performances of one or more exercise routines (e.g., with or without an electronic exercise machine).

Reference is made to FIG. 2B illustrating an exemplary configuration for two paired units of electronic exercise equipment 200A and 200B, consistent with some disclosed embodiments. Electronic exercise equipment 200A and 200B may correspond to electronic exercise equipment 200 of FIG. 2D. FIG. 2B illustrates three wall studs 103, 105, and 107, indicated as dashed lines. In some embodiments, T-bar 204 may be configured to extend between and connect to an additional vertically wall-mountable beam 202B mounted on a third stud 107 adjacent to second stud 105 and on a side of the second stud 105 opposite the first stud 103. In some embodiments, vertically wall-mountable beam 202A, the additional vertically wall-mountable beam 202B, and the T-bar 204 cooperate for form an H-configuration, with the T-bar 204 configured to resist torquing of both the vertically wall-mountable beam 202A and the additional vertically wall-mountable beam 202B.

Figure 3:
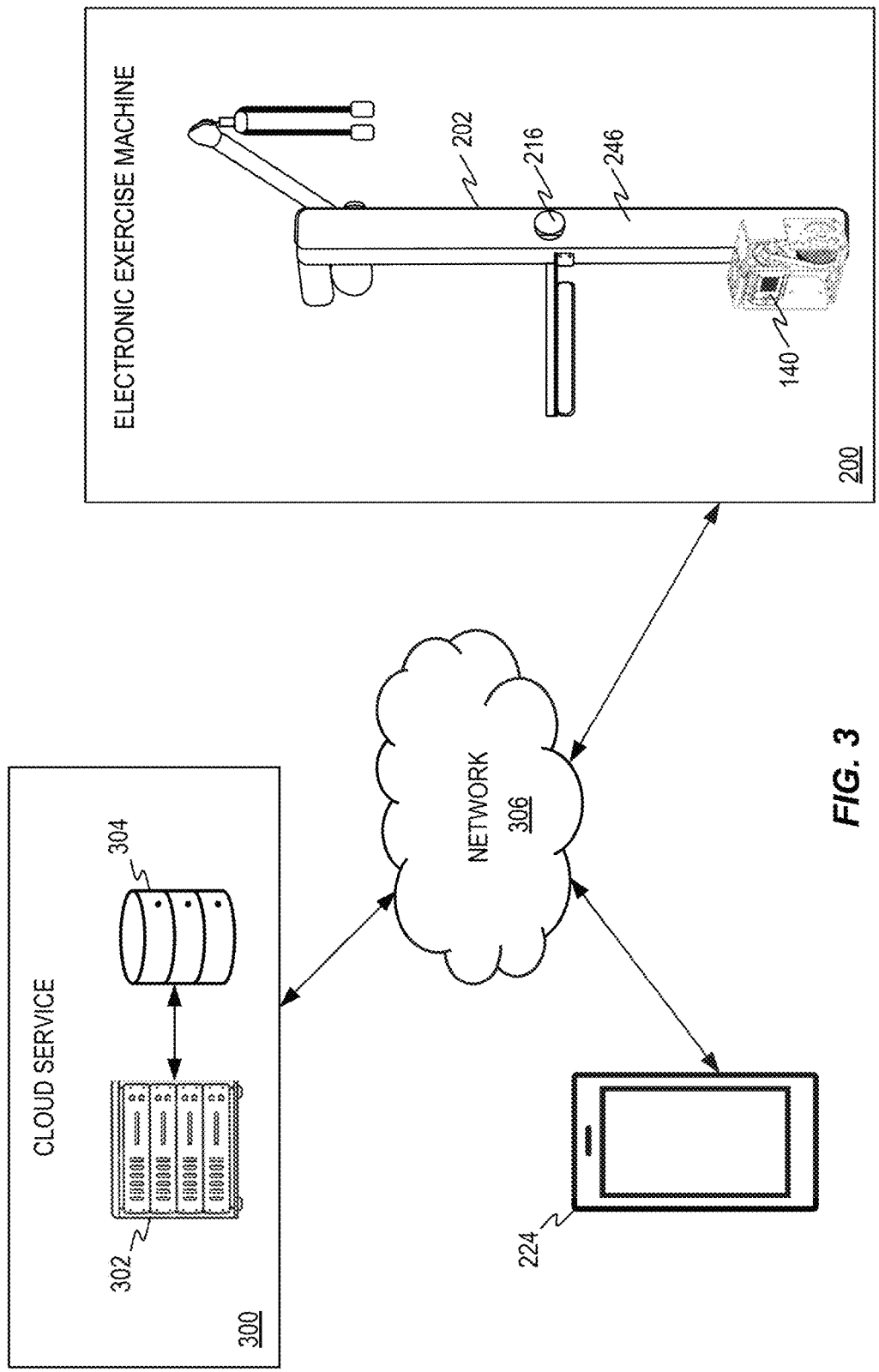
FIG. 3 is a schematic network diagram, consistent with some embodiments of the present disclosure.

FIG. 3 is a schematic illustration of a cloud service 300 associated with wall-mountable electronic exercise machine 200, consistent with some embodiments of the present disclosure. Cloud service 300 includes at least one server 302 (e.g., including at least one processor), and a data structure 304 connected to a communications network 306. Cloud service 300, wall-mountable electronic exercise machine 200 and mobile communications device 224 may communicate via a communications network 306. In some embodiments, communications network 306 may include a dedicated communications network, such as a Bluetooth communications channel connection mobile communications device 224 with at least one processor 112 of electronic exercise machine 200. In some embodiments, a light sensor (e.g., a camera) associated with mobile communications device 224 may capture images (e.g., of a user performing an exercise routine with or without wall-mountable electronic exercise machine 200). Cloud service 300 may store and analyze the images or videos, for example, to allow a first user of a first instance of wall-mountable electronic exercise machine 200 compete with a second user (e.g., of a second instance of wall-mountable electronic exercise machine 200), to provide feedback and/or instructions to a user performing an exercise routine, and/or provide any other service associated with performances of exercise routines (e.g., with or without wall-mountable electronic exercise machine 200).

Some disclosed embodiments involve initially accessing data. Data, in this context, may include exercise related data including any information that has a bearing on at least one of an exercise, an exercise routine, and individual or a class of individuals associated with an exercise schedule, historical exercise information, or details about a subject individual such as age, height, weight, medical conditions, injuries, restrictions, and/or medical information. Data may include information about an amount of resistance associated with an exercise. Any of such data is "initially accessed" if it precedes some subsequent operation. (I.e., initial accessing does require that the data was not previously accessed.)

In some embodiments, data may be accessed by a processor issuing one or more inquiries to one or more memories or databases in communication with the processor. In addition or alternative to the examples provided above, in some embodiments, the exercise-related data may include an exercise name, an exercise target muscle, an exercise effect, a prohibited condition of the exercise, available/possible resistances, a recommended number of repetitions and sets, a recommended duration of time, a recommended exercise machine adjustment (e.g., a height and/or angle of an arm of the exercise machine, available accessories for the exercise, recommended physiological parameters for user safety, conditions in which the workout should be aborted, and any set up information that may guide a user to perform the exercise or instruct the user to perform or stop performing a task. In some embodiments, the exercise-related data may be preset by an entity such as a manufacturer, owner, operator, trainer, or other entity having control over exercise-related data. In some embodiments, the an initial set of exercise-related data may be preset or determined according to industry standards, scientific research, experience, or a combination thereof.

In some embodiments, the exercise-related data may be associated with an individual's past exercise history. Past exercise history includes any information related to one or more prior exercises performed by the individual. Non-limiting examples of past exercise history include an identification of exercises previously performed by an individual, resistance associated with past exercises performed, historical changes in resistance or exercises, prior injuries or difficulties, In some embodiments, the past exercise history may include past exercise schedule and the degree of execution of the past exercise schedule. In some embodiments, past exercise history may include exercises performed on other machines. The past exercise history may be uploaded from one or more devices, such as smartphone 224, using one or more applications on the device.

In some embodiments, past exercise history may be associated with movements performed on the same exercise machine that is being used for the current exercise session. For example, a processor such as processor 112 may record in memory 114 that a user exercised using a specific exercise schedule on a certain date. If the processor 112 determines that the user completed the exercise schedule with ease (e.g., performed the exercise schedule with high quality, taking short breaks between sets, holding the arm(s) of the exercise machine without much shaking, and/or maintained a low heart rate throughout the scheduled exercise), the processor 112 may then decide that this exercise schedule might be adjusted to be more challenging (e.g., more resistance, longer duration, more repetitions and sets, higher target heart rate, or using indicators that may indicate the needs of additional efforts.) On the other hand, if the processor 112 determines that the user completed the exercise schedule with much difficulties, (e.g., performed the exercise schedule with low or declining quality, taking long breaks between sets, holding the arm(s) of the exercise machine with much shaking, and/or detected high heart rate during the scheduled exercise,) or even left the exercise schedule without finishing it, the processor 112 may decide that this exercise schedule might be adjusted to be less challenging (e.g., less resistance, shorter duration, fewer repetitions and sets, lower target heart rate, exercise on fewer days every week, or using indicators that may indicate the needs of lower effort.)

In some embodiments, the exercise-related data may include both general exercise data and user specific data. In some embodiments, the exercise machine may recognize a user and use only past exercise history tied to this user. In some embodiments, the exercise machine may recognize a user by asking the user to log in. In some embodiments, the exercise machine may recognize a user by pairing with an identified near field communication (NFC) device, e.g., a smart phone, a smart watch, a wristband, or any NFC enabled device that may be linked to an identity. In some embodiments, the exercise machine may recognize a user by using biometrics of the user, for example, fingerprints, facial recognition, iris scan, voice recognition, body weight, gait analysis, or any other biometrics that can be used to identify a person. Note that such recognition, in some embodiments, does not need to be done with high confidence (i.e., the level of certainty at an airport security checkpoint). It only needs to distinguish a limited number of frequent users. For example, the exercise machine may distinguish a husband from a wife by measuring their body weight. In some embodiments, different ways of recognizing a user may be combined for a higher accuracy.

In some embodiments, a user may set up the exercise machine with an exercise goal. The exercise goal may be a general goal, for example, general fitness, weight management, body building, strength, physical therapy. The exercise goal may also be a SMART goal that is "specific, measurable, attainable, relevant, timely." For example, a user may set up the exercise machine by stating that the exercise goal is to "lose ten pounds of weight in a month." The exercise machine may analyze the exercise goal and the user's physical conditions to determine which exercises to select for an exercise session, and accordingly determine a recommended exercise schedule.

Some disclosed embodiments may involve an exercise session or an exertion session. In some embodiments, an exercise session or exertion session may involve a selection of exercises, exercise intensity, duration, number of repetitions, number of sets, starting time, exercise schedule-related factors, and one or more goals. In some embodiments, an exercise session may include a series of varied electronically controlled exercises selected to further an exercise goal. An exercise goal refers to a specific objective or target that an individual sets for themselves in relation to their physical fitness or exercise routine and/or that is set by a computing device. For example, a computing device (e.g., one or more processors) may set a customized exercise goal based on inputs about an individual. In a broadest sense, an exercise goal may be to perform a defined amount of work. An exercise goal may additionally or alternatively include an amount of work for differing exercises or targeting differing regions of the body or muscles. Some exercise goals may additionally or alternatively include burning a number of calories in a workout or over a series of workouts. Additionally or alternatively, an exercise goal may include one or more of weight loss, strength building, endurance improvement, flexibility and mobility and/or athletic performance or any other goal associated with performance qualities. For example, an exercise goal may be associated with a desired strength level, a desired user weight, a target resistance level for one or more movements of an exercise, or any other definable target or desired metric associated with fitness of a user.

An electronically controlled exercise refers to a form of physical activity or workout routine that utilizes electronics to control, monitor, and/or enhance the exercise experience. For example, an electronically controlled exercise includes an exercise where variable resistance is electronically preset. Electronic control may also involve pre-setting other variables such as duration, equipment configuration, electronic coaching, and any other feature that is electronically controllable. Electronic control in some embodiments may involve altering any variable during an exercise routine and/or across a series of sessions.

A series of varied electronically controlled exercises refers to a group of differing exercises that are controlled, as discussed above. The differing exercises may vary in that they are directed to differing parts of the body, differing muscles, or differing manners of exercising the same muscles. Exercises may be additionally or alternatively be varied with respect to a required movement of the exercise equipment, a muscle group targeted by the exercise, a required pose or orientation of the user while interacting with the exercise equipment, or by differentiating other aspects of exercises that result in multiple different exercises.

The series of varied exercises may be a selection from a pool of available exercises on the exercise machine. In some embodiments, the series of varied electronically controlled exercises may be sequenced. In some embodiments, the exercise schedule may refer a particular exercise session, or a particular exercise session within a group of exercise sessions (e.g., spread out over a period of time such as days.) Exercises may be electronically controlled by the exercise equipment by, for example, regulating a resistance level associated with one or more movements of the exercise equipment, by providing feedback or instruction associated with an exercise to a user via an output device.

Some disclosed embodiments involve applying a resistance using a resistance motor of the electronic exercise equipment. A resistance motor refers to a motor that applies a resistive force. A brushless DC motor (BLDC motor) is one non-limiting example of a motor that can be used to provide resistance. Such a motor may be integrated into the resistance mechanism of the exercise equipment, such as through a flywheel or pulley system. By varying the voltage or current applied to the motor, the resistance level can be adjusted, providing users with different workout intensities. A motor controller may receive input signals via a user interface or smart gym system and regulate the motor's speed and torque output accordingly. This allows users (or a program) to select and adjust the desired resistance level during workouts.

In general, altering the resistance on the resistance motor may change a difficulty or intensity of the exercise. For example, increasing the resistance may increase a simulated amount of weight that must be lifted or force that must be exerted on the exercise equipment in order to complete the exercise movement. The electronic exercise equipment may include one or more resistance motors that generate a resistive force that the individual must overcome to perform the exercise. In some embodiments, the resistance motor may include one or more electromagnets, such as the resistance motors discussed herein.

Some disclosed embodiments involve adjusting operation of the electronic exercise equipment, such as by changing or modifying the way the exercise equipment, any part thereof, or any program associated therewith operates. It may involve adjusting one or more settings, parameters, or configurations to alter how the equipment operates. Such changes may impact one or more parameters of the exercise, such as changing an intensity of the exercise. In some embodiments, altering a mode of operation may change the exercise to a different exercise.

For example, adjusting a resistive force of the resistance motor changes the amount of force required to perform an exercise. In some embodiments, the mode of operation may be altered by changing a configuration (or instructing a user to change a configuration) of the exercise equipment through, for example a height or angle adjustment (e.g., altering an angle of the arm 212 relative to the exercise equipment). In turn, this alters the manner in which the user performs a movement, or changes a direction that the user faces when performing a movement with the exercise equipment.

Some disclosed embodiments involve outputting instructions for adjusting the electronic exercise equipment. In general, the exercise equipment may provide instructions to a user via one or more output devices in the exercise equipment in a device (e.g., a smartphone) paired with the exercise equipment. The instructions may be provided to users to follow during the exercise session, and in some embodiments, before or after the exercise session, to set up the equipment before a session, and to stow the equipment after use. In some embodiments, outputted instructions may be associated with a change in exercise (e.g., providing instructions adjust parameters of the machine to enable a switch to a different exercise movement. In some embodiments, outputted instructions may be associated with aspects of the exercise other than adjusting the exercise equipment, including a change during a current exercise such as, for example, a change in a number of repetitions, sets, durations, intensity, resistance level, or time of rest between sets of the same exercise movement.

In some disclosed embodiments, outputting instructions involve displaying instructions on an electronic display associated with the electronic exercise equipment. Instructions refers to guidance, such as guidance on how to perform an exercise, how to position oneself, or how to configure the exercise equipment. Instructions may be provided in the form of one or more of text, audio, graphics, videos, clips, or images. For example, a display on a piece of exercise equipment or on a paired device may present video instructions, visual images or videos on a display device. A paired device may include a mobile phone or smartphone, tablet, laptop, wearable device, and any other portable or handheld communications device capable of displaying information or providing audible information to a user and communicating with one or more processors of the electronic exercise equipment. The mobile communications device may be paired to the electronic exercise equipment, and may communicate with the exercise equipment via a wired or wireless connection. In some embodiments, the mobile communications device and the exercise equipment may communicate via an intermediary device or system, such as the mobile communications device communicating with the exercise equipment via a local or remote server.

A speaker on either the equipment or a paired device may provide audible queues, spoken instructions output by a speaker, or any other form of communication that can enable a user to understand how to adjust a part of the electronic exercise equipment. An electronic display may be associated with the electronic exercise equipment by being built into the equipment, or by being physically or communicatively attached to the exercise equipment.

By way of non-limiting example, one or more components of an electronic exercise machine, such as machine 200 in FIG. 2A, may provide instructions. For example, with reference to system architecture 100 of FIG. 1A, one or more components of output interface 118 of an electronic exercise machine may display or present instructions to a user.

In some disclosed embodiments, adjusting the exercise session includes outputting instructions for adjusting the electronic exercise equipment. An adjustment of a session may involve changing exercises, and that in turn may involve outputting instructions to effectuate the exercise change. The instructions may be output as described earlier, to guide the user in modifying the equipment (e.g., adjust the equipment for a different exercise. Thus, in the context of a home gym exercise equipment exemplified in the figures, the instructions that may be associated with adjusting an angle or position of an arm of the electronic exercise equipment. In some embodiments, the instructions may be associated with adjusting a height of an arm of the electronic exercise equipment. The instructions may inform a user as to how far to move the arm and in which direction, to reach the required height and/or angle. In some embodiments, the exercise equipment may include one or more sensors for tracking a real-time position of the arm, to provide feedback to the user about how close the arm is to its required angle or height. Such feedback may be provided in the form of updated instructions, or as an indication separate from the outputted instructions.

Some disclosed embodiments involve adjusting an exercise session by altering a time of the exercise session and in a manner furthering the exercise goal. Altering a time refers to either shortening or lengthening a duration of the exercise session. In a manner furthering a goal refers to compensating in some way for the time alteration to thereby advance the goal. For example, if altering a time involves shortening a session, then the manner of alteration may involve increasing a resistance level of one or more exercises in the shortened time, to make up for the user adopting a shorter workout. For example, resistance may be increased in one or more exercises so that an amount of work consistent with a goal is achieved by making the user work harder for a shorter period of time.

In some embodiments, at least one processor may adjust an exercise session by taking into account the alternative duration, the exercise-related data, the record of the series, and the exercise goal. For example, if a goal is to burn a particular number of calories in a session or to achieve a particular amount of total work or total work in one or more exercises, resistance, speed of repetitions, time between repetitions, and/or any other variable might be changed to minimize the impact on the goal. Thus, the manner of alteration may not ensure that the goal is met, it might help close the gap in achieving the goal. In other embodiments, the manner of furthering the exercise goal may be a manner that maintains the goal. For example, one or more of the aforementioned variables may be altered so that the goal is achieved for the session, despite the altered duration.

Some disclosed embodiments involve a metaverse gym. The metaverse refers generally to virtual three-dimensional environments in which users represented by avatars interact. The metaverse is poised to change many aspects of life. Some disclosed embodiments include a gym experience where a user may physically exercise at a first location (e.g., home), with their exercises being expressed via an avatar in virtual gym. In this way, multiple individuals exercising in separate locations (e.g., at home), can participate in a shared gym experience.

Some embodiments provide a non-transitory computer readable medium containing instructions that when executed by at least one processor cause the at least one processor to communicate with a plurality of remote sensors associated with disbursed exercise equipment and to simulate a virtual training experience. The operations may include generating a simulated exercise environment. For instance, at least one processor may generate a simulated exercise environment viewable by a plurality of wearable extended reality appliances, allowing multiple participants to be simultaneously emersed in the simulated exercise environment.

The at least one processor may present a first avatar in the simulated exercise environment, associated with a first participant located in a first physical location. The at least one processor may present a second avatar in the simulated exercise environment, associated with a second participant located in a second physical location remote from the first physical location. The at least one processor may receive from at least one first sensor associated with a first piece of exercise equipment in the first physical location first signals representing first physical exertions by the first participant. For example, the first piece of exercise equipment may be a first instance of T-shaped wall-mounted electronic exercise machine 200, and the first sensor may include a camera. In some embodiments, the camera may be associated with a first mobile communications device of the first participant. The camera may capture images of the first participant performing first exercise exertions on the first piece of exercise equipment.

The at least one processor may cause the first avatar to simulate, in the simulated exercise environment, the first physical exertions in response to the first signals. The at least one processor may receive from at least one second sensor associated with a second piece of exercise equipment in the second physical environment second signals representing second physical exertions by the second participant. For example, the second piece of exercise equipment may be a second instance of T-shaped wall-mounted electronic exercise machine 200, and the second sensor may include a camera (e.g., associated with a second mobile communications device of the second participant). The camera may capture images of the second participant performing second exercise exertions on the second piece of exercise equipment.

The at least one processor may cause the second avatar to simulate, in the simulated exercise environment, the second physical exertions based on the second signals. The at least one processor may enable the first participant to view from the first physical location the simulations of the first physical exertions and the second physical exertions in the simulated exercise environment (e.g., using the first wearable extended reality appliance). The at least one processor may enable the second participant to view from the second physical location the simulations of the first physical exertions and the second physical exertions in the simulated exercise environment (e.g., using the second wearable extended reality appliance). The at least one processor may enable the first participant and the second participant to communicate with each other during a common exercise session in the simulated exercise environment, thereby allowing the first and second participants to exercise in separate locations while participating in a shared gym experience.

In some embodiments, the simulated exercise environment may contain a simulation of a piece of exercise equipment (e.g., virtual exercise equipment) and the first physical exertions and the second physical exertions may be simulated on the simulation of the piece of exercise equipment, e.g., via the first and second wearable extended reality appliances. In some embodiments, the first signals may be associated with tension on a first cable of the first (e.g., physical) piece of exercise equipment, and the second signals may be associated with tension on a second cable of the second (e.g., physical) piece exercise equipment.

In some embodiments, the first avatar and the second avatar may mask identities of the first participant and the second participant. Alternatively, the first avatar and the second avatar simulate identities of the first participant and the second participant.

In some embodiments, the first signals and the second signals reflect limb motion of the first participant and the second participant, respectively. The at least one processor may use the first signals and the second signals to respectively simulate via the first avatar and the second avatar the limb motion of the first participant and the second participant.

In some embodiments, the first signals and the second signals reflect posture of the first participant and the second participant, respectively. The at least one processor may use the first signals and the second signals to provide posture feedback to the first participant and the second participant.

In some embodiments, the at least one processor may monitor of the first signals and the second signals by a trainer (e.g., a human or virtual trainer). The at least one processor may enable the trainer to provide feedback based on the first signals and the second signals. In some embodiments, the at least one processor may enable a competition between the first participant and the second participant. The competition may involve the first participant and the second participant respectively interacting simultaneously with the first piece of exercise equipment and the second piece of exercise equipment.

In some embodiments, the first signals and the second signals each include image data and resistance data (e.g., associated with the first and/or second exercise equipment). The first piece of exercise equipment may include free weights. The at least one processor may determine from the first signals repetitions occurring with the free weights. The at least one processor may determine from the first signals and indication of form of the first participant. The at least one processor may determine from the first signals an indication of posture of the first participant. The at least one processor may determine from the first signals an indication of tempo of the first participant. The at least one processor may determine from the first signals an indication of repetitions of the first participant. The at least one processor may count the repetitions only when the first physical exertions meet a threshold. The at least one processor may output the simulated exercise environment and the first and second avatars in a format enabling virtual reality presentation.

Disclosed herein are systems, methods, and non-transitory computer readable media relating to simulation of virtual training experience using electronic exercise equipment such as electronic exercise machines. Some disclosed embodiments relate to software applications for using an electronic exercise machine. Some disclosed embodiments relate to operation of a modular electronic exercise machine, allowing integration of a plurality of individual electronic exercise machines. Some disclosed embodiments relate to performance of exercise routines. Some disclosed embodiments relate one or more combinations software applications, and/or operation of modular electronic exercise machines with associated mechanical features.

The disclosed embodiments that follow may be performed using at least one processor. The at least one processor may be associated with one or more of electronic exercise equipment, a mobile communication device, a wearable extended reality appliance, and/or a remote cloud server. In some embodiments, a plurality of processors may operate together in a distributed fashion by communicating over a communications network. For example, a processor of a mobile communications device may operate together with a cloud service and one or more processors of one or more exercise machines to track, analyze, and/or provide feedback for exercise routines performed by a user. The disclosed embodiments that follow may involve performance of one or more image processing techniques, e.g., to analyze image data for simulating one or more virtual training experiences based on detected physical exertions. Such image processor techniques may include, for example, preprocessing of an acquired image for noise reduction, contrast enhancement, and/or resizing, and/or one or more edge and/or contour detection, pattern recognition, feature detection and/or extraction, blob detection, template matching, and/or any other image processing technique.

Some disclosed embodiments involve communicating with a plurality of remote sensors associated with dispersed exercise equipment and simulating a virtual training experience. Exercise equipment refers to a device, machine, tool, and/or accessory for facilitating physical activity, strength training, cardiovascular exercise, flexibility training, and/or overall fitness as described and exemplified elsewhere herein. Dispersed exercise equipment refers to a plurality of pieces of exercise equipment that may be distributed in different locations. For example, dispersed exercise equipment may include an elliptical machine located in a commercial gym and a weight machine located at a home of an individual. As another example, disbursed exercise equipment may include a first electronic (e.g., wall-mounted) weight machine at a first location and a second electronic (e.g., wall-mounted) weight machine at a second location. As a further example, a set of free weights may be located at an office gym and an electronic weight machine may be located at a home location. A sensor refers to a device and/or component for detecting and/or responding to one or more physical changes and/or stimuli in an environment, as described elsewhere herein. Sensor data may include information about temperature, pressure, motion, or other parameters depending on the type of sensor. Example sensors include thermistors, pressure sensors, motion sensors, and the like. A remote sensor refers to a sensor located at a distance from at least one processor, such that receiving information detected by a remote sensor may involve communication over a communications network.

A plurality of remote sensors associated with dispersed exercise equipment refers to multiple sensors linked and/or related to a plurality of distributed pieces of exercise equipment. In some embodiments, different pieces of dispersed pieces of exercise equipment may be associated with one or more different types of sensors. For instance, a camera may be associated with a first piece of exercise equipment at a first location and a motion sensor may be associated with a second piece of exercise equipment at a second location. In some embodiments, different pieces of dispersed pieces of exercise equipment may be associated with one or more sensors of the same type. For example, a first camera may be located in proximity to a first piece of exercise equipment at a home location, and a second camera may be located in proximity to a second piece of exercise equipment located at a commercial gym. As another example, a first motion sensor integrated with a first wearable appliance may sense exercise motion of a first user using a first piece of exercise equipment at a first location, and a second motion sensor integrated with a second wearable appliance may sense exercise motion of a second user using a second piece of exercise equipment at a second location. As a further example, a first load cell associated with a first resistance motor of a first electronic weight machine located in a first location may sense a first weight lifted at the first location, and a second load cell associated with a second resistance motor of a second electronic weight machine located in a second location may sense a second weight lifted at the second location.

Communicating with a plurality of remote sensors associated with dispersed exercise equipment refers to receiving electronic signals from a plurality of sensors linked and/or related to distributed pieces of exercise equipment via a wired and/or wireless communications network. Simulating refers to replicating, emulating, and/or reproducing events, exercises, or other actions. A virtual training experience refers to an exercise routine facilitated using electronic media and/or content. A virtual training experience may include rendering of digital content during a performance of an exercise routine, such as displaying one or more digital images, video and/or outputting audio content. For example, at least one processor may receive data from a plurality of sensors associated with dispersed exercise equipment and use the data to generate digital content for simulating a virtual training experience. The at least one processor may output the digital content using one or more electronic output devices. Such output devices may include, for example, a speaker, an electronic display, a haptic output device, an extended reality appliance and/or any other output device.

Some disclosed embodiments involve generating a simulated exercise environment. Generating refers to creating and/or producing. An exercise environment refers to a surrounding and/or a setting in which a physical activity may occur. An exercise environment may include a physical space and/or an atmosphere or conditions within a space.

Some examples of an exercise environment may include a fitness facility equipped with various exercise machines, a natural or landscaped outdoor area with trails, a dedicated space within a home equipped with exercise equipment, a specialized facility for group exercise classes, a digitally-created or simulated environment for virtual reality (VR) or augmented reality (AR) workouts or and any other type of setting in which physical activity takes place. A simulated exercise environment refers to a digitally recreated space and/or surrounding for performing an exercise routine. Some examples of a simulated exercise environment may include a simulated running track, a simulated cycling tour, a simulated fitness class, and/or any other type of simulated environment that mimics or represents a setting where exercise may occur. For example, at least one processor may use image data received from a remote image sensor to generate outdoor scenery for viewing while riding a stationary bicycle in a gym. As another example, at least one processor may receive audible exercise instructions from a microphone located at a remote gym, and output the audible exercise instructions via a speaker at a home gym to simulate a remote exercise class.

Figure 4:
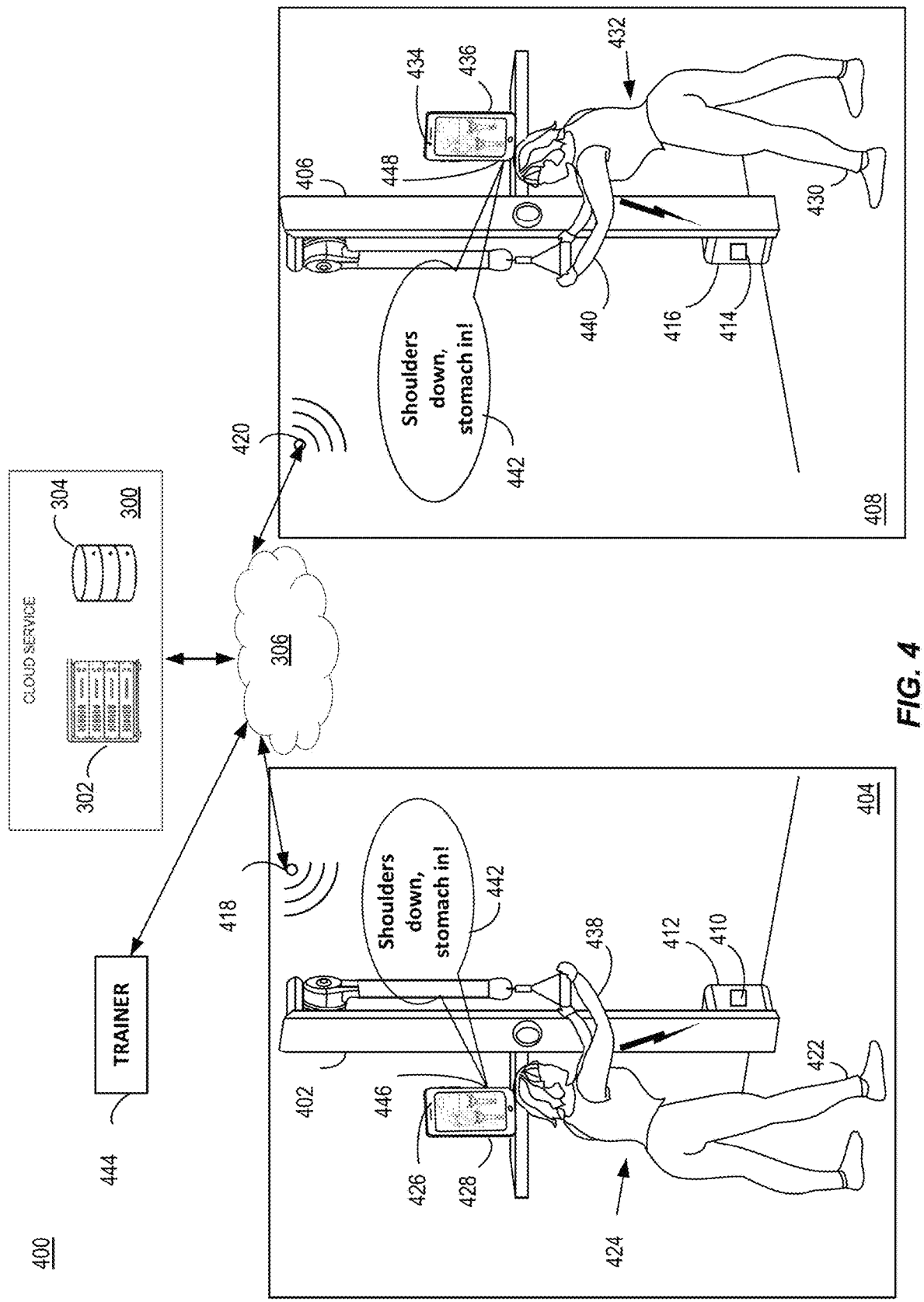
FIG. 4 illustrates an exemplary network diagram of a system for communicating with a plurality of remote sensors associated with dispersed exercise equipment and simulating a virtual training experience, consistent with some embodiments of the present disclosure.

By way of a non-limiting example, reference is made to FIG. 4, illustrating an exemplary network diagram of a system 400 for communicating with a plurality of remote sensors associated with dispersed exercise equipment and simulating a virtual training experience, consistent with some embodiments of the present disclosure. System 400 may include a first piece of exercise equipment 402 in a first physical location 404, and a second piece of exercise equipment 406 in a first physical location 408. For example, first and second pieces of exercise equipment 402 and 406 may include a wall-mounted electronic weight machine. First piece of exercise equipment 402 and second piece of exercise equipment 406 may each include at least one processor (e.g., processor 112 in FIG. 1A) in communication with a cloud service 300 over a communications network 306, using a first Wi-Fi sensor 418 and a second Wi-Fi sensor 420, respectively. First piece of exercise equipment 402 may include a first potentiometer 410 associated with a first resistance motor 412 for transmitting resistance data to cloud service 300 via communications network 306. Second piece of exercise equipment 406 may include a second potentiometer 414 associated with a second resistance motor 416 for transmitting resistance data to cloud service 300 via communications network 306. A first participant 422 may perform first physical exertions 424 on first piece of exercise equipment 402 at first location 404. A first image sensor 426 of a first mobile communications device 428 may record first physical exertions 424 by first participant 422 at first location 404 and transmit associated image data to cloud service 300 via communications network 606. A second participant 430 may perform second physical exertions 432 on second piece of exercise equipment 406 at second location 408. A second image sensor 434 of a second mobile communications device 436 may record second physical exertions 432 by second participant 430 at second location 408 and transmit associated image data to cloud service 300 via communications network 606. System 400 may enable communicating with a plurality of remote sensors (e.g., first and second potentiometers 410 and 414 and image sensors 412 and 416, respectively) associated with dispersed exercise equipment (e.g., first and second pieces of exercise equipment 402 and 406) and simulating a virtual training experience.

Figure 5:
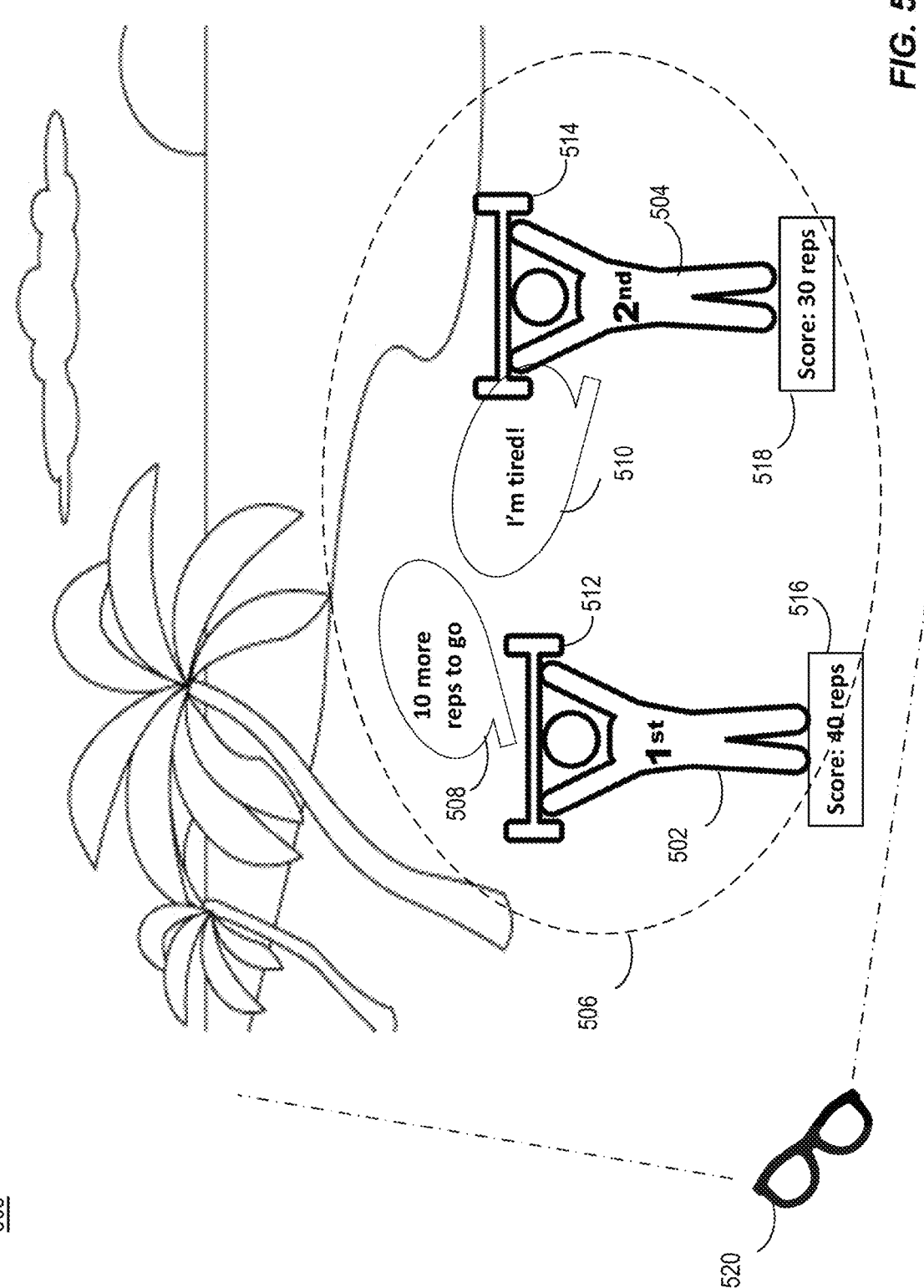
FIG. 5 illustrates a simulated virtual training experience, consistent with some embodiments of the present disclosure.

By way of another non-limiting example, reference is made to FIG. 5 illustrating a simulated exercise environment 500 for a virtual training experience, consistent with some embodiments of the present disclosure. Simulated exercise environment 500 may include a beach background for performing exercise routines.

Some disclosed embodiments involve presenting a first avatar in the simulated exercise environment, wherein the first avatar is associated with a first participant located in a first physical location. An avatar refers to a digital representation and/or embodiment of a person and/or entity in a virtual environment and/or digital platform, as described elsewhere herein. For example, an avatar may include a three-dimensional image, an animated image, a photo, a sketch of a person, or a person's alter ego, sometimes used in a virtual world. A physical location refers to the specific place or position of an object or entity in physical space. A physical location may include a tangible, real-world location that may be described using coordinates such as latitude and longitude, or by referencing landmarks or addresses. Some examples of physical locations may include a gym, an office, a personal home, and/or or any other type of physical location. A participant refers to an individual taking part in an event and/or an activity, and/or using a service. In the context of electronic exercise equipment, a participant may include an individual interacting with a computer system, software application, and/or online platform associated with the exercise equipment. Participants may perform various actions such as using the exercise equipment, entering data, requesting information, or controlling the behavior of the system through input devices like keyboards, mice, touchscreens, or voice commands as described and exemplified elsewhere herein. Presenting refers to showing, displaying, outputting, and/or rendering. Presenting may include displaying information on an electronic screen, outputting audio data via a speaker, outputting haptic data via a haptic output device, and/or any other presentation of data. For example, presenting may include presenting results of a computation, showing visualizations of data, or displaying user interface elements for interaction and/or any other type of presenting. Presenting a first avatar in a simulated exercise environment refers to rendering image, video, and/or audio data associated with an avatar using one or more output devices. For example, at least one processor may activate selected pixels of an electronic display to cause a sequence of images of an avatar exercising in a commercial gym to appear as an animation, and output associated audio data via a speaker. A first avatar associated with a first participant located in a first physical location refers to an avatar linked and/or related to a first participant situated in a specific place. For example, at least one processor may receive image data of a participant exercising at a commercial gym and may use the image data to generate a sequence of images of an avatar performing the exercise at a commercial gym, thereby presenting an avatar in a simulated environment.

Some disclosed embodiments involve presenting a second avatar in the simulated exercise environment, wherein the second avatar is associated with a second participant located in a second physical location remote from the first physical location. Second avatar may be understood similar to the first avatar, second participant may be understood similar to the first participant, and second physical location may be understood similar to the first physical location as described and exemplified above.

For example, at least one processor associated with a cloud server may generate a simulated commercial gym for presenting to a first participant and a second participant via a first mobile communications device and a second mobile communications device, respectively. The at least one processor may cause a simulation of first avatar exercising in the commercial gym to be displayed on the first mobile communications device, and may cause a simulation of second avatar exercising in the commercial gym to be displayed on the second mobile communications device.

Some disclosed embodiments involve the first avatar and the second avatar masking identities of the first participant and the second participant. The second avatar may be a second instance of the same, similar, or different type of avatar as those described above with respect to the first communications channel. Masking identities refers to techniques used to obfuscate or hide sensitive information, such as personal data, network addresses, or cryptographic keys, to protect them from unauthorized access or disclosure. Masking identities may also refer to the process of anonymizing or pseudonymizing data to protect the privacy of individuals. This can involve replacing identifying information with pseudonyms or aggregating data to make it less identifiable. For example, in online gaming, or online forums and communities, users may create avatars to represent themselves instead of using their real identities, such as 514 shown in FIG. 5. Anonymizing or pseudonymizing data may also include creating an avatar that looks different from the user's actual appearance, in order to protect that user's identity and appearance.

Some disclosed embodiments may involve the first avatar and the second avatar simulating identities of the first participant and the second participant. An identity refers to characteristics, traits, and/or attributes that distinguish an individual and/or entity from others. For instance, an identity may be associated with an appearance, a body shape, an exercise type, a style of clothing, a brand of clothing and/or exercise equipment, a specific location, and/or any other distinguishing characteristic. By way of example, an identity may include a friend, an associate, a trainer, a coach, a partner, and/or any other individual. Simulating identities refers to creating realistic-seeming recreations of individuals, e.g., to protect a real identity. Simulating an identity may refer to the digital representation of an individual or entity within a system or network. By way of example, at least one processor may use a personal profile of a participant, including a name, one or more images, and/or personal information to produce a replica of the participant. By another way of another example, at least one processor may create a plurality of personas representing different players in an interactive game. By way of a further example, at least one processor may user a plurality of images of a participant to create a three-dimensional avatar having similar facial features to the participant.

By way of a non-limiting example, in FIG. 5, at least one processor (e.g., included in cloud server 302) may present a first avatar 502 in simulated exercise environment 502. First avatar 502 may be associated with first participant 422 (FIG. 4) located in first physical location 404. At least one processor may present a second avatar 504 in simulated exercise environment 502. Second avatar 504 may be associated with second participant 430 located in second physical location 408. In some embodiments, first avatar 502 and second avatar 504 may mask identities of first participant 422 and second participant 430. In some embodiments, first avatar 502 and second avatar 504 may simulate identities of first participant 422 and second participant 430 (e.g., with labels thereon).

Some disclosed embodiments involve receiving from at least one first sensor associated with a first piece of exercise equipment in the first physical location first signals representing first physical exertions by the first participant. Physical exertion refers to expenditure of energy during physical activity. Intensity of exertion may be measured by, for example, a rate of body oxygen consumption, a heart rate, a breathing rate, a number of steps taken, a body temperature, a hydration level, and/or any other vital sign or statistic (e.g., a biomarker), as described and exemplified elsewhere herein. A signal refers to a physical phenomenon or event that can be used to convey information. Signals can take various forms, such as sound waves, light waves, electrical voltages, or other physical quantities that can be measured and/or transmitted. In some embodiments, a signal may refer to a message and/or event generated by a process or program to indicate a change in state or to request attention from another part of the system. Signals representing first physical exertions by the first participant refers to signals conveying information characterizing and/or embodying an exercise routine performed by the first participant. Such signals may include, for example, optical signals associated with images captured of a participant performing an exercise routine, audio signals associated with sound captured of a participant performing an exercise routine, signals associated with one or more vital signs or statistics, current and/or voltage signals associated with one or more settings of an electronic exercise machine, and/or any other type of signals representing physical exertion of a participant. Receiving refers to accepting, obtaining, and/or gaining access to. In some embodiments, receiving may involve acknowledging the receipt of an item and/or information and may involve physical and/or digital interactions. Receiving from at least one first sensor associated with a first piece of exercise equipment in the first physical location refers to obtaining sensed data from a sensor linked and/or related to a piece of exercise equipment located in a particular place. For example, at least one processor may receive image data from a camera located in proximity to an exercise machine recording a participant involved in a physical exertion. As another example, at least one processor may receive biometric data from a wearable appliance worn by a participant involved in a physical exertion. As a further example, at least one processor may receive speedometer data from an electronic treadmill used by a participant. By way of an additional example, the at least one processor may receive a signal, analog or digital signal representing heart rate from the first optical sensor, associated with the first exercise equipment at first physical location that represents the first participant's physical exertions. By way of a further example, the at least one processor may receive a signal, analog or digital signal representing force exerted from the first strain gauge or load cell sensor, associated with the first exercise equipment at first physical location that represents the first participant's physical exertions.

Some disclosed embodiments involve, in response to the first signals, causing the first avatar to simulate, in the simulated exercise environment, the first physical exertions. In response refers to consequent to, and/or as a result of. In response to the first signal refers to based one, and/or consequent to detecting and/or receiving the first signal. Causing refers to triggering and/or inducing. Causing the first avatar to simulate, in the simulated exercise environment, the first physical exertions refers to generating an animation of the first avatar reproducing the first physical exertions in the simulated environment. For example, a first participant may exercise at home. At least one processor may acquire first image data of the first participant performing an exercise routine at home, and may acquire second image data of a commercial gym. In response to receiving the first and/or second image data, the at least one processor may use the first and second image data to generate an animation of an avatar performing the exercise routine in a simulated environment corresponding to the commercial gym. By way of another example, a heart rate monitor sensor may detect an increase in heart rate during a workout, and may sends a signal to at least one processor associated with a piece of exercise equipment. In response to the signal, the at least one processor may cause the first avatar to appear to pant and/or sweat.

Some disclosed embodiments involve receiving from at least one second sensor associated with a second piece of exercise equipment in the second physical location second signals representing second physical exertions by the second participant. Receiving second signal may be understood similar to receiving first signal as described above. Second sensor associated with a second piece of exercise equipment may be understood similar to the first piece of exercise equipment. Physical location may be understood similar to the first physical location as described and exemplified above.

Some disclosed embodiments involve based on the second signals, causing the second avatar to simulate, in the simulated exercise environment, the second physical exertions. Based on refers to in association with, and/or related to. For example, at least one processor may use second signals to generate a second avatar. Causing the second avatar to simulate, in the simulated exercise environment, the second physical exertions may be understood as described earlier regarding the first avatar and the first physical exertions. Thus, at least one processor (e.g., associated with a cloud server) may receive a plurality of signals from a plurality of sensors associated with different pieces of exercise equipment situated in different physical locations. The at least one processor may use the received signals to generate a first avatar replicating a first exercise routine performed by a first participant in a first location, and generate a second avatar replication a second exercise routine performed by a second participant in a second location.

By way of an example, a first participant may perform a weight training routine using an (e.g., wall-mounted) electronic weight machine located at a first home location. A second participant may perform a running routing using an electronic treadmill located in a second home location. At least one processor may receive first image data and first exertion data associated with the weight training routine, and may receive second image data and second exertion data associated with the electronic treadmill. The at least one processor may use the first image data and first exertion data to generate a first avatar performing the weight training routine at a simulated five-star spa, and may use the second image data and second exertion data to generate a second avatar performing the running routine at the simulated five-star spa.

Some disclosed embodiments involve the first signals and the second signals each include image data and resistance data. Image data refers to a digital representation of visual information formatted as pixels and captured using an image sensor (e.g., a camera). Image data may include pixels, data streams, digital images, digital video streams, data derived from captured images, and data that may be used to construct one or more 3D images, a sequence of 3D images, 3D videos, or a virtual 3D representation. Image data may be formatted using one or more file formats, such as JPEG, PNG, GIF, and/or BMP image formats, and/or MP4, AVI, MKV, MOV, WMV, FLV, WebM, and/or MPEG video formats. Resistance data refers to information associated with a force and/or effort exerted by one or more participants while exercising. For example, the resistance data may indicate the weight lifted or the tension in the exercise equipment as described and exemplified elsewhere herein.

By way of a non-limiting example, in FIGS. 4 and 5, at least one processor (e.g., associated with server 302) may receive from at least one first sensor (e.g., first potentiometer 410) associated with first piece of exercise equipment 402 in first physical location 404 first signals representing first physical exertions 424 by first participant 422. In response to the first signals, at least one processor may cause first avatar 502 to simulate, in simulated exercise environment 500, first physical exertions 424.

At least one processor may receive from at least one first sensor (e.g., second potentiometer 414) associated with second piece of exercise equipment 406 in second physical location 408 second signals representing second physical exertions 432 by second participant 430. In response to the second signals, at least one processor may cause second avatar 504 to simulate, in simulated exercise environment 500, second physical exertions 432. In some embodiments, the first signals and the second signals each include image data (e.g., acquired using first image sensor 426 and second image sensor 434) and resistance data (e.g., acquired using first potentiometer 410 and second potentiometer 414).

Some disclosed embodiments involve enabling the first participant to view from the first physical location the simulations of the first physical exertions and the second physical exertions in the simulated exercise environment. Enabling refers to the process of allowing and/or facilitating an action and/or process. For example, enabling may include providing one or more resources and/or permissions for carrying out a task. To view refers to see and/or observe. For example, a participant may view visual content using an electronic display. Enabling the first participant to view from the first physical location the simulations of the first physical exertions and the second physical exertions in the simulated exercise environment refers to facilitating the first participant to see the first avatar performing the first physical exertion and the second avatar performing the second physical exertion in the simulated environment while located in the first physical location.

Some disclosed embodiments involve enabling the second participant to view from the second physical location the simulations of the first physical exertions and the second physical exertions in the simulated exercise environment. Second physical exertion may be understood similar to the first physical exertion as described above. By way of non-limiting example, the at least one processor simulate the exercise environment and the physical exertions such as warm-up exercise, and flexibility training, associated with the first participant in home gym and the second participant in a commercial gym. The at least one processor enable the second participant from the commercial gym to view the warm-up exercise and flexibility training displayed in a graphical user interface on a touch-sensitive display of the exercise equipment in the commercial gym.

By way of non-limiting example, a first participant may perform a running routine on an electronic treadmill at a first gym. At least one processor may receive first image data of the first participant and a running pace from a speedometer associated with the electronic treadmill over a communications network. A second participant may perform a cycling routine on a stationary bike at a second gym. At least one processor may receive second image data of the second participant and a heart rate from a wearable appliance worn by the second participant over a communications network. The at least one processor may use the first image data and the running pace to generate a first avatar simulating the running routine on a simulated track and the second image data and the heart rate data to generate a second avatar simulating the cycling routine on the simulated track. The at least one processor may cause the first avatar and the second avatar to be displayed via a first mobile device of the first participant and via a second mobile device of the second participant. In this manner, the first participant and the second participant may each view a simulation of the running routine and the cycling routine on the simulated track.

By way of a non-limiting example, in FIG. 4, at least one processor (e.g., associated with cloud server 302) may enable first participant 422 to view from first physical location 404 the simulations of first physical exertions 424 and second physical exertions 432 in simulated exercise environment 500. For example, simulations of first physical exertions 424 and second physical exertions 432 may be displayed using first mobile communications device 428 in first physical location 404. Similarly, at least one processor may enable second participant 430 to view from second physical location 408 the simulations of first physical exertions 424 and second physical exertions 432 in simulated exercise environment 500. For example, simulations of first physical exertions 424 and second physical exertions 432 may be displayed using second mobile communications device 434 in second physical location 408.

Some disclosed embodiments may involve enabling the first participant and the second participant to communicate with each other during a common exercise session in the simulated exercise environment. Enabling refers to facilitating and/or permitting. An exercise session refers to a structured period of physical activity undertaken for the purpose of achieving a fitness goal. An exercise session may include one or more warm-up routines, exertion routines, and cool-down routines. A common exercise session refers to a shared exercise session performed by at least two participants, e.g., concurrently for a shared experience. By way of example, interactive cycling may involve the first and second participants cycling at the same time. By way of another example, a simulated group fitness classes may be conducted, allowing participants to join a simulated class simultaneously with other participants and follow along with a live or pre-recorded instructor. Enabling the first participant and the second participant to communicate with each other refers to facilitating an exchange of information between the first and second participant. The information may be exchanged as an audible conversation between the first and second participants, as an audible conversation between the first and second avatars, via a chat box and/or text messages, and/or using any other medium for exchanging information. Enabling the first participant and the second participant to communicate with each other during a common exercise session in the simulated exercise environment refers to conveying information from the first participant to the second participant via the simulated exercise environment and conveying information from the second participant to the first participant via the simulated exercise environment. For example, at least one processor may receive speech uttered by the first participant from a microphone located the first environment and cause the first avatar to simulate the speech which may be outputted by a speaker. Similarly, at least one processor may cause speech uttered by the second participant to be simulated by the second avatar, allowing the first and second avatars to communicate as proxies for the first and second participants. Additionally or alternatively, at least one processor may convert detected speech to text and may display the text on first and second mobile devices associated with the first and second participants. As an example, two participants engaged in cycling physical exertion from two different locations may send messages via mobile communication devices associated with the first and second participants at the first and second physical locations, respectively. By way of another example, the participants may communicate and exchange the exercise related data through the exercise equipment associated application.

By way of a non-limiting example, in FIGS. 4 and 5, at least one processor (e.g., associated with cloud server 302) may enable first participant 422 and second participant 430 to communicate with each other during a common exercise session 506 in simulated exercise environment 500. For example, first participant 422 and second participant 430 may communicate with each other via first avatar 502 and second avatar 504 (e.g., see comment bubbles 508 and 510).

In some disclosed embodiments, the simulated exercise environment containing a simulation of a piece of exercise equipment and wherein the first physical exertions and the second physical exertions are simulated on the simulation of the piece of exercise equipment. A simulation of a piece of exercise equipment refers to a digital reproduction of the piece of exercise equipment. For example, a simulation of a piece of exercise equipment may include a digital animation of an electronic weight machine. The first physical exertions and the second physical exertions are simulated on the simulation of the piece of exercise equipment refers to digitally reproducing the first and second physical exertions on a digital reproduction of a piece of exercise equipment. By way of example, at least one processor may simulate a spinning class (e.g., an exercise environment) and may simulate first and second spinning bicycles located at the first and second physical locations, as through located together in the simulated spinning class.

By way of a non-limiting example, in FIGS. 4 and 5, simulated exercise environment 500 may contain a simulation of a piece of exercise equipment (e.g., first virtual barbell 512 and second virtual barbell 514). First physical exertions 424 and second physical exertions 432 may be simulated on the simulation of the piece of exercise equipment (e.g., first virtual barbell 512 and second virtual barbell 514).

Some disclosed embodiments involve the first signals being associated with tension on a first cable of the first piece of exercise equipment, and the second signals being associated with tension on a second cable of the second piece exercise equipment. A cable may include a rope, cord, chain, belt, and/or any other band or cordage having a tensile strength for withstanding repeated applications of tension as described and exemplified elsewhere herein. A cable may be made of a plurality of elongated metal, plastic, and/or nylon fibers. In some disclosed embodiments, a first end of a cable may be connected to a resistance motor and a second end of the cable may be connected to an accessory for engaging with a hand and/or foot. Tension on a cable refers to a force exerted on a cable due to stretching and/or pulling on the cable. Tension may be used to simulate the resistance or force exerted by a piece of exercise equipment. For example, the tension may mimic resistance provided by a weight machine or a resistance band and or any other type of tension. First signals being associated with tension on a first cable of the first piece of exercise equipment, and the second signals being associated with tension on a second cable of the second piece exercise equipment refers to first and second sensors (e.g., a motion sensors and/or cameras) associated with the first and second cables for measuring tension thereon, and transmitting signals indicative of the tension to at least one processor. For example, a first participant may pull on an end of a first cable and exert tension causing the first signal to be transmitted. The second participant may pull on an end of the second cable and exert tension causing the second signal to be transmitted. At least one processor may receive the first and second signals and determine cable motion and/or tension based on the signals.

By way of a non-limiting example, in FIG. 4, the first signals may be associated with tension on a first cable (e.g., see cable 206 in FIG. 2A) of first piece of exercise equipment 402. Second signals may be associated with tension on a second cable e.g., see cable 206 in FIG. 2A) of second piece exercise equipment 406.

Some disclosed embodiments involve each sensor includes an image sensor, wherein the first signals and the second signals respectively reflect limb motion of the first participant and the second participant, and wherein the operations further include using the first signals and the second signals to respectively simulate via the first avatar and the second avatar the limb motion of the first participant and the second participant. Each sensor includes an image sensor refers to cameras located in proximity to the first and second pieces of exercise equipment. Limb motion refers to a movement or motion of a bodily appendage, such as an arm and/or a leg. Limb motion may be used to track and analyze bodily motion during exercise. For instance, leg motion may be associated with running, cycling, stepping, and/or pushing weights using the legs. Arm motion may be associated with rowing, lifting, pulling, and/or pushing weights using the arms. First signals and the second signals respectively reflect limb motion of the first participant and the second participant refers to image data acquired of the limbs of the first and second participants during performance of exercise routines depicting and/or portraying motion of the limbs. Using the first signals and the second signals to respectively simulate via the first avatar and the second avatar the limb motion of the first participant and the second participant refers to replicating the limb motion of the first and second participants via simulated limbs of the first and second avatars, based on image data received from the image sensors. For example, at least one processor may use image data reflective of the first participant raising the arms to lift a weight to cause an avatar to raise virtual arms to lift a virtual weight. Similarly, at least one processor may use image data reflective of the second participant turning the legs on a stationary bicycle to cause an avatar to turn virtual legs on a virtual bicycle.

By way of a non-limiting example, in FIG. 4. each sensor may include an image sensor (e.g., image sensors 426 and 434). The first signals and the second signals respectively may reflect limb motion of first participant 422 and second participant 430. For example, the limb motion may involve first arms 438 of first participant 422 and second arms 440 of second participant 430. At least one processor (e.g., included in cloud server 302) may use the first signals and the second signals to respectively simulate via first avatar 502 and second avatar 504 the limb motion of first participant 422 and second participant 430.

In some disclosed embodiments, the at least one first sensor and the at least one second sensor each include an image sensor, wherein the first signals and the second signals respectively reflect posture of the first participant and the second participant, and wherein the operations further include using the first signals and the second signals to provide posture feedback to the first participant and the second participant. A first sensor and the at least one second sensor each include an image sensor may be understood as described earlier. A posture refers to a position and/or alignment of differing parts of a body. A posture may be used to monitor and/or analyze the position of the body. A posture may be upright, bent, tilted, twisted, and may affect balance, stability, mobility, and/or ergonomics. Incorrect posture may lead to injury, falling, fatigue, and/or inability to reach an exercise goal. First signals and second signals respectively reflect posture of the first participant and the second participant refers to image data acquired by the first and second image sensors depicting the postures of the first and second participants. For example, at least one processor may analyze the first and second signals to detect if a participant is slouching and/or leaning, instead of standing upright. Posture feedback refers to an evaluation, input, and/or assessment of a position and/or alignment of a participant. Using the first signals and the second signals to provide posture feedback to the first participant and the second participant refers to analyzing image data associated with the first and second signals to characterize a posture of the first and/or second participants, and providing an evaluation regarding the characterization. For example, at least one processor may determine that the first participant is slouching during an exercise routine and may transmit a message to straighten the spine.

By way of non-limiting example, posture feedback may involve one or more image sensors associated with the first and second exercise equipment transmitting data on the first and second participant's postures, respectively. The at least one processor may process the image data and analyze with respect to the participant's exercise related data to determine a user's posture. Result of the analysis is displayed on the mobile device to warn the user of improper posture.

By way of a non-limiting example, in FIG. 4, at least some of the first signals may include image data captured using first image sensor 426, and at least some of the second signals may include image data captured using second image sensor 434. The first signals and the second signals respectively may reflect posture of first participant 422 and second participant 430. At least one processor (e.g., associated with cloud server 302) may use the first signals and the second signals to provide posture feedback 442 to first participant 422 and second participant 430. For example, posture feedback 442 may be outputted via speakers 446 and 448 included in first mobile communications device 428 and second mobile communications device 426, respectively.

Some disclosed embodiments involve monitoring of the first signals and the second signals by a trainer, and wherein the operations further comprise enabling the trainer to provide feedback based on the first signals and the second signals. Monitoring refers to the process of observing, checking, or supervising something over time to gather information or track its progress. Monitoring signals associated with an exercise routine may ensure correct and/or proper performance of the exercise routine. A trainer refers to an individual providing instruction, coaching, motivation, and/or guidance, e.g., for performing one or more exercise routines. In some embodiments, a trainer may be associated with a software application and/or a communications device. For example, a training application may be installed on a communications device associated with a trainer, permitting the trainer to communicate with one or more clients, subscribers, and/or trainees via a communications network. In the context of exercise equipment a trainer may provide instruction, guidance, and motivation to individuals or groups to use exercise equipment, perform exertion routines and help them achieve their fitness goals. Trainers may work in gyms, fitness centers, and/or private settings, and may specialize in different areas such as strength training, cardio, flexibility, or sports-specific training. A trainer may guide a participant how to use an exercise machine. In some embodiments trainer may be human. In some embodiments trainer may be virtual, e.g., a digital simulation of a human. Enabling a trainer to provide feedback based on the first signals and the second signals refers to providing a trainer information associated with the first and second signals permitting the trainer to provide advice, an assessment, and/or guidance. For example, image data acquired by a camera may indicate that a participant is not sitting centered on a spinning bike. At least one processor may analyze the image data and display the image data with annotations showing a non-centered position. A trainer may view the annotated image data and communicate to the participant to center her body on the spinning bike. As another example, image sensors associated with the first and second exercise equipment may transmit the first and second signals representing tension of the cable and the force exerted on cable. The at least one processor process the data and enable the trainer to view the data, for example, on a graphical user interface displayed on a trainer's mobile device. The trainer may send message through the application to the first and or second participant, e.g., to raise and/or reduce a resistance, and/or increase and/or decrease a weightlifting pace.

By way of a non-limiting example, in FIG. 4, a trainer 444 may communicate with cloud service 300 via communication network 306. Trainer 444 may monitor the first signals and the second signals. At least one processor (e.g., included in cloud server 302) may enable trainer 444 to provide feedback 442 based on the first signals and the second signals.

Some disclosed embodiments involve enabling a competition between the first participant and the second participant. Competition refers to a rivalry or contest between individuals, groups, or entities who are seeking to achieve the same goal, such as winning a game, acquiring a resource, or achieving recognition. Enabling refers to allowing or facilitating a certain action or process as described above. For example, by simulating the exercise activities of the first and second participants, and permitting each participant to view the exercise activities simultaneously performed by the first and second participants, each participant may be able to compare one or more performance metrics of the exercise activities and determine which participant outperformed the other. By way of a non-limiting example, tension sensors transmit the first and second signal that presents resistive force exerted on the cable of the first and second exercise equipment. The at least one processor process the data obtained during a common exercise session such as shared weightlifting exertion session. The at least one processor enable the first and second participant to view simultaneously the first and second avatar in the simulated environment and physical exertion on the first and second mobile device displays. The first and second participant may view competition result in real-time on the display.

By way of a non-limiting example, in FIGS. 4 and 5, at least one processor (e.g., associated with cloud server 302) may enable a competition between first participant 422 and second participant 430. For example, the at least one processor may present a first score 516 and a second score 518 associated with first avatar 502 and second avatar 504, respectively.

Some disclosed embodiments involve the first participant and the second participant respectively interacting simultaneously with the first piece of exercise equipment and the second piece of exercise equipment. Simultaneous refers to occurring at the same time, e.g., concurrently. Interaction refers to engagement, reciprocal actions and/or influence between two or more entities. Simultaneous interaction refers to the ability to interact with multiple entities or systems at the same time. The first participant and the second participant respectively interacting simultaneously with the first piece of exercise equipment and the second piece of exercise equipment refers to the first participant using the first piece of exercise equipment at the same time that the second participant uses the second piece of exercise equipment. For example, the first and second participants may both lift weights using first and second electronic weight machines at the same time.

By way of a non-limiting example, in FIG. 4, first participant 422 and second participant 430 respectively may interact simultaneously with first piece of exercise equipment 402 and the second piece of exercise equipment 506.

In some disclosed embodiments, the first piece of exercise equipment includes free weights, wherein the at least one first sensor includes an image sensor, and wherein the operations further include determining from the first signals repetitions occurring with the free weights. Free weights refer to a weight that is not attached to a machine or apparatus, e.g., for use in resistance training exercises. Free weights may include but not limited to dumbbells, barbells, kettlebells, and weight plates as described and exemplified elsewhere herein. Repetitions refers to recurring and/or repetitive motions. In some embodiments, a repetition may include a completion of a single, full range of motion of an exercise. A repetition is typically a unit of measurement used to track progress and set goals. For example, in weightlifting, a repetition of a bicep curl would involve lifting the free weight from the starting position to the top position (fully contracting the bicep muscle) and then lowering it back to the starting position. Determining refers to figuring out or establishing something, e.g., with certainty, often by analyzing information or evidence. Determining may involve calculating or evaluating the performance of the participants. For example, determining may involve calculating the number of repetitions, the speed of the movements, or the accuracy of the form. For example, the image sensor may transmit a signal that includes image of the participant's arm in up and down position with respect to the exercise equipment. The at least one processor analyzes the signal to obtain the number of bicep curl repetition by counting the number of times that a participant's arm performs a full or partial motion of a bicep curl with a free weight. As another example, image sensor transmit signal including pixelating data of the participant's limbs position. From the pixel data the at least one processor detects whether the data is associated with the starting or ending point of a physical exertion. Physical exertion such as bench press has predefined starting and ending limb position. The at least one processor count repetition by detecting image signals presenting starting point followed by ending point limbs' position of the participant.

Figure 12:
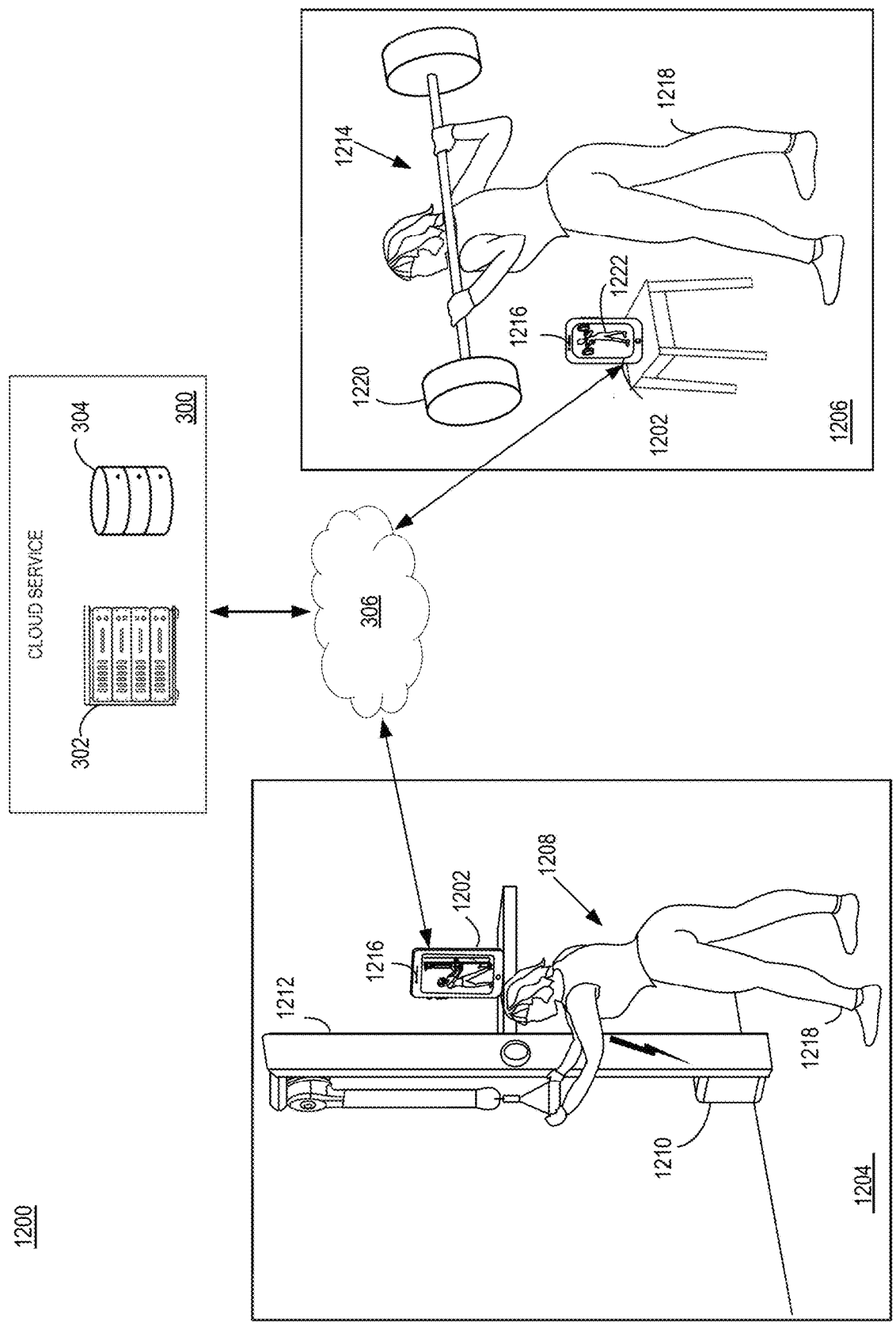
FIG. 12 is an exemplary network diagram for exercise routine monitoring in differing spaces, consistent with some embodiments of the present disclosure.

By way of a non-limiting example, in FIG. 12, the first piece of exercise equipment may include free weights 1220. The at least one first sensor may include an image sensor (e.g., image sensor 1218). At least one processor (e.g., included in cloud server 302) may determine from the first signals repetitions occurring with free weights 1220.

Some disclosed embodiments involve determining repetition from the first signals and indication of form of the first participant. Form refers to a pose, posture, balance, and/or alignment of a participant. In some embodiments, form may indicate engagement of certain muscles, and lack of engagement of other muscles. In the context of exercise equipment and fitness, form refers to the technique or posture used when performing an exercise. Indication refers to a sign, signal, or piece of information that provides guidance, direction, or insight. An indication of form refers to information relating to a form of an individual during exercise. For example, an image of a participant slouching may indicate a lack of engaging core muscles during exercise. An image of a participant overextending may indicate an incorrect position relative to an exercise machine. An indication of form may be used to provide feedback to a participant. For example, the indication of form may involve a visual or auditory signal that indicates whether the participant is performing the exercise correctly.

Some disclosed embodiments involve determining from the first signals an indication of posture of the first participant. As previously described determining may involve calculating or evaluating the performance of the participants. As previously described and exemplified, posture refers to the position in which someone holds their body when standing or sitting. By way of a non-limiting example, the first sensor may be image sensor transmitting image of the first participants during physical exertion. The at least one processor compare and analyze the image signal to detect the alignment of spine and limbs of the participant. As a result the at least one processor may measure and detect participant posture based on image signal received from an image sensor. In some embodiments, an image sensor may be included in a piece of exercise equipment, mounted in proximity to a piece of exercise equipment, and/or may be included in a mobile communications device, such as a mobile phone and/or a wearable appliance.

Some disclosed embodiments involve determining from the first signals an indication of tempo of the first participant. Tempo refers to a speed and/or pace at which something is done or the rate at which something moves or progresses. Tempo indication may be used to specify physical exertion routine. For example, in strength training, a participant may be advised to perform the exercises with a specific tempo, such as a 2-0-2 tempo. The tempo indicates that they should take two seconds to lift the weight, pause for zero seconds at the top, and then take two seconds to lower the weight back to the starting position. The tempo helps control the movement and ensures that the muscles are being worked effectively. By way of a non-limiting example, the at least one processor analyzes the image signal received from image sensor and determine the pace of participants movement. The pace of participants movement is calculated based on the image signal and the indication of tempo is displayed on the participant's mobile device.

Some disclosed embodiments involve determining from the first signals an indication of repetitions of the first participant. Determining from the first signal an indication of repetitions (as described earlier) of the first participant refers to calculating a number of recurring motions by the first participant. For example, at least one processor may analyze image data acquired over time of a participant performing an exercise routing and may search for one or more patterns (e.g., repeating images). The at least one processor may determine a number of repetitions based on a number of detected recurring patterns.

Some disclosed embodiments involve counting the repetitions only when the first physical exertions meet a threshold. A threshold refers to an (e.g., upper and/or lower) baseline and/or boundary. Meeting a threshold may include reaching a specified level or value, e.g., in relation to a fitness goal. For example, a weightlifting repetition may only be counted if a cable is extended by a minimal length, for a minimal amount of time, and/or released over a minimal amount of time. At least one processor may analyze image data to identify when a threshold is not met, and may dismiss and/or remove a repetition from being counted in response.

By way of a non-limiting example, in FIG. 4, at least one processor (e.g., included in cloud server 302) may determine repetition from the first signals and indication of form of first participant 422. In some embodiments, at least one processor may determine from the first signals an indication of posture of first participant 422. For instance, the at least one processor may analyze image data acquired by image sensor 426. In some embodiments, at least one processor may determine from the first signals an indication of repetitions of first participant 422 (e.g., see first score 516 in FIG. 5). In some embodiments, at least one processor may count the repetitions only when first physical exertions 424 meet a threshold. For example, the threshold may include a length of extending cable 206 (see FIG. 2A).

Some disclosed embodiments involve outputting the simulated exercise environment and the first and second avatars in a format enabling virtual reality presentation. Virtual reality presentation refers to using multimedia technology to simulate an immersive user experience. Virtual reality presentation may be implemented using a virtual reality headset displaying virtual content in an immersive manner. A format enabling virtual reality presentation refers to a specific data structure and/or encoding scheme that allows the data to be interpreted and displayed within a virtual reality environment, e.g., using a virtual reality device. By way of example, the format enabling virtual reality presentation may include 3D graphics data, audio data, and other sensory data. At least one processor may generate virtual content for presenting the first and second avatars using a virtual reality appliance.

By way of a non-limiting example, in FIGS. 4 and 5, at least one processor (e.g., included in cloud server 302) may output simulated exercise environment 500 and first and second avatars 502 and 504 in a format enabling virtual reality presentation (e.g., using smart glasses 520).

Some disclosed embodiments involve causing the generated simulated exercise environment to be presented on at least one mobile computing device. A mobile computing device refers to a portable device that is capable of wireless communication. A mobile device may include smartphones, tablets, wearable devices (e.g., smartwatches), portable media players, and/or any other transportable electronic device. The mobile communications device may be paired to the electronic exercise equipment and may communicate with the exercise equipment via a wired or wireless connection. In some embodiments, the mobile communications device and the exercise equipment may communicate via an intermediary device or system, such as the mobile communications device communicating with the exercise equipment via a local or remote server.

FIG. 6 illustrates a flowchart of an exemplary process 600 for communicating with a plurality of remote sensors associated with dispersed exercise equipment and simulating a virtual training experience, consistent with embodiments of the present disclosure. In some embodiments, process 600 may be performed by at least one processing device (e.g., included in with cloud server 302 in FIG. 3) may to perform operations or functions described herein. In some embodiments, some aspects of process 600 may be implemented as software (e.g., program codes or instructions) that are stored in a memory (e.g., memory 114) or a non-transitory computer readable medium. In some embodiments, some aspects of process 600 may be implemented as hardware (e.g., a specific-purpose circuit). In some embodiments, process 600 may be implemented as a combination of software and hardware.

Process 600 may include a step 602 of generating a simulated exercise environment. By way of a non-limiting example, in FIGS. 4 and 5, at least one processor (e.g., included in cloud server 302) may generate simulated exercise environment 500.

Process 600 may include a step 604 of presenting a first avatar in the simulated exercise environment, wherein the first avatar is associated with a first participant located in a first physical location. By way of a non-limiting example, in FIGS. 4 and 5, at least one processor (e.g., included in cloud server 302) may present first avatar 502 in simulated exercise environment 500. First avatar 502 may be associated with first participant 422 located in first physical location 404.

Process 600 may include a step 606 of presenting a second avatar in the simulated exercise environment, wherein the second avatar is associated with a second participant located in a second physical location remote from the first physical location. By way of a non-limiting example, in FIGS. 4 and 5, at least one processor (e.g., included in cloud server 302) may present second avatar 504 in simulated exercise environment 500. Second avatar 504 may be associated with second participant 430 located in second physical location 408.

Process 600 may include a step 608 of receiving from at least one first sensor associated with a first piece of exercise equipment in the first physical location first signals representing first physical exertions by the first participant. By way of a non-limiting example, in FIGS. 4 and 5, at least one processor (e.g., included in cloud server 302) may receive from a first sensor 410 associated with first piece of exercise equipment 402 in first physical location 404, first signals representing first physical exertions 424 by first participant 422.

Process 600 may include a step 610 of in response to the first signals, causing the first avatar to simulate, in the simulated exercise environment, the first physical exertions. By way of a non-limiting example, in FIGS. 4 and 5, in response to the first signals, at least one processor (e.g., included in cloud server 302) may cause first avatar 502 to simulate, in the simulated exercise environment 500, the first physical exertions 424.

Process 600 may include a step 612 of receiving from at least one second sensor associated with a second piece of exercise equipment in the second physical location second signals representing second physical exertions by the second participant. By way of a non-limiting example, in FIGS. 4 and 5, at least one processor (e.g., included in cloud server 302) may receive from second sensor 414 associated with second piece of exercise equipment 406 in second physical location 408 second signals representing second physical exertions 432 by second participant 430.

Process 600 may include a step 614 of based on the second signals, causing the second avatar to simulate, in the simulated exercise environment, the second physical exertions. By way of a non-limiting example, in FIGS. 4 and 5, based on the second signals, at least one processor (e.g., included in cloud server 302) may cause second avatar 504 to simulate, in simulated exercise environment 500, the second physical exertions 432.

Process 600 may include a step 616 of enabling the first participant to view from the first physical location the simulations of the first physical exertions and the second physical exertions in the simulated exercise environment. By way of a non-limiting example, in FIGS. 4 and 5, at least one processor (e.g., included in cloud server 302) may enable first participant 422 to view from first physical location 404 the simulations of the first physical exertions 424 and the second physical exertions 433 in simulated exercise environment 500, e.g., as first and second avatars 502 and 504 displayed on mobile communications device 428.

Process 600 may include a step 618 of enabling the second participant to view from the second physical location the simulations of the first physical exertions and the second physical exertions in the simulated exercise environment. By way of a non-limiting example, in FIGS. 4 and 5, at least one processor (e.g., included in cloud server 302) may enable second participant 430 to view from second physical location 408 the simulations of first physical exertions 424 and second physical exertions 432 in simulated exercise environment 500, e.g., as first and second avatars 502 and 504 displayed on mobile communications device 428.

Process 600 may include a step 620 of enabling the first participant and the second participant to communicate with each other during a common exercise session in the simulated exercise environment. By way of a non-limiting example, in FIGS. 4 and 5, at least one processor (e.g., included in cloud server 302) may enabling first participant 422 and second participant 430 to communicate with each other during a common exercise session 506 in simulated exercise environment 500, e.g., using comment bubbles 508 and 510.

Some disclosed embodiments provide a system for dynamically adjusting an exercise routine upon detecting an injury. A workout routine may consist of a series of exercises, as described and exemplified herein. When an injury occurs during a workout routine, a software application may permit a user to report a location of the injury on the body. Thereafter, all subsequent exercises in the routine will be adapted to avoid causing further injury.

Some embodiments provide a non-transitory computer readable medium containing instructions that when executed by at least one processor cause the at least one processor to perform dynamic injury-related adjustments during exercise. The at least one processor may initiate an exercise routine, e.g., by prompting a user. The exercise routine may include a series of varied electronically controlled exercises on exercise equipment. Differing exercises may work differing groups of muscles. The at least one processor may instruct a user to engage in one of the series of varied electronically controlled exercises using the exercise equipment. The at least one processor may receive from the user an electronic indication of injury. For instance, a user may input an indication of injury via a user interface of a mobile device. The electronic indication of injury may include an indication of at least one injured muscle. The at least one processor may, in response to the received electronic indication of injury, change the series of varied electronically controlled exercises to limit use of the injured muscle. In some embodiments, the electronic indication includes an identification of a specific injured muscle.

In some embodiments, the at least one processor may initiate the exercise routine by selecting the series of varied electronically controlled exercises. In some embodiments, the at least one processor may change the series by determining in the series predetermined exercises that engage the injured muscle and substituting other exercises for the predetermined exercises that engage the injured muscle. The at least one processor may instruct the user to engage in one of the series of varied electronically controlled exercises by outputting for display directions for performing at least the one exercise of the series. For instance, the at least one processor may cause the directions to be displayed via a user interface of a mobile device. The at least one processor may send signals to mobile communications device connected to the exercise equipment, e.g., via a wired and/or wireless connection.

In some embodiments, the at least one processor may output an anatomical map. The at least one processor may receive an electronic indication by receiving a selection from the anatomical map. In some embodiments, the at least one processor may determine from the anatomical map an identification of the injured muscle. In some embodiments, the at least one processor may present an injury button, and in response to activation of the injury button, cause a display of the anatomical map. In some embodiments, the at least one processor may change the series of varied electronically controlled exercises to avoid the injured muscle during a subsequent exercise routine. In some embodiments, the at least one processor may, prior to initiation of a subsequent exercise routine, query the user on the status of the injured muscle. When a response to the query indicates improvement, the at least one processor may reinstate exercises that engage the injured muscle.

Disclosed herein are systems, methods, and non-transitory computer readable media relating to performance and adaptation of exercise routines, optionally using electronic exercise equipment such as electronic exercise machines. Some disclosed embodiments relate to performing dynamic injury-related adjustments during exercise. FIGS. 7A through 9 provide exemplary embodiments of related disclosed systems, methods, and non-transitory computer readable media. For example, consistent with some disclosed embodiments, a system, method, or non-transitory computer-readable medium may facilitate a user to initiate an exercise routine that includes a series of varied electronically controlled exercises on exercise equipment. The varied electronically controlled exercises may include differing exercises that work differing groups of muscles. The system, method, or non-transitory computer-readable medium may further cause the user to be instructed to engage in one of the series of varied electronically controlled exercises using the exercise equipment. After the user sustains an inquiry, the system, method, or non-transitory computer-readable medium may receive from the user an electronic indication of injury. For example, the electronic indication of injury may include an indication of at least one injured muscle. In response to the received electronic indication of injury, The system, method, or non-transitory computer-readable medium may cause a change in the series of varied electronically controlled exercises to limit use of the injured muscle.

Some disclosed embodiments include a non-transitory computer readable medium containing instructions that when executed by at least one processor cause the at least one processor to perform dynamic injury-related adjustments during exercise.

A non-transitory computer readable medium may refer to any type of physical memory on which information or data readable by a processor can be stored. For example, non-transitory computer readable medium may include Random Access Memory (RAM), Read-Only Memory (ROM), volatile memory, nonvolatile memory, hard drives, CD ROMs, DVDs, flash drives, disks, any other optical data storage medium, any physical medium with patterns of holes, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located on a portable device or at a remote location. Additionally, one or more computer-readable storage media may be utilized in implementing a computer-implemented method. Accordingly, the term computer-readable storage medium should be understood to include tangible items and exclude carrier waves and transient signals.

A processor may refer to any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The at least one processor may be associated with a computer system. Consistent with disclosed embodiments, the at least one processor may be located, embedded, installed, positioned, or otherwise associated with the exercise equipment, a user's mobile communication device, or both, as described and exemplified elsewhere in this disclosure.

A user may refer to a person who interacts with the exercise equipment directly, via the user's mobile communication device, or using both. Exercise equipment may refer to any apparatus or device designed and used for physical exercise, strength training, cardiovascular exercises, flexibility training, and/or rehabilitation purposes, as described and exemplified elsewhere in this disclosure. A mobile communication device may refer to a portable device that can receive and transmit information. For example, a mobile communications device may include a smartphone, a tablet, a smartwatch, or any other portable device capable of receiving signals from the exercise equipment.

Some disclosed embodiments include at least one cloud server configured to communicate with the mobile communication device and/or the exercise equipment, as disclosed and exemplified elsewhere in this disclosure. The cloud server may be provided by one or more third-party vendors who manage and maintain the underlying infrastructure allowing users to access and use the services via the internet. Non-limiting examples of types of cloud services include Infrastructure as a Service (IaaS), Platform as a Service (PaaS), and Software as a Service (SaaS).

The cloud server may provide data storage and/or computational services to one or more client devices via a communications network, as described an exemplified elsewhere in this disclosure. For example, a cloud server may store data and software associated with the exercise equipment and/or mobile communications devices (e.g., client devices) and/or execute program code instructions associated with using the exercise equipment. In another example, a cloud server may store data and/or execute program code instructions for implementing a plurality of operational modes for the exercise equipment (e.g., in association with one or more exercise routines), creating an interface between a mobile communications device and the exercise equipment, and/or pairing two or more pieces of modular exercise equipment. As used herein, an exercise routine may refer to a structured and repetitive set of physical movements that may be directed to one or more muscle groups with the goal of improving or maintaining physical fitness, health, and/or specific athletic abilities.

In another example, a cloud server may store data and execute program code instructions associated with performances of exercise routines. For example, a cloud server may store results or achievements and/or provide feedback associated with performances of exercise routines (e.g., by a single or by multiple users), provide instructions for using the exercise equipment and/or for implementing differing modes of operation of the exercise equipment, facilitate interactions between remote users performing exercise routines (e.g., with or without the exercise equipment), and/or provide any other service associated with performances of exercise routines.

In addition to the disclosed cloud servers, user data may be stored in one more physical locations via one or more remote servers, as discussed an exemplified elsewhere in this disclosure. The remote server may be a physical server. A physical server may refer to a tangible piece of hardware designed to host and manage software applications, data, or servers. The physical remote server may be located in a physical location, whereas the cloud server may be virtual. Similar to the cloud server, the one or physical remote servers may store data such as, but not limited to, the user's height, weight, age, preferred exercise routine, injury information, and/or recovery information, consistent with the current disclosure. The one or more physical remote servers may store data associated with one or more users in one or more databases (e.g., a relational database) using appropriate database structures (e.g., one or more database records). The at least one processor in the exercise equipment may communicate with one or more servers while the user is performing an exercise routine. In this example, the exercise equipment may provide for display via one or more connected or associated display devices (e.g., via a paired device, such as a smartphone, smartwatch, tablet, or other computing device), consistent with this disclosure, information related to the user's exercise routine, such as the type of exercise, the number of repetitions, and the user's desired resistance. For example, the user's mobile communication device may communicate with the server while the user is performing one or more exercise routines. The operations discussed in this disclosure may be performed on the at least one cloud server, the at least one remote server, and/or on the user's mobile communications device.

Instructions, in the context of those that operate or control a computing device, refer to a set of commands or orders that are capable of being interpreted and executed by the at least one processor. For example, instructions may include commands that control the operation of a computer or direct its processor to perform specific operations. As used herein, instructions may refer to commands that the at least one processor receives in response to the user interacting with the user's mobile communication device or exercise equipment. Operations may refer to a series of actions or steps taken in order to achieve a particular end. Here, operations may include initiating an exercise routine, receiving an indication of injury from the user, and adjusting the exercise routine based on the indicated injury, as discussed herein.

In some embodiments, the at least one processor may receive instructions to initiate an exercise routine. As used herein, executed refers to carrying out commands by a computer or a processor. For example, when a program is executed, the processor performs one or more of the instructions in the program. Perform refers to an action of carrying out or accomplishing an action, task, or function, as described and exemplified elsewhere in this disclosure. For example, a processor may execute instructions stored in a computer-readable medium.

Dynamic refers to something that is not static. For example, something that is dynamic may change or adjust (e.g., based on external factors or stimuli). An injury refers to damage to a muscle or other tissue of the user. Here, an injury may refer to straining, severing, or pulling a muscle or ligament, breaking a bone, and/or any other tissue or biological damage that may occur from exercising. An adjustment refers to an alteration. Accordingly, dynamic injury-related adjustments refer to modifications made to an exercise routine based on the injury status of the user. Dynamic injury-related adjustments may be performed by a processor associated with a computer system, wherein the at least one processor may be associated with the exercise equipment, the user's mobile communication device, or both. In one example, the user may have a shoulder injury. In another example, the user may have a back injury. Consistent with disclosed embodiments, the at least one processor may amend, update, or otherwise adjust the user's exercise routine to reduce stress and/or strain on the user's injured muscles, as discussed herein.

Exercise refers to physical activity performed to sustain or improve physical health and/or to become stronger and healthier, as described and exemplified elsewhere in this disclosure. Exercise may be performed by the user associated with a computer system. For example, exercise may include activities such as running, lifting weights, doing yoga, or any other physical activity. In another example, the user may interact with the computer system either directly through the exercise equipment, and/or an application on the user's mobile communication device.

Some disclosed embodiments include initiating an exercise routine including a series of varied electronically controlled exercises on exercise equipment, wherein differing exercises work differing groups of muscles. Initiating refers to beginning, starting, or introducing something, especially regarding the beginning of a process, action, or sequence of events. As discussed herein, an exercise routine may refer to a structured and repetitive set of physical movements that may be directed to one or more specific muscle groups with the goal of improving or maintaining physical fitness, health, or specific athletic abilities. The set of physical movements may be designed to be performed in a specific order. An exercise routine may include aerobic and/or anaerobic movements. Accordingly, initiating an exercise routine may involve beginning or selecting a series of exercises for the user to perform. Selecting, for example, a series of exercises, may refer to choosing one or more options from a plurality of options. In this example, the at least one processor may receive a request from the user to perform a certain workout, such as a chest workout. As used herein, a workout may generally refer to a user's exercise routine. In one example, a chest workout may involve exercising one or more muscles located in the user's chest region, including one or more pectoral muscles, wherein the exercise may be directed to strengthening those muscles.

The at least one processor may provide for display on a graphical user interface (GUI) of the mobile communications device one or more exercises for the user to select. A GUI may refer to a type of user interface that allows users to interact with electronic devices or software through graphical icons, visual indicators, and/or on-screen elements such as windows, buttons, menus, and dialog boxes, rather through text-based commands. GUIs may provide an alternative to text-based user interfaces and may make it easier for users to navigate and operate devices or software by providing intuitive visual representations of functionality and options. The user may select the chest workout from a plurality of workouts directed to various muscle groups by selecting one or more interactive elements. An interactive element may refer to any component or feature within a system, interface (here, a GUI), or environment that allows one or more users to actively engage with and/or manipulate content or functionality.

The one or more interactive elements may each launch a micro application directed to initiating a certain workout. A micro application may refer to a specialized application designed to perform one task or use case with the only objective of doing it well. Here, a micro application may be directed to initiating a chest workout. The user may select one or more interactive elements to initiate an exercise routine, here a chest workout.

Consistent with disclosed embodiments, a user may also initiate an exercise routine by selecting one or more exercises from a touch screen associated with a built-in display on the exercise equipment. The built-in display may be mounted or otherwise affixed to the main structure of the exercise equipment using bolts, screws, soldering, and/or adhesives. Here, the at least one processor may be located in the built-in display and may communicate with the mobile communications device, the cloud server, and/or the remote server to retrieve information related to the user's selected exercise routine.

A series such as, for example, a series of exercises, refers to a number of exercises presented and/or performed in a sequence (e.g., one after another). As used herein, a series may refer to one or more selections from a pool of available exercises on the one or more pieces of exercise equipment, as described and exemplified elsewhere in this disclosure. Varied refers to incorporating different types of elements (e.g., at least one that differs from another). As used herein, varied may refer to the plurality of exercises the user may engage in when using the exercise equipment. Electronically controlled exercises refer to physical activity or a workout routine directed by a processor or controller. For example, electronics may be used to control, monitor, and/or enhance the user's exercise experience, as described and exemplified elsewhere in this disclosure.

A series of varied electronically controlled exercises on exercise equipment may therefore refer to a plurality of differing exercises performed on the same or on different pieces of exercise equipment. For example, a series of varied electronically controlled exercises may include multiple types of resistance training using one or more bands, cables, straps, weights, dumbbells, and/or barbells, wherein the at least one processor may control the amount of resistance, i.e., how heavy the bands and/or weights feel to the user. Here, the user may perform different exercises using the resistance bands, such as a flat bench press, an incline bench press, or a one-arm cable press. In another example, the user may engage in one or more exercises on an electrically controlled treadmill, wherein the treadmill is set to adjust speed at various time intervals.

Differing exercises refers to at least two physical movements that are not the same, as described and exemplified elsewhere in this disclosure. Work refers to any physical movement used to strengthen one or more muscle groups. Non-limiting examples of muscle groups may include chest muscles, back muscles, leg muscles, and/or arm muscles. In one example, the exercise routine may combine exercises that work a group of muscles with exercises that work another group of muscles. In this example, the exercise routine may combine varied back workouts such as pull-ups, rows, and pull-downs, with leg workouts such as squats, lunges, and deadlifts.

Figure 7A:
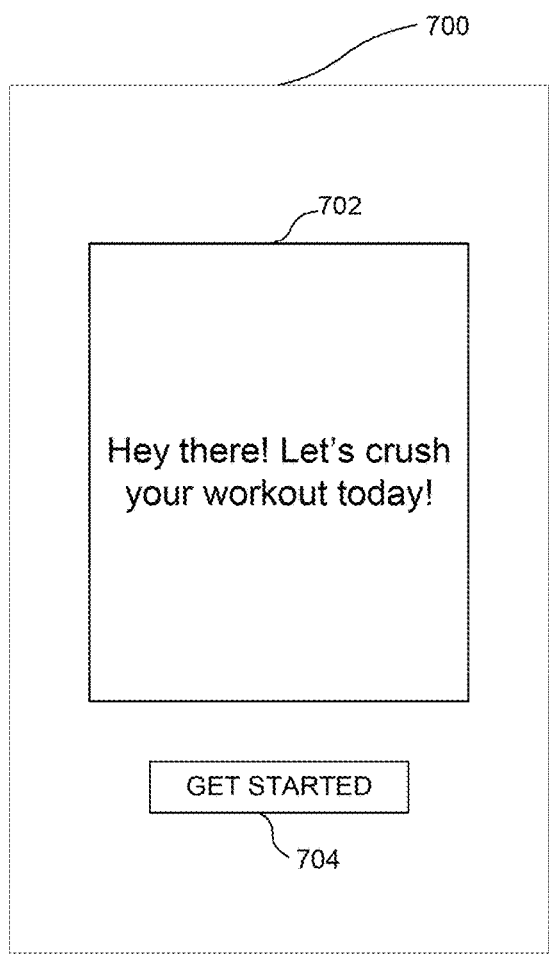
FIG. 7A illustrates an exemplary graphical user interface for initiating an exercise routine, consistent with some disclosed embodiments.

By way of example FIG. 7A illustrates an exemplary graphical user interface for initiating an exercise routine, consistent with disclosed embodiments. The user may interact with the exercise equipment using their mobile communication device. In this example, the mobile communication device may contain GUI 700. GUI 700 on the mobile communication device may contain welcome message 702 and begin workout button 704. Begin workout button 704 may also be a tile or another interactive element designed to launch a micro-application directed to initiating an exercise routine. Begin workout button 704 may contain a message prompting the user to begin their workout. In this example, begin workout button 704 may contain a message such as "Get Started," or "Begin Workout." The at least one processor may receive an instruction to initiate an exercise routine when the user presses, selects, or otherwise interacts with (e.g., via a voice command) begin workout button 704.

In some embodiments, initiating the exercise routine includes selecting the series of varied electronically controlled exercises. Selecting may refer to the user choosing one or more works from a plurality of exercise routines. The at least one processor, in response to receiving a request to initiate an exercise routine, may provide for display on the GUI a plurality of exercise routines for the user to choose from. In one example, the user may select an exercise routine via a GUI on the user's mobile communication device. In another example, the user may select an exercise routine via a touch screen interface on a built-in display on the exercise equipment.

Figure 7B:
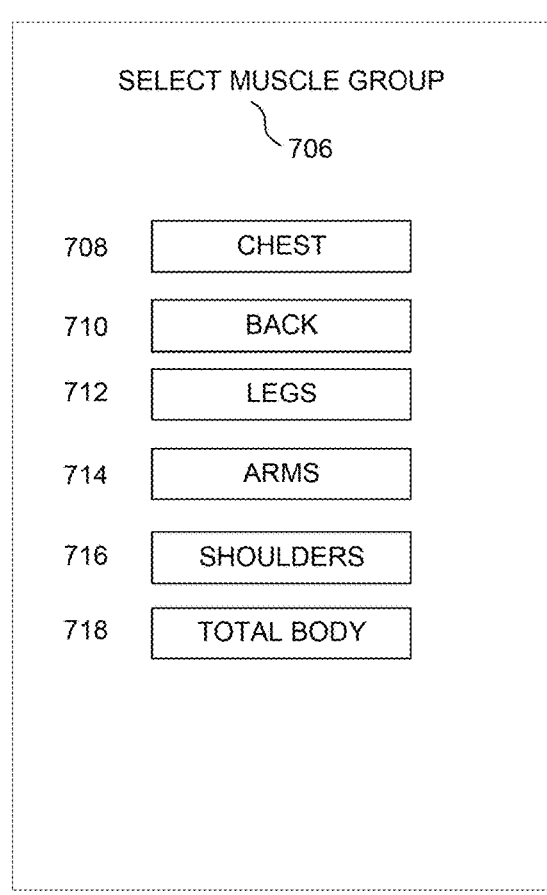
FIG. 7B illustrates an exemplary graphical user interface for selecting an exercise, consistent with some disclosed embodiments.

By way of example, FIG. 7B illustrates an exemplary graphical user interface for selecting an exercise routine, consistent with disclosed embodiments. In this example, the at least one processor may provide for display on the GUI a header or prompt, such as select muscle group header 706. A header may generally refer to text that appears at the top of a page, here, the GUI. Select muscle group header 706 may contain a message prompting the user to select a muscle group. In this example, select muscle group header 706 may read "Select Muscle Group," "Choose Muscle Group," or "Which Muscles Would You Like to Exercise Today?" The at least one processor may prompt the user to select one or more muscle groups from a plurality of muscle groups 708 through 718. The user may select one or more muscle groups via a tile, button, toggle, or any other interactive element. In a non-limiting example, the user may select a chest workout 708, a back workout 710, a legs workout 712, an arms workout 714, a shoulders workout 716, and/or a total body workout 718. The user may select a single muscle group 708-718, or multiple muscle groups. Each workout 708-718 may correspond to a different muscle group.

The user may similarly begin a workout by interacting with a touch screen on the built-in display affixed to the exercise equipment, wherein the at least one processor provides for display on the touch screen interactive elements similar to those discussed in relation to FIG. 7A and FIG.

7B. In this example, the at least one processor located in the exercise equipment may communicate with at least one cloud server or remote server to retrieve relevant information to the user's exercise route. Here, exercise routine information, such as, in a non-limiting example, the type of exercise, the duration of the exercise, and the difficulty of the exercise, may be stored on the at least one cloud server or remote server.

Some disclosed embodiments include instructing the user to engage in one of the series of varied electronically controlled exercises using the exercise equipment. Instructing the user refers to directing or commanding the user to do something. As used herein, instructing may refer to the at least one processor directing the user to perform a task, through directions provided via a user interface. The instructions may direct the user to engage in at least one of a series of varied electronically controlled exercises using the exercise equipment. As used herein, engaging may refer to how the user interacts or otherwise uses the exercise equipment. The user may be guided to engage with the exercise equipment directly, via the user's mobile communication device, or both. In one example, the at least one processor may instruct the user to perform a bench-pressing motion using the exercise equipment. In another example, the at least one processor may direct the user to perform a lunging motion using the exercise equipment. In yet another example, the at least one processor may direct the user to perform a rowing motion using the exercise equipment. The at least one processor may be located on the exercise equipment, or may be located within a user's mobile communications device.

In some embodiments, instructing the user occurs via a mobile communications device of the user. As discussed herein, a mobile communications device may refer to a portable device that can receive and transmit information. In one example, the at least one processor may be associated with the user's mobile communications device and may provide the GUI for display. The at least one processor may present instructions for the user to follow during their exercise routine. In one example, the at least one processor may direct the user to perform multiple repetitions and sets of a bench press on the exercise equipment via instructions displayed on the user's mobile communications device. In another example, the at least one processor may direct the user to perform multiple pull-ups using the exercise equipment, wherein instructions to perform the exercise are displayed on the GUI of the user's mobile communications device.

Instructing the user may also occur via at least one processor associated with a built-in display on the exercise equipment. A built-in display may refer to one or more screens that are mounted to the exercise equipment. Mounting may refer to permanently or semi-permanently affixing an object in its operating position. For example, mounting may refer to affixing the built-in display in its operating position on the exercise equipment. In one example, the built-in display may be affixed to the main structure of the exercise equipment. The main structure may refer to the backbone of the exercise equipment, which supports the exercise equipment's weight. In one example, the main structure may be located on a vertically wall-mountable beam.

In this example, the at least processor associated with the exercise equipment may communicate with the mobile communications device to transmit workout instructions to the user. In yet another example, both the exercise equipment and the mobile communications device may contain at least one processor, wherein each processor provides for display a GUI or touch screen to instruct the user. In this example, the user may be able to access exercise instructions using both the exercise equipment and the user's mobile communications device simultaneously.

Figures 7C, 7D:
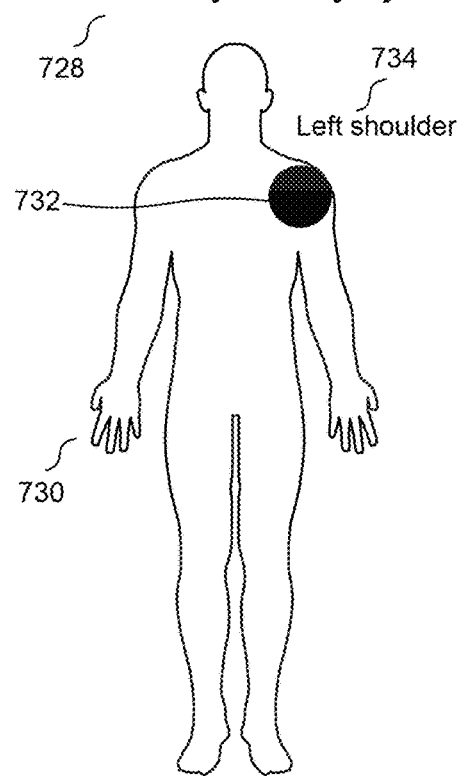
FIG. 7C illustrates an exemplary graphical user interface for engaging in a series of varied electronically controlled exercises, consistent with some disclosed embodiments.
FIG. 7D illustrates an exemplary graphical user interface for identifying an injury, consistent with some disclosed embodiments.

By way of example, FIG. 7C illustrates an exemplary graphical user interface providing information for engaging in a series of varied electronically controlled exercises, consistent with disclosed embodiments. In this example, the at least one processor may provide for display of a header or prompt on GUI 700, such as current workout header 720. Current workout header 720 may display the current exercise routine that the user is performing in. For example, current workout header 720 may display "Today's Chest Workout" if the user selected a chest workout 708. In this example, the at least one processor provides the GUI for display on the user's mobile communication device. The at least one processor may instruct the user to engage in at least one electronically controlled exercise 722. In this example, the processor may instruct the user to perform four sets of ten repetitions each of a chest press.

In some embodiments, instructing the user to engage in one of the series of varied electronically controlled exercises includes outputting for display directions for performing at least the one exercise of the series. As described and exemplified elsewhere in this disclosure, outputting for display may refer to the process of providing instructions or information to the user. Outputting for display may also include providing directions via a graphical user interface (GUI) on the user's mobile communication device, a built-in display on the exercise equipment, or both. Directions for performing may refer to specific guidelines provided to the user to correctly execute an exercise. For example, directions for performing may include step-by-step instructions, visual aids, or audio cues. One exercise of the series may refer to a specific activity included in the varied electronically controlled exercises. For example, one exercise of the series may include a cardio exercise, a strength training exercise, or a flexibility exercise.

In one example, the at least one processor may provide written instructions for how to perform a certain exercise routine, such as a deadlift. In another example, the at least one processor may provide for display a video showing the user how to perform a certain exercise.

Outputting may be performed by the at least one processor associated with the exercise equipment. In this example, the at least one processor associated with the exercise equipment may communicate with the cloud server and/or physical remote server to retrieve relevant exercise information, here, how to perform the exercise, and display that information to the user. Additionally or alternatively, the outputting may be performed by the at least one processor associated with the user's mobile communication device. In this example, information related to performing the exercise may be stored in the memory of the user's mobile communication device.

Referring to FIG. 7C, the at least one processor may instruct the user to perform one or more exercises 722, such as performing multiple repetitions and sets of a chest press or bench press. In this example, the at least one processor instructs the user to perform a chest press for four sets of ten repetitions each. In another example, the at least one processor may instruct the user to perform chest flys for four sets of ten repetitions each. Consistent with disclosed embodiments, the processor may provide for display on the GUI directions 724 for performing the at least one exercise 722. In one example, the at least one processor may retrieve instructions for performing the exercise from the cloud server and/or remote server. In another example, the directions for performing the exercise may be stored on the user's mobile communications device.

Directions 724 may include a button or other interactive element displayed on the GUI, and the user may press or otherwise interact with the button to learn more about the exercise 722. In one example, the at least one processor may provide for display text directions for performing exercise 722. In another example, the at least one processor may provide for display a video showing the user how to perform exercise 722.

In some embodiments, instructing includes sending signals to a mobile communications device connected to the exercise equipment. Sending may refer to the process of transmitting information to a device. Here, sending may refer to transmitting information to the user's mobile communication device. Signals may refer to an electrical or electromagnetic wave that carries information such as voice, video, or data, as described and exemplified elsewhere in this disclosure. A mobile communications device may refer to a portable electronic instrument designed to facilitate information transmission to other devices or networks, as described an exemplified elsewhere in this disclosure. In one example, at least one processor located in the exercise equipment may send signals to the user's mobile communication device, and vice versa. In one example, the at least one processor located in the exercise equipment may send signals to a mobile communications device connected to the exercise equipment to instruct the user to engage in a specific exercise. In another example, the at least one processor located in the exercise equipment may send signals to the cloud server and/or remote server to retrieve information related to an exercise the user may have selected using their mobile communications device. Connected may refer to a link established between two or more devices to enable communication. Here, connected may refer establishing a link between the exercise equipment and the user's mobile communication device to enable communication between the two devices.

In some embodiments, the connection is wired. A wired connection may include one or more physical components (e.g., wires) that are connected. A wire may refer to metal drawn out into the form of a thin flexible thread or rod for purposes of carrying electrical current. The wire may form an electrical connection between the exercise equipment and the mobile communication device. An electrical connection may refer to a wired connection, wireless connection, or combination of the two, that permits the flow of electrical current between two components. In one example, the wire is made of copper and may be insulated by a PVC or XLPE insulator. In another example, the wire may be a Universal Serial Bus (USB) type wire with appropriate connectors. In yet another example, the wired connection may be an Ethernet connection.

In some embodiments, the connection is wireless. A wireless connection may include transmitting signals via one or more networks. Further, a wireless connection may refer to any way of transmitting signals between two devices where the two devices are not required to be physically connected to one another. The two devices may communicate using a wireless communication protocol. The wireless communication protocol may be WiFi (IEEE 802.11-based), radio frequency (RF, such as ZigBee or ZWave), radio frequency identification (RFID, such as Active Reader Passive Tag or Active Reader Active Tag), Bluetooth, Near Field Communication (NFC), or any other wireless pairing protocol usable for short-range communication.

In a non-limiting example, the exercise equipment may contain a power source. A power source may include any element, device, or system for providing electrical energy to an electrical load or a circuit. In this example, the exercise equipment may be wirelessly connected to the mobile communication device. The exercise equipment and the mobile communication device may form an electrical connection using a wireless power transfer standard. For example, the wireless power transfer standard may include Qi, AirFuel Resonant, near-field magnetic coupling (NFMC), radio frequency (RF), or other suitable wireless charging protocol.

Some embodiments include receiving from the user an electronic indication of injury, wherein the electronic indication of injury includes an indication of at least one injured muscle. Receiving refers to at least one processor obtaining or accepting information. The information may be obtained from a paired or linked mobile communication device, the exercise equipment, or both.

For example, at least one processor in the exercise equipment may receive an input or command from the mobile communication device, and vice versa. The at least one processor may receive a command via a Graphic User Interface (GUI) of the user's mobile communication device to perform a task. In another example, the received input may occur via one or more controls located on the exercise equipment. For instance, the user may provide input via a touch screen user interface or other built-in display and/or via a mobile communications device paired to the exercise equipment. The at least one processor may also receive input via a voice command. Electronic indication of injury may refer to information indicating an injury. The indication may be an icon, a marking, a designation of an injury location, a measurement, a sign, and/or a signal conveying information about a state and/or level of a physical phenomenon, as described and exemplified elsewhere in this disclosure. For example, the electronic indication of injury may convey that the user strained, pulled, or otherwise damaged or injured at least one muscle or ligament. The user may indicate that they are injured by providing input via the GUI associated with the mobile communications device, and/or the touch screen associated with the exercise equipment.

In some embodiments, the electronic indication of injury may be generated automatically by one or more processor, such as a processor of the electronic exercise equipment, a processor of a mobile communications device in communication with the electronic exercise equipment, or a processor of a cloud service. In some embodiments, at least one processor may obtain sensor data that is associated with an injury or a likelihood of injury. For example, a processor may receive image data from an image sensor, as described and exemplified elsewhere in this disclosure. The image sensor may be located in, embedded in, or otherwise associated with the built-in display of the exercise equipment and/or the user's mobile communication device. The processor may analyze image data received from the image sensor, wherein image data refers to, for example, pixel data streams, digital images, digital video streams, and/or data derived from captured images, as described an exemplified elsewhere in this disclosure. Captured image data may be stored via the memory associated with the user's mobile communications device, via a cloud server, and/or via a physical server. The at least one processor may, for example, based on the stored image data, determine whether the user's facial expressions are abnormal, based on comparisons of the received image data to previously-captured image data associated with typical facial expressions of the user and/or one or more other users. Based on an analysis of the user's facial features and determined facial expressions, the processor may determine that the user is likely in pain that is not normal for a workout, and may generate an indication of an injury.

As another example, at least one processor may determine, using collected sensor data, whether a user's posture is abnormal based on stored image data. In this example, the at least one processor may determine that the user's posture or body movements are abnormal based on an average range or motion of the user, wherein the average range of motion is based on aggregated stored image data. In some embodiments, analysis of one or more features and body parts in collected image data may allow a processor to determine that a user is holding a particular muscle, limb, or part of their body, further indicative of an injury.

In some embodiments, the image sensor may be associated with the user's mobile communication device. In this example, the image sensor may interpret image data to determine that the user is abnormally straining one or more face muscles, and/or is demonstrating incorrect posture. In this example, a user may be performing an exercise with the user's right arm, such as a cable fly. The at least one processor may determine that the user, on average, moves their right arm 20 cm, 30 cm, or 40 cm to correctly perform the exercise. In this example, the image senor may determine that the user only moved their arm 10 cm or 15 cm, indicating that the user's range of motion is limited and that they may be injured. In some embodiments, one or more processors may employ a machine learning or AI system or service to analyze sensor data to generate an indication of injury, using one or more models trained with sensor data indicative of injuries.

In some embodiments, the electronic indication of injury may involve the at least one processor receiving audio data via an audio sensor, as described an exemplified elsewhere in this disclosure. Audio data refers to any sound, exhibited by the user, the exercise equipment, or both, that the at least one processor may convert into an electrical signal. The audio sensor may be located, embedded in, or otherwise associated with the at least one piece of exercise equipment, the user's mobile communications device, or both. As described and exemplified elsewhere in this disclosure, the audio sensor may include one or more microphones. In one example, the electronic indication of injury may include the audio sensor detecting a groan or gasp from the user. In another example, the audio sensor may detect that the user a slammed one or more weights, indicating that the user dropped the weights accidentally. Captured audio data may be stored via the memory associated with the user's mobile communications device, via a cloud server, and/or via a physical server. The at least one processor may, for example, based on the stored audio data, determine whether the user's audible physical exertions are abnormal, indicating an injury. In this example, the audio sensor may determine that a user typically grunts during while performing a certain exercise routine. Here, the audio sensor may determine that the user grunted louder and/or more often than normal, or alternatively, abnormally gasped or groaned, similarly indicating an injury.

In some embodiments, the electronic indication of injury may also involve the at least one processor receiving mechanical data via a mechanical sensor, as described an exemplified elsewhere in this disclosure. The mechanical sensor includes any device that detects some sort of mechanical deformation or movement and translates that detection into an electrical signal. Captured mechanical data may be stored via the memory associated with the user's mobile communications device, via a cloud server, and/or via a physical server. The mechanical sensor may be located, embedded in, or otherwise associated with the exercise equipment.

In some embodiments, obtained mechanical sensor data may indicate a speed or acceleration at which a user moves a portion of the electronic exercise equipment, for example, a wall-mounted cable exercise machine, as described and exemplified elsewhere in this disclosure. The at least one processor may store the speed at which the user performs movements, i.e., mechanical data, to determine an average speed at which the user lifts and lowers weights. In this example, the at least one processor may determine that the user lowered the weights faster than normal based on data received by the mechanical sensor, indicating that the user dropped the exercise equipment. A determination that the user dropped the exercise equipment may be associated with an injury while performing the exercise movement. In another example, the at least one processor may determine that the cables associated with the exercise equipment, here, a wall-mounted cable exercise machine, are wobbling or vibrating more than normal, wherein normal refers to a typical level of wobbling or vibration during exercise. Excess wobbling may indicate that the user is having difficulty grasping, gripping, or otherwise using the exercise equipment. In some embodiments, one or more sensors may monitor mechanical properties of the cable, and determine that the cable retracted suddenly in an uncontrolled manner, indicating that the user suffered an injury and let go of the cable or could no longer control it.

In some embodiments, one or more processors may analyze obtained sensor data in combinations that may be indicative of an injury, such as by analyzing image and audio data to identify, for example limping in combination with groaning, or any other posture or body position in combination with a sound from the user that may indicate an injury. In some embodiments, image and/or audio data may be analyzed in conjunction with mechanical sensor data of the operation of the electronic exercise equipment. For example, mechanical sensor data may be analyzed to determine that a user let go of a cable, and image data may be analyzed to indicate that at the same time, the user grabbed a muscle of the arm that was holding the cable. Thus, the disclosed embodiments may provide robust devices and techniques for automatically generating indications of injury, thereby assisting the user to prevent further injury and also to prevent damage to the electronic exercise equipment due to improper use when the user is injured or impaired.

By way of example, FIG. 7D illustrates an exemplary graphical user interface for identifying an injury, consistent with disclosed embodiments. In this example, the at least one processor may provide for display on GUI 700 a header or prompt, such as injury header 728. Injury header 728 may prompt the user to identify at least one injured muscle. Non-limiting examples of language to be included in injury header 728 may include "Where is your injury?" "Please identify your injury," and/or any other message that may prompt the user to identify a specific injured muscle. Consistent with disclosed embodiments, the at least one processor may receive an electronic indication of injury based on image, audio, and/or mechanical sensor data, and the user may not be required to interact with the GUI to indicate they are injured.

In some embodiments, receiving occurs during the exercise routine. During the exercise routine may refer to a time while the user is in the midst of performing one or more exercises, such as between sets or between repetitions. In this example, the user may interact with one or more icons, buttons, tiles, and/or other interactive elements associated with the GUI of the mobile communication device to signal to the at least one processor that the user injured one or more muscles.

In some disclosed embodiments, the electronic indication includes an identification of a specific injured muscle. Identification of the injured muscle may refer to the process of determining which muscle or muscle group has been injured. For example, the identification may be based on the user's input, the system's analysis of the user's performance, or a combination of both. In one example, based on a user's input via the GUI on the mobile communications device, the at least one processor may retrieve data from the cloud server and/or remote server to identify the specific injured muscle. In some embodiments, the at least one processor may identify the injured muscle based on the exercise the user is performing and received image, audio, and/or mechanical data. For example, the user may be performing chest flys, and the at least one processor may determine, based on received image, audio, and/or mechanical data, that the user is exhibiting a shorter range of motion that normal. Based on the user's range of motion and the selected exercise, the at least one processor may determine that the injury is related to one or more chest muscles, such as the pectoral muscle.

A specific injured muscle may refer to a single muscle or a larger group of muscles. In one example, the user may indicate that they pulled their bicep. In another example, the user may indicate that they strained their hamstring. In yet another example, the user may indicate that they pulled their quad. In yet another example, the user may notate a portion of the body where pain is felt, and the system may be preprogrammed to identify the muscle or muscle group associated with the notated body portion.

In some disclosed embodiments, the operations further include outputting an anatomical map, wherein receiving an electronic indication includes a selection from the anatomical map. An anatomic map may refer to visual representation of the human body. For example, an anatomical map may include a front and back view of a human figure, and the user may indicate through interacting with the body map where pain is felt. In some embodiments, muscles or muscle groups may be highlighted and labeled. In another example, the anatomical map may be zoomed in on only the muscle group that the user is currently exercising. In this example, the anatomical map may be in zoomed in on the user's chest if the user was engaged in a chest workout prior to the injury indication, and may be zoomed in on the user's legs if the user was engaged in a leg workout prior to the injury indication. In yet another example, the anatomical map may be three dimensional. The anatomical map may be in black and white, grayscale, or in color. Selection from the anatomical map may refer to the user or the system choosing a specific muscle or muscle group from the anatomical map. For example, a selection may involve the user clicking on a specific muscle or area of pain on the body map, or the system highlighting a muscle based on the user's performance.

In some embodiments, operations include determining from the anatomical map an identification of the injured muscle. Determining may refer to performing a look up correlating an area of designated injury with an associated muscle or muscle group. This may occur, for example, using a look up table or using artificial intelligence. The look up may be based on the user's input of an area of injury via a GUI, and/or may be based on movement data captured by an image sensor, and audio sensor, and/or a mechanical sensor. The user may select one or more portions of the anatomical map, highlighting an injured area (or muscle or muscles). Based on the user's selection, the at least one processor may decide which muscle or muscles are injured.

In some embodiments, operations include presenting an injury button, and in response to activation of the injury button, causing a display of the anatomical map. An injury button may refer to a user interface element that the user can interact with to indicate an injury. For example, the injury button may be a physical button or a touch screen element on the exercise equipment, a virtual button on the user's mobile communication device, and/or a voice command. Presenting may refer to a process of displaying or making available information. As used herein, presenting may refer to the process of displaying or making available an injury button, via a GUI associated with the user's mobile communication device or via a display on the exercise equipment. In one example, presenting may involve displaying the anatomical map, showing a list of exercises, or providing options for adjusting the exercise routine. Activation may refer to the process of initiating a function or action by interacting with the user interface element. For example, activation may involve the user pressing the injury button, speaking a voice command, or making a gesture. A display of the anatomical map may refer to the visual presentation of the anatomical map on a screen or other display device. For example, the display may include a front and back view of a human figure, with different muscles or muscle groups highlighted and labeled.

In some embodiments, an injury button may not initially be presented on the GUI, or may be presented in a deactivated state that is not selectable. For example, the image button may be presented on the GUI based on image data, audio data, and/or mechanical sensor data received by at least those respective sensors. In this example, the at least one processor may determine from captured mechanical data at the user dropped weights while performing an exercise using the exercise equipment, such as a wall-mounted cable exercise machine. In response to the determination that the user dropped weights, the at least one processor may present the injury button for display on the GUI.

Referring to FIG. 7C, GUI 700 may contain an injury button 726. The user may select injury button 726 at any time during an exercise routine. In one example, the user may select injury button 726 as soon as the user feels discomfort in one or more joints, muscles, bones, and/or other parts of the user's body. In another example, the user may complete the exercise routine before selecting the injury button 726.

Referring to FIG. 7D, GUI 700 may contain an anatomical map 730. The user may interact with anatomical map 730 to identify a specific injured muscle. In this example, the user may select their left shoulder 732 from anatomical map 730, and the at least one processor may therefore receive an indication that the user's left shoulder is injured. Based on the specific muscle that the user selects, the processor may provide for display on GUI 700 a shaded portion of anatomical map 730, wherein the shaded portion reflects the selected muscle. In this example, the left shoulder 732 is shaded. In another example, the injured area may be highlighted, colored, or otherwise displayed to stand out to the user. The GUI 700 may display text 734 confirming that the user selected the correct muscle. In this example, text 734 may display "left shoulder" based on the user's selection. The user may select more than one muscle that they injured.

In one example, the user may select both the user's left shoulder and the user's left pectoral muscle. If the user is in pain or discomfort, but does not know the exact location or cause, the user may select a larger muscle group on anatomical map 730. For example, the user may select that their entire left leg or right leg is injured.

In some embodiments, the electronic indication of injury is received from the mobile communications device of the user. Users may interact with their mobile communications devices to indicate that they are injured. A user may select an interactive element via the GUI to indicate that they are injured. In one example, the user may select injury button 726. The at least one processor may be located in the user's mobile communications device, in the electronic exercise equipment, or in the cloud, and may determine that the user is injured based on the user's input via the GUI.

The user may also indicate injury via a touch screen on a built-in display associated with the exercise equipment. In one example, the built-in display may be affixed to or may be embedded within the main structure of the exercise equipment. The user may interact with the built-in display on the exercise equipment to indicate injury. In this example, the at least one processor associated with the exercise equipment may communicate with a cloud server and/or remote server to retrieve information related to the user's injury, such as, but not limited to, the injury location, severity, and/or exercises to be avoided or substituted in response to the injury. The built-in display may contain a touch screen or other GUI similar to that associated with the mobile communication device, as described in FIGS. 7A through 7F. In this example, the at least one processor associated exercise equipment may be positioned, located, or embedded within the built-in display and may communicate with the mobile communications device.

In response to the received electronic indication of injury (e.g., received from one or more inputs via a mobile communications device), some disclosed embodiments include changing the series of varied electronically controlled exercises to limit use of the injured muscle. A response to the received electronic indication of injury refers to feedback related to the indication of injury. In one example, the at least one processor may respond to the received electronic indication of injury based on the user interacting with the injury button only. In another example, the at least one processor may respond to the received electronic indication of injury based on the user selecting both the injury button and selecting a part of the user's body that is injured, such as the user's shoulder. In yet another example, the at least one processor may respond to the received electronic indication of injury, wherein the electronic indication of injury is based on data received via the image sensor, audio sensor, and/or mechanical sensor.

Changing the series of varied electronically controlled exercises refers to updating or otherwise amending one or more exercises to prevent further injury and/or to minimize use of injured muscles. Changing the series of varied electronically controlled exercises may also refer to stopping the exercise routine entirely. In one example, the user may indicate that they injured their arm or leg during a workout. Based on this indication of injury, the at least one processor may prompt the user to stop the exercise routine or continue the exercise routine. Limit refers to restricting the amount of something. As used herein, limit may refer to restricting the use and motion of the injured muscle.

By way of example, FIG. 7E illustrates an exemplary graphical user interface for adjusting an exercise based on the user's injury, consistent with disclosed embodiments. As mentioned in relation to FIG. 7D, the user may select an injured muscle from anatomical map 730. Based on the user's selection, the at least one processor may provide for display on GUI 700 a header or prompt, such as continue workout header 736. In this example, continue workout header 736 may contain text directed to whether the user is interested in continuing with their workout, based on their injury. For example, continue workout header 736 may contain language such as "continue workout?" or "pause workout?" The GUI may present an option 738 for continuing the workout, and an option 740 for pausing or stopping the workout. In this example, option 738 may display text such as "yes," whereas option 740 may display text such as "no." Options 738 and 740 may be interactive elements such as a button or tile.

In some embodiments, changing the series includes determining in the series predetermined exercises that engage the injured muscle, and substituting other exercises for the predetermined exercises that engage the injured muscle in a different manner or that avoid engaging the injured muscle. Predetermined exercises may refer to a plurality of exercises stored in memory. The exercises may be stored in memory of the exercise equipment, the user's mobile communication device, and/or the cloud. The predetermined exercises may be associated with a specific muscle or muscle group based on factory settings, user input, or both. For example, of the plurality of exercises stored in a memory, the at least one processor may associate a bench press exercise with chest and shoulder muscles. In another example, the at least one processor may associate a lateral pull-down exercise with back muscles.

Substituting may refer to replacing something, such as an item or object, with another. As used herein, substituting may refer to replacing one exercise in the series with another. For example, the processor may substitute an exercise that engages the injured muscle with another exercise that does not engage the injured muscle. Other exercises may refer to low-impact activities, strength training exercises, or flexibility exercises that do not strain the injured muscle or that impose less exertion or strain on the injured muscle.

By way of example, FIG. 7F illustrates an exemplary graphical user interface for performing dynamic injury-related adjustments during exercise, consistent with disclosed embodiments. In this example, the at least one processor may receive a request to continue with the workout based on the user selecting option 738. Based on the specific muscle that the user indicates is injured, the processor may update or otherwise change the previously selected series of varied electronically controlled exercises to limit or avoid the use of the injured muscle. The at least one processor may substitute an exercise that engages the injured muscle with another exercise that does not engage the injured muscle. In this example, the user selected a chest workout 708, and indicated that their left shoulder 732 was injured. The at least one processor may provide for display on the GUI a header or prompt, such as amended workout header 742. Amended workout header 742 may indicate that the at least one processor updated, amended, or otherwise changed the series of varied electronically controlled exercises. In one example, amended workout header 742 may display text such as "Amended Chest Workout," or "Updated Chest Workout Based on Shoulder Injury."

The at least one processor may instruct the user to engage in at least one amended electronically controlled exercise, such as one arm cable press 744 based on the user's selected injured left shoulder 732. Previously, the processor may have instructed the user to perform multiple repetitions and sets of a chest press 722 or bench press. Instead, the at least one processor may instruct the user to perform one or more exercises that avoid or limit use of the user's injured shoulder, such as multiple repetitions and/or sets of one arm cable press 744. In this example, the processor substitutes the one arm cable press exercise 744 for the chest press exercise 722 to reduce strain on the user's injured left shoulder 732. Consistent with disclosed embodiments, the at least one processor may provide for display on the GUI 700 directions 746 for performing the at least one adjusted exercise, such as one arm cable press 744. GUI 700 may contain injury button 748, in the event that the user injures another muscle during the amended exercise. Consistent with disclosed embodiments, it may be understood that the operations discussed in relation to FIG. 7F may similarly be performed via the at least one processor located in the exercise equipment, wherein the touch screen as part of the built-in display on the exercise equipment may be similar to the GUI on the user's mobile communication device. In this example, the at least one processor associated with the exercise equipment may communicate with the cloud server and/or the remote server to retrieve information related to substitute exercises.

Some disclosed embodiments may include changing the series of varied electronically controlled exercises to avoid the injured muscle during a subsequent exercise routine. A subsequent exercise routine refers to an exercise routine that the user performs later or after the current exercise routine. A subsequent exercise routine may be used to continue the user's exercise regimen after an injury has been reported and adjustments have been made. Avoiding the injured muscle may refer to the process of modifying the exercise routine to limit use of the injured muscle. The subsequent exercise routine may additionally or alternatively involve exercises that avoid the injured muscle or muscles.

In one example, the user may be performing a chest exercise routine, and may subsequently perform a back exercise routine. It is possible that one or more of the same muscles may be used between subsequent exercise routines. For example, a chest exercise routine may use one or more of the same muscles as a subsequent back exercise routine. The at least one processor may recognize that the user may use one or more of the same muscles between subsequent exercise routines, and may amend the subsequent exercise routine to avoid the injured muscle in the subsequent exercise routine. In one example, the user may indicate during an exercise routine that they have injured their shoulder. Consistent with disclosed embodiments, the at least one processor may substitute an exercise that is less stressful on the user's shoulder, such as a one arm cable press, for the previous exercise that put more stress on the user's shoulder, such as a chest press or bench press. The user may then subsequently select a back workout. In this example, the at least one processor may have instructed the user to perform one or more sets of pull-ups, which may put additional strain on the user's shoulder. Here, the at least one processor may substitute a less stressful exercise, such as a dumbbell bent-over row, for the more stressful pull-up exercise.

Some disclosed embodiments involve, prior to initiation of a subsequent exercise routine, querying the user on the status of the injured muscle, and wherein, when a response to the query indicates improvement, reinstating exercises that engage the injured muscle. Prior to initiation refers to performing certain actions before the start of an exercise routine. Here, these actions may include querying the use on the status of the injured muscle. Querying may refer to asking for or prompting information from the user. For example, querying may include electronically prompting the user for information about the status of an injured muscle before initiating a subsequent exercise routine. A status of an injured muscle may refer to the current condition of a muscle previously reported as injured by the user. For example, the status of the injured muscle may include information about the severity of the injury, the type of injury, the severity of pain and/or recovery progress.

A response to a query refers to information provided about the status of an injured muscle. The query may be issued by the at least one processor as part of the exercise equipment or the mobile communication device, and the user may respond to the query using an interactive element on the GUI on the user's mobile communication device or via a built-in display on the exercise equipment. Indicates improvement refers to a positive change. For example, indicates improvement may refer to a positive change in the status of the user's injured muscle. Reinstating may refer to reintroducing, restoring, or returning something to a previous position, condition, or state, after it has been removed, suspended, or discontinued. As used herein, reinstating exercises refers to reintroducing exercises that engage the injured muscle once improvement has been indicated. For example, the reinstating of exercises may involve gradually increasing the intensity or frequency of exercises that engage the injured muscle.

The at least one processor may provide for display on the GUI associated with the mobile communication device a prompt for the user to update their injury status. The user may update their injury status by selecting an interactive element on the GUI, such as a button or tile. After receiving a request to update injury status, the at least one processor may provide one or more options for the user to update their injury status. The at least one processor may provide for display of a header prompting the user to provide updates regarding the user's injury status. In one example, the at least one processor may present a plurality of options for the user to update their injury status, wherein each option is a selectable interactive element on the GUI. In this example, the at least one processor may present three options for the user to select, wherein the user may indicate that their injury is feeling better, about the same, or worse. In this example, the user may indicate that their injury is feeling better. Alternatively, the user may indicate that their injury is feeling worse. Consistent with disclosed embodiments and depending on the user's input, the at least one processor may maintain the currently substituted exercise, add more exercises that reduce strain or stress on the injured muscle, or gradually reinstate exercises from the original exercise routine.

In another example, the at least one processor may provide for display on the GUI of the mobile communication device a scale to indicate the status of the user's injury. The scale may be from 1 to 10, 1 to 20, 1 to 50, 1 to 10, or any range in between. In the example where the scale is from 1 to 10, a selection of 1 may indicate that the user is in significant pain, and/or that the injury has gotten worse. A selection of 5 may indicate that the user's injury is feeling about the same. A selection of 10 may indicate that the user's injury has healed, and the user is ready to resume their regularly scheduled workout routine. Depending on the user's input, the at least one processor may maintain the currently substituted exercise, add more exercises that reduce strain or stress on the injured muscle, or gradually reinstate exercises from the original exercise routine.

Figure 8A:
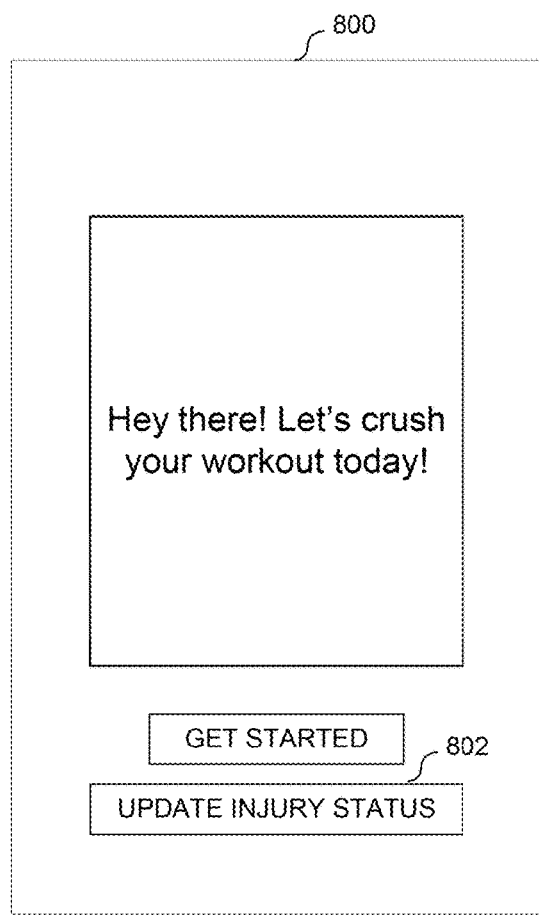
FIG. 8A illustrates an exemplary graphical user interface for querying the user on the status of the one or more injured muscles, consistent with some disclosed embodiments.

By way of example, FIG. 8A illustrates an exemplary graphical user interface for querying the user on the status of the one or more injured muscles. GUI 800 may display a button, such as injury update button 802, prompting the user to update their injury status. Injury update button 802 may also be a tile or other interactive element that allows the user to update their injury status.

Figure 8B:
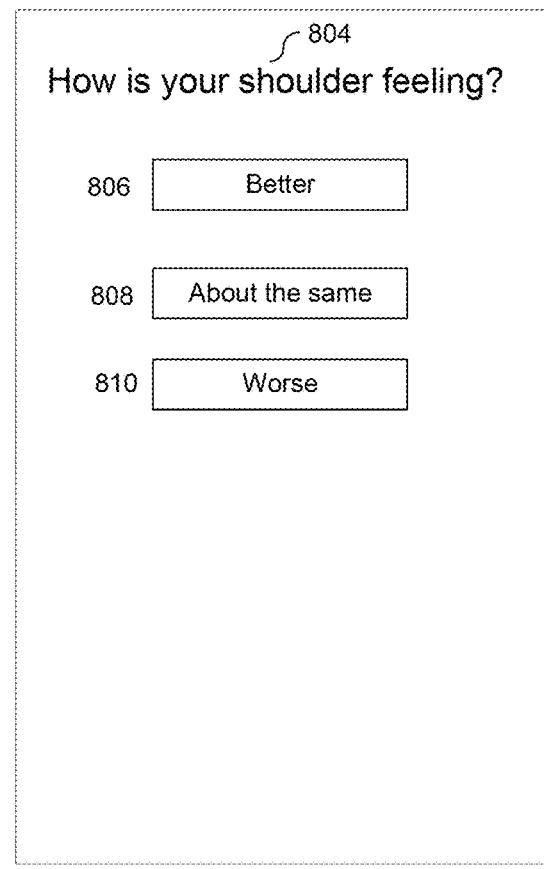
FIG. 8B illustrates an exemplary graphical user interface for updating the user's injury status, consistent with some disclosed embodiments.

By way of example, FIG. 8B illustrates an exemplary graphical user interface on the user's mobile communication device for updating the user's injury status. In this example, GUI 800 may display a header or prompt, such as injury update header 804. Injury update header 804 may prompt the user to provide feedback, via the GUI, regarding the status of the user's injury. Injury update header 804 may include text such as "How is your injured muscle feeling," "Has your injury improved," and/or "Please evaluate your injury on a scale from 1 to 10." In this example, based on the user's shoulder injury 728, injury update header 804 may display "How is your shoulder feeling" text. GUI 800 may also display options for the user to select how their injury has improved. In this example, the user may select that their injury is feeling better using "better" button 806, their injury is about the same using "about the same" button 808, or that their injury is feeling worse using "worse" button 810. Consistent with disclosed embodiments, the at least one processor may change the series of electronically controlled exercises based on the user's input. In this example, the processor may gradually reintroduce shoulder-based workouts if the user selects the "better" button 806. In another example, the processor may keep the same amended workouts if the user selects "about the same" button 808. In yet another example, the processor may further reduce shoulder-focused workouts if the user selects "worse" button 810.

Consistent with some disclosed embodiments, it may be understood that the operations discussed in relation to FIG. 8A and FIG. 8B may similarly be performed via the at least one processor associated with the exercise equipment, wherein the touch screen is part of the built-in display on the exercise equipment and may be similar to the GUI on the user's mobile communication device. In this example, the at least one processor on the exercise equipment may communicate with the cloud server and/or the remote server to store the user's inputs regarding the user's updated injury information.

Figure 9:
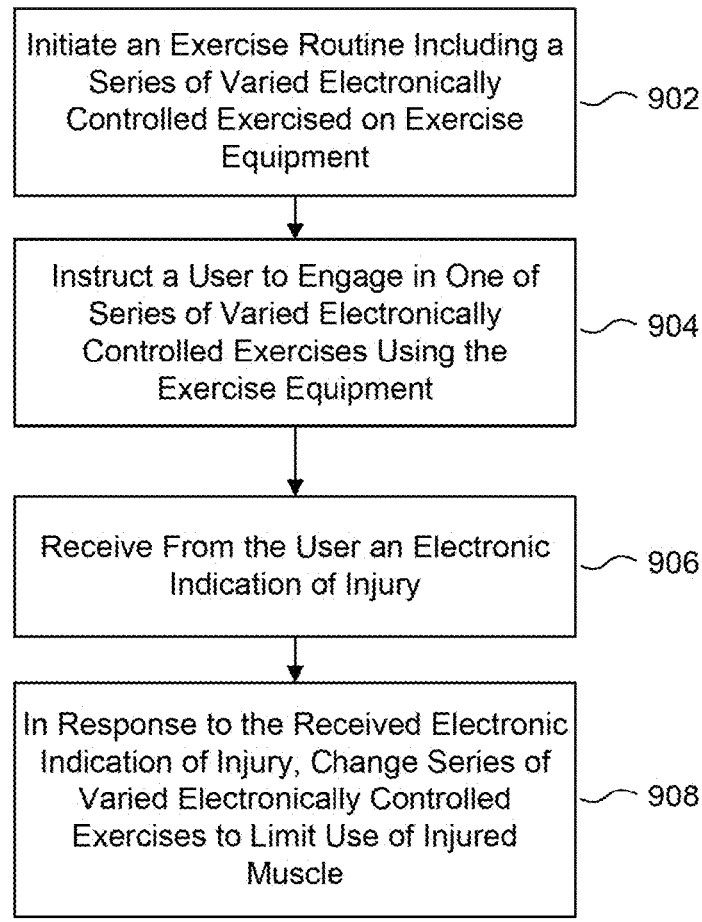
FIG. 9 is a flowchart illustrating an exemplary method of performing dynamic injury-related adjustments during exercise, consistent with some disclosed embodiments.

FIG. 9 is a flowchart illustrating an exemplary method 900 of performing dynamic injury-related adjustments during exercise. As illustrated in step 902, the processor may initiate an exercise routine. The exercise routine may include a series of varied electronically controlled exercises on exercise equipment, wherein differing exercises work differing groups of muscles. As illustrated in step 904, the processor may instruct the user to engage in one of the series of varied electronically controlled exercises using the exercise equipment. At step 906, the processor may receive an electronic indication of injury. The electronic indication of injury may include an indication of at least one injured muscle. In one example, the electronic indication may be based on user input via a GUI and/or touch screen associated with the exercise equipment, and/or the GUI associated with the user's mobile communication device. At step 908, the processor may, in response to the received electronic indication of injury, change the series of electronically controlled exercises to limit use of the injured muscle.

Some disclosed embodiments involve automated workout routines built around disliked exercises. One impediment to follow-through in exercise routines is a dislike of particular exercises. For example, if an individual dislikes arm curls and a typical automated exercise routine includes arm curls, the individual might be discouraged from working out altogether. Some disclosed embodiments provide a system for permitting an individual to identify disliked exercises. In response, a software application may build an exercise routine omitting the disliked exercises and substituting in their stead other exercises that work the same muscles as are worked by the disliked exercises.

Some embodiments provide a non-transitory computer readable medium containing instructions that when executed by at least one processor cause the at least one processor to perform operations for dynamically modifying automated electronic exercise equipment usage instructions. The operations may be implemented by at least one processor.

The at least one processor may receive a selection of a fitness a goal associated with a user of electronic exercise equipment configured for implementing an automated exercise program. The fitness goal may be typically associated with a series of exercises in the automated exercise program. The at least one processor may electronically prompt the user to identify disliked movements. For instance, the at least one processor may display exercise names for selection, display graphical images for selection, and/or display animations for selection.

The at least one processor may identify alternative movements to the disliked movements. The alternative movements may be chosen from a group consisting of movements that work muscles typically worked by the disliked movements. The at least one processor may build an alternative automated exercise program including the alternative movements. The alternative automated exercise program may omit the disliked movements while enabling attainment of the fitness goal. The at least one processor may sequentially output for presentation on a display, prompts for performing the alternative automated exercise program. The at least one processor may obtain feedback on performance of the alternative automated exercise program from at least one sensor monitoring the electronic exercise equipment.

In some embodiments, the at least one processor may store indications of the identified disliked movements (e.g., in a memory), and apply the alternative automated exercise program to a subsequent exercise session based on the stored indications. In some embodiments, the exercise program may include exercise sequences for a series of sessions extending over a plurality of days.

In some embodiments, the at least one processor may modify the alternative automated exercise program based on the obtained feedback. For instance, modifying may include changing at least one of an exercise sequence in a day in the subsequent day in the series of days.

In some embodiments, the at least one processor may introduce the disliked movements into the alternative automated exercise program based on the feedback. In some instances, the alternative automated exercise program includes instructions for altering resistance for application by the electronic exercise equipment. In some embodiments, the at least one processor may initiate an exercise routine including a series of varied electronically controlled exercises on exercise equipment, where differing exercises work differing groups of muscles.

In some instances, the disliked movements correspond to an injury. The at least one processor may prompt the user to report the injury. The alternative automated exercise program may be configured to minimize further injury.

In some embodiments, the at least one processor may prompt the user with an option to reinstitute disliked movements. In some embodiments, the at least one processor may provide a graphical user interface that presents a series of movements and permits the user to accept or reject each movement. In some instances, the series of movements includes a swipe in one direction to accept a movement, and a swipe in another direction to reject a movement.

Some disclosed embodiments involve dynamically modifying automated electronic exercise equipment usage instructions. Modifying refers to changing or altering in some way. Modifying may involve creating, deleting, or changing one or more files or data records in a database. In some embodiments, modifying may involve supplementing data in a file with additional data. In some embodiments, modifying instructions may involve changing, adding, or deleting data or metadata associated with stored automated electronic exercise equipment usage instructions. In some embodiments, modifying usage instructions may involve changing an order of the usage instructions, shortening, lengthening, or changing the usage instructions in any other manner consistent with disclosed embodiments. Dynamically modifying refers to constantly changing. Modifications that are dynamic may involve changes performed at constant intervals, or at irregular intervals. Usage instructions refer to orders for using something. For example, usage instructions may involve orders informing a user how to use a piece of electronic exercise equipment or how to perform a movement. In some embodiments, dynamically modifying usage instructions may involve constantly changing the usage instructions in response to new data or information. In such embodiments, an amount or frequency of constant changes may be directly proportional to the receipt and amount of new information or data. As disclosed herein, usage instructions may be dynamically modified based on information about disliked exercises.

Electronic exercise equipment refers to electronic devices used for exercising, as described and exemplified elsewhere herein. For example, electronic exercise equipment may include a wall-mounted electronic exercise machine that applies a resistive force to a cable, as described elsewhere herein. Something that is automated requires little or no human intervention. An automated device may use technology to perform tasks with little or no human intervention. Automation may involve the use of machines, computers, or other systems to control and operate processes automatically. Automated electronic exercise equipment refers to electronic exercise equipment that performs one or more operations with little or no human intervention. Automated electronic exercise equipment may adjust one or more parameters with little or no human intervention, such as by changing resistance or speed. Automated electronic exercise equipment may also collect information automatically such as monitoring a user's heart rate or analyzing information about a user's form, and provide feedback on performance. Such features can enhance the user's experience by allowing the user to focus on performing the exertion to improve fitness, without needing to constantly change device settings or provide data, thereby making workouts more efficient and effective.

By way of non-limiting example, FIG. 2A illustrates an electronic exercise machine 200 that may be automated by automatically changing operational parameters. For example, a motor 140 may automatically apply a predetermined amount of resistance to a cable 206 without human intervention. Thus, a user of the electronic exercise machine 200 may perform exercise movements without needing to manually add weights to the cable or adjust a tensioning device.

Some disclosed embodiments involve receiving a selection of a fitness goal associated with a user of electronic exercise equipment configured for implementing an automated exercise program. Selection refers to a choosing of something. Receiving a selection includes obtaining a choice. A received selection may be an indication of a choice among a predefined set of alternatives. For example, one or more inputs may identify a particular fitness goal among a set of displayed or outputted fitness goal options. In some embodiments, a received selection may be an indication or choice provided in response to an open-ended prompt. In some embodiments, one or more processors may choose one or more fitness goals based on a set of parameters or data associated with an individual.

A fitness goal refers to an objective and/or plan for a level of physical conditioning, wellness, and/or vigor, as described and exemplified elsewhere herein. A fitness goal may be set individually by a user, or determined for the user by a third party. An exercise program refers to a set of related exercises. The exercises may be related by a common fitness goal, such as improving cardiovascular health or strengthening a particular muscle group. The exercises of an exercise program may have a common characteristic such as a similar time length, exercise style such as high intensity interval training, or other characteristic associated with the movements of the exercises. An automated exercise program refers to a set of pre-programmed workout routines or sequences that are designed to be used with exercise equipment and are controlled by the equipment itself, as described and exemplified elsewhere herein.

Implementing refers to putting a plan, decision, or idea into effect or action. Implementing may involve carrying out one or more steps to make the decision, idea, or plan happen or to achieve a specific goal. Implementing an automated exercise program refers to putting a set of pre-programmed workout routines or sequences into action. In some embodiments, an electronic exercise machine may implement an automated exercise program by providing a set of instructions for a user to perform exercises in a sequence.

By way of non-limiting example, referring to FIG. 1A, an electronic exercise machine may provide instructions using one or more of electronic display 128, haptic indicator 130, speaker 132, and/or light indicator 134. Additionally or alternatively, a connected mobile communications device such as a smartphone 224 (shown in FIG. 1B) may provide instructions and feedback for performing exercises using an interface and output device of the smartphone 224. In such embodiments, the instructions and feedback may be determined via an app running on smartphone 224, or using a processor 112 of the electronic exercise machine (shown in FIG. 1A).

In some disclosed embodiments, the fitness goal is typically associated with a series of exercises in the automated exercise program. A series of exercises refers to multiple exercises in a sequence, as described and exemplified elsewhere herein. A series of exercises may involve different physical activities or movements performed in a particular order as part of a workout or training regimen. Such exercises are often designed to target different muscle groups or aspects of fitness, such as strength, endurance, flexibility, or coordination. For example, a series of exercises may be a pre-programmed workout routine or set of instructions provided by the equipment, such as a treadmill might have a "hill climb" series of exercises that gradually increase the incline and speed to simulate climbing a hill. For example, a strength training machine might have a series of exercises targeting different muscle groups, with instructions on how to perform each exercise safely and effectively. A fitness goal that is typically associated with a series of exercises refers to a fitness goal and multiple exercises that share common characteristics and are often associated with one another. For example, a fitness goal of improving cardiovascular health may be associated with a characteristic of elevated heart rate exercises, and may thus be associated with a series of exercises designed to elevate a user's heart rate.

Some disclosed embodiments involve the exercise program including exercise sequences for a series of sessions extending over a plurality of days. A sequence refers to successive associated things. Exercise sequences refer to successive associated exercises. For example, an exercise sequence for an upper body workout may involve successive exercises that are all associated with upper body muscle groups. A session refers to a period devoted to an activity. Sessions may involve periods of time devoted to exercising. A series of sessions refers to a number of related or similar periods of time devoted to exercising. In some embodiments, a series of sessions may extend over a plurality of days such that each of the plurality of days includes at least one exercise session. In some embodiments, the series of sessions may extend over a plurality of days, with days of no exercise, or rest, included in the plurality of days.

Some disclosed embodiments involve electronically prompting the user to identify disliked movements. A user refers to an individual, as described and exemplified herein. A user may interact with a product, system, or service. In the context of exercise equipment, a user typically refers to the person who is using the equipment for physical exercise or fitness purposes. Users of exercise equipment can range from individuals working out at home to members of a gym or fitness facility as described and exemplified elsewhere herein.

Prompting refers to causing a course of action. Electronically prompting refers to an electronic device causing a course of action. Electronic exercise equipment disclosed herein my electronically prompt an action by providing a graphical user interface requesting an input or response from a user. In some embodiments, electronically prompting may involve providing an interface, audible message or sound, or a haptic or light indicator, to cause the user to provide an input to the electronic exercise equipment. Identifying refers to selecting, establishing a choice, or choosing. One or more processors may receive an input from a user that identifies something. For example, processor 112 may receive a touch or voice input from a user that establishes or points out exercises that the user dislikes, such as by selecting from a list or manually inputting the exercises. Electronically prompting the user to identify thus refers to an electronic device causing the user to establish or point out. In some embodiments, electronically prompting may involve providing a query, cue or stimulus that elicits a specific response or action from a user. Prompting may involve one or more actions or messages that encourage users to take specific actions or provide input. For example, a software program might prompt the user to enter or select a name or description of an exercise.

Disliked movements refer to physical exercises or activities that the user does not enjoy or finds unpleasant. These could be exercises that are exceedingly challenging for the user, uncomfortable, boring, or simply not preferred by the individual. For example, user may dislike using a certain type of weightlifting movement because it causes discomfort. Such disliked movements can vary from person to person based on individual preferences, fitness levels, and physical limitations. Identifying disliked movements may involve receiving or gathering information that enables one or more processors to point out one or more exercises that the user does not enjoy. In some embodiments, one or more processors may receive an input via a touchscreen, microphone, or other input device, associated with an identification of a disliked movement. In some embodiments one or more sensors of the electronic exercise equipment or of a connected mobile communications device may receive information associated with identification of a disliked movement.

Some disclosed embodiments involve electronically prompting the user to identify disliked movements includes displaying exercise names for selection. A name refers to words by which something is known. Exercise names refer to words by which the exercises are known. In some embodiments, exercise names may describe and differentiate different between different types of exercise movements. In some embodiments, exercise names may include an identification of the muscle(s), muscle groups, or body region associated with the exercise. In some embodiments, exercise names may reflect the targeted muscles or muscle groups, equipment or props used, a direction of the movement, and/or a specific motion or action involved in the exercise. In some embodiments, a display of an electronic exercise equipment or a connected mobile communications device may provide one or more exercise names associated with the series of exercises in the exercise program. Unlike the display of graphical images, the display of exercise names may be substantially all textual in nature, using alphanumeric characters to identify the exercises as opposed to visual representations of the exercises.

Some disclosed embodiments involve electronically prompting the user to identify disliked movements by displaying graphical images for selection. Graphical images refer to information expressed in pictures, diagrams, or visual representations. Graphical images may include pictures, photographs, drawings, charts, diagrams, and other visual elements that depict movements associated with exercises in an exercise program. Some disclosed embodiments involve electronically prompting the user to identify disliked movements includes displaying animations for selection. An animation refers to a moving image. Animations displayed for selection may include animations of the movement. For example, an animation for a cable triceps extension may include a moving image of an individual performing the triceps extension movement. In some embodiments, the animation may be a moving image of the electronic exercise equipment.

In some embodiments, an electronic prompt to the user to identify disliked movements may involve prompting the user to confirm or acknowledge a disliked movement automatically identified by the processor without needing human input or intervention. Electronic exercise equipment may include one or more sensors such as mechanical sensors (such as 124 in FIG. 1A), audio sensors (such as 122 in FIG. 1A), and light sensors (such as 126 in FIG. 1A), among other sensor types. Additionally, sensor devices that are external to the electronic exercise equipment may be in communication with a processor that controls the electronic exercise equipment. By way of non-limiting example, FIG. 2A shows a mobile communications device 224 in communication with an electronic exercise machine 200 via a communication link 226, where the mobile communications device 224 may include a camera, audio sensor, and other sensors capable of observing a user while using electronic exercise machine 200.

In some embodiments, one or more processors may receive sensor data indicative of the user's performance and behavior during various exercise movements, and automatically identify disliked movements. For example, a mechanical sensor in the electronic exercise equipment may sense a reduced or lacking level of effort by the user to move a cable 206, or detect a limited range of travel (range of motion) of the cable via one or more sensors. In some embodiments, an analysis of movement characteristics of the cable may indicate a user's lack of desire to perform a particular movement, and cause the processor to identify the disliked movement. For example, mechanical sensor data may indicate a slow acceleration of the cable for a particular movement, despite the user accelerating the cable more quickly while performing other movements with similar or greater resistance levels. As another example, mechanical sensor data may be analyzed to determine that the user did not complete all instructed repetitions of a particular movement, even though sensor data for other movements indicated that the user should be capable of performing the movement. Additionally, or alternatively, sensors in the electronic exercise equipment or the mobile communications device may capture visual and/or audio data for the user. One or more processors may analyze the captured audio/visual data to identify images, movement, or sounds associated with a user disliking a movement. For example, visual data may be analyzed to determine whether the user's facial expressions indicate the user is unhappy or bored while performing a movement. In some embodiments, visual data may indicate that the user failed to complete all repetition of a movement, and optionally determine whether the user walked away from the machine during the movement. As another example, audio data may be analyzed to detect sounds and speech associated with content or discontent with a movement. In some embodiments, certain words, phrases, and sounds such as sighs may be associated with a user disliking a movement. One or more processors may analyze data gathered throughout an exercise session, and establish a range of the user's content/discontent for the session. The one or more processors may identify movements that fall at the "content" end of the range, and identify movements that fall at the "discontent" end of the range, to identify disliked movements. In some embodiments, the one or more processors may track and analyze collected sensor data across multiple exercise sessions, and analyze collected data to identify disliked movements. In some embodiments, the one or more processors may compare sensor data for the same movement collected during different exercise sessions. The one or more processors may determine, based on the comparison whether the user's attitude toward a particular movement has changed over time, towards liking the movement or disliking the movement, using the types of analysis discussed above.

For instance, one or more processors may calculate one or more statistical aspects of monitored cable motions and/or motor resistance levels for different movements performed and/or partially performed during a plurality of exercise sessions over time. For example, one or more sensors may obtain data indicative of a length the cable has extended or retracted during a movement. As another example, one or more sensors may measure an amount of effort, force, or power exerted by the user on the cable while performing the movement. One or more processors may analyze the calculated values and detect one or more anomalies and/or trends indicated preferences for certain movements, and/or aversions for one or specific movements. For example, based on cable motion and/or motor resistance settings (e.g., correlated to image data) one or more processors may detect a tendency of a user to perform fewer than a recommended number of repetitions of a specific movement. In some embodiments, one or more processors may compare obtained data and analysis outputs from the obtained data to prior data for the user or one or more other users. Based on the detection, the one or more processors may automatically identify an aversion (e.g., dislike) for the specific movement. Thus, the disclosed embodiments may automatically identify disliked movements to enhance the user's experience, improve the accuracy of one or more rule sets or algorithms used to identify disliked movements, and provide enhanced operation of the electronic exercise equipment through effective user results.

Figure 10A:
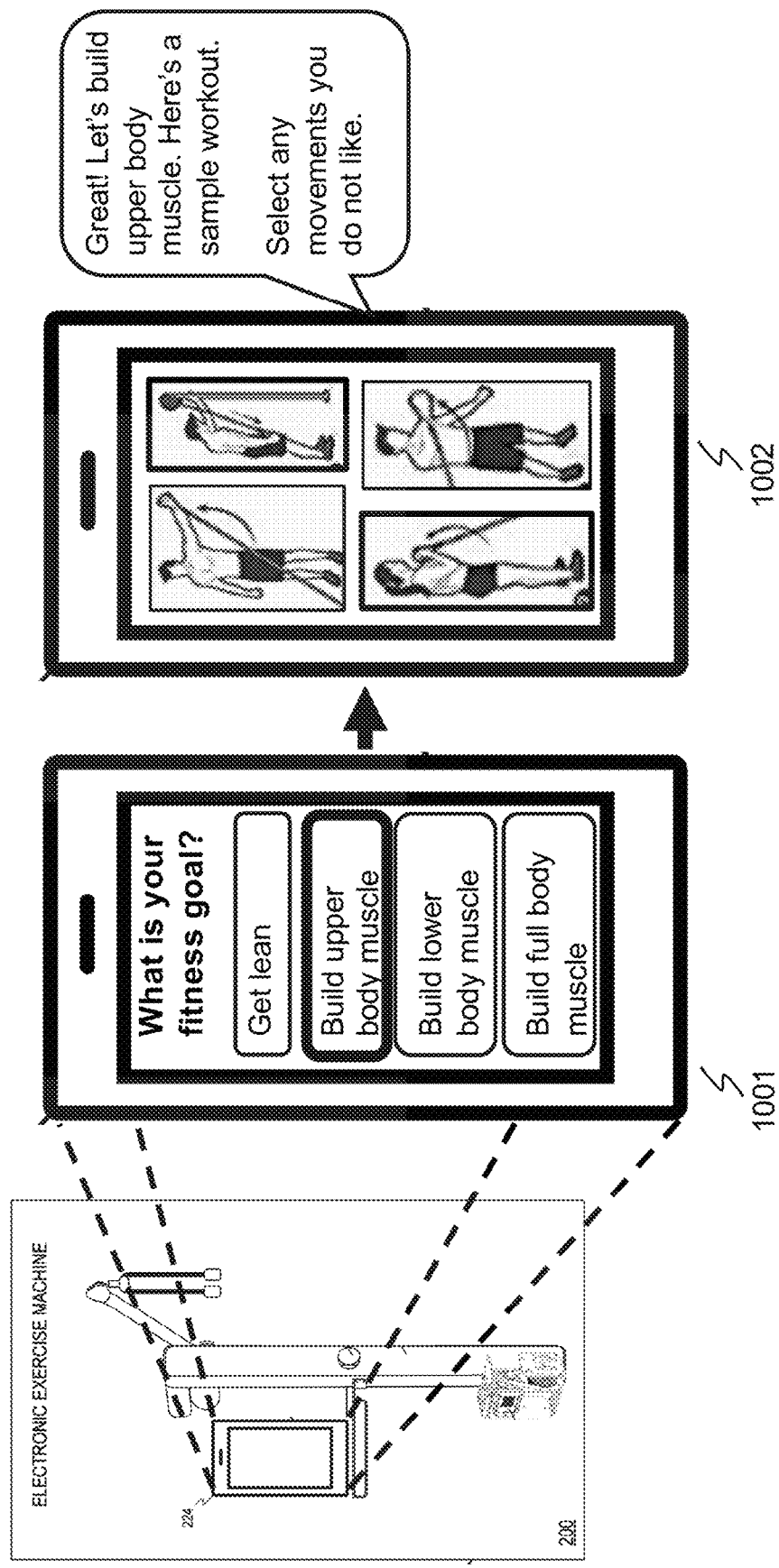
FIG. 10A is a diagram illustrating exemplary graphical user interfaces for dynamically modifying automated electronic exercise equipment usage instructions, consistent with disclosed embodiments.

By way of non-limiting example, FIG. 10A is a diagram illustrating exemplary graphical user interfaces for dynamically modifying automated electronic exercise equipment usage instructions, consistent with disclosed embodiments. A user (not shown) may interact with electronic exercise equipment such as electronic exercise machine 200, to exercise toward achieving a fitness goal. In some embodiments, a mobile communications device 224 attached and/or in communication with the electronic exercise machine 200 may present one or more graphical user interfaces prompting the user to provide inputs and take one or more actions. One or more of a processor of the mobile communications device 224, the electronic exercise machine 200, or a cloud service 300 (not shown) may provide for display a first GUI 1001, prompting the user to identify a fitness goal. In the example shown, a number of predetermined fitness goals may be presented for selection. In some embodiments, the processor may provide an open-ended query and a prompt to enter a free form response, from which the processor may determine one or more fitness goals. In some embodiments, one or more processors may apply techniques such as natural language processing, string matching, parsing, and other language processing techniques to identify a fitness goal from an open ended input.

The processor(s) may provide for output a second GUI 1002, displaying information associated with a series of exercises for an automated exercise program associated with the selected fitness goal. In the example shown, graphical images for the movements for the series of exercises in the exercise program are displayed, to prompt a user to select disliked movements. The processor may prompt, visually and/or audibly, the user to identify any disliked movements among the series of exercises.

Some disclosed embodiments involve identifying alternative movements to the disliked movements, wherein the alternative movements are chosen from a group consisting of movements that work muscles typically worked by the disliked movements. Alternative movements refer to other possible movements. Alternative movements may involve different exercises or physical activities that can be performed as a substitute for a disliked movement. In some embodiments, several movements may be associated with a certain muscle or group of muscles. For example, one or more electronic records may store information for exercises and movements that includes an indication of the muscle(s) that are worked by the respective exercise or movement. Muscle refers to a tissue in the body that is responsible for producing movement. Muscles are composed of fibers that contract and relax to generate force, allowing for various types of movement. In the context of the disclosed embodiments, muscle refers to the specific muscles or muscle groups targeted by the equipment during exercise. For example, a leg press machine targets the muscles of the legs, including the quadriceps, hamstrings, and glutes. Understanding the muscles involved in each exercise can help individuals target specific areas of the body for strength training, muscle building, or rehabilitation purposes. Work refers to physical movement used to strengthen one or more muscles, as described and exemplified elsewhere herein. Work (ing) muscles therefore involves physical movement used to strengthen contractive tissue. Muscles typically worked by the disliked movements refer to movements that are associated with at least a threshold level of physical effort by one or more particular muscles. One or more processors may identify one or more alternative movements that involve physical movement used to strengthen the muscle(s) associated with the disliked movements. As a result, the disclosed embodiments can identify alternative movements that will achieve similar fitness goals but offer variety, challenge, or a different approach to training.

Some disclosed embodiments involve building an alternative automated exercise program including the alternative movements, wherein the alternative automated exercise program omits the disliked movements while enabling attainment of the fitness goal. An automated exercise program is described and exemplified elsewhere.

An alternative automated exercise program refers to an automated exercise program having one or more alternative movements or exercises. For example, one or more disliked movements from an automated exercise program may be modified, substituted, or otherwise changed to one or more alternative movements, resulting in an alternative automated exercise program. Alternative programs may offer variety and flexibility, allowing users to switch between different workout styles, intensities, or focuses based on their preferences and fitness goals, and to avoid disliked movements.

Figure 10B:
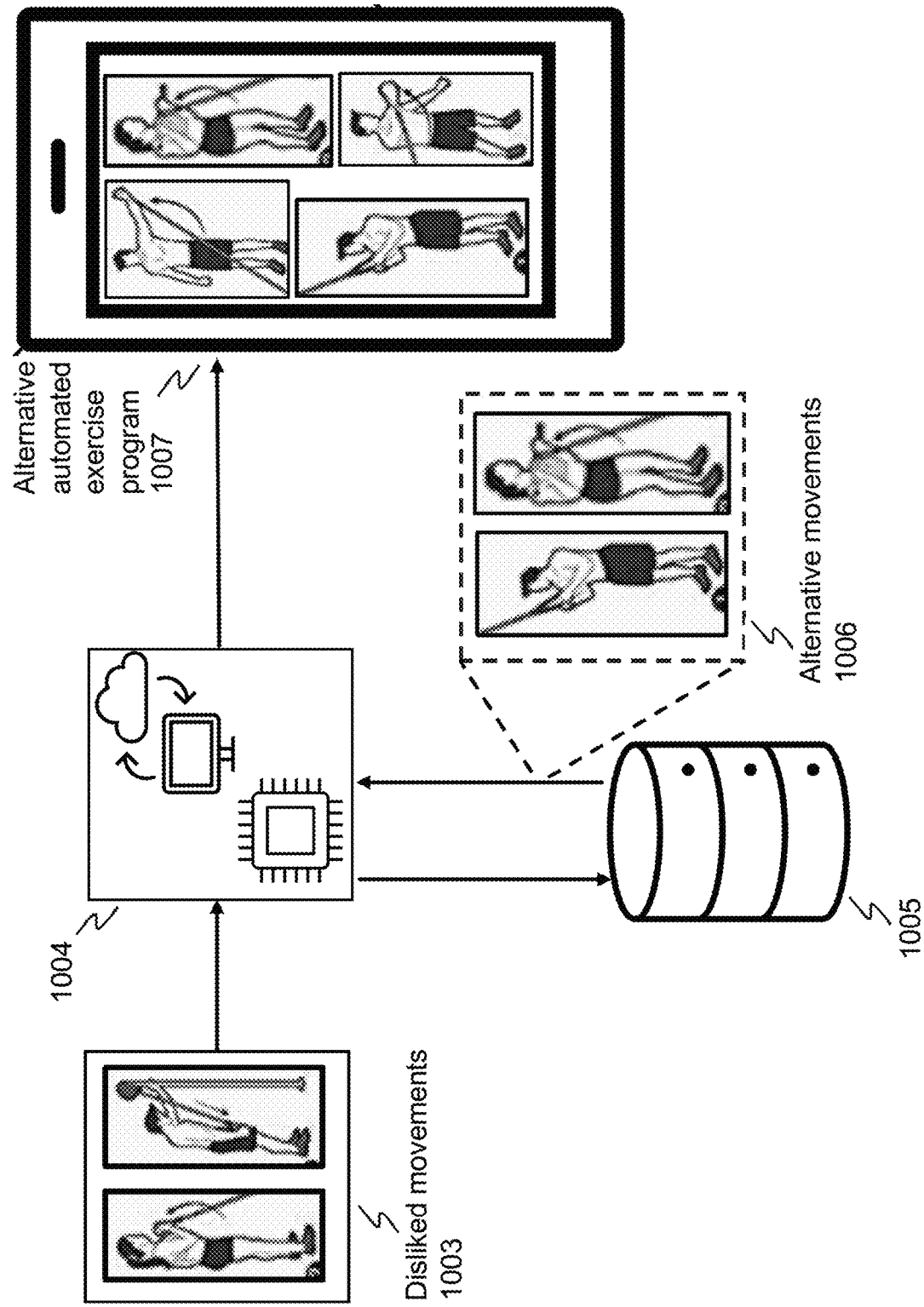
FIG. 10B is a diagram illustrating portions of a process for dynamically modifying automated electronic exercise equipment usage instructions, consistent with disclosed embodiments.

By way of non-limiting example, FIG. 10B illustrates portions of a process of dynamically modifying automated electronic exercise equipment usage instructions, consistent with disclosed embodiments. One or more processors of a mobile communication device, electronic exercise equipment, and/or a cloud service (collectively represented by 1004) may receive identification of one or more disliked movements 1003 from a user. The one or more processors 1004 may identify one or more alternative movements to the disliked movements. The one or more processors may query one or more storage locations such as a database 1005 to identify a group of movements that work muscles typically worked by the disliked movements. The one or more processors 1004 may then identify one or more alternative movements 1006 from the identified group. Using the alternative movements 1006, the one or more processors may then build an alternative automated exercise program 1007 including the alternative movements.

An alternative automated exercise program may cause a processor of electronic exercise equipment to operate differently. For example, implementing an alternative movement may cause the processor to set different resistance levels associated with the alternative movement, display different instructions for performing the alternative movement, and may affect one or more techniques of determining a user's physical fitness level.

The alternative automated exercise program omits disliked movements. Omitting refers to leaving out or excluding. Omitting may involve excluding certain items or groups of items. For example, omitting may involve excluding certain elements, data, or instructions from a process or output. For example, omitting may involve excluding certain data points or variables from analysis or calculations. With respect to the disclosed embodiments, one or more processors may omit the disliked movements identified by a user and/or a processor. For example, an automated exercise program may omit the particular movements identified by a user as disliked movements. In some embodiments, a processor (such as processor 112) may identify one or more other movements that have similar patterns or other attributes, and omit the identified other movements.

The alternative automated exercise program may be designed to enable attainment of the fitness goal. Attainment refers to achieving or reaching a goal. Attainment of the fitness goal thus refers to achieving or reaching the fitness goal. By way of example, attainment may include reaching a threshold level of performance or achieving a certain goal. A processor may evaluate attainment by comparing one or more measured metrics of a user's performance to one or more metrics of a fitness goal. The processor may determine that the user has attained a fitness goal when the measured metrics meet or exceed the fitness goal metrics, or when the measured metrics are within a predetermined margin of the fitness goal metrics. Enabling attainment of the fitness goal refers to making attainment of the fitness goal possible. A processor may enable attainment by identifying and selecting alternative movements that are associated with the same fitness goal, or are associated with working the same muscle(s) as the disliked exercises.

Some disclosed embodiments involve the alternative automated exercise program including instructions for altering resistance for application by the electronic exercise equipment. In some embodiments, the processor may enable attainment of the fitness goal by adjusting one or more operational parameters of the electronic exercise equipment to cause the user to perform the identified alternative movements. For example, the processor may alter resistance applied by the electronic exercise equipment. Altering resistance may involve reducing or increasing resistance. Resistance is described and exemplified elsewhere. Resistance may be applied by one or more components of the electronic exercise equipment to simulate a force applied to the user, or to simulate an amount of weight being displaced by the user. In some embodiments, resistance may be reduced in an alternative movement that is associated with a higher difficulty level than the disliked movement. In some embodiments, an alternative movement may be associated with a significantly lower difficultly level, and the resistance applied in the alternative movement or other movements in the program may be increased to compensate for the easier movement. In this way, the user may be able to achieve the same fitness goal without needing to perform the disliked movements, thereby enhancing the user's experience with the electronic fitness equipment.

Some disclosed embodiments involve sequentially outputting for presentation on a display prompts for performing the alternative automated exercise program. A display refers to a device or component that is described and exemplified elsewhere herein. Outputting refers to providing, as described and exemplified elsewhere. Outputting may involve providing information, data, or analysis results. Sequentially refers to a particular order, one after the other, following a sequence. Sequentially outputting refers to providing information in a particular order or sequence, or providing prompts one after another. As an example, a processor may sequentially output information that causes a display to show prompts for performing one movement or exercise after another, in a particular order or sequence. Presentation on a display refers to showing something visually. An output for presentation on a display may therefore involve providing something that can be seen or viewed on a display. In some embodiments, a built-in display of electronic exercise equipment may display the prompts. In some embodiments, a processor may send signals that cause an external device to display prompts.

Some disclosed embodiments involve sequentially outputting, for presentation on a display, prompts for performing the alternative automated exercise program by sending second signals to the mobile communications device of the user to thereby cause a presentation of the prompts on a display of the mobile communications device of the user. In some embodiments, a mobile communications device may serve as a primary or secondary display device for an exercise machine. A display screen of the mobile communications device may sequentially display prompts in response to one or more outputs of a processor of electronic exercise equipment.

Figure 10C:
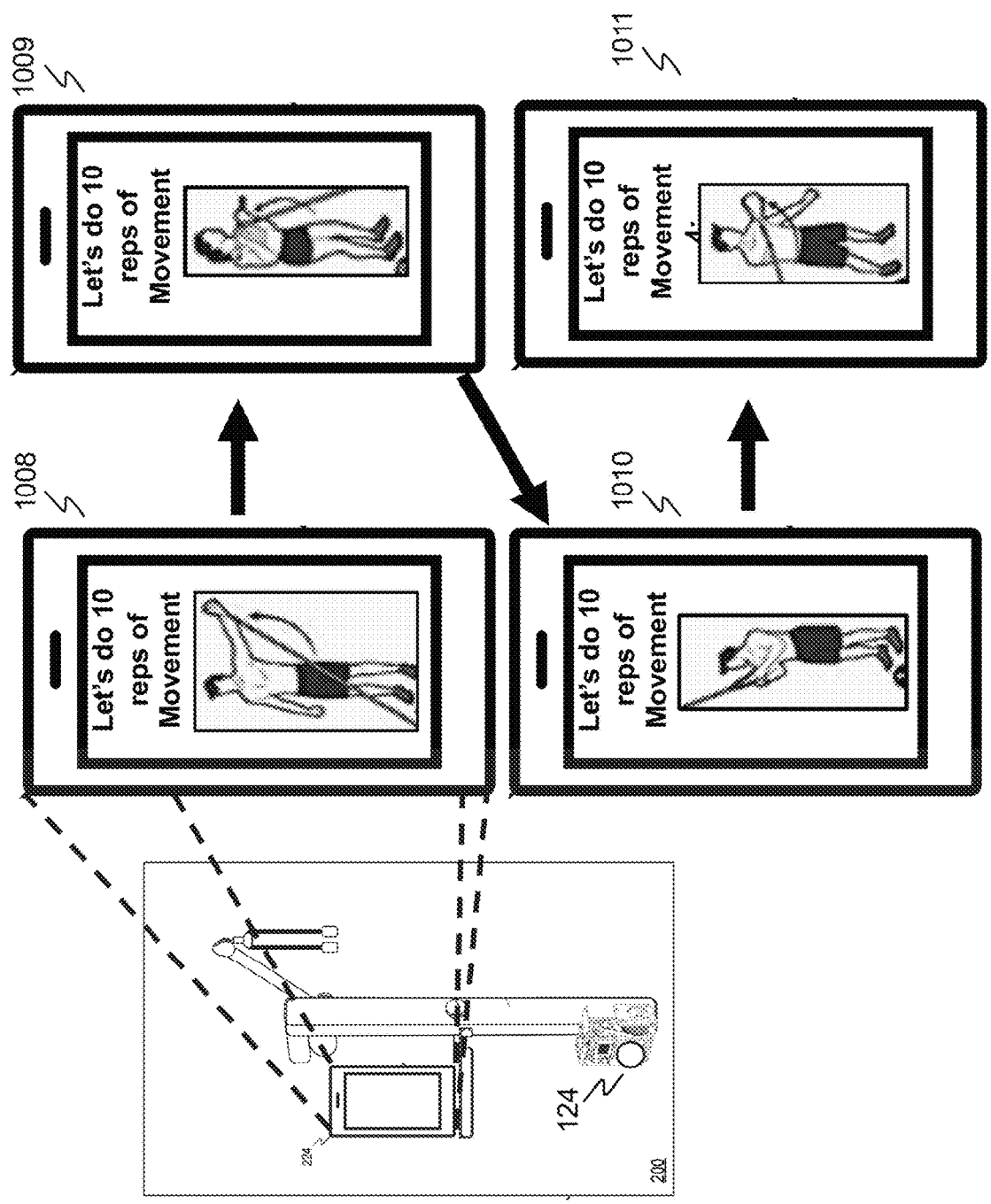
FIG. 10C is a diagram illustrating exemplary graphical user interfaces sequentially presenting prompts for performing exercise movements, consistent with disclosed embodiments.

By way of non-limiting example, FIG. 10C is a diagram illustrating exemplary graphical user interfaces that sequentially present prompts for performing exercise movements, consistent with disclosed embodiments. A display device (not shown) of the electronic exercise machine 200, or display of a mobile communications device 224, may sequentially present prompts for performing the alternative automated exercise program 1007 built with respect to FIG. 10B. The alternative automated exercise program 1007 illustrated in the figures includes four exercises. As shown in FIG. 10C, the mobile communications device may sequentially present GUIs 1008, 1009, 1010, and 1011 displaying prompts for a user to perform the four movements of the alternative automated exercise program 1007.

Some disclosed embodiments involve obtaining feedback on performance of the alternative automated exercise program from at least one sensor monitoring the electronic exercise equipment. Feedback refers to information about a reaction. Such information may include data output from a sensor, information extracted from data analysis of data associated with a reaction to something, or any other form of information indicative of a reaction. Feedback on performance refers to information about performance, such as performance of an exercise movement. In some embodiments, a processor may gather information representing feedback on performance of an individual performing exercise movements. Such information may be gathered by the electronic exercise equipment, a sensor associated with the electronic exercise equipment, and/or a device in communication with the electronic exercise equipment, such as a mobile communications device. A sensor refers to a device which detects or measures something, as described and exemplified elsewhere herein. Monitoring refers to observing or checking, as described and exemplified elsewhere. In some embodiments, the electronic exercise equipment may include at least one sensor that detects or measures a force exerted by the electronic exercise equipment. For example, a sensor may monitor a resistance level applied to a cable, or may monitor another type of force applied to a user via the electronic exercise equipment. In some embodiments, the electronic exercise equipment may include at least one sensor that detects or measures a force exerted by the user upon the electronic exercise equipment. For example, a sensor may measure a pressing force applied by the user to one or more components of the electronic exercise equipment. In some embodiments, a sensor may measure or detect a characteristic of a force, such as a speed of a movement, acceleration of movement, a continuity of an applied force, a rate of change of a force, an orientation or vector of a force, or any other measurable characteristic or parameter of a force. Such sensor measurements may enable a processor to objectively quantify a user's performance metrics while performing the alternative automated exercise program. Thus, feedback may be used to improve or refine stored information regarding the user's progress toward attaining fitness goals, as well as information regarding the effectiveness of certain exercise movements, and information regarding usage of the electronic exercise equipment.

By way of non-limiting example, FIG. 10C shows an electronic exercise machine 200 having a mechanical sensor 124, that may monitor one or more parameters of use of the machine, to obtain feedback about the user's performance of the alternative automated exercise program.

Some disclosed embodiments involve storing indications of the identified disliked movements. Storing involves saving or retaining data in a persistent form, as described and exemplified elsewhere herein. Storing indications of the identified disliked movements refers to saving or retaining data about the disliked movements identified in response to one or more prompts, as previously disclosed. Such indications may include data or metadata stored in association with a data entry or file for the movement, indicating to at least one processor that the movement is disliked.

Some disclosed embodiments involve applying the alternative automated exercise program to a subsequent exercise session based on the stored indications. A subsequent exercise session refers to an exercise session at a future or later time period. In some embodiments, one or more processors may store the alternative automated exercise program in association with a user's ongoing exercise program, such that the alternative automated exercise program may become the regular program for subsequent sessions. A processor of the electronic exercise equipment or a mobile communications device may apply the alternative automated exercise program by automatically setting one or more operational parameters and device settings corresponding to the alternative movements, and not the omitted movements. For example, a processor may cause the electronic exercise machine 200 to automatically set a resistance level and provide usage instructions associated with the alternative movements, and not the omitted movements.

Some disclosed embodiments involve modifying the alternative automated exercise program based on the obtained feedback. In some embodiments, at least one processor may evaluate the obtained feedback to determine whether one or more movements in the alternative automated exercise program are too easy or too difficult for the user. For example, obtained feedback may indicate that the user performs movements of the alternative program faster than a threshold pace, or above a threshold acceleration of the electronic exercise equipment. The processor may determine that the alternative program is too easy, and may modify the alternative program by increasing a resistance level for one or more movements, increasing a number of repetitions, instructing the user to lengthen a time period of each repetition, or any other modification that increases the difficulty of the alternative program for the user. On the other hand, obtained feedback such as mechanical sensor data monitoring a cable may indicate that the user is struggling to complete movements, and the alternative program is too difficult. For example, obtained feedback may indicate that tension on a cable of the electronic exercise equipment moves at inconsistent speeds, or a range of motion of the user is reduced, or the user is "cheating" to complete repetitions. The processor may modify the alternative program to decrease the difficulty for the user, such as reducing a tension level, reducing a number of repetitions, or making other modifications to lower the exercise difficulty. In this way, the disclosed embodiments may operate in a closed loop of identifying disliked movements, implementing alternative movements, and using obtained feedback to indicate to one or more processors whether to maintain the alternative automated exercise program, or modify it further.

In some embodiments, modifying the alternative automated exercise program may involve the processor swapping one or more movements for another movement that is associated with a higher or lower difficulty level, depending on trends observed in the obtained feedback. In some embodiments, such modifying includes changing at least one of an exercise sequence in a day in the subsequent day in the series of days. In some embodiments, the processor may change an exercise sequence of the current exercise session. Some disclosed embodiments involve introducing the disliked movements into the alternative automated exercise program based on the feedback. The processor may determine that a predetermined number of workouts have been completed since the user identified the disliked movements, a predetermined length of time has passed since the user identified the disliked movements, or any other rule or threshold has been satisfied that is associated with introducing the disliked movements. In some embodiments, the feedback obtained from one or more sensors in the electronic exercise equipment may indicate that the user's fitness or strength has increased beyond a threshold level, causing the processor to introduce the disliked movements back into the user's exercise program. In some embodiments, obtained feedback may indicate that the user is failing to progress toward their fitness goal, and the processor may introduce the disliked movement as a potential solution for overcoming a fitness plateau.

Some disclosed embodiments involve initiating an exercise routine including a series of varied electronically controlled exercises on exercise equipment, wherein differing exercises work differing groups of muscles. Electronically controlled exercises refer to exercises or workouts that are controlled or regulated by electronic devices or systems. This may include but not limited to using technology to adjust resistance levels, monitor performance, provide feedback, or guide users through a workout. For example, a stationary bike with electronically controlled resistance allows users to adjust the resistance level using electric and/or computerized components, rather than manually adjusting a knob or lever that tensions a belt or applies pressure to a flywheel Differing exercises refer to at least two physical movements that are not the same, as described and exemplified elsewhere.

In some disclosed embodiments, the disliked movements correspond to an injury. An injury refers damage to a muscle or other tissue of the user, as described and exemplified elsewhere herein. Disliked movements that correspond to an injury may include movements that have caused damage to a muscle or other tissue of the user, or movements that a user expects will cause such damage. An injury may involve harm or damage to the body caused by an accident, fall, or another traumatic event, such as muscle strains, joint sprains, bruises, cuts, and falls. Injuries can range from minor cuts and bruises to more serious conditions such as fractures, sprains, strains, or dislocations. Injuries can occur during physical activity, sports, or everyday activities. In the context of exercise equipment, an injury may involve harm or damage to the body that occurs while using exercise equipment due to improper use of the equipment, overexertion, or accidents.

Some disclosed embodiments involve prompting the user to report the injury. At least one processor may cause a device such as the electronic exercise equipment or a mobile communications device to prompt the user to provide information about the injury. Report refers to providing an account of something. Reporting an injury may involve providing an account of the injury by providing information about the occurrence or expected occurrence of the injury. In some embodiments, a graphical user interface may include a prompt for the user to report an injury. In some embodiments, reporting an injury may involve indicating a type of injury associated with a particular movement or exercise. In some embodiments, reporting an injury may simply involve identifying a movement, in response to a prompt to report movements associated with an injury.

By way of non-limiting example, FIG. 7D, illustrates an exemplary graphical user interface for identifying an injury, consistent with disclosed embodiments, as described elsewhere.

Some disclosed embodiments involve the alternative automated exercise program being configured to minimize further injury. In some embodiments, at least one processor may change a series of exercise in the automated exercise program, to limit use of the injured muscle, as described and exemplified elsewhere. The at least one processor may take other various actions to minimize further injury. For example, an alternative automated exercise program may be adjusted to reduce an amount of stress placed on the injured tissue, by avoiding movements that work the injured muscle or tissue, or by reducing an intensity or duration of movements associated with the injury. In some embodiments, the processor may identify movements associated with muscles surrounding or supporting the injured area, that may strengthen the user to prevent future injury. The one or more processors may employ one or more lookup tables, rule sets, artificial intelligence systems, or other data processing and analysis techniques, to adjust the alternative automated exercise program in a manner that minimizes and avoids further injury to the user.

By way of non-limiting example, FIG. 7F illustrates an exemplary graphical user interface for performing dynamic injury-related adjustments during exercise, as described elsewhere herein. FIG. 7F illustrates an example of an alternative automated exercise program that may be configured to minimize further injury.

By way of another non-limiting example, FIG. 2A shows an example of an electronic exercise machine 200, consistent with disclosed embodiments. In some embodiments a processor such as processor 112 (shown in FIG. 1A) of the electronic exercise machine 200, or a processor of smartphone 224, may modify an automated exercise program to create an alternative automated exercise program omitting disliked exercises that may be associated with a reported injury. The processor may provide for display an adjusted set of prompts to perform movements that omits the disliked movements. In some embodiments, an altered automated exercise program may include movements with parameters adjusted to account for the reported injury, and to minimize further injury. For example, in some embodiments, the processor may reduce an amount of tension applied to a cable for movements that are identified as being associated with an injury or a risk of further injury.

Some disclosed embodiments involve prompting the user with an option to reinstitute disliked movements. Reinstitution refers to putting back into place. Reinstitution may also involve reintroducing, restoring, reestablishing, or otherwise bringing back a disliked movement that was previously-omitted. Reinstituting disliked movements may be similar to reinstating exercises, disclosed elsewhere herein. An option to reinstitute refers to an option to put back into place. Reinstitution may include resuming a disliked movement that was temporarily removed or omitted from an exercise program. In some embodiments, a processor may cause an electronic exercise equipment output device (such as a screen, speaker, or other output device) to provide a prompt with an option for the user to reinstate one or more disliked movements. The option may be provided individually for reach disliked movement, or may be provided as a single option for reinstituting all disliked movements at the same time. In some embodiments, the option may be provided during performance of the alternative automated exercise program. In some embodiments, the user may be prompted with the option to reinstitute disliked movements before or after performing a workout in the exercise program. In some embodiments, a settings menu may include an option to reinstitute disliked movements after a predetermined time period or after a predetermined number of workout sessions that omit the disliked movements.

By way of non-limiting example, FIGS. 8A and 8B illustrates exemplary graphical user interfaces that may be associated with reinstituting movements. The examples illustrated in FIGS. 8A and 8B relate to movements that are omitted due to injury. Other graphical user interfaces may similarly prompt a user to indicate whether disliked movements should be reinstituted.

Some disclosed embodiments involve providing a graphical user interface (GUI) that presents a series of movements and permits the user to accept or reject each movement. A series of movements is similar to a series of exercises as described and exemplified elsewhere, and similar to movements that are described and exemplified elsewhere. A GUI that permits refers to a GUI that allows something to happen. For example, a GUI that allows a user to take action may involve an interactive GUI having one or more interactive GUI elements that are selectable, clickable, or can be manipulated in any other way, to permit input from the user. In some embodiments, a GUI that allows the user to take action may provide a prompt for a user to speak or make a gesture, that may be detected by a microphone and/or camera in communication with at least one processor. To accept refers to an answer in the affirmative. A user may accept a movement by agreeing or consenting to the movement, admit the movement into the user's electronic exercise program, or otherwise provide an indication that the user is willing to perform the movement. To reject refers to an answer in the negative. A user may reject a movement by refusing the movement, eject the movement, delete the movement, or otherwise indicate an unwillingness to perform the movement.

Some disclosed embodiments involve the series of movements including a swipe in one direction to accept a movement, and a swipe in another direction to reject a movement. A swipe refers to a brief rapid movement. A swipe may move from one side to the other side of a space or display, or up or down on the screen or in the space. A swipe may look like a sweeping motion, a wave, or a flick. In some embodiments, a user may swipe using one or more fingers against a touchscreen. In some embodiments, a user may swipe using one or more fingers or a hand in the air in front of one or more cameras. Some embodiments may involve detecting a swipe to dynamically modify automated electronic usage instructions. A direction refers to a general trajectory. A direction may involve a particular orientation or course in which a swipe gesture is made. By way of example, one direction may include left to right, top to bottom, or any other trajectory. A processor may interpret a swipe in one direction as a specific command or function to accept or reject a movement. A processor may also interpret a swipe in another direction as a different command or function. Another direction may be a second direction that is different than the one (or first) direction. For example, a swipe in another direction may be interpretated as a command to reject a movement.

Some disclosed embodiments involve electronically prompting the user to identify disliked movements by sending first signals to a mobile communications device of the user. A mobile communications device is described and exemplified elsewhere. Prompting is described and exemplified elsewhere. Electronically prompting refers to prompting using an electronic device. Sending first signals to a mobile communications device refers to transmitting signals to the mobile communications device, as described and exemplified elsewhere. In some embodiments, the mobile communications device may be paired to the electronic exercise equipment and may communicate with the exercise equipment via a wired or wireless connection as described and exemplified elsewhere herein. A processor of the electronic exercise equipment may send one or more signals to the mobile communications device, causing the mobile communications device to provide one or more prompts to the user to identify disliked movements.

By way of non-limiting example, processor 112 (shown in FIG. 1A) of an electronic exercise machine 200 (shown in FIG. 2A) may send one or more signals to a mobile communications device 224, shown in FIG. 2A. The signals may cause mobile communications device 224 to provide one or more prompts electronically to a user. For example, a display screen of mobile communications device 224 may display a graphical user interface prompting a user to identify disliked movements on the display screen. As another example, a display or speaker may output a visual and/or audible prompt to a user to identify disliked movements. In some embodiments, indications of disliked movements may be provided to the electronic exercise machine 200 via the mobile communications device 224. In some embodiments, mobile communications device 224 may provide electronic prompts for a user to indicate disliked movements directly to the input interface 116 (shown in FIG. 1A) of electronic exercise machine 200, such as by prompting the user to manipulate dial 216 on the electronic exercise machine 200, or interact with a display or other input interface of electronic exercise machine 200 (not shown in FIG. 2A).

Figure 11:
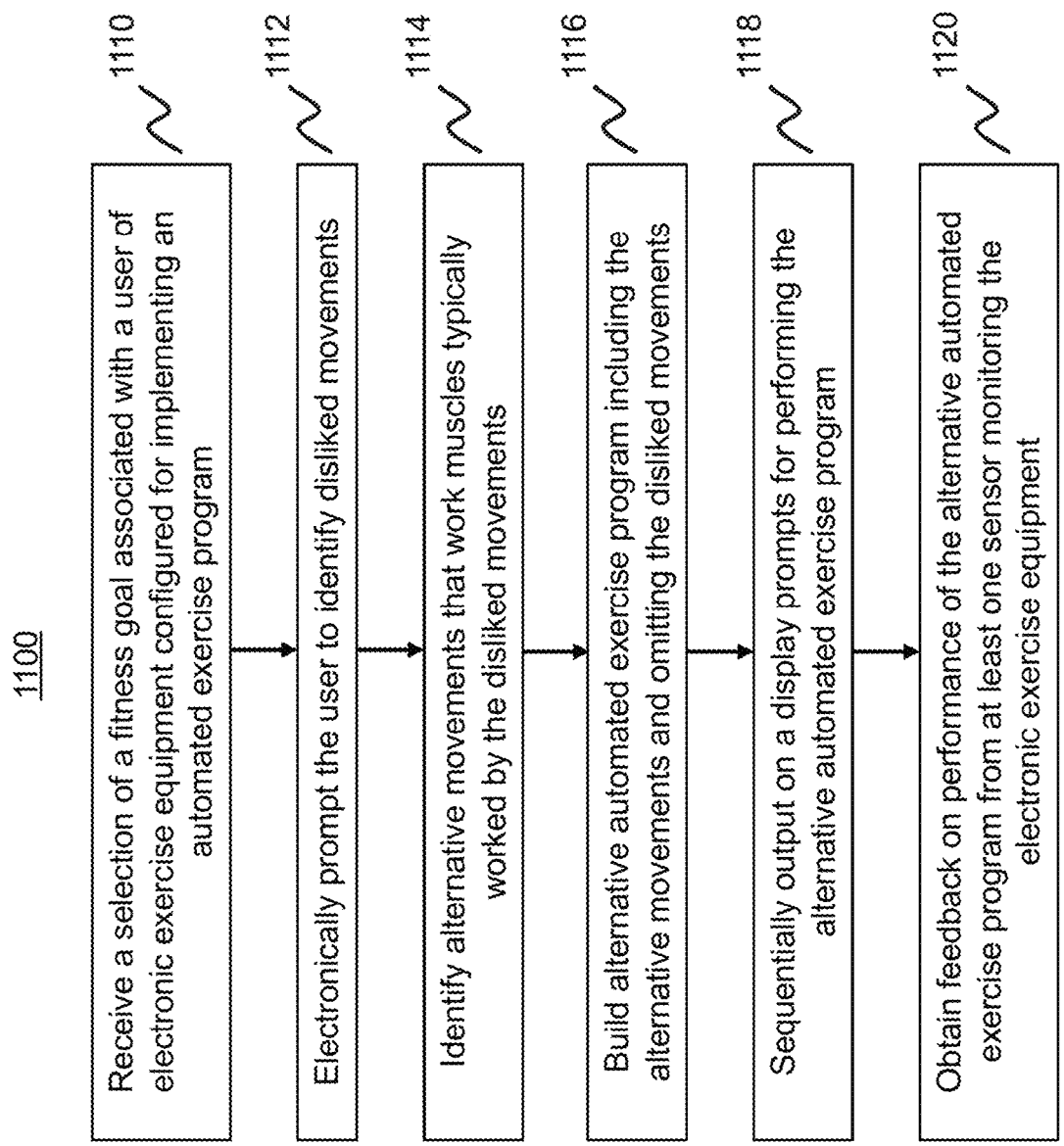
FIG. 11 is a flowchart illustrating an exemplary method for dynamically modifying automated electronic exercise equipment usage instructions, consistent with disclosed embodiments.

By way of non-limiting example, FIG. 11 illustrates a flowchart of an exemplary method for modifying automated electronic exercise equipment usage instructions, consistent with embodiments of the present disclosure. In some embodiments, process 1100 may be performed by at least one processing device (e.g., processor 112 associated with an electronic exercise machine, a processor associated with a mobile communications device 224, and/or a processor associated with cloud service 300) may to perform operations or functions described herein. In some embodiments, some aspects of process 1100 may be implemented as software (e.g., program codes or instructions) that are stored in a memory (e.g., memory 114) or a non-transitory computer readable medium. In some embodiments, some aspects of process 1100 may be implemented as hardware (e.g., a specific-purpose circuit). In some embodiments, process 1100 may be implemented as a combination of software and hardware.

Process 1100 may include a step 1110 of receiving a selection of a fitness a goal associated with a user of electronic exercise equipment. The electronic exercise equipment may be configured to implement an automated exercise program, wherein the fitness goal is typically associated with a series of exercises in the automated exercise program.

Process 1100 may include a step 1112 of electronically prompting a user to identify disliked movements. For example, an output device of an electronic exercise machine 200 or a connected mobile communications device 224 (shown in FIG. 2B) may provide a visual and/or audible prompt for a user to provide an input identifying disliked movements, consistent with the disclosed embodiments.

Process 1100 may include a step 1114 of identifying alternative movements to the disliked movements, wherein the alternative movements are chosen from a group consisting of movements that work muscles typically worked by the disliked movements. In some embodiments, a processor of an electronic exercise machine, a cloud service, and/or a mobile communications device may apply one or more rule sets or query a database of movements to identify alternative movements that are associated with the same or similar muscles as the disliked movements.

Process 1100 may include a step 1116 of building an alternative automated exercise program including the alternative movements. In some embodiments, the alternative automated exercise program may omit the disliked movements that were identified by the user. The alternative automated exercise program may include the alternative movements substituted in place of the omitted exercises, to enable the user to attain the same fitness goal. For example, the alternative automated exercise program may include the alternative movements that are expected to work the same or similar muscles as the omitted exercises, so that the alternative automated exercise program remains directed to the user's original fitness goal.

Process 1100 may include a step 1118 of outputting for presentation on a display prompts for performing the alternative automated exercise program. In some embodiments, a processor may output one or more prompts for performing the alternative exercise program. Such prompts may be output by an output device of electronic exercise equipment. In some embodiments, a display of a mobile communications device may present the prompts. For example a mobile communications device 224 in communication with an electronic exercise machine 200, shown in FIG. 2A, may provide prompts for a user to perform movements. As another example, FIG. 4 illustrates a mobile communications device 428 presenting prompts on a display to perform movements using exercise equipment 402.

Referring again to FIG. 11, process 1100 may include a step 1120 of obtaining feedback on performance of the alternative automated exercise program from at least one sensor monitoring the electronic exercise equipment. In some embodiments, one or more sensor devices may obtain feedback on performance. For example, electronic exercise machine 200 may include one or more sensors as described herein, for measuring a parameter of the machine such as a force applied to part of the machine a user, such as a force or speed of force applied by a user to cable 206. In some embodiments, feedback may be obtained using one or more sensors in the electronic exercise machine 200, or in a mobile communications device 224 in communication with the electronic exercise machine. For example, as illustrated in FIG. 5, a user may indicate that they are tired during a movement, such as by the user saying, "I'm tired!" An image or sound sensor of the electronic exercise equipment or a mobile communications device may detect the spoken feedback, and associate the obtained feedback about the user's performance with the current movement. In some embodiments, feedback may also be obtained from user responses to one or more prompts from the electronic exercise machine 200 and/or mobile communications device 224.

Some disclosed embodiments involve an application (app) that bridges commercial and home gyms. To facilitate continuity between commercial gym and home gym experiences, some disclosed embodiments include a software application that tracks experiences in one environment and translate the experiences into instructions in a second environment where the exercise equipment differs from the equipment in the first environment. In this way, regardless of whether a subject is at home or at a commercial gym, the subject can be guided to achieving a workout goal.

In this manner, a personal workout may be recorded, e.g., via an electronic device (e.g., a mobile device or an electronic exercise machine), and introduced for performance elsewhere. This may allow tracking exercise activity on a platform associated with an electronic exercise machine. Based on the input, a workout of the user may be modified accordingly. For example, if a user previously focused on legs exercises in a gym, a subsequent workout may be modified to focus on another part of the body.

Some embodiments provide a non-transitory computer readable medium containing instructions that when executed by at least one processor cause the at least one processor to perform operations for coordinating multi-space exertion routines. The at least one processor may receive from a mobile communications device during a first time period an indication of a first space in which the mobile communications device is located. The at least one processor may receive from the mobile communications device first data reflective of a first exercise routine during the first time period, wherein the first exercise routine is associated with a fitness goal. For instance, the first data may reflect output of a resistive motor, output from an image sensor, and/or output from a resistive motor and an image sensor.

The at least one processor may receive from the mobile communications device at a second time different from the first time, an indication of a second space in which the mobile communications device is located. The at least one processor may output to the mobile communications device, instructions for performing a second exercise routine to facilitate advancement of the fitness goal. The at least one processor may receive from the mobile communications device second data reflective of the second exercise routine which conforms to the fitness goal, where at least the first or the second exercise routine is preformed using at least one exercise equipment. For instance, the second data may be obtained via manual input on the mobile communications device. In some embodiments, the at least one processor may prompt input of data recording performance of the second exercise routine, and the second data may be, for example, reflective of output from an image sensor.

In some embodiments, the at least one exercise equipment includes an electronic home gym and a non-electronic commercial gym equipment. In some embodiments, the first exercise routine is performed using the electronic home gym and the second exercise routine is performing using the non-electronic commercial gym equipment. The at least one processor may simulate via the commercial gym equipment, the first exercise routine.

In some embodiments, the first exercise routine is performed using the non-electronic commercial gym equipment and the second exercise routine is performed using the electronic home gym. The at least one processor may simulate via the electronic home gym, the first exercise routine.

In some embodiments, the first exercise equipment includes a non-electronic commercial gym equipment, and the second exercise equipment includes electronic home gym equipment. The at least one processor may simulate via the electronic home gym equipment the first exercise routine.

In some embodiments, the at least one processor may receive input indicative of the fitness goal. In some instances, the at least one processor may provide instructions configured to cause muscles recruited during the first exercise routine to be recruited during the second exercise routine.

In some embodiments, at least one of the first exercise equipment and the second exercise equipment includes electronic resistance. The mobile communications device may pair with the at least one of the first exercise equipment and the second exercise equipment and to send signals configured to alter the electronic resistance. In some instances, at least one of the first exercise equipment and the second exercise equipment includes free weights.

In some embodiments, the at least one processor may transmit signals to the mobile communications equipment to simulate via an avatar, at least some of the first exercise routine and at least some of the second exercise routine. In some embodiments, the at least one processor may output signals to the mobile communications device to present challenges. In some embodiments, the at least one processor may log the first data and the second data. In some embodiments, the at least one processor may output a report reflective of the first data and the second data.

To facilitate continuity between exercising experiences in a commercial gym and a home gym, embodiments are disclosed for a software application for bridging a home gym experience and a commercial gym experience. The software application may track a first exercise experience using first exercise equipment available in a first environment and use the exercise experience as a basis for instructions for a second exercise experience using second exercise equipment available in a second environment. The first and second exercises experiences may both conform to meeting a common exercise goal. For example, if a user performed hamstring exercises in a commercial gym using commercial gym equipment, the software application may guide the user to perform hamstring exercises at home using home gym equipment.

The disclosed embodiments that follow may be performed using at least one processor. The at least one processor may be associated with one or more of electronic exercise equipment, a mobile communication device, a wearable extended reality appliance, and/or a remote cloud server. In some embodiments, a plurality of processors may operate together in a distributed fashion by communicating over a communications network. For example, a processor of a mobile communications device may operate together with a cloud service and one or more processors of one or more exercise machines to track, analyze, and/or provide feedback for exercise routines performed by a user.

Some disclosed embodiments involve coordinating multi-space exertion routines. Coordinating refers to organizing, scheduling, and/or managing. An exertion routine refers to an exercise schedule and/or workout regime. An exertion routine may include a structured series of physical activities designed to improve fitness, health, and/or athletic performance. An exertion routine may challenge the body's muscles, cardiovascular system, and/or overall physical capacity in a systematic manner. An exertion routine may include one or more warm up exercises, cardiovascular exercises, strength training, flexibility training, and/or cool down exercises. Some examples of exertion routines may include one or more of a series of weightlifting exercises, a set of laps for swimming in a pool, a series of stretching exercises, a running drill, a set of yoga poses, a series of pullups, pushups, and/or sit-ups, and/or any other form of exercise. Multi-space exertion routines refer to performance of exertion routines in a plurality of different locations. Such locations may include, for example a home, a gym, a workplace, a hotel, a spa, and or any other location for performance of exercise routine. By way of example, an individual may perform similar exercise routines at home and at a work gym. By way of another example, an individual may wish to continue a daily exercise routine while on vacation at a hotel.

Some disclosed embodiments involve receiving from a mobile communications device during a first time period an indication of a first space in which the mobile communications device is located. Receiving refers to obtaining, acquiring, and/or gaining access to. A mobile communications device refers to portable electronic equipment for exchanging information over distance. A mobile communications device may include one or more transceivers for communicating over a wired and or wireless communication network, a graphical user interface, a touch-sensitive display, a microphone, a speaker, and/or one or more cameras. A mobile communication device may include memory for storing instructions and at least one processor for executing the instructions. In some embodiments, a mobile communication device may implement a software application in conjunction with at least one other processor and/or memory associated with a cloud server. During a time period refers to over a course of a duration and/or interval of time. A time period may include several seconds, several minutes, and/or several hours, at a specific time of day, a specific day of the week, a specific month of the year. In some embodiments, a time period may include at least 10 minutes, at least 20 minutes, at least half an hour, at least an hour, at least two hours, and/or any other duration for an exercise routine. An indication refers to a signal, and/or notification conveying information. A space refers to a region, an area, a location, a room, a floor, and/or a building. Some examples of a space may include a room in a house, a park, a commercial gym, a health club, and/or any other space for performance of exercise routines. In some embodiments, a space may include areas within range of a local communication network, such as a Wi-Fi, Bluetooth, Zigbee, Near-field Communication (NFC) network, and/or any other type of local network. For example, establishment of a Bluetooth connection between a mobile communication device and an electronic home gym mounted on a wall of a home may be an indication that a space where the mobile communication device is located is within Bluetooth range of the wall where the electronic home gym is mounted. A first space refers to a particular space. An indication of a first space in which a mobile communications device is located refers to signals associated with a location where the mobile communications device may be positioned (e.g., during a first time period). For instance, the information may include location data, such as GPS data, motion data, network connectivity data, cellular data, image data, and/or any other type of data for identifying a particular space. By way of an example, at least one processor may receive network data (e.g., associated with a home Wi-Fi network) indicating location of a mobile communications device at a home location during a first time period. By way of another example, at least one processor may receive GPS data indicating location of a mobile communication device at a commercial gym during a second time period.

By way of a non-limiting example, reference is made to FIG. 12 which illustrates an exemplary system 1200 for performance of exercise routines in a plurality of different spaces during different time periods, consistent with some embodiments of the present disclosure. System 1200 may include a mobile communications device 1202 located in a first space 1204 during one time period, and located in a second space 1206 during a second time period. System 1200 may additionally include cloud service 300, including a server 302 coupled to a data structure 304. Mobile communications device 1202 may communicate with cloud service 300 via network 306. At least one processor (e.g., included in cloud server 302) may receive from mobile communications device 1202 during the first time period an indication of first space 1204 in which mobile communications device 1202 is located. For instance, at least one processor may receive GPS data from an associated sensor, and an identifier for a local Wi-Fi network available in first space 1204 from mobile communications device 1202.

Figure 13:
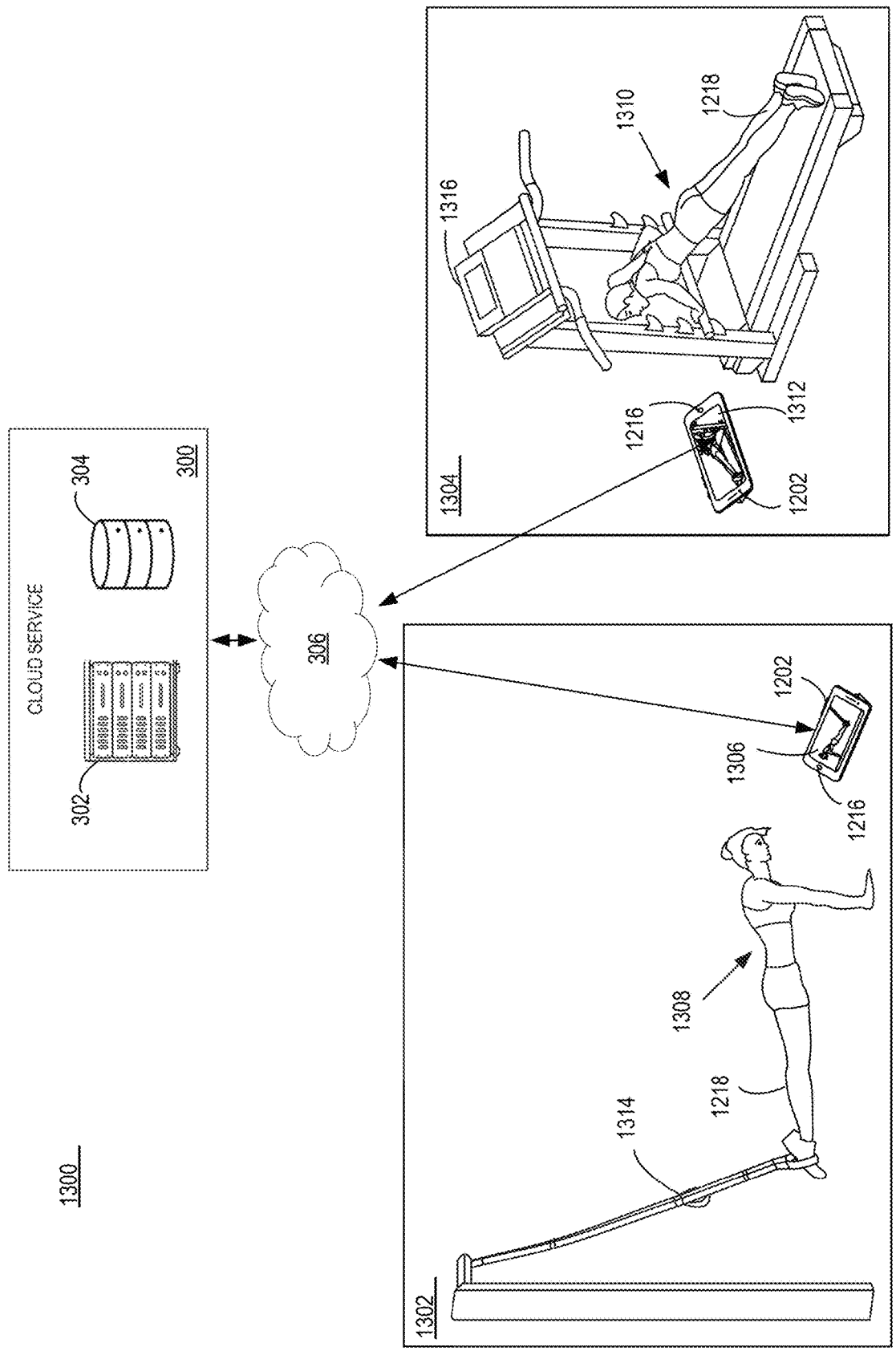
FIG. 13 is another exemplary network diagram for exercise routine monitoring in differing spaces, consistent with some embodiments of the present disclosure.

By way of another non-limiting example, reference is made to FIG. 13 which illustrates another exemplary system 1300 for performance of exercise routines in a plurality of different spaces during different time periods, consistent with some embodiments of the present disclosure. System 1300 may be substantially similar to system 1200 of FIG. 1 with the notable difference that at least one processor may receive from mobile communications device 1202 during the first time period an indication of a first space 1302 in which mobile communications device 1202 is located. For instance, at least one processor may determine the first space 1302 based on GPS data and image data received from mobile communications device 1202 over network 306, where the image data may be acquired by a camera 1216 of mobile communications device 1202.

Some disclosed embodiments involve receiving from the mobile communications device first data reflective of a first exercise routine during the first time period, wherein the first exercise routine is associated with a fitness goal. An exercise routine may be understood similar to an exertion routine, as described earlier. A fitness goal refers to an objective and/or plan for a level of physical conditioning, wellness, and/or vigor. A fitness goal may include improvements in strength, tone, endurance, balance, coordination, flexibility, stamina, agility, a heart rate, a cardiovascular rate, blood pressure, weight loss, bone density, and/or any other measure of fitness. In some embodiments, an exercise routine and/or a fitness goal may be associated with a season and/or stage, such as a training season, a competing stage, or a recovery stage for an exercise. A fitness goal may be determined based on a user input, and/or based on analysis of data. Such data may include, for example, search data, membership in a group, data associated with purchased items (e.g., athletic gear and/or health foods), and/or any other type of data. For example, at least one processor may receive data indicating that a user joined a rowing club and purchased a pair of rowing shoes. Based on this data, the at least one processor may determine that the user wishes to improve her rowing skills as a fitness goal, e.g., by lifting weights and/or practicing on a rowing machine. First data reflective of a first exercise routine during a time period refers to information associated with performance of an exercise regimen over a duration of time. Such data may be digitally encoded and may include, for example, motion data, heart rate data, body temperature data, breathing rate data, oxygen intake, and or any other information indicative of performance of an exercise regimen over a time period. At least one processor may receive from one or more sensors, information associated with an individual performing an exercise routine over a time period (e.g., at least 10 minutes, at least 20 minutes, at least half an hour, at least an hour, or over any other time duration). The at least one processor may use the information to determine the exercise routine. For example, over a period of time, one or more of an accelerometer, a gyroscope, and/or a magnetometer may provide data indicative of a number of steps walked and/or run, a photoplethysmogram (PPG) sensor may measure a heart rate, and image data acquired by an image sensor may be analyzed to determine a weightlifting and or stretching exercise. An exercise routine associated with a fitness goal refers to an exercise routine designed and/or tailored to achieve a physical conditioning and/or wellness objective. By way of example, a stretching routine may be associated with improved flexibility, a weightlifting routine may be associated with improved strength, and a running routine may be associated with improved endurance. Thus, at least one processor (e.g., associated with a cloud server) may receive from a mobile communication device information associated with an exercise regimen performed over a first time period in association with achievement of a level of physical conditioning. At least one processor may associate a fitness goal with an exercise routine based on data received from a user, historical data associating different exercise routines with fitness goals, and/or any other information enabling association of an exercise routine with a fitness goal.

By way of a non-limiting example, in FIG. 12, at least one processor (e.g., included in cloud server 302) may receive from mobile communications device 1202 first data reflective of a first exercise routine 1208 during the first time period. The first data may include, for example, data from a resistance motor 1210 of an electronic exercise machine 1212 during performance of first exercise routine 1208 in first space 1204 during the first time period. For example, first exercise routine 1208 may include a series of weight-bearing exercises performed by user 1218 in first space 1204. First exercise routine 1208 may be associated with a fitness goal.

By way of a non-limiting example, in FIG. 13, at least one processor (e.g., a processor of server 302 associated with cloud service 300) may receive from mobile communications device 1202 first data 1306 reflective of a first exercise routine 1308 during the first time period. First data 1306 may include, for example, a video acquired by a camera 1216 of mobile communications device 1202 including images of user 1218 performing first exercise routine 1308 in first space 1302 during the first time period. For example, first exercise routine 1308 may include a series of pushups performed by user 1218 in first space 1302. First exercise routine 1308 may be associated with a fitness goal.

Figure 15:
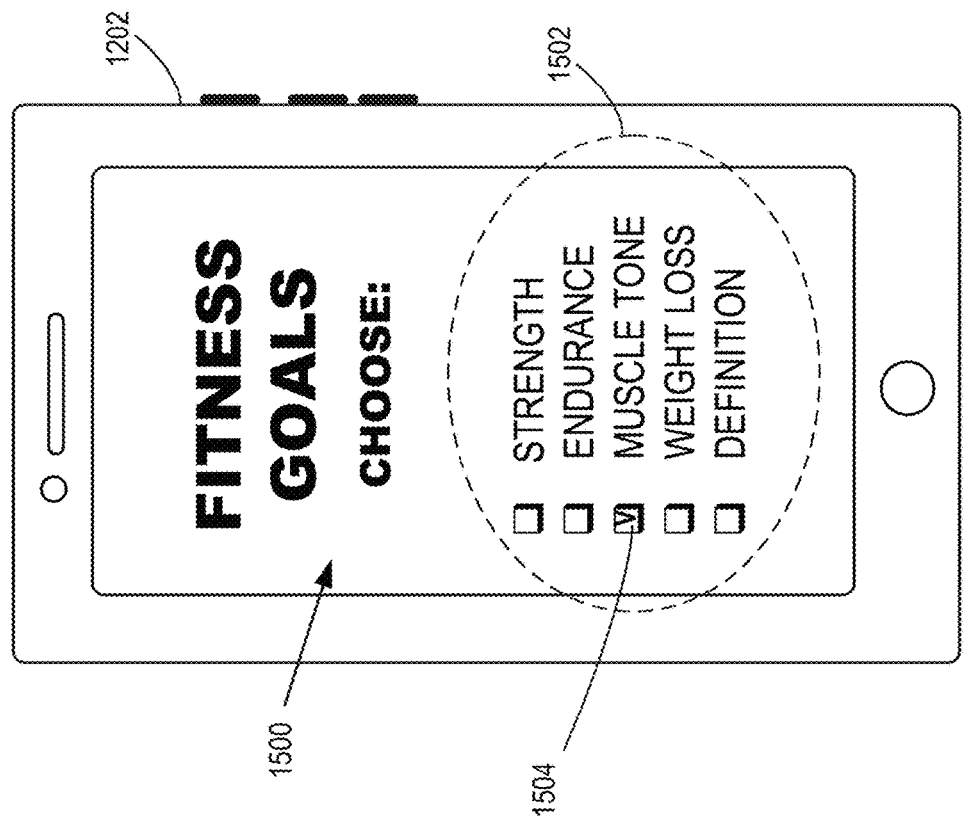
FIG. 15 illustrates an exemplary user interface displayed on mobile communication device for indicating a fitness goal, consistent with some embodiments of the present disclosure.

By way of another non-limiting example, reference is made to FIG. 15 illustrating an exemplary user interface 1500 displayed on mobile communications device 1202 for indicating a fitness goal, consistent with some embodiments of the present disclosure. User interface 1500 may display a plurality of fitness goals 1502 for selection by user 1218 (FIG. 13), such as strength, endurance, tone, weight loss, and/or definition. In the example shown, user 1218 may select fitness goal 1504 (e.g., "Muscle Tone"). Upon receiving a selection of fitness goal 1504 from user, mobile communications device 1202 may transmit an indication of fitness goal 1504 to the at least one processor over network 306. The at least one processor may associate fitness goal 1504 with first exercise routine 1308.

Some disclosed embodiments involve receiving from the mobile communications device at a second time different from the first time, an indication of a second space in which the mobile communications device is located. A second time different from the first time refers to another time duration before or after a first time duration, as described earlier. An indication of a second space in which the mobile communications device is located refers to signals associated with another location where the mobile communications device may be positioned, as described earlier. For example, on Monday, at least one processor may receive network connectivity data from a mobile device indicating the mobile device is at a home location, and on Tuesday, the at least one processor may receive GPS data from the mobile device indicating the mobile device at a work location. In some embodiments, the first and second time periods may be associated with a similar time of day but different days of the week, or the same day of the week but during different weeks of a month. For example, an individual may exercise at home on Mondays, and exercise at a health club on Tuesdays. As another example, an individual may be on holiday on the first Monday of the month and may work out at a hotel gym, and exercise at home on the second Monday of the month after returning home from the holiday.

By way of a non-limiting example, in FIG. 12, at least one processor (e.g., included in cloud server 302) may receive from mobile communications device 1202 at a second time different from the first time period, an indication of second space 1206 in which mobile communications device 1202 may be located. For example, the at least one processor may determine second space 1206 based on an identity of a Wi-Fi connection communicated by mobile communications device 1202.

By way of another non-limiting example, in FIG. 13, at least one processor may receive from mobile communications device 1202 at a second time different from the first time period, an indication of second space 1304 in which mobile communications device 1202 may be located. For example, at least one processor may determine second space 1304 based on GPS data communicated by mobile communications device 1202.

Some disclosed embodiments involve outputting to the mobile communications device, instructions for performing a second exercise routine to facilitate advancement of the fitness goal. Outputting to a mobile communications device refers to transmitting and/or sending to a mobile communications device over a wired and/or wireless communication network. In some embodiments, outputting may include outputting for display on a mobile communication device. Instructions for performing a second exercise routine refers to directions, guidelines, and/or advice for accomplishing and/or completing another exercise routine, different than the first exercise routine. Such instructions may include for example, one or more types of exercise (e.g., pushups and bench presses), a number of repetitions and/or sets, rest times, a heart rate threshold, a form, a pose, a posture, a limb extension, a hand, arm, and/or leg orientation, a type of accessory for using with an exercise machine, one or more settings for an exercise machine, and/or any other information for facilitating performance of an exercise routine. To facilitate advancement of a fitness goal refers to furthering and/or aiding progress towards meeting a fitness objective. For example, the second exercise routine may work similar muscles as the first exercise routine. As another example, the second exercise routine may achieve similar cardiovascular exertion as the first exercise routine. As a further example, the second exercise routine may achieve similar flexibility and/or balancing ability as the first exercise routine. Thus, at least one processor may transmit to a mobile communication device guidelines and/or directives for performing another exercise routine at a different location for achieving similar exercise objectives as the first exercise routine that was performed at the first location. For example, the first exercise routine may include running on a treadmill for half an hour and the second set exercise routine may include running uphill for fifteen minutes to cause a similar cardiovascular exertion during the first exercise routine and the second exercise routine. As another example, the first exercise routine may include lifting free weights in a home gym for a fixed number of repetitions and the second exercise routine may include pulling on a cable coupled to a resistance motor to simulate weightlifting in a commercial gym for a similar number of repetitions. As another example, the first exercise routine may include stretching on a yoga mat at home, and the second exercise routine may include stretching using a Pilates machine at a commercial gym.

Some disclosed embodiments involve outputting to the mobile communications device, instructions for performing a second exercise routine associated with at least one of the fitness goal and the first exercise routine. For example, the second exercise routine may be similar to the first exercise routine, e.g., a similar type of exercise (weightlifting, endurance), and/or may work similar muscles. As another example, the second exercise routing may complement the first exercise routine. For instance if the first exercise routine includes interval training for long distance running (e.g., a fitness goal), the second exercise routine may include hill repeats and/or a tempo run. As a further example, if the first exercise routine includes leg circles using a first Pilates machine, the second exercise routine may include leg springs using a second Pilates machine.

Figure 14:
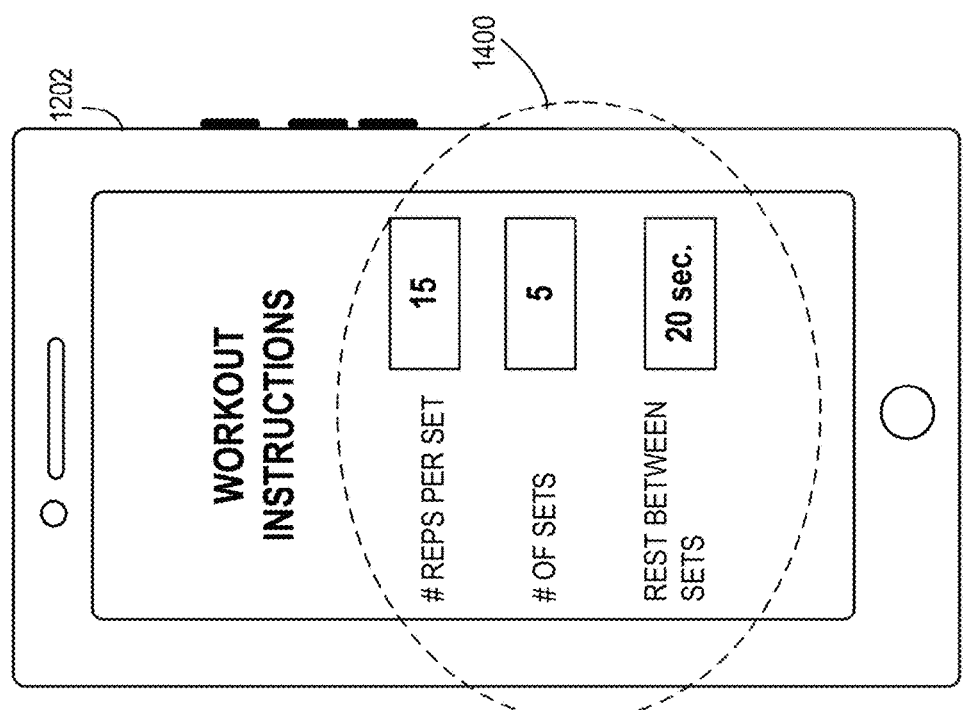
FIG. 14 illustrates an exemplary set of instructions displayed on a user interface of a mobile communications device for performance of an exercise routine to facilitate advancement of a fitness goal, consistent with some embodiments of the present disclosure.

By way of a non-limiting example, reference is made to FIG. 14 illustrating an exemplary set of instructions 1400 displayed on a user interface of a mobile communications device for performance of an exercise routine to facilitate advancement of a fitness goal, consistent with some embodiments of the present disclosure. At least one processor (e.g., included in cloud server 302) may output to mobile communications device 1202, instructions 1400 for performing a second exercise routine, such as second exercise routine 1214 in FIG. 12 or a second exercise routine 1310 in FIG. 13.

For instance, in FIG. 12, at least one processor may analyze data from resistance motor 1210 while user 1218 performs first exercise routine 1208 during the first time period. Based on the analysis, at least one processor may determine a type of exercise (e.g., weight-bearing exercise), a number of repetitions (e.g., 15), a number of sets (e.g., 5), and a rest period between sets (e.g., 20 second). Instructions 1400 (FIG. 14) may assist user 1218 (FIG. 12) to perform second exercise routine 1214 (FIG. 12) at second space 1206 (FIG. 12).

As another example, in FIG. 13, at least one processor may analyze first data 1306 (e.g., a video) recording the performance of first exercise routine 1308 in first space 1302 during the first time period. Based on the analysis, at least one processor may determine a type of exercise (e.g., pushups), a number of repetitions (e.g., 15), a number of sets (e.g., 5), and a rest period between sets (e.g., 20 second). Instructions 1400 (FIG. 14) may assist user 1218 to perform second exercise routine 1310 at second space 1304.

In some embodiments, at least one processor may determine instructions 1400 (FIG. 14) to include substantially the same exercises as in first exercise routine 1208 (FIG. 12). In some embodiments, at least one processor may determine instructions 1400 (FIG. 14) to include more exercises as in first exercise routine 1208 (e.g., to ramp up second exercise routine 1214). In some embodiments, at least one processor may determine instructions 1400 (FIG. 14) to include fewer exercises as in first exercise routine 1208 (e.g., to scale down second exercise routine 1214).

Some disclosed embodiments involve receiving from the mobile communications device second data reflective of the second exercise routine which conforms to the fitness goal. Second data reflective of the second exercise routine maybe understood as described earlier regarding first data reflective of first exercise routine, where the second data and the second exercise routine are different than the first data and the first exercise routine. For example, the second data may include on or more of image data, text, selection of one or more elements displayed on a graphical user interface, voice data, and/or any other type of data which may be analyzed to determine an exercise routine. A second exercise routine which conforms to the fitness goal refers to another set of physical activities for meeting the objective of the first exercise routine. For example, the second exercise routine may work similar muscles, achieve a similar cardiovascular rate, achieve similar flexibility, and/or achieve any other exercise goal as the first exercise routine. Some disclosed embodiments involve receiving from the mobile communications device second data reflective of the second exercise routine, e.g., independent of a fitness goal. For instance, a second exercise routine may follow a first exercise routine without being associated with a particular fitness goal.

By way of a non-limiting example, in FIG. 12, at least one processor (e.g., included in cloud server 302) may receive from mobile communications device 1202 second data 1222 reflective of second exercise routine 1214 performed during the second time period. Second data 1222 may include, for example, a video acquired by camera 1216 of mobile communications device 1202 including images of user 1218 performing second exercise routine 1214 in second space 1206 during the second time period.

By way of another non-limiting example, in FIG. 13, at least one processor may receive from mobile communications device 1202 second data 1312 reflective of second exercise routine 1310 performed during the second time period. Second data 1312 may include, for example, a video acquired by camera 1216 of mobile communications device 1202 including images of user 1218 performing second exercise routine 1310 in second space 1304 during the second time period.

In some disclosed embodiments at least the first or the second exercise routine is preformed using at least one exercise equipment. Exercise equipment refers to one or more devices, machines, tools, and/or accessories for facilitating physical activity, strength training, cardiovascular exercise, flexibility training, and/or overall fitness. Exercise equipment may come in various forms, sizes, and/or functionalities, each tailored to different fitness goals, preferences, and/or levels of experience. Some examples of exercise equipment may include a treadmill, a stationary bike, and elliptical trainer, free weights, weight machines, resistance bands, kettle bells, a yoga mat, a foam roller, a stretching strap, a medicine ball, a BOSU ball, a TRX suspension trainer, and/or a wall mounted or free standing device providing resistance using a motor. Thus, at least one of the first exercise machine and the second exercise machine may involve using some type of exercise equipment. In some embodiments, the first exercise routine uses a first type of exercise equipment and the second exercise routine uses a second type of exercise equipment. In some embodiments, the first exercise routine uses exercise equipment and the second exercise routine is performed without exercise equipment. In some embodiments, the first exercise routine is performed without exercise equipment and the second exercise routine is performed using exercise equipment.

By way of an example, a fitness goal may include strengthening quadriceps for completing a marathon. During a first time period, at least one processor associated with an exercise software application may receive from a mobile communication device, location data associated with a home of a user and image data associated with performance of a series of squats for strengthening quadriceps (e.g., a first exercise routine). The at least one processor may use the data to estimate a weight of the user and the number of repetitions and/or sets performed. During a second time period, the at least one processor may receive from the mobile communication device, location data associated with a commercial gym including a plurality of exercise machines. The at least one processor may select a specific machine for working quadriceps similar to the performance of squats, and transmit instructions to the mobile communication device informing the user which machine to use for working the quadriceps. In some instances, at least one processor may additionally determine one or more of a weight setting, a number of repetitions, a number of sets, and/or any other exercise factor such that performance of the second exercise routine at the commercial gym strengthens quadriceps for completing a marathon. For example, the at least one processor may indicate a weight setting of a resistance motor corresponding to the estimated weight of the user, and a similar number of repetitions for performing on the exercise machine as the number of squats that were performed at home.

By way of another example the first location may include a commercial gym and the first exercise routine may include a spinning on an exercise bike in a spinning class. At least one processor may receive data indicative of a cardiovascular rate achieved during the first exercise routine and transmit instructions for performing a second exercise routine on a home electronic gym to achieve a cardiovascular rate similar to what was achieved during the spinning class.

By way of a non-limiting example, in FIG. 12, first exercise routine 1208 may be performed using exercise equipment 1212 (e.g., an electronic wall-mounted weight machine). In some embodiments, exercise equipment 1212 may include at least one processor in communication with cloud service 300 and/or with mobile communications device 1202 over network 306. Second exercise routine 1214 may be performed using second exercise equipment 1220 (e.g., barbells).

By way of another non-limiting example, in FIG. 13, first exercise routine 1308 may be performed using first exercise equipment 1314 (e.g., a TRX machine). Second exercise routine 1310 may be performed using second exercise equipment 1316 (e.g., an electronic treadmill).

In some disclosed environments, the at least one exercise equipment includes at least one of an electronic home gym and a non-electronic commercial gym equipment. An electronic home gym refers to a device and/or apparatus integrating one or more electronic and/or digital components for providing a workout experience within a home. An electronic home gym may include, for example, a motorized treadmill, a motorized elliptical trainer, a motorized rowing machine, a motorized (e.g., wall mounted or free standing) weight machine, a motorized vibration plate, and/or a balance board with electronic feedback. In some embodiments, an electronic home gym may include one or more of an interactive user interface, software associated with performance of one or more exercise routines, integration with extended reality technology, connectivity to a cloud server, and/or tracking sensors. Tracking sensors may include, for example, a heart rate monitor, an inertial measurement unit (IMU) and/or GPS sensor for measuring a number of steps taken, distance travelled, calories burned, and/or sleep patterns, a blood pressure monitor, an Electrodermal Activity (EDA) Sensors for measuring electrical conductivity of skin, a temperature sensor, an electrocardiogram (ECG and/or EKG) sensor, a pulse oximeter, a respiratory rate monitor, and/or a muscle activity sensor. Non-electronic gym equipment refers to an (e.g., purely) mechanical device and/or apparatus that does not rely on electronics for operation and/or monitoring. Some examples of non-electronic commercial gym equipment may include free weights, a selectorized and/or plate-loaded machine, resistance bands, kettle bells, and/or BOSU ball, a suspension trainer, mechanical cardio equipment (e.g., a mechanical stationary bicycle, treadmill, stepping machine, and/or rowing machine), a flat and/or inclined bench, a power and/or squat rack, a yoga mat, and/or a non-electronic balancing board. Non-electronic commercial gym equipment refers to non-electronic gym equipment (as described earlier) offered by a business oriented enterprise, such as a health club, spa, and/or fitness center.

By way of a non-limiting example, in FIG. 12, first exercise equipment 1212 may include an electronic home gym, and second exercise equipment 1220 may include non-electronic commercial gym equipment. By way of another non-limiting example, in FIG. 13, first exercise equipment 1314 may include non-electronic commercial gym equipment, and second exercise equipment 1316 may include an electronic home gym.

In some disclosed embodiments, the first exercise routine is performed using the electronic home gym and wherein the second exercise routine is performing using the non-electronic commercial gym equipment, and wherein the instructions are configured to simulate via the commercial gym equipment, the first exercise routine. A first exercise routine performed using an electronic home gym refers to the first exercise routine (as described earlier) achieved and/or carried out using an electronic gym (as described earlier) located at a home of a user. A second exercise routine performing using non-electronic commercial gym equipment refers to the second exercise routine (as described earlier) achieved and/or carried out using non-electronic commercial gym equipment (as described earlier). To simulate refers to replicate, mimic, and/or imitate. Instructions configured to simulate via a commercial gym equipment, a first exercise routine refers to directives for replicating and/or emulating the first exercise routine using non-electronic commercial gym equipment instead of an electronic home gym. For example, a first exercise routine may include a first series of weightlifting exercises performed on a home electronic resistance motor machine using a specific resistance setting. A second exercise routine may include a second series of weightlifting exercises performed using a free weight in a fitness center. At least one processor may use the first resistance setting and the first series of weightlifting exercises to determine one or more instructions for selecting a free weight at the fitness center and performance of the second series of weightlifting exercises in a manner to conform to the fitness goal.

By way of a non-limiting example, in FIG. 12, first exercise routine 1208 may be performed using exercise equipment 1212 (e.g., a wall-mounted weight machine of an electronic home gym), and second exercise routine 1214 may be performing using non-electronic commercial gym equipment 1220 (e.g., a barbell). Instructions 1400 (see FIG. 14) may simulate via non-electronic commercial gym equipment 1220, first exercise routine 1208. For example, first exercise routine 1208 may include five sets of weight-bearing pulls using exercise equipment 1212, each including fifteen repetitions, with 20 second of rest between each set. The at least one processor may convert first exercise routine 1208 to five sets of weight lifts using exercise equipment 1220.

In some disclosed embodiments, the first exercise routine is performed using the non-electronic commercial gym equipment and wherein the second exercise routine is performing using the electronic home gym, and wherein the instructions are configured to simulate via the electronic home gym, the first exercise routine. A second exercise routine performed using an electronic home gym refers to the first exercise routine (as described earlier) achieved and/or carried out using an electronic gym (as described earlier). A first exercise routine performing using non-electronic commercial gym equipment refers to the second exercise routine (as described earlier) achieved and/or carried out using non-electronic. Instructions configured to simulate via an electronic home gym, a first exercise routine refers to directives for replicating and/or emulating the first exercise routine using an electronic home gym instead of non-electronic commercial gym equipment. For example, a first exercise routine may include a first series of balancing exercises performed on a BOSU ball in a commercial gym. A second exercise routine may include a second series of balancing exercises performed using an electronic balancing board of an electronic home gym. At least one processor may use the first series of balancing exercises performed on the BOSU ball to determine one or more instructions for performance of the second series of balancing exercises using the electronic balancing board in a manner to conform to the fitness goal.

By way of a non-limiting example, in FIG. 13, first exercise routine 1308 may be performed using non-electronic commercial gym equipment 1412 (e.g., a TRX machine) and second exercise routine 1310 may be performed using second exercise equipment 1316 (e.g., an electronic treadmill of an electronic home gym). Instructions 1400 (see FIG. 14) may simulate via second exercise equipment 1316, first exercise routine 1308. For instance, first exercise routine 1308 may include five sets of push-ups, with fifteen repetitions in each set, and 20 second rest between each set.

In some disclosed embodiments, the first data reflects output of a resistive motor. A resistive motor (e.g., an electronic resistive motor and/or braking motor) refers to a motor for converting electrical energy into mechanical energy through the use of resistance. A resistive motor may incorporate a resistive element (e.g., a resistive wire and/or resistor bank) and a controller for controlling motor speed and/or torque. The resistive element may be connected in series with the motor windings to provide an additional load to a motor circuit. Output of a resistive motor refers to data communicated by a resistive motor, e.g., during operation, or data captured by a sensor associated with the resistive motor. Such data may include, for example, power consumption (e.g., for monitoring energy usage and efficiency), torque output (e.g., tracking a resistance level during a workout to monitor intensity and/or progress over time), motor speed, a resistance level (e.g., to match a fitness goal and/or preferences), temperature (e.g., to prevent overheating), feedback to a software application (e.g., for enabling an interactive and/or adaptive workout experience), diagnostic information for maintenance and/or repairs, and/or any other information associated with a resistive motor. For example, at least one processor may receive output from a resistive motor to determine a type and/or mode of exercise, a resistance level, range of motion, a number of repetitions, a duration, a speed, and/or any other attribute associated with performance of an exercise routine. In some embodiments, output of a resistive motor may include data associated with a cable connected thereto. Such data may include, for example, a speed and/or acceleration of an extension and/or retraction of a cable, a length of a cable extended and/or retracted via an associated spool, a duration between a cable extension and a cable retraction, or the reverse, and/or any other data associated with a cable connected to a resistance motor.

By way of example, in FIG. 12, the first data may reflect output of resistive motor 1210. For example, resistive motor 1210 may generate resistance in response to a force exerted by user 1218 such that data associated with resistance generated by resistive motor 1210 may be indicative of forces exerted by user 1218 on exercise equipment 1212.

In some disclosed embodiments, the first data is reflective of output from an image sensor. An image sensor refers to a detector for converting light reflected off an object to digital data. An image sensor may include a charged coupled device (CCD) camera, a CMOS camera, an IR camera, and/or any other type of camera. In some embodiments, an image sensor may be included in a mobile communication device (e.g., paired to an electronic exercise machine) of a user performing an exercise routine. In some embodiments, an image sensor may be included in an electronic exercise machine used for performance of an exercise routine. In some embodiments, an image sensor may be a standalone camera, e.g., mounted on a wall of a home and/or a commercial gym. In some embodiments, an image sensor may be included in a wearable device of a user performing an exercise routine, e.g., in front of a mirror. At least one processor may receive image data from an image sensor over a wired and/or wireless communication network and perform one or more image processing techniques on the image data to determine one or more attributes associated with performance of an exercise routine. The image processing techniques may include, for example, preprocessing of an acquired image for noise reduction, contrast enhancement, and/or resizing, and/or one or more edge and/or contour detection, pattern recognition, feature detection and/or extraction, blob detection, template matching, and/or any other image processing technique. Attributes associated with performance of an exercise routine that may be determined based on analyzing image data may include, for example, a pose, a posture, an orientation, and/or an extension of a user, a type and/or mode of exercise, and/or a number of repetitions, a speed for completing repetitions, a duration of rest periods between repetitions, and/or any other attribute associated with performance of an exercise routine.

By way of a non-limiting example, in FIG. 13, first data 1306 may be reflective of output from image sensor 1216 (e.g., configured with mobile communications device 1202).

In some disclosed embodiments, the first data is reflective of output from a resistive motor and an image sensor. Data reflective of output from a resistive motor and an image sensor refers to information provided from a combination of a resistance motor and an image sensor, as described earlier. At least one processor may use data received from a combination of an image sensor and a resistance motor to determine one or more attributes associated with performance of an exercise routine, as described earlier. For example, for a particular exercise routine, at least one processor may determine an exercise mode and a number of repetitions performed using data outputted by a resistance motor, and determine a posture and/or orientation of a user performing the particular exercise routine using data outputted from an image sensor.

By way of a non-limiting example, in FIG. 12, the first data may be reflective of output from resistive motor 1210 and image sensor 1216 (e.g., configured with mobile communications device 1202).

In some disclosed environments, the second data is obtained via manual input on the mobile communications device. To obtain refers to receive, to acquire, and/or to gain access, e.g., to data. A manual input refers to entry of data by a human operator. A user may input data manually via an (e.g., graphical) user interface of an electronic device using an input system. Such an input system may include a keyboard, an electronic mouse, a touchscreen, a microphone, an electronic stylus, a camera, and/or any other input system. Second data obtained via manual input on a mobile communications device refers to the second data received via a user interface of a mobile communications device. For instance, a user may enter the second data by typing on an associated touch screen, selecting one or more elements of an associated graphical user interface, speaking into an associated microphone, and/or using an associated camera. As one example, a user may use a user interface of a mobile communication device to enter a type of weightlifting exercise performed, a number of number repetitions and/or sets lifted, a weight setting, and/or an exercise duration. As another example, a user may use a camera of a mobile communication device to record a video of performance of the second exercise routine in the second space, and/or a microphone to dictate a description of the second exercise routine.

Figure 16:
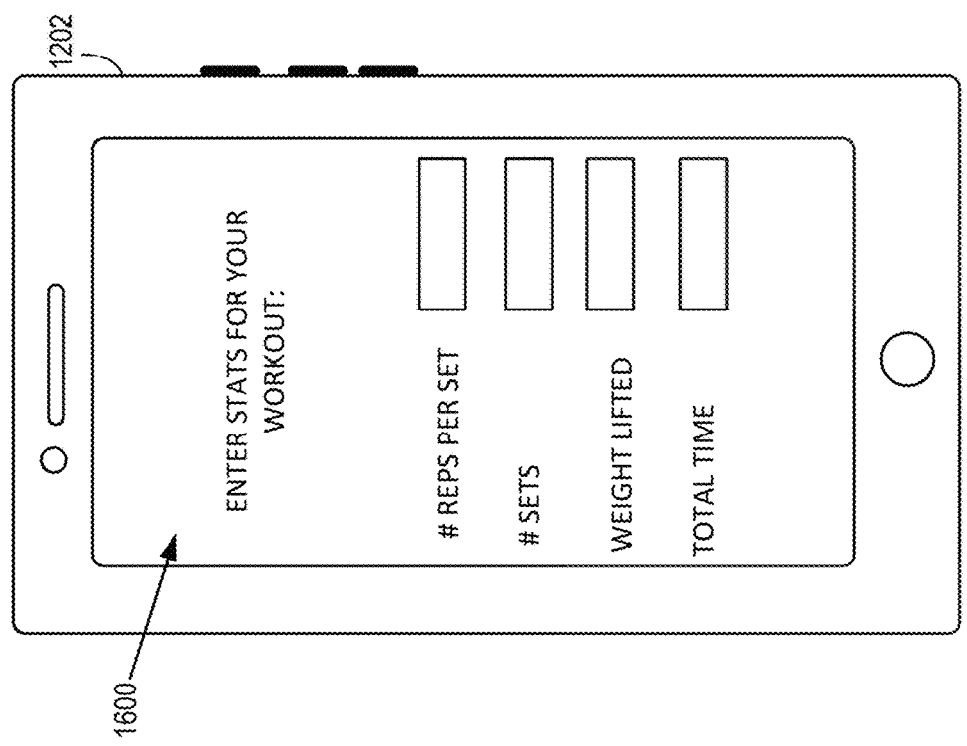
FIG. 16 illustrates an exemplary user interface displayed on mobile communication device for receiving manual input, consistent with some embodiments of the present disclosure.

By way of example, reference is made to FIG. 16 illustrating an exemplary user interface 1600 displayed on mobile communications device 1202 for receiving manual input, consistent with some embodiments of the present disclosure. At least one processor (e.g., included in cloud server 302) may obtain the second data via manual input on mobile communications device 1202. For example, user 1218 may manually enter a number of repetitions per set, a number of sets, an amount of weight lifted, and a total exercise time via graphical user interface 1600.

Some disclosed embodiments involve prompting input of data recording performance of the second exercise routine. Data recording performance of a second exercise routine may include image, audio, text, metadata, and/or any other type of data chronicling, documenting, and/or logging an exercise routine. Prompting input of data refers to actively soliciting and/or requesting information from a user. At least one processor may prompt a user for data using a dialog box (e.g., a text prompt), a notification, an auditory cue (e.g., a voice prompt), a graphical element, and/or any other type of interface for requesting data from a user. By way of an example, at least one processor may display a prompt on a mobile communications device requesting a user to enter data. Such a prompt may include, for example, one or more fields for entering text, and/or one or more buttons for engaging a camera and/or microphone for receiving visual and/or audio data from the user. For instance, the user may select a button to begin recording a performance of a second exercise routine using a camera of a mobile communication device to produce a video file. The video file may include images of the user performing the second exercise routine, as well as associated metadata indicating the second space, a time, a date, a duration, and/or any other metadata associated with the second exercise routine. The user may upload the video file via an interface of a software application installed in the mobile communication device for subsequent analysis (e.g., by a cloud server).

Figure 17:
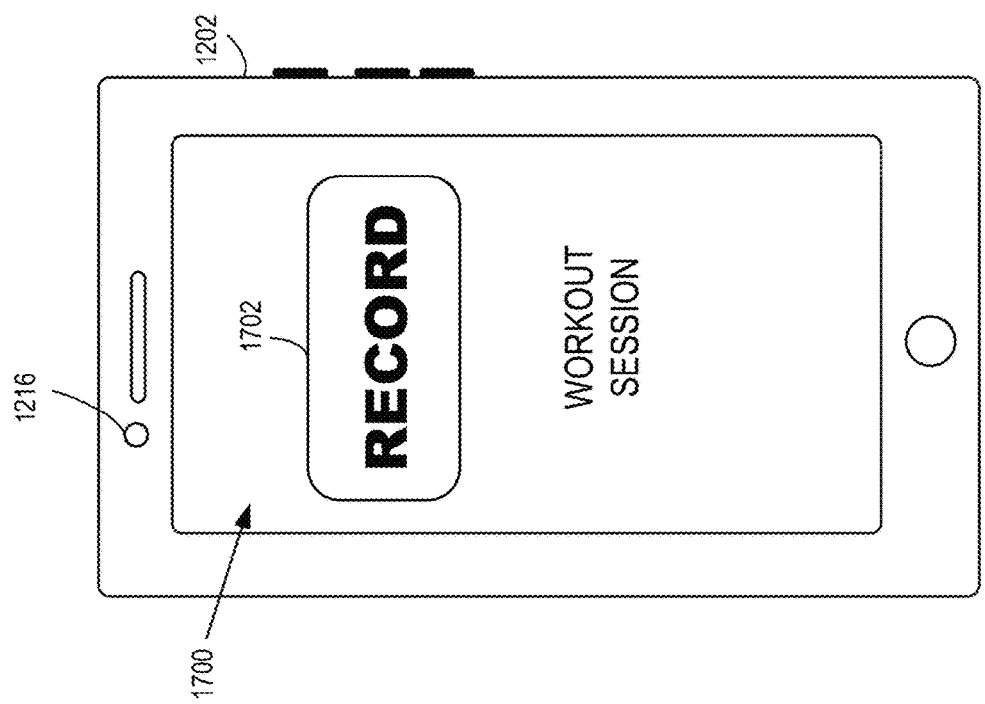
FIG. 17 illustrates an exemplary user interface displayed on mobile communication device for recording a performance of an exercise routine, consistent with some embodiments of the present disclosure.

By way of example, reference is made to FIG. 17, illustrating an exemplary user interface 1700 displayed on mobile communications device 1202 for recording a performance of an exercise routine, consistent with some embodiments of the present disclosure. At least one processor (e.g., included in cloud server 302) may display user interface 1700 prompting input of data for recording performance of the second exercise routine (e.g., second exercise routine 1214 of FIG. 12 or second exercise routine 1310 of FIG. 13). User 1218 may respond to the prompt by selecting a record button 1702, which may invoke camera 1216 to capture images of the second exercise routine.

In some disclosed embodiments, the second data is reflective of output from an image sensor. An image sensor refers to a camera, as described earlier. Output from an image sensor refers to electronic signals produced by an image sensor based on detected light. For example, one or more image sensors may be positioned at a second space for recording at least a portion of a performance of an exercise routine. The one or more image sensors may be associated with a mobile communication device, exercise equipment, and/or a standalone camera, as described earlier.

By way of example, in FIG. 13, second data 1312 reflective of second exercise routine may be reflective of output from image sensor 116 (e.g., e.g., of mobile communication device 1202).

Some disclosed embodiments involve receiving input indicative of the fitness goal. Receiving input indicative of the fitness goal refers to obtaining and/or gaining access to an objective for performance of an exercise routine, as described earlier. In some embodiments, a user may enter a fitness goal via a user interface on a mobile communication device as typed text, spoken words, and/or a selection from a menu. For instance, a software application may offer a menu listing a plurality of fitness goals, as described earlier, permitting a user to select one or more fitness goals from the menu. In some embodiments, receiving input indicative of a fitness goal includes receiving one or more inputs from one or more software applications tracking user behavior over time. Such user behavior may include a search history, membership in one or more groups (e.g., athletic, sporting, weight loss, wellness), a history of purchases (e.g., for weight loss programs, sporting gear, and/or a health club membership), and/or any other user behavior indicative of a fitness goal.

By way of an example, In FIG. 15, at least one processor (e.g., a processor of server 302 associated with cloud service 300) may receive input (e.g., via user interface 1500 displayed on mobile communications device 1202) reflective of fitness goal 1504 (e.g., to improve muscle tone).

In some disclosed embodiments, the instructions are configured to cause muscles recruited during the first exercise routine to be recruited during the second exercise routine. Muscles recruited during an exercise routine refers to a process by which a nervous system activates and/or controls particular muscles to cause a specific movement. For example, lifting weights with the arms may recruit one or more of the Biceps Brachii, Brachialis, Brachioradialis, Triceps Brachii, Deltoid, Forearm, and/or Rotator Cuff Muscles. Lifting weights with the legs may recruit one or more of the Quadricep, Hamstring, Gluteus Maximus, Adductors, Abductors, Calves, and/or Hip Flexor muscles. Similarly, performing abdominal exercises may recruit one or more of the Rectus Abdominis, External Obliques, Internal Obliques, Transversus Abdominis, Erector Spinae, and/or Hip Flexor muscles. Muscles recruited during the first exercise routine to be recruited during the second exercise routine refers to enlisting similar muscles for performance of the second exercise routine that were enlisted for performance of the first exercise routine. For instance, recruiting the same and/or similar muscles may enable continuity of an exercise regime at different times, different locations, and/or using different exercise equipment. By way of an example, if a user enlists the Bicep, Deltoid, and Forearm muscles while performing a set of bicep curls with a barbell during a first exercise routine, at least one processor may determine instructions for performing a set of resistance band curls that also enlist the Bicep, Deltoid, and Forearm muscles for the second exercise routine. By way of another example, if a user enlists the Pectoralis Major and Anterior Deltoid muscles while performing a set of bench presses using a bench during a first exercise routine, at least one processor may determine instructions for performing a set of cable chest presses using a cable machine that also enlist the Pectoralis Major and Anterior Deltoid muscles for the second exercise routine.

By way of a non-limiting example, in FIG. 12, instructions 1400 (see FIG. 14) may cause muscles recruited during first exercise routine 1208 to be recruited during second exercise routine 1214. For example, first and second exercise routines 1208 and 1214 may recruit biceps, triceps, and forearm muscles.

In some disclosed embodiments, at least one of the first exercise equipment and the second exercise equipment includes electronic resistance, and wherein the mobile communications device is configured to pair with the at least one of the first exercise equipment and the second exercise equipment and to send signals configured to alter the electronic resistance. Electronic resistance refers to an impedance and/or load generated by a circuit. Exercise equipment including electronic resistance refers to exercise equipment simulating a non-electronic load and/or weight (e.g., caused by a mass, an elastic band, and/or any other non-electronic load and/or weight) using electronic circuitry. In some embodiments, the electronic circuitry may include a resistance motor. For example, an electronic weight machine may simulate weight using resistance, allowing to control (e.g., increase and/or decrease) a simulated weight electronically rather than adding and/or removing weight plates of a non-electronic weight machine. Consequently, electronic weight machines may be less bulky and safer than non-electronic weight machines. As another example, an electronic resistance machine may simulate a non-electronic resistance band, allowing the increase and/or decrease resistance electronically rather than replacing a resistance band for each different level of resistance. A mobile communications device paired with exercise equipment refers to a mobile communications device linked and/or communicatively coupled with at least one processor associated with exercise equipment. A mobile communications device may be paired to a processor of exercise equipment by establishing a wired and/or wireless communication channel therebetween to enable an exchange of information. For example, a mobile communications device may be paired to a processor of exercise equipment using a USB and/or Ethernet cable, and/or using a wireless (e.g., Bluetooth, Wi-Fi, NFC, and/or Zigbee) channel. Once paired, at least one processor of the mobile communications device may be used to control one or more settings of the first exercise equipment and/or the second exercise equipment. Send signals to alter electronic resistance refers to transmitting one or more commands to a controller of a resistance motor to increase and/or decrease an associated resistance level, to thereby simulate an increase and/or decrease in weight. For example, pairing a mobile communications device to a processor of exercise equipment including a resistance motor may permit a user to control the resistance of the motor via an associated user interface of a software application. At least one processor of the mobile communications device may receive one or more resistance settings inputted by the user and transmit signals associated with the settings via a communication channel to a controller of a resistance motor paired therewith. The controller may use the signals for increasing and/or decreasing resistance on the resistance motor in a manner consistent with the settings provided by the user.

By way of a non-limiting example, as illustrated in FIG. 12, first exercise equipment 1212 may include electronic resistance (e.g., motor 1210). Mobile communications device 1202 may pair with first exercise equipment 1212 to send signals for altering the electronic resistance. For instance, user 1218 may set electronic resistance for motor 1210 using a graphical user interface displayed on mobile communications device 1202.

Some disclosed embodiments involve transmitting signals to the mobile communications device to simulate via an avatar, at least some of the first exercise routine and at least some of the second exercise routine. An avatar refers to a digital representation and/or embodiment of a person and/or entity in a virtual environment and/or digital platform. An avatar may include a two-dimensional image (e.g., displayed on a conventional screen), a three-dimensional model (e.g., displayed using an extended reality appliance), and/or a text-based representation. Transmitting signals to a mobile communications equipment to simulate via an avatar, at least some of an exercise routine refers to communicating information to a mobile communications device for displaying an avatar mimicking and/or imitating the exercise routine. Such information may include, for example, graphics, metadata, animation data, visual appearance data, data associated with the first and/or second exercise routines, and/or any other data for simulating an avatar. By way of an example, at least one processor may transmit a graphics file to a mobile communications device causing a display of an avatar performing a series of bench presses. The avatar may guide an associated user visually and/or audibly by demonstrating a pose, posture, pace, number of repetitions and/or sets, and/or provide any other guidance for performance of an exercise routine. In some embodiments, an avatar may additionally encourage a user during performance of an exercise routine.

By way of example, reference is made to FIG. 18 illustrating an exemplary user interface 1800 displayed on mobile communications device 1202 for simulating an avatar performing an exercise routine, consistent with some embodiments of the present disclosure. At least one processor (e.g., included in cloud server 302) may transmit signals to mobile communications device 1202 to simulate via an avatar 1802, at least some of first exercise routine 1308 (see FIG. 13) and at least some of second exercise routine 1310.

In some disclosed embodiments at least one of the first exercise equipment and the second exercise equipment includes free weights. Free weights refer to hand held weights that may be disconnected from an exercise machine. Some examples of free weights may include dumbbells, barbells, kettle balls, and/or weight plates. For example, at least one processor may map a resistance setting of an electronic weight machine used in a first exercise routine performed in a first space to one or more free weights for performing a second exercise routine in a second space, or the reverse.

By way of example, in FIG. 12, second exercise equipment 1220 may include free weights (e.g., a barbell).

Some disclosed embodiments involve outputting signals to the mobile communications device to present challenges. Challenges refer to competitions and/or tournaments inviting a plurality of users to compete against each other. A challenge may involve two or more persons. In some embodiments, a challenge may involve a single person competing against an avatar or performance predetermined performance thresholds or performance thresholds customized to the user. In some embodiments, challenges may encourage community participation and/or support. Challenges may compare levels of fitness, strength, endurance, flexibility, and/or other measures of athleticism. For instance, one or more participants may set a specific goal, and invite other participants to compete against each other to meet the specific goal. By way of some examples, challenges may request participants to complete a certain number of weightlifting repetitions within a time frame, run a certain distance, and/or complete a number of steps on a stepping machine, Challenges may be organized by individuals, fitness influencers, gyms, and/or organizations, and they often encourage community participation and support. In some embodiments, results of a challenge may be displayed on a physical and/or virtual leader board.

Figure 19:
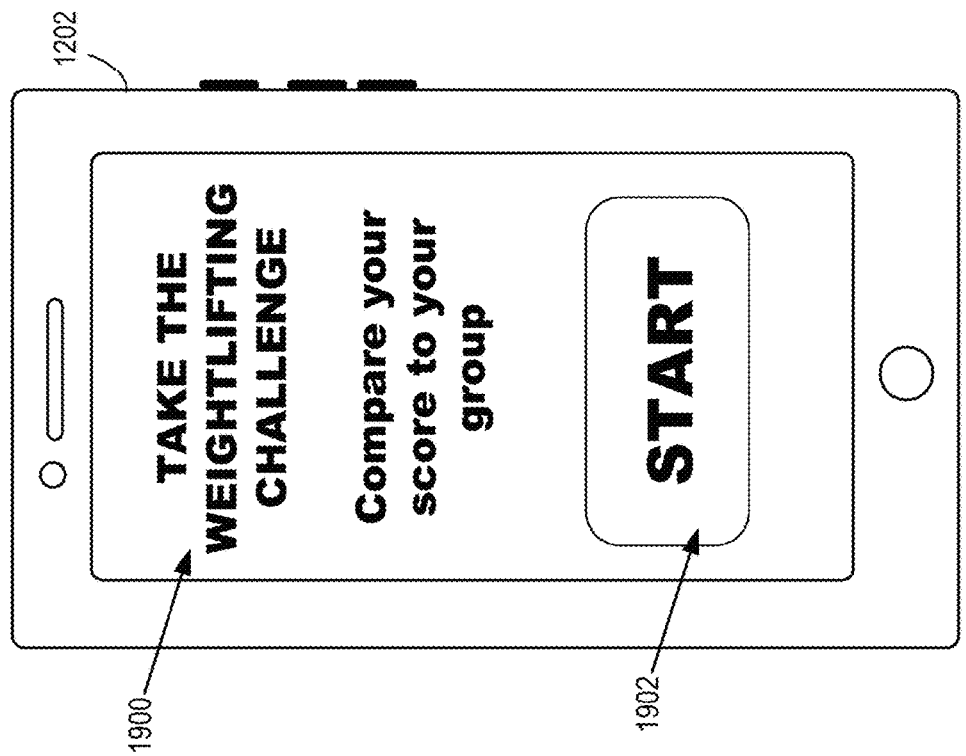
FIG. 19 illustrates an exemplary user interface displayed on mobile communication device for presenting exercise challenges, consistent with some embodiments of the present disclosure.

By way of a non-limiting example, reference is made to FIG. 19 illustrating an exemplary user interface 1900 displayed on mobile communications device 1202 for presenting exercise challenges, consistent with some embodiments of the present disclosure. At least one processor (e.g., included in cloud server 302) may output signals over network 306 to mobile communications device 1202 to present one or more challenges via a button 1902. For example, the challenges may permit user 1218 to compare statistics of first exerciser routine 1208 and/or second exercise routine 1214 to similar exercise routines performed by other users.

Some disclosed embodiments involve logging the first data and the second data. Logging refers to recording, compiling, and/or collecting information for storage in memory. Logging may include recording a time-based record of interactions and/or communication for analysis, trouble shooting, and/or identification of trends In some embodiments, a learning engine may be applied to logging data collected over multiple time periods to extract trends and/or predictions for determining instructions for subsequent (e.g., third and fourth) exercise routines. For example, at least one processor may use a log of the first data and the second data to improve and/or tailor a subsequent exercise for meeting a fitness goal. A log may include a record of performed exercise sessions, including details such as a date, a time, a duration, a type of exercise, a location where an exercise session was performed, associated environmental factors, an intensity level, a heart rate (e.g., average and/or maximum), a body temperature (e.g., average and/or maximum, and/or any other details associated with performance of an exercise routine.

By way of a non-limiting example, in FIG. 13, at least one processor (e.g., included in cloud server 302) may log first data 1306 and second data 1312 in data structure 304.

Some disclosed embodiments involve outputting a report reflective of the first data and the second data. Outputting may refer to transmitting, presenting, causing to be presented, and/or sending, as described earlier. A report reflective of the first data and the second data refers to a summary, an account, and/or an overview. A report may include one or more conclusions and/or statistics based on (e.g., a log of) the first data and the second data. For example, a report may include personal information, a summary of an activity log (e.g., based on logging first data and second data, as described earlier), workout metrics, progress tracking, biometric data, one or more exercise goals (as described earlier), analysis and/or recommendations, visualizations, and/or information associated with compliance with one or more recommended exercise routines. Personal information may include, for example, a name, an age, a gender, a weight, a height, a medical history, user preferences, and/or any other personal information. Workout metrics may include, for example, a distance and/or elevation covered, a speed and/or pace, a number of repetitions and/or sets, a weight and/or resistance level, heartrate data, and/or calories burned. Progress tracking may include, for example, a comparison of current data with data from previous workouts to track progress over time, e.g., to determine an improvement in performance, a change in body composition, and/or progress towards reaching a fitness goal. Biometric data may include, for example, body weight, body fat percentage, muscle mass, and/or any other biometric data. Analysis and/or recommendations may include, for example, interpretations of the first data and the second data by at least one processor for providing insights for improvement and/or adjustments to exercise routines for achieving specific goal. Visualizations may include one or more graphs, charts, tables, and/or any other visual representations of data.

Figure 20:
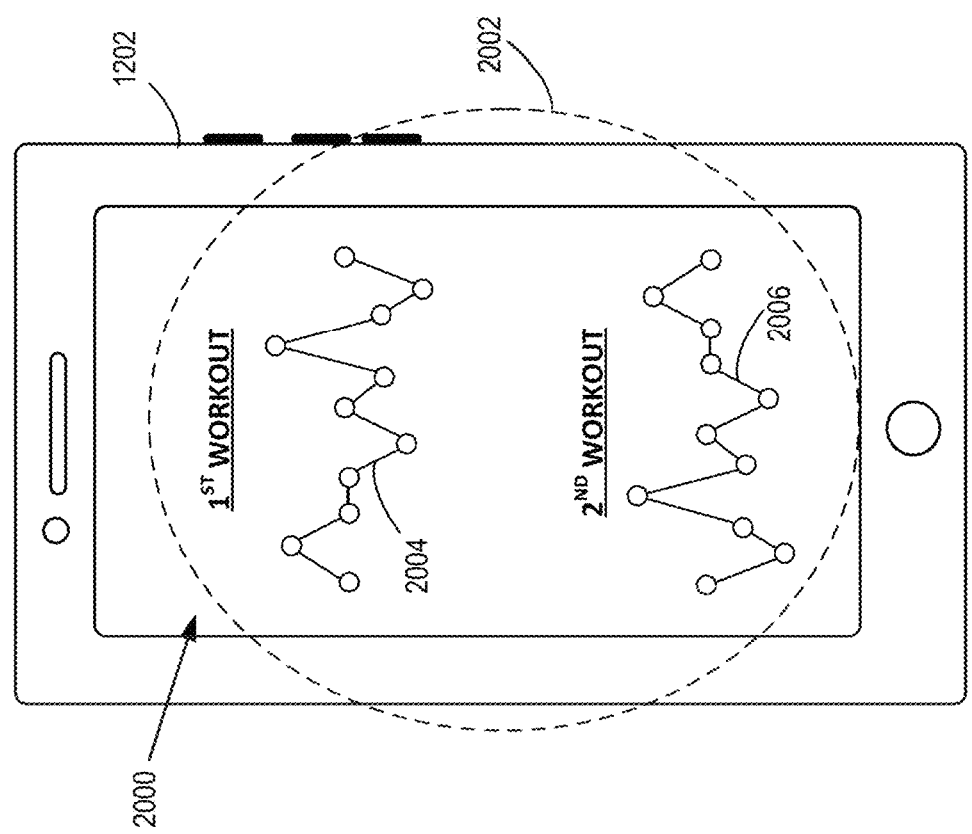
FIG. 20 illustrates an exemplary user interface displayed on mobile communication device for presenting a report, consistent with some embodiments of the present disclosure.

By way of a non-limiting example, reference is made to FIG. 20 which illustrates an exemplary user interface 2000 displayed on mobile communications device 1202 for presenting a report 2002, consistent with some embodiments of the present disclosure. For example, report 2002 may include a first chart 2004 corresponding to first exercise routine 1208 (FIG. 12) and a second chart 2006 corresponding to second exercise routine 1214 (FIG. 12), permitting user 1218 (FIG. 12) to track and compare performances of similar exercises performed in first space 1204 (FIG. 12) and in second space 1206 (FIG. 12).

Figure 21:
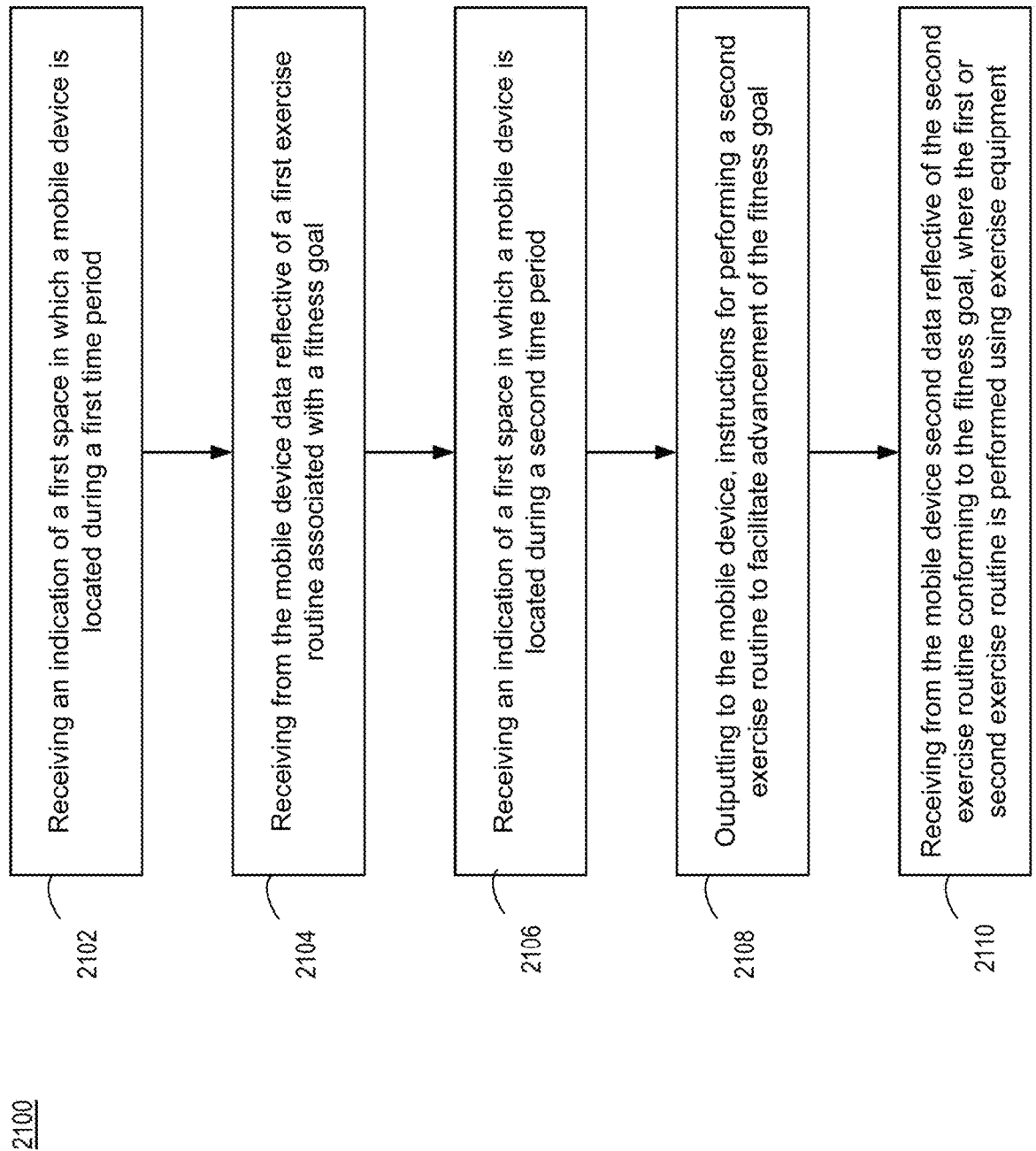
FIG. 21 is a flowchart of an example process for performance of exercise routines in a plurality of different spaces during different time periods, consistent with embodiments of the present disclosure.

FIG. 21 illustrates a flowchart of an exemplary process 2100 for performance of exercise routines in a plurality of different spaces during different time periods, consistent with embodiments of the present disclosure. In some embodiments, process 2100 may be performed by at least one processing device (e.g., included in cloud server 302) may to perform operations or functions described herein. In some embodiments, some aspects of process 2100 may be implemented as software (e.g., program codes or instructions) that are stored in a memory (e.g., memory 114) or a non-transitory computer readable medium. In some embodiments, some aspects of process 2100 may be implemented as hardware (e.g., a specific-purpose circuit). In some embodiments, process 2100 may be implemented as a combination of software and hardware.

Process 2100 may include a step 2102 of receiving from a mobile communications device during a first time period an indication of a first space in which the mobile communications device is located. By way of a non-limiting example, in FIG. 12, at least one processor (e.g., included in cloud server 302) may receive from mobile communications device 1202 during a first time period an indication of first space 1204 in which mobile communications device 1202 may be located Process 2100 may include a step 2104 of receiving from the mobile communications device first data reflective of a first exercise routine during the first time period, wherein the first exercise routine is associated with a fitness goal. By way of a non-limiting example, in FIG. 12, at least one processor (e.g., included in cloud server 302) may receive from mobile communications device 1202 first data reflective of first exercise routine 1208 during the first time period. For example, the first data may be associated with resistance motor 1210. The first exercise routine may be associated with fitness goal 1504 (see FIG. 4).

Process 2100 may include a step 2106 of receiving from the mobile communications device at a second time different from the first time, an indication of a second space in which the mobile communications device is located. By way of a non-limiting example, in FIG. 12, at least one processor (e.g., included in cloud server 302) may receive from mobile communications device 1202 at a second time different from the first time, an indication of second space 1206 in which the mobile communications device 1202 may be located.

Process 2100 may include a step 2108 of outputting to the mobile communications device, instructions for performing a second exercise routine to facilitate advancement of the fitness goal. By way of a non-limiting example, in FIG. 12, at least one processor (e.g., included in cloud server 302) may output to mobile communications device 1202, instructions 1400 (see FIG. 14) for performing second exercise routine 1214 to facilitate advancement of fitness goal 1504 (FIG. 15).

Process 2100 may include a step 2110 of receiving from the mobile communications device second data reflective of the second exercise routine which conforms to the fitness goal, wherein at least the first or the second exercise routine is performed using at least one exercise equipment. By way of a non-limiting example, in FIG. 12, at least one processor (e.g., included in cloud server 302) may receive from mobile communications device 1202 second data 1222 reflective of second exercise routine 1214 which conforms to fitness goal 1504. At least one of first exercise routine 1208 or second exercise routine 1214 may be performed using at least one exercise equipment. For example, first exercise routine 1208 may be performed using first exercise equipment 1212 and second exercise routine 1214 may be performed using second exercise equipment 1220.

Some disclosed embodiments involve simultaneous client channels with a common trainer. Some embodiments may provide capability for a single trainer to open a number of simultaneous training session with different clients, enabling the single trainer to provide individualized training to each client. Each channel permits two data streams-one for exertion data originating from the exercise equipment and another for dialogue data (e.g., chat, video, voice).

Some embodiments provide a non-transitory computer readable medium containing instruction that when executed by at least one processor cause the at least one processor to perform overlapping individualized data transfer operations.

The at least one processor may establish a first communications channel between a trainer application and a first piece of electronic exercise equipment associated with a first client. The first communications channel may be configured to convey a first dialogue data stream and to convey a first exertion data stream from at least one first sensor associated with the first piece of electronic exercise equipment.

The at least one processor may establish a second communications channel between the trainer application and a second piece of electronic exercise equipment associated with a second client. The second communications channel may be configured to convey a second dialogue data stream and to convey a second exertion data stream from at least a second sensor associated with the second piece of electronic exercise equipment.

The at least one processor may enable a first selection, via the trainer application, of the first communications channel. In response to the first selection, the at least one processor may open the first dialogue data stream and the first exertion data stream between the first client and the trainer thereby enabling the first trainer to view first exertion data while simultaneously conducting a dialogue with the first client. While the first dialogue data stream is open, the at least one processor may block at least a return path of second dialogue data stream from the trainer application to the second client, preventing dialogue from the trainer application to the second client.

The at least one processor may enable a second selection, via the trainer application, of the second communications channel. In response to the second selection, the at least one processor may open the second dialogue data stream and the second exertion data stream between the first client and the trainer thereby enabling the first trainer to view first exertion data while simultaneously conducting a dialogue with the first client. While the second dialogue data stream is open, the at least one processor may block at least a return path of the first dialogue data stream from the trainer application to the first client, preventing communication from the trainer application to the first client.

In some embodiments, the first dialogue data stream and the second dialogue data stream include video data. In some embodiments, when the first channel is open, the at least one processor may convey audio from the second client to the trainer application, while blocking audio transmission from the trainer application to the second client. In some embodiments, when the first channel is open, the at least one processor may convey video from the first client to the trainer application, while blocking video transmission from the trainer application to the second client.

In some embodiments, the at least one processor may, when the first channel is open, log the second exertion data stream from the second channel for later presentation on the trainer application when the second channel is open. The at least one processor may, when the second channel is open, logging the first exertion data stream from the first channel for later presentation on the trainer application when the first channel is open.

In some embodiments, the electronic exercise equipment includes at least one resistive motor for exerting tension on a movable part such as an arm or a cable, and the first exertion data stream and the second exertion data stream reflect applied resistive forces. In some embodiments, the trainer application provides a plurality of windows differentiating dialogue data from exertion data.

Online training applications may permit a single trainer interact with a plurality of clients and/or subscribers. However, a trainer and/or client may wish to engage in a dialogue without revealing the dialogue to the other clients. Disclosed embodiments may permit a single trainer to open a plurality of communication channels for conducting multiple, simultaneous training session with different clients. Each communication channel may carry a data stream for conveying exertion data, permitting a trainer to monitor exertion of each client during an exercise session. Each communication channel may additionally carry a dialogue stream for enabling a dialogue between the trainer and a specific client. To avoid a situation where a trainer conducts a dialogue with multiple clients simultaneously (e.g., leading to interference and/or lack of confidentiality), disclosed embodiments permit a trainer to select a specific client for engaging in a dialogue. Selection of a specific channel may cause at least a return path of other dialogue streams to be blocked, e.g., to prevent a second client from hearing speech aimed at a first client.

The disclosed embodiments may be performed using a plurality of processors associated with one or more pieces of electronic exercise equipment, mobile communication devices, and/or a remote cloud server. In some embodiments, a plurality of processors may operate together in a distributed fashion by communicating over a communications network. For example, processors associated with a plurality of mobile communications devices may operate together with a cloud service and one or more processors of one or more pieces of electronic exercise machines to implement a trainer application between a trainer and a plurality of clients (e.g., trainees).

Some disclosed embodiments involve performance of overlapping individualized data transfer operations. Data transfer operations refers to actions and/or process for exchanging information. Data transfer operations may include formatting data for communication via a communications network (e.g., the Internet), using a communications network to establish a link between two or more electronic devices, and/or transmitting and/or receiving information over a link established between two or more electronic devices. In some embodiments, data transfer operations may include copying data from one location to another location. For example, data transfer may include exchanging information between a remote server and a local computing device, exchanging information between two local computing devices, exchanging information between two or more memory locations and/or registers, and/or any other data transfer. Overlapping refers to concurrent, simultaneous, and/or parallel. Individualized refers to personal, singular, and/or associated with a specific (e.g., private) entity. In some embodiments, individualized may include adapting to needs and/or special circumstances associated with an individual. Overlapping individualized data transfer operations refers to concurrent and/or parallel data transfer processes, each process being associated with a different individual. In some embodiments, individualized overlapping data transfer may include multiple concurrent exchanges of information between at least three entities in a manner to reduce latency. For example, a first processor may receive data from a second processor while concurrently transmitting data to a third processor. In some embodiments, overlapping data transfer may include initiating a new data transfer operation before the previous data transfer has completed for reduced idle time.

Some disclosed embodiments involve establishing a first communications channel between a trainer application and a first piece of electronic exercise equipment associated with a first client. Establishing refers to creating, constructing, and/or setting up. A communications channel refers to a link, route, and/or pathway for conveying information. A communications channel may include any combination of wired and/or wireless links. A wired link may include, for example, an Ethernet cable, a coaxial cable, a fiber optics cable, a twisted pair cable, a universal serial bus (USB) cable, a High-Definition Multimedia Interface (HDMI) cable, a serial cable, and/or a powerline communication cable. A wireless link may include, for example, a Wi-Fi channel, a Bluetooth channel, a Zigbee channel, a channel of a cellular network, a Near Field Communication (NFC) channel, a radio frequency identification (RFID) channel, a channel linked to a satellite, a wireless sensor network (WSN) channel, and/or an infrared channel. Establishing a communications channel refers to creating a link for conveying information between two or more entities. Establishing a communications channel may involve implementing one or more protocols, such as handshake protocols, a transmission control protocol (TCP), a user datagram protocol (UDP), a hypertext transfer protocol (HTTP), a secure sockets layer and/or transport layer security (SSL/TLS) protocol, a dynamic host configuration protocol (DHCP), a domain name system (DNS) protocol, a Bluetooth protocol stack, a Wi-Fi protocol, and/or any other communication protocol. In some embodiments, a communications channel may include a dedicated link of a communications network between two or more entities for a period of time. A piece of electronic exercise equipment refers to a unit for facilitating physical activity to advance a fitness goal using one or more electronic circuits, as described and exemplified elsewhere. Some examples of pieces of electronic exercise equipment may include an electronic treadmill, an electronic (e.g., wall-mounted) weight machine, an electronic rowing machine, an electronic (e.g., stationary) bicycle, an electronic step machine, an electronic elliptical machine, and/or any other type of electronic exercise equipment. A client refers to a user and/or individual. In some embodiments, a client may include first portion of a software application for installing on an electronic device associated with a private user, where a second portion of the software application may be installed on a server. In some embodiments, a client may include a device associated with a client, such as a personal tablet, a mobile communication device, a personal computer, a wearable appliance, a piece of electronic exercise equipment, and/or any other personalized electronic device. In some embodiments, A client refers to a computer program or device that requests services or resources from another program or server.

A trainer refers to an individual capable of teaching and/or coaching one or more other individuals. For example, a fitness trainer may assist one or more individuals reach a fitness goal, as described elsewhere herein. An application refers to a program and/or piece of software designed and/or written to fulfill a particular purpose. A trainer application refers to a software application for providing guidance, instructions, tips, schedules, and/or plans for fitness-related activities. For example, a trainer application may include a first code portion installed on a first communication device and/or a first piece of electronic exercise equipment associated with a trainer, multiple instances of a second code portion installed on multiple second communication devices and/or a second pieces of electronic exercise equipment associated with a plurality of clients, and a third code portion installed on a cloud server in communication with the first communication device and/or first piece of electronic exercise equipment, and the multiple second communication devices and/or second pieces of electronic exercise equipment. The first code portion may include functionalities that may not be available on the multiple instances of the second code portion, such as monitoring exercise routines of a plurality of clients, broadcasting data (e.g., audio, visual, and/or text, and/or any other type of data) to a plurality of clients, selection of specific communication channels, and/or blocking and/or partial blocking of selected communications channels. A trainer application may enable a trainer to exchange data with the client while accessing resources with the cloud server. For example, such resources may include a profile, history, and/or preferences associated with one or more clients, information associated with one or more exercise routines (e.g., recommendations, risks, injuries), alternative exercises, warm-up and/or warm-down routines, a list of subscribers, a list of advertisers, a list of promotions, a list of music tracks, and/or any resource associated with a trainer application. Some examples of trainer applications may include a workout tracker, a strength training application, a cardio training application, a running and/or biking tracker, a weightlifting application, an activity tracker, a personalized exercise tracker, and/or a live workout class application. In some embodiments, a trainer application may include software code distributed between a plurality of devices.

Establishing a first communications channel between a trainer application and a first piece of electronic exercise equipment associated with a first client may involve creating a link for exchanging information between at least one electronic device associated with a training application and a piece of electronic exercise equipment used by a first individual. For example, a communications channel may be established between one or more of a server associated with a training application, a mobile communications device and/or a piece of electronic exercise equipment associated with a trainer, and a mobile communications device and/or a piece of electronic exercise equipment associated with a client.

Some disclosed embodiments involve a first communications channel being configured to convey a first dialogue data stream and to convey a first exertion data stream from at least one first sensor associated with the first piece of electronic exercise equipment. A sensor refers to a device and/or component that for detecting and/or responding to one or more physical changes and/or stimuli in an environment, as described and exemplified elsewhere. A sensor may convert environmental data (e.g., light, sound, temperature, and/or motion) to electronic signals for communicating via a communications channel. Some examples of sensors may include, a speedometer, a heart rate monitor, an inertial measurement unit (IMU) and/or GPS sensor for measuring a number of steps taken, distance travelled, calories burned, and/or sleep patterns, a blood pressure monitor, an Electrodermal Activity (EDA) sensor for measuring electrical conductivity of skin, a temperature sensor, an electrocardiogram (ECG and/or EKG) sensor, a pulse oximeter, a respiratory rate monitor, and/or a muscle activity sensor, a current sensor, a voltage sensor, a pressure sensor, a camera, a microphone, and/or any other type of sensor. A sensor associated with a first piece of electronic exercise equipment refers to a sensor for measuring one or more physical phenomena associated with performance of an exercise routine using a first piece of electronic exercise equipment. One or more sensors may be integrated within a piece of electronic exercise equipment, integrated within a wearable device and/or a mobile communications device paired to a piece of electronic exercise equipment, and/or may be a stand-alone sensor in communication with a trainer application. For example, a speedometer may be integrated within an electronic spinning machine to detect an exercise speed, and a current and/or voltage sensor may be integrated with a resistance motor of an electronic weight machine to detect a weigh lifted. As another example, a camera may be mounted on a wall near a wall-mounted electronic weight machine to detect a number of exercise repetitions, and a heart rate monitor may be worn by a user exercising using a piece of electronic exercise equipment to measure heart exertion. As an additional example, a microphone may be worn by an individual exercising using a piece of electronic exercise equipment. Convey refers to communicate and/or transfer. For example, convey may involve passing and/or sending a message, data over a networked connection.

A data stream refers to a continuous flow of information between a source and at least one destination. A source and/or a destination for a data stream may include a device, a system, and/or a software application. A data stream may be generated, transmitted, and/or processed over time. A data stream may include a continuous sequence of data elements and/or events arriving in a sequential order. A data stream may bypass storage in memory, and may be forwarded directly to an output device, for reduced latency. A dialogue refers to a two-way exchange of words (e.g., a conversation) between two persons, e.g., via one or more electronic devices. A dialogue data stream refers to a stream of data including digitally encoded words exchanged between two individuals using electronic media. A dialog stream may be associated with duplex communication, allowing for two-way communication between parties. A duplex communication channel may be full-duplex, allowing simultaneous two-way communication or half-duplex, allowing sequential two-way communication. A dialog stream may be associated with an audio sensor (e.g., a microphone) for sensing speech, and with an audio output device (e.g., a speaker) for rendering speech. For example, a first microphone may detect one or more words uttered by a first individual, and convert the uttered words to a first audio stream for conveying to a speaker of a second individual, and a second microphone may detect one or more words uttered by the second individual, and convert the uttered words to a second audio stream for conveying to a speaker of the first individual to thereby produce a two-way communication including a dialogue data stream.

Exertion refers to working, laboring, and/or investing energy, e.g., to achieve a goal, as described and exemplified elsewhere. Exertion data refers to information associated with performance of one or more physical activities, e.g., using a piece of electronic exercise equipment, as described and exemplified elsewhere herein. Some examples of exertion data may include one or more biomarkers, such as a heart rate, a breathing rate, an oxygen intake, a body temperature, a blood pressure level, a number of calories burned, a hydration level, and/or any other biomarker. Some additional examples of exertion data may include one or more measurements associated with a piece of electronic exercise equipment, such as a resistance level of a resistance motor indicating a weight lifted, an incline level (e.g., for a treadmill and/or stationary bicycle), an exercise duration, a distance covered, an elevation attained, an exercise pace, and/or any other measurement associated with a piece of electronic exercise equipment. Some further examples of exertion data may include a velocity, an acceleration, an orientation, a number of repetitions per exercise set, a rest period between exercise sets, and/or any other type of data associated with physical exertion. An exertion data stream refers to a stream of data carrying information associated with performance of an exercise routine. One or more sensors associated with a piece of electronic exercise equipment may continually sense exertion data during performance of an exercise routine, and continually transmit the sensed exertion data over a communication channel.

A first communications channel being configured to convey a first dialogue data stream and to convey a first exertion data stream from at least one first sensor associated with the first piece of electronic exercise equipment refers to a first link for exchanging speech data and exertion data (as described earlier) between a client and an exercise application. A communications channel may accommodate a plurality of data streams between two entities, each stream conforming to a different data type. For instance, an audio stream may include metadata permitting at least one processor to identify data as audio data for outputting via a speaker, and exertion data may include metadata permitting at least one processor to identify data as exertion data for analysis and/or output via an electronic screen. By way of example, a microphone of a mobile communications device may sense speech uttered by an individual exercising on an electronic stationary bicycle, and a speedometer may sense a spinning rate of the electronic stationary bicycle. The microphone may convert the sensed speed to an audio stream, and the speedometer may convert the sensed spinning rate to an exertion stream. At least one processor may transmit the audio stream and the exertion stream via a communications channel to at least one processor associated with a trainer application. By way of another example, a microphone associated with a headset may sense speech uttered by an individual exercising on an electronic rowing machine, and a heart rate monitor may sense a heart rate of the individual. The microphone may convert the sensed speed to an audio stream, and the heart rate monitor may convert the sensed heart rate to an exertion stream for transmission by at least one processor to a trainer application.

Figure 22:
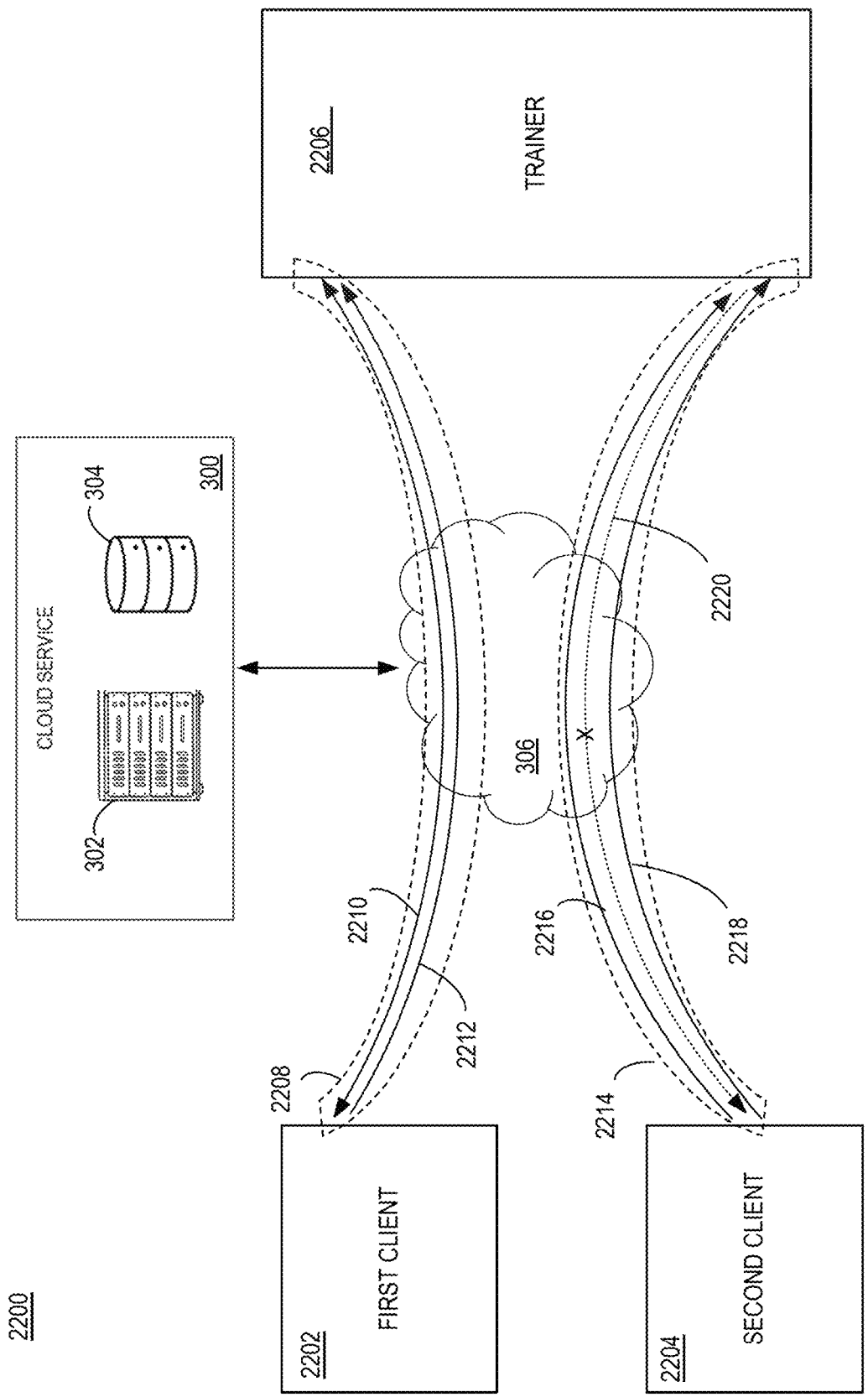
FIG. 22 illustrates an exemplary network diagram of a system for performing overlapping individualized data transfer operations, consistent with some embodiments of the present disclosure.

By way of a non-limiting example, reference is made to FIG. 22 illustrating an exemplary network diagram of an implementation of a system 2200 for performing overlapping individualized data transfer operations, consistent with some embodiments of the present disclosure. System 2200 may include a first client 2202, a second client 2204, a trainer application 2206, and a cloud service 300 communicating via communications network 306. First client 2202 and second client 2204 may include one or more of a piece of electronic exercise equipment, a mobile communication device, a wearable appliance, a tablet computer, a software application associated with trainer application 2206, and/or any other communication device and/or software application. For example, first client 2202 may include wall-mounted electronic weight machine 402 and second client 2202 may include wall-mounted electronic weight machine 406 in FIG. 4. At least one processor (e.g., 112, shown in FIG. 1A) may establish a first communications channel 2208 between trainer application 2206 and first piece of electronic exercise equipment 2202. First communications channel 2208 may convey a first dialogue data stream 2210 and a first exertion data stream 2212 from at least one first sensor associated with first piece of electronic exercise equipment (e.g., see image sensor 426 of mobile communication device 428 associated with electronic weight machine 402 in FIG. 4).

Some disclosed embodiments involve establishing a second communications channel between the trainer application and a second piece of electronic exercise equipment associated with a second client. The second communications channel may be a second instance of the same, similar, or different type of communications as those described above with respect to the first communications channel. The second client may be a second device of the same or similar type as those described above with respect to the first client. Some disclosed embodiments involve the second communications channel being configured to convey a second dialogue data stream and to convey a second exertion data stream from at least a second sensor associated with the second piece of electronic exercise equipment. The second dialogue data stream may be a second instance of the same, similar, or different type of dialogue data stream as those described above with respect to the first dialogue data stream. The second exertion data stream may be a second instance of the same, similar, or different type of exertion data stream as those described above with respect to the first exertion data stream. The second sensor may be a second device of the same or similar type as those described above with respect to the first sensor.

Thus, a trainer application may concurrently communicate with a plurality of clients via different communications channels. For instance, an exercise trainer may be associated with a first code portion of a trainer application configured for monitoring, coaching, and/or advising one or more client (e.g., exercise trainees). A first client may be associated with a first instance of a second code portion of the trainer application configured for tracking a progress of a first exercise routine. The first client may communicate with the exercise trainer using a first communications channel. Concurrently, a second client may be associated with a second instance of the second code portion of the trainer application. The second client may communicate with the exercise trainer using a second communications channel concurrent with the first client communicating with the exercise trainer using the first communications channel.

By way of a non-limiting example, in FIG. 22, at least one processor (e.g., 112) may establish a second communications channel 2214 between trainer application 2206 and second client 2204. Second communications channel 2214 may convey a second dialogue data stream 2216 and a second exertion data stream 2218 from at least one second sensor associated with second client 2204 (e.g., see image sensor 434 of mobile communication device 436 associated with electronic weight machine 406 in FIG. 4).

Some disclosed embodiments involve enabling a first selection, via the trainer application, of the first communications channel. Enabling refers to permitting and/or allowing. A selection refers to a choice, a decision, and/or an election. A selection may be made using an input device in conjunction with a user interface of a trainer application. Such input devices may include, for example, a microphone (e.g., for an audible selection), a keyboard, a touch-sensitive screen, a camera (e.g., for gesture-based selection), an electronic mouse, a stylus, and/or any other input device. Enabling a first selection, via a trainer application of the first communications channel refers to permitting a user (e.g., a trainer) to choose the first communications channel from a plurality of available communications channels. For example, a trainer application may include a user interface for presenting a plurality of available communications channels and for receiving a selection of a specific communications channel from the plurality as a user input via one or more input devices. For instance, a user interface may include a voice user interface (VUI) coupled to a microphone for receiving an audio selection, a graphical user interface (GUI) for receiving a touch-based selection via a touch-sensitive screen, and/or an electronic selection using a stylus and/or electronic mouse, a gesture-based interface for receiving a gesture selection using a camera, a keyboard for receiving text-based selection, and/or any other interface for receiving a selection using an input device.

Figure 23:
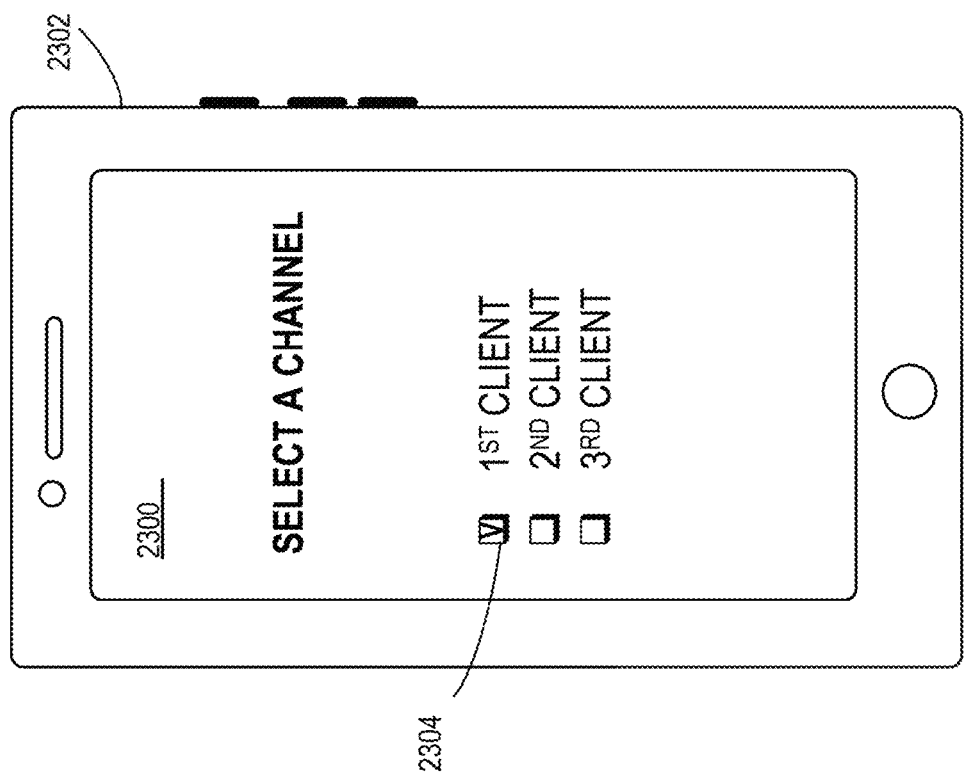
FIG. 23 illustrates a user interface for enabling a selection of a communications channel, consistent with some embodiments of the present disclosure.

By way of a non-limiting example, reference is made to FIG. 23 illustrating a user interface 2200 for enabling a selection of a communications channel, consistent with some embodiments of the present disclosure. Trainer application 2206 (FIG. 22) may display user interface 2200 on a mobile communication device 2302 of a trainer. User interface 2200 may enable a first selection 2304, via trainer application 2206, of first communications channel 2208. For example, first selection 2204 may be made by touching a touch-sensitive screen.

In some disclosed embodiments, in response to the first selection, the first dialogue data stream and the first exertion data stream are open between the first client and the trainer thereby enabling the first trainer to view first exertion data while simultaneously conducting a dialogue with the first client. In response to the first selection refers to consequent to, and/or based on the first selection. An open data stream refers to a dedicated channel that may be available to send and receive a flow of data between two end points. An open data stream may include a continuous flow of data that may be actively transmitted between two or more devices, systems, and/or applications. The first dialogue data stream and the first exertion data stream are open between the first client and the trainer refers to a channel established between the first client and the trainer being open for conveying two separate data streams of data flowing therethrough, where a first one of the two data streams may include a one-way stream of exertion data from the first client to the trainer, and the second one of the two data streams may include a two-way flow of audio data associated with a dialogue exchanged between the first client and the trainer. Simultaneously refers to concurrently, at the same time, and/or in parallel. Conducting a dialogue with the first client refers to holding and/or engaging in a two-way conversation with the first client. To view first exertion data refers to receive, read, observe, and/or notice information associated with an effort applied by a client to perform an exercise routine. Exertion data may be viewed, for example, using a graphical user interface of an (e.g., mobile) communications device. For instance, exertion data may be displayed as a chart and/or table itemizing one or more indications of exertion, as described earlier. Thus, based on a selection by a trainer of a first communication channel, at least one processor may maintain a one-way exertion data stream from the first client and the trainer, and concurrently, maintain a two-way dialogue data stream between the first client and the trainer. The exertion data stream may permit the trainer to monitor an exertion level of the first client and the dialogue data stream may permit the trainer and the first client to converse. For instance, the trainer may provide individual guidance to the first client, and the first client may respond to the individual guidance.

By way of a non-limiting example, in FIG. 22, in response to first selection 2304 (FIG. 23), first dialogue data stream 2210 and first exertion data stream 2212 may be open between first client 2202 and trainer application 2206 thereby enabling viewing via trainer application 2206 of first exertion data stream 2212 while simultaneously conducting a dialogue with first client 2202 (e.g., via first dialogue stream 2210). For instance, first exertion data stream 2212 may include a flow of exertion data associated with a piece of electronic exercise equipment from first client 2202 to trainer application 2206, and first dialogue stream 2210 may include a two-way flow of audio data exchanged between first client 2202 and a trainer associated with trainer application 2206.

In some disclosed embodiments, while the first dialogue data stream is open, at least a return path of the second dialogue data stream from the trainer application to the second client is blocked, preventing dialogue from the trainer application to the second client. While a first dialogue data stream is open refers to throughout a time period during which a communications channel is available to convey a two-way flow of audio data between the first client and the trainer, e.g., via a duplex communication channel. A return path of a second dialogue data stream from a trainer application to a second client refers to an audio stream associated with speech uttered by the trainer addressing the second client, e.g., in response to an audio stream associated with speech uttered by the second client addressing the trainer. For example, a duplex communication channel for a dialogue data stream may include two paths, a first path for carrying audio data from a client to a trainer, and a second path (e.g., a return path) for carrying audio data from the trainer to the client, e.g., in response to audio data from the client to the trainer. Thus, a return path may refer to one of two paths included in a duplex communication channel. Blocked refers to obstructed, interrupted, and/or prevented. At least one processor may prevent data from flowing along a blocked data stream, e.g., by storing the data in a buffer for subsequent transmission or by discarding the data. Preventing dialogue from the trainer application to the second client refers to averting, stopping, and/or prohibiting dialogue data to flow from the trainer to the second client. For example, at least one processor may store and/or discard audio data associated with the return path from the trainer to the second client while the first communication channel is selected. In some embodiments, when a return path of the second dialogue data stream from the trainer application to the second client, the trainer may still receive exertion data and/or audio data from the second client. Thus, in some instances, only speech from the trainer to the second client (or any other client other than the first client) may be blocked.

For example, upon selection of a first communication channel, at least one processor may open an (e.g., two-way) dialogue data stream for conveying first dialog data between a trainer and a first client. Speech uttered by the trainer may be captured by a microphone and converted to an audio data stream, which may flow to the first client via the first communication channel. Concurrently, a second communication channel may be open between the trainer and a second client. The second communication channel may be used to convey exertion data and/or dialogue data between the second client to the trainer. To prevent the second client from receiving speech intended for the first client, at least one processor may block a return path of the second communication channel, blocking speech intended for the first client from reaching the second client. Thus, a dialogue stream between the second client and the trainer may at most include a one-way flow of data from the second client to the trainer.

By way of a non-limiting example, in FIG. 22, while first dialogue data stream 2210 is open (e.g., for two-way communication between client 2202 and trainer application 2206), at least a return path 2220 of second dialogue data stream 2216 from trainer application 2206 to second client 2204 may be blocked (e.g., see "X" on dotted return path 2220 indicated blockage) preventing a flow of audio data from the trainer application 2206 to the second client 2204.

Some disclosed embodiments involve enabling a second selection, via the trainer application, of the second communications channel, wherein in response to the second selection, the second dialogue data stream and the second exertion data stream are open between the second client and the trainer thereby enabling the trainer to view first exertion data while simultaneously conducting a dialogue with the second client, and wherein while the second dialogue data stream is open, at least a return path of the first dialogue data stream from the trainer application to the first client is blocked, preventing communication from the trainer application to the first client. Enabling a second selection, via the trainer application, of the second communications channel may be understood as described above for the first channel. For example, during a first time period a trainer may select a first communication channel for engaging in dialogue with a first client, and during a second time period a trainer may select a second communication channel for engaging in dialogue with a second client. In response to the second selection, the second dialogue data stream and the second exertion data stream are open between the second client and the trainer may be understood as described earlier for the first channel. For example, based on a selection of the second communication channel, at least one processor may enable exertion data and two-way dialogue data to flow between the second client and the trainer. Thereby enabling the trainer to view first exertion data while simultaneously conducting a dialogue with the second client may be understood as described earlier for the first channel. While the second dialogue data stream is open, at least a return path of the first dialogue data stream from the trainer application to the first client is blocked, preventing communication from the trainer application to the first client may be understood as described earlier for the first channel. For example, selection of the second channel may permit the trainer to view exertion of the second client and engage in two-way dialogue with the second client. In some instances, selection of the second channel may permit the trainer to view exertion of the second client and exertion of the first client concurrently. In some instances, selection of the second channel may permit the trainer to receive audio data from the first client and the second client concurrently. In some instances, selection of the second channel may only block audio data from the trainer to any client other than the second client, and may permit other data streams (e.g., including exertion data and/or speech data originating from one or more clients) to continue to flow.

Figure 24:
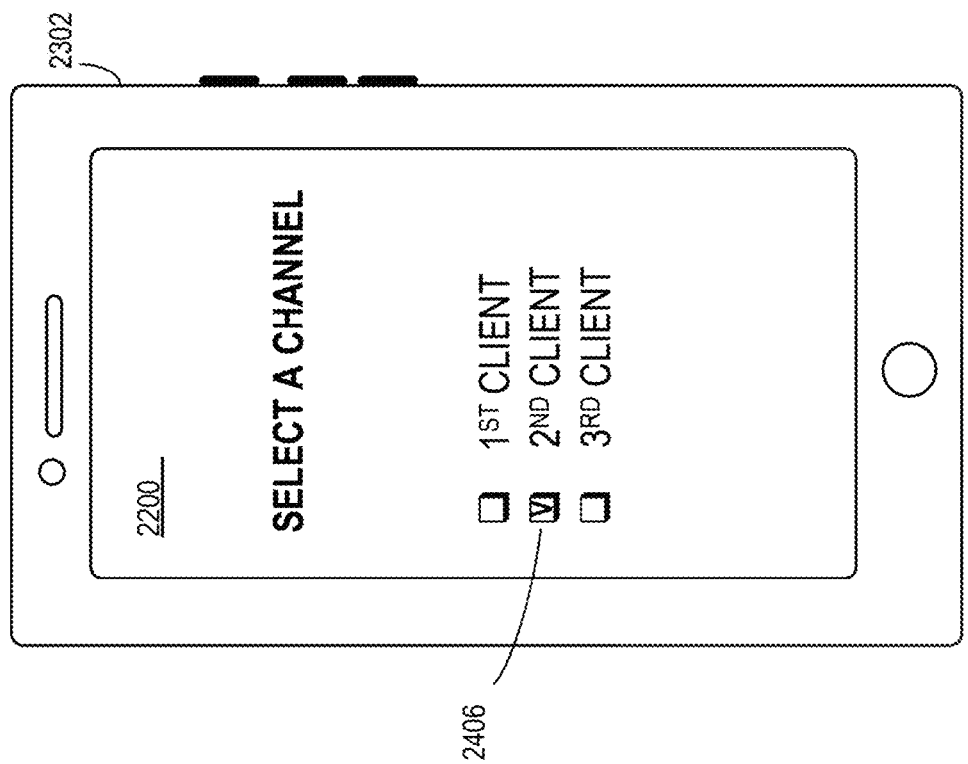
FIG. 24 illustrates the user interface of FIG. 23 for enabling another selection of a communications channel, consistent with some embodiments of the present disclosure.

By way of a non-limiting example, reference is made to FIG. 24 illustrating user interface 2200 for enabling another selection of a communications channel, consistent with some embodiments of the present disclosure. User interface 2200 may enable a second selection 2406, via trainer application 2206 (FIG. 22), of second communications channel 2214.

In some disclosed embodiments, the first dialogue data stream and the second dialogue data stream include video data. Video data refers to a sequence of images, that when presented according to the sequence, convey motion. Video data may include a plurality of frames, each frame capturing a real and/or virtual occurrence at an instant in time. Formats for video data may include MP4, AVI, MOV, WMV, FLV (Flash video), MKV (Matroska video), WEBM, MPEG, 3GP/3G2, and/or AVC video. Video data may include a corresponding audio track, recording sounds that may have occurred while capturing a sequence of images. For example, a video recorder of a mobile communications device may capture speech of a dialogue by enlisting a microphone for capturing sounds and an image sensor (e.g., a camera) for capturing sequential images concurrent with sounds. Playing back the video data may permit hearing speech concurrent with viewing the speaking party. Implementing a trainer application may involve capturing one or more videos of a trainer and a client, permitting each of the trainer and client to hear and view speech uttered by the other one of the trainer and client.

Figure 25:
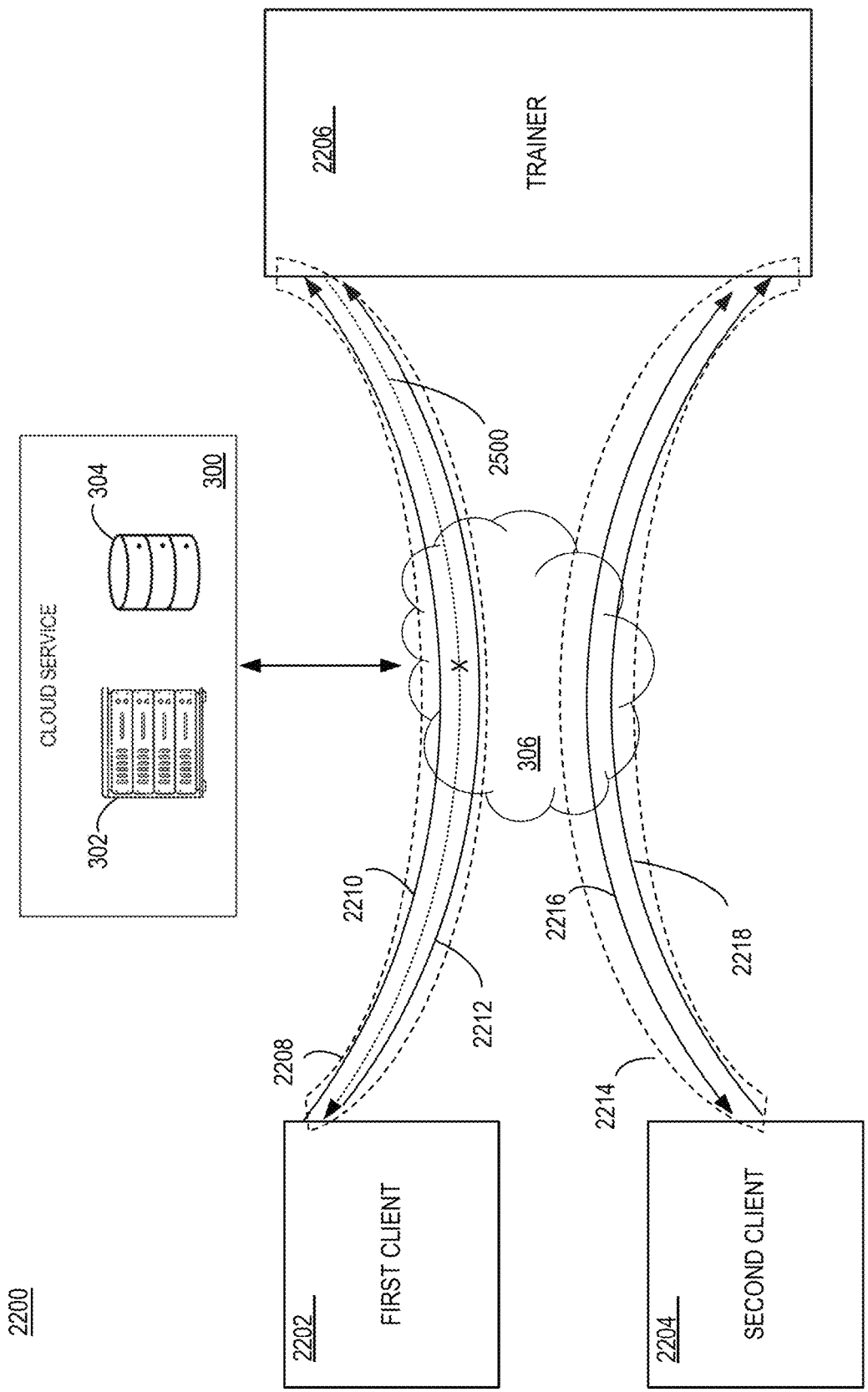
FIG. 25 illustrates another exemplary network diagram for performing overlapping individualized data transfer operations, consistent with some embodiments of the present disclosure.

By way of another non-limiting example, reference is made to FIG. 25 illustrating the exemplary network diagram of FIG. 22 for performing overlapping individualized data transfer operations, consistent with some embodiments of the present disclosure. In response to second selection 2406, second dialogue data stream 2216 and second exertion data stream 2218 may be open between second client 2204 and trainer application 2206, thereby enabling viewing via trainer application 2206, second exertion data 2218 while simultaneously conducting a dialogue with second client 2204 (e.g., see two-way communication via second dialogue data stream 2216). While second dialogue data stream is open 2216, at least a return path 2500 of first dialogue data stream 2210 from trainer application 2206 to first client 2202 may be blocked (e.g., see "X" and dotted line indicating blockage). The blockage may prevent (e.g., speech) communication from trainer application 2206 to first client 2202. In some embodiments, first dialogue data stream 2210 and the second dialogue data stream 2216 may include video data.

In some disclose embodiments, when the first channel is open, the operations further include conveying audio data from the second client to the trainer application, while blocking audio transmission from the trainer application to the second client. When the first channel is open refers to within a time period during which a two-way dialogue stream may flow through the first channel. In some embodiments, when the first channel is open refers to when the first dialogue data stream and the first exertion data stream are open between the first client and the trainer application. Conveying refers to transmitting and/or communicating. Audio data refers digital information representing sound. Audio data may be produced by a microphone configured to sense sound and convert the sensed sound to electronic signals. Some examples of audio data formats may include WAV, MP3, AAC, FLAC, OGG, AIFF, WMA, and/or PCM. Conveying audio data from the second client to the trainer application refers to permitting audio data to flow from the second client to the trainer application during a period that the first channel may carry two-way audio data between the first client and the trainer. Thus the trainer may receive audio data from the first and second clients, concurrently. Blocking audio transmission from the trainer application to the second client refers to preventing audio data from the trainer application to flow to the second client. Thus, upon receiving a selection of the first channel, at least one processor may permit a trainer to receive audio data and exertion data from the first and second clients, via the first and second communication channels, respectively. However, only the first client may receive audio data from the trainer since a return path for audio data from the trainer to the second client may be blocked. Consequently, the trainer may hear speech by the first and second clients concurrently using first and second audio data streams originating from the first and second clients, and may be able to monitor the exertion of the first and second clients concurrently based on the first and second exertion data streams. However, only the first client may receive an audio stream from the trainer, enabling only the first client to hear speech by the trainer.

By way of a non-limiting example, in FIG. 22, when first channel 2208 is open (e.g., when first dialogue data stream 2210 and first exertion data 2212 stream are open between first client 2202 and trainer application 2206), at least one processor (e.g., 112) may convey audio data second client 2204 to trainer application 2206 (e.g., via, one-way dialog data stream 2216 while blocking audio transmission from the trainer application 2206 to second client 2204, e.g., by blocking return path 2220.

In some disclose embodiments, when the first channel is open, the operations further include conveying video data from the first client to the trainer application, while blocking video transmission from the trainer application to the second client. This may be understood as described above where video data may replace the audio data. Thus, upon receiving a selection of the first channel, at least one processor may permit a trainer to receive video data and exertion data from the first and second clients, via the first and second communication channels, respectively. However, only the first client may receive video data from the trainer since a return path for video data from the trainer to the second client may be blocked. Consequently, the trainer may hear and view speech spoken by the first and second clients concurrently using first and second video data streams originating from the first and second clients, and may be able to monitor the exertion of the first and second clients concurrently based on the first and second exertion data streams. However, only the first client may receive a video stream from the trainer, enabling only the first client to hear and view speech spoken by the trainer.

Some disclosed embodiments involve, when the first channel is open, logging the second exertion data stream from the second channel for later presentation on the trainer application when the second channel is open. Logging refers to the act of keeping a log of events that occur in a computer system. Logging may include storing an audio, visual, and/or any other data stream in memory for subsequent transmission and/or rendering. Later presentation on the trainer application refers to subsequent and/or eventual rendering via an output device associated with a trainer. For example, an audio stream may be stored in memory for subsequent retrieval and playback. when the first channel is open, logging the second exertion data stream from the second channel for later presentation on the trainer application when the second channel is open refers to storing data streams associated with the second client throughout a time period during which the first channel is open (e.g., selected), and retrieving the stored data streams for rendering on one or more output devices when the first channel is no longer selected.

Some disclosed embodiments involve, when the second channel is open, logging the first exertion data stream from the first channel for later presentation on the trainer application when the first channel is open. When the second channel is open, logging the first exertion data stream from the first channel for later presentation on the trainer application when the first channel is open may be understood as described above for when the first channel is open. Thus a trainer may defer and/or postpone receiving data from one or more clients during a training session by selecting to exclusively interact with either a first client or a second client (or additional clients).

By way of a non-limiting example, in FIG. 22, when first channel 2208 is open, (e.g., when first dialogue data stream 2210 and first exertion data 2212 stream are open between first client 2202 and trainer application 2206), at least one processor (e.g., 112, or a processor of mobile communications device 224) may convey video data from first client 2202 to trainer application 2206 (e.g., via first dialogue data stream 2210), while blocking video transmission from trainer application 2206 to second client 2204 (e.g., by blocking return path 2220). In some embodiments, at least one processor (e.g., included in server 302) may log second exertion data stream 2218 from second channel 2214 for later presentation on trainer application 2206 when second channel 2214 may open. For example, at least one processor may store logged second exertion data stream 2218 in data structure 304. Referring to FIG. 25, when second channel 2214 may open, at least one processor may log first exertion data stream 2214 from first channel 2208 for later presentation on trainer application 2206. For example, at least one processor may store logged first exertion data stream 2214 in data structure 304.

In some disclosed embodiments, the first piece of electronic exercise equipment and the second piece of electronic exercise equipment each include a resistive motor for exerting tension on a cable, and wherein the first exertion data stream and the second exertion data stream reflect cable-applied resistive forces. A resistive motor (e.g., a resistance motor) may be understood as described elsewhere herein. A first piece of electronic exercise equipment and a second piece of electronic exercise equipment each include a resistive motor refers to each of the first and second pieces of electronic exercise equipment configured to apply resistance using a resistive motor. For example, the first and second pieces of electronic exercise equipment may include electronic weight machines, electronic treadmills, electronic rowing machines, electronic stationary bicycles, and/or any other electronic exercise machine associated with resistance. Tension on a cable refers to a pulling and/or stretching force applied to a cable, as described elsewhere herein. To reflect refers to embody, to express, and/or to represent. Cable-applied resistive forces refer to a force by a resistive motor that may be applied to a cable to counter an opposite force applied on the cable by a user and/or client. A cable-applied resistive force applied by a resistive motor may simulate a resistive force applied to a cable by a weight in response to a user pulling on the cable. A resistive motor may include a plurality of settings, each associated with a different resistance level. Monitoring cable-applied resistive forces for a piece of electronic exercise equipment may permit a trainer to monitor an exertion of an associated client.

By way of a non-limiting example, in FIG. 4, first piece of electronic exercise equipment 402 and second piece of electronic exercise equipment 406 may each include a resistive motor 412 and 416, respectively, for exerting tension on a cable (see cable 206 in FIG. 2A). In FIG. 22, first exertion data stream 2212 and second exertion data stream 2218 may reflect cable-applied resistive forces, e.g., exerted on the cable by the resistive motor in response to a pulling motion.

In some disclosed embodiments, the trainer application provides a plurality of windows differentiating dialogue data from exertion data. A window refers to a user interface element for framing and/or organizing content. For example, a software chat application may include a first window to display text messages between a trainer and a first user, and a second window to display text messages between a trainer and a second user. Differentiating refers to distinguishing and/or discriminating. A trainer application providing a plurality of windows differentiating dialogue data from exertion data refers to a user interface of a trainer application displaying multiple frames, each dedicated to displaying a different type of data. A first window may be dedicated to display exertion data for a plurality of clients (e.g., as charts and/or graphs), and a second window may be dedicated to display dialogues between the trainer and a plurality of clients.

Figure 26:
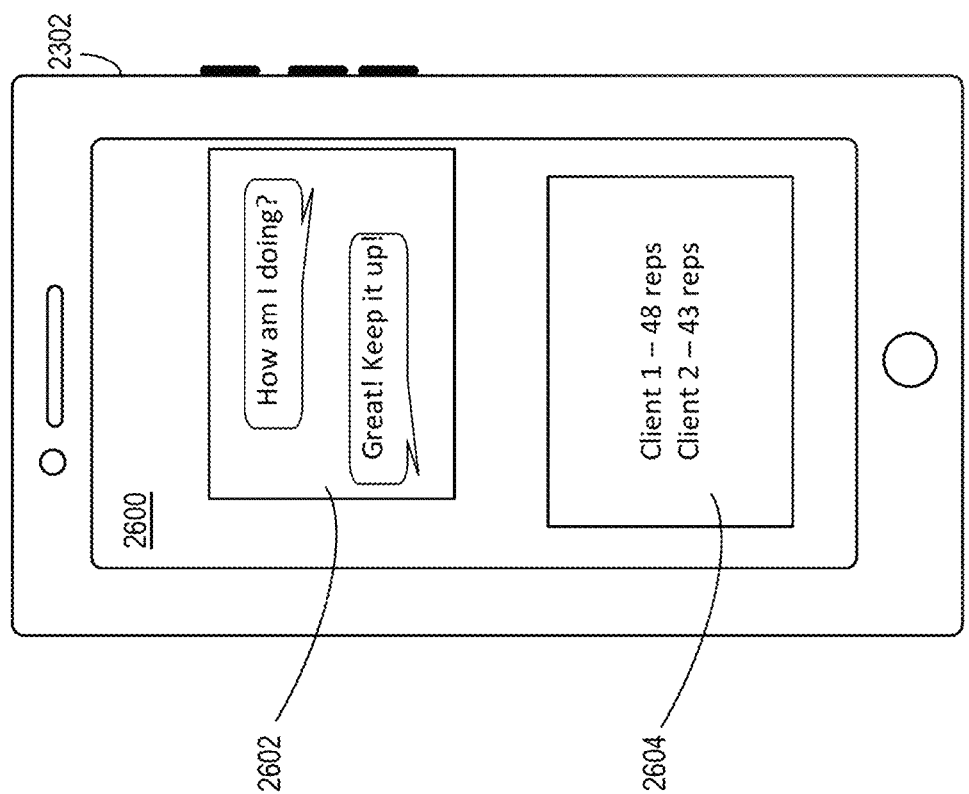
FIG. 26 illustrates an exemplary user interface including a plurality of windows, consistent with some embodiments of the present disclosure.

By way of a non-limiting example, reference is made to FIG. 26 illustrating a user interface 2600 including a plurality of windows, consistent with some embodiments of the present disclosure. Trainer application 2206 may be installed on mobile communications device 2302 of the trainer, and may present user interface 2600. User interface 2600 may include a first window 2602 displaying dialogue data with first client 2202, and a second window 2604 displaying exertion data associated with first client 2202 and second client 2204, thereby differentiating dialogue data from exertion data.

In some disclosed embodiments, the first communications channel is established between a first mobile communications device associated with the first client and a trainer mobile communications device running the trainer application, and wherein the second communications channel is established between a second mobile communications device associated with the second client and the trainer mobile communications device. A mobile communications device refers to a portable computing device capable of communicating via a wired and/or wireless communication network, as described and exemplified elsewhere. A mobile communications device may be capable of wireless communication and run one or more mobile applications. A mobile communications device may include a smartphone, a tablets, a wearable device (e.g., a smartwatch, smart glasses) a portable media players, and/or any other portable electronic communication device. A mobile communications device may pair to an electronic exercise equipment and may communicate with the exercise equipment via a wired or wireless connection. In some embodiments, the mobile communications device and the exercise equipment may communicate via an intermediary device or system, such as the mobile communications device communicating with the exercise equipment via a local or remote server. Thus in some embodiments, communication between a trainer and a plurality of clients may be established using associated mobile communication devices.

By way of a non-limiting example, in FIG. 22, first communications channel 2208 may be established between a first mobile communications device associated with first client 2206 (e.g., see mobile communication devices 428 associated with first participant 422 in FIG. 4) and trainer mobile communications device 2302 running trainer application 2206. Second communications channel 2214 may be established between a second mobile communications device associated with second client 2204 (e.g., see mobile communication devices 436 associated with second participant 430 in FIG. 4) and trainer mobile communications device 2302 running trainer application 2206.

Figure 27:
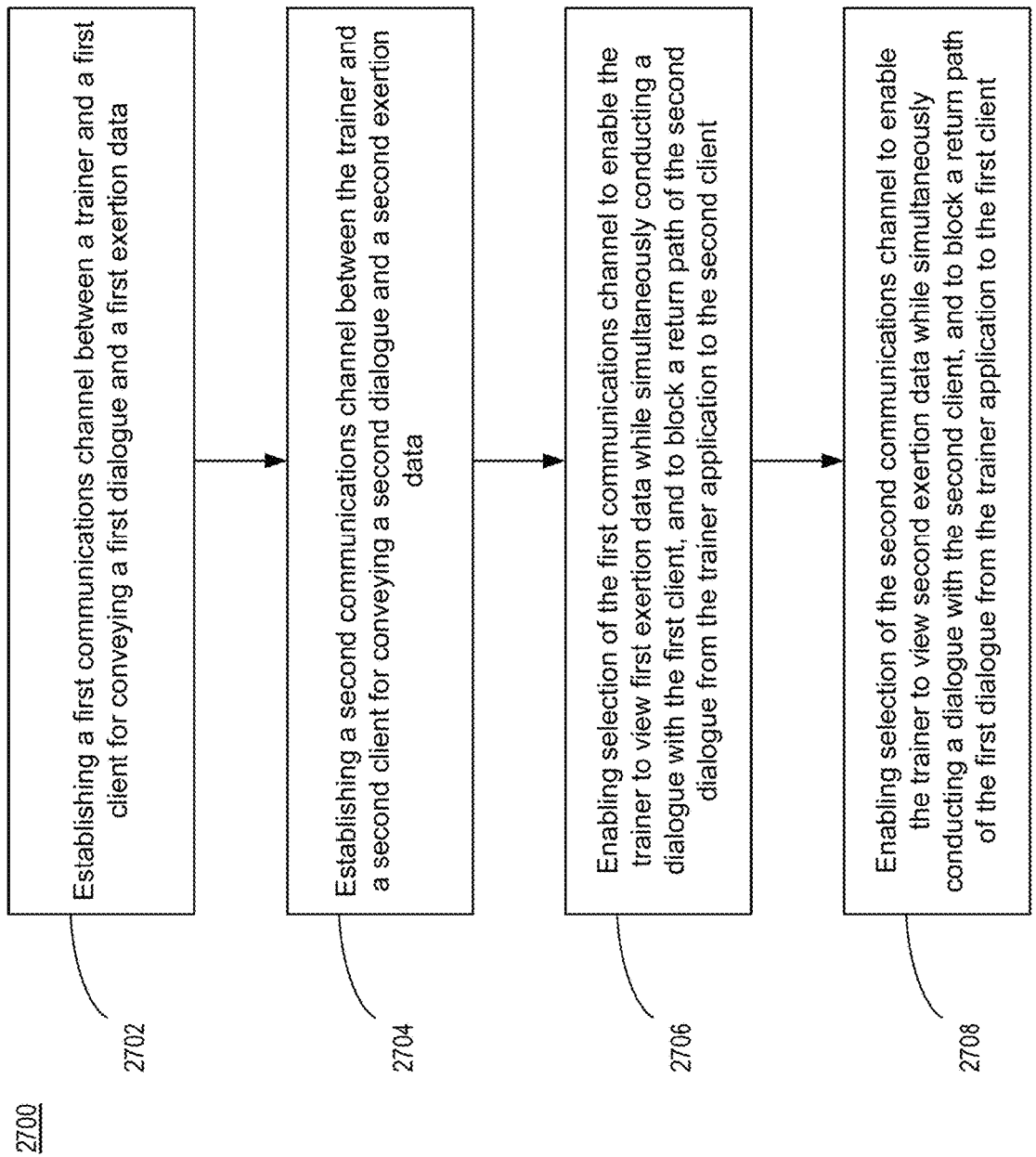
FIG. 27 is a flowchart of an exemplary process for performing overlapping individualized data transfer operations, consistent with embodiments of the present disclosure.

FIG. 27 illustrates a flowchart of an exemplary process 2700 for performing overlapping individualized data transfer operations, consistent with embodiments of the present disclosure. In some embodiments, process 2700 may be performed by at least one processing device (e.g., included in with cloud server 302 in FIG. 3) may to perform operations or functions described herein. In some embodiments, some aspects of process 2700 may be implemented as software (e.g., program codes or instructions) that are stored in a memory (e.g., memory 114, or a memory of mobile communications device 224) or a non-transitory computer readable medium. In some embodiments, some aspects of process 2700 may be implemented as hardware (e.g., a specific-purpose circuit). In some embodiments, process 2700 may be implemented as a combination of software and hardware.

Process 2700 may include a step 2702 of establishing a first communications channel between a trainer application and a first piece of electronic exercise equipment associated with a first client, the first communications channel being configured to convey a first dialogue data stream and to convey a first exertion data stream from at least one first sensor associated with the first piece of electronic exercise equipment. By way of a non-limiting example, in FIG. 22, at least one processor (e.g., 112, or a processor of mobile communications device 224) may establish first communications channel 2208 between trainer application 2206 and first piece of electronic exercise equipment 2202. First communications channel 2208 may convey a first dialogue data stream 2210 and a first exertion data stream 2212 from at least one first sensor associated with first piece of electronic exercise equipment (e.g., see image sensor 426 of mobile communication device 428 associated with electronic weight machine 402 in FIG. 4).

Process 2700 may include a step 2704 of establishing a second communications channel between the trainer application and a second piece of electronic exercise equipment associated with a second client, the second communications channel being configured to convey a second dialogue data stream and to convey a second exertion data stream from at least a second sensor associated with the second piece of electronic exercise equipment.

By way of a non-limiting example, in FIG. 22, at least one processor (e.g., 112, or a processor of mobile communications device 224) may establish second communications channel 2214 between trainer application 2206 and second client 2204. Second communications channel 2214 may convey a second dialogue data stream 2216 and a second exertion data stream 2218 from at least one second sensor associated with second client 2204 (e.g., see image sensor 434 of mobile communication device 436 associated with electronic weight machine 406 in FIG. 4).

Process 2700 may include a step 2706 of enabling a first selection, via the trainer application, of the first communications channel, wherein in response to the first selection, the first dialogue data stream and the first exertion data stream are open between the first client and the trainer thereby enabling the trainer to view first exertion data while simultaneously conducting a dialogue with the first client, and wherein while the first dialogue data stream is open, at least a return path of the second dialogue data stream from the trainer application to the second client is blocked, preventing dialogue from the trainer application to the second client.

By way of a non-limiting example, in FIG. 23, user interface 2200 may enable a first selection 2304, via trainer application 2206, of first communications channel 2208. In response to first selection 2304 (FIG. 23), first dialogue data stream 2210 and first exertion data stream 2212 may be open between first client 2202 and trainer application 2206 thereby enabling viewing via trainer application 2206 of first exertion data stream 2212 while simultaneously conducting a dialogue with first client 2202 (e.g., via first dialogue stream 2210). while first dialogue data stream 2210 is open (e.g., for two-way communication between client 2202 and trainer application 2206), at least a return path 2220 of second dialogue data stream 2216 from trainer application 2206 to second client 2204 may be blocked (e.g., see "X" on dotted return path 2220 indicated blockage) preventing a flow of audio data from the trainer application 2206 to the second client 2204.

Process 2700 may include a step 2708 of enabling a second selection, via the trainer application, of the second communications channel, wherein in response to the second selection, the second dialogue data stream and the second exertion data stream are open between the second client and the trainer thereby enabling the trainer to view second exertion data while simultaneously conducting a dialogue with the second client, and wherein while the second dialogue data stream is open, at least a return path of the first dialogue data stream from the trainer application to the first client is blocked, preventing communication from the trainer application to the first client. By way of a non-limiting example, in FIG. 24, user interface 2200 may enable a second selection 2406, via trainer application 2206 (FIG. 22), of second communications channel 2214. In FIG. 25, in response to second selection 2406, second dialogue data stream 2216 and second exertion data stream 2218 may be open between second client 2204 and trainer application 2206, thereby enabling viewing via trainer application 2206, second exertion data 2218 while simultaneously conducting a dialogue with second client 2204 (e.g., see two-way communication via second dialogue data stream 2216). While second dialogue data stream is open 2216, at least a return path 2500 of first dialogue data stream 2210 from trainer application 2206 to first client 2202 may be blocked (e.g., see "X" and dotted line indicating blockage). The blockage may prevent (e.g., speech) communication from trainer application 2206 to first client 2202. In some embodiments, first dialogue data stream 2210 and the second dialogue data stream 2216 may include video data.

Some disclosed embodiments involve workout scoring using image and exertion data. Several variables contribute to how well an exercise is performed, including form, posture, number of repetitions, duration, and exertion level relative to a goal. Some disclosed embodiments provide a system that analyzes image data and exertion data to generate an exercise score. Such a score may better enable individuals to track their workout progress.

Some embodiments include a non-transitory computer readable medium storing instructions that cause the at least one processor to perform exercise scoring operation. The at least one processor may store an exercise goal for a particular individual. The at least one processor may receive from a sensor on a piece of electronic exercise equipment, exertion data. The at least one processor may receive from at least one image sensor monitoring use of the piece of electronic exercise equipment, image data reflecting form and posture of the particular individual during an exercise set. The at least one processor may generate a score for the exercise set by performing an aggregate analysis of the exercise goal, the exertion data, and the image data reflecting the form and posture. The at least one processor may output the score.

In some embodiments, the exercise set includes a group of repetitions of a same exercise, and wherein the score evaluates the group of repetitions. In some embodiments, the exercise set includes a series of groups of repetitions of differing exercises and wherein the score evaluates the series of groups. In some embodiments, performance of the aggregate analysis includes only counting repetitions when a threshold exertion level is detected. In some embodiments, the image data is video and wherein detecting a threshold exertion level includes image analysis of the video. In some embodiments, the at least one processor may automatically adjust the exercise goal as performance improvements are detected over time. In some embodiments, the at least one processor may generate the exercise goal. Generating the exercise goal may include administering a baseline test and receiving baseline image data and baseline exertion data.

In some embodiments, the score is generated based on at least three of detected exercise duration, intensity, form, posture, effectiveness, progress, and the exercise goal. In some embodiments, the at least one processor may output in real time during the exercise set, a repetition count. In some instances, the image data includes video data and wherein the repetition count is derived at least in part from the video data. In some instances, the repetition count only includes repetitions that pass a threshold determined based on analysis of the video data.

Some disclosed embodiments involve exercise scoring operations. Exercise includes activity requiring physical effort that may sustain or improve health or fitness. Scoring refers to a process of determining, calculating, generating, and/or assigning a numerical value (e.g., score) to a datum point or entity based on one or more data, criteria, or algorithms. Exercise scoring refers to scoring an exercise set based on one or more data, criteria, or algorithms. For example, exercise scoring may include evaluating the performance of an individual during an exercise set by generating a numerical score based at least on one or more of received data and/or an exercise scoring algorithm. In some embodiments, exercise scoring may include scoring exercises performed by an individual using electronic exercise equipment, including smart electronic exercise equipment, such as the computerized electronic exercise equipment disclosed herein. For example, exercise scoring may include performance scoring in real-time and/or progress over time scoring, as described and exemplified elsewhere herein. Exercise scoring operations involve one or more operations, activities, or tasks associated with evaluating an individual performing an exercise set. For example, at least one processor may analyze data, including data received from one or more sensors, to generate a score for an exercise set. Further, the at least one processor configured to perform exercise scoring operations may be part of a server, a mobile communication device, electronic exercise equipment, or any other suitable processor.

By way of a non-limiting example, FIG. 3 shows an exemplary schematic network diagram with electronic exercise machine 200, cloud service 300, and mobile communications device 224 that are configured to communicate with each other via communications network 306. In some embodiments, cloud service 300 may comprise a server 302 and a database 304. Server 302 may comprise at least one processor configured to perform exercise scoring operations, as described and exemplified herein. Additionally or alternatively, in some embodiments, mobile communications device 224 may comprise at least one processor configured to perform exercise scoring operations, as described and exemplified herein. Further, in some embodiments, exercise scoring operations may be performed by at least one processor in server 302, mobile communications device 224, electronic exercise equipment such as electronic exercise machine 200, or any combination of the foregoing.

Figure 28A:
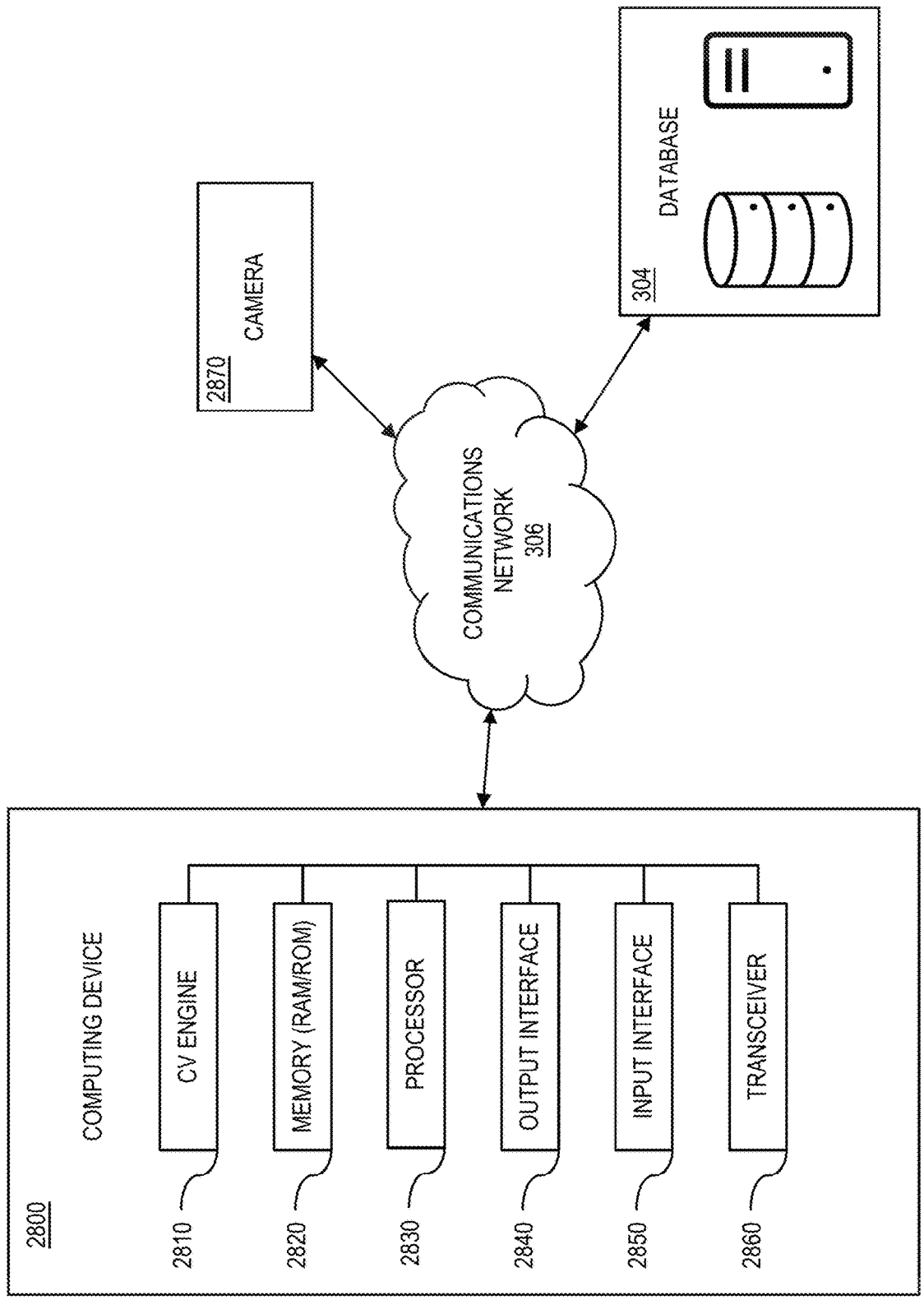
FIGS. 28A-28B are exemplary schematic network diagrams, consistent with disclosed embodiments.

Further and by way of a non-limiting example, FIG. 28A shows an exemplary schematic network diagram with computing device 2800, camera 2870, and database 304 that are configured to communicate with each other via communications network 306. In some embodiments, computing device 2800 may correspond to one or more processors in server 302, mobile communication device 224, electronic exercise machine 200, or any combination of the foregoing. Further, in some embodiments, computing device 2800 may be configured to store code with instructions for causing at least one processor to perform exercise scoring operations stored in a non-transitory computer readable medium in, for example, memory 2820. Operations may be performed based on instructions executed by, for example, at least one processor such as processor 2830.

Some disclosed embodiments involve storing an exercise goal for a particular individual. Storing involves a process of saving or retaining data in a persistent form, such as on a physical or digital storage medium. For example, storing may include saving or retaining data in a non-transitory computer readable medium, such as flash memory of electronic exercise equipment or cloud-based memory in communication with electronic exercise equipment. A goal refers to an objective, target, or desired outcome of an action. An exercise goal refers to data associated with an objective or target for a particular exercise set. For example, an exercise goal may include a target exercise score, a target number of repetitions, a target height, a target weight, or a target exercise duration. Further, an exercise goal may be generated by at least one processor executing exercise scoring operations, inputted by an individual, predefined and stored in a memory, any combination of the foregoing, or any other suitable means of defining an exercise goal.

A particular individual refers to a specific person. For example, a particular individual may include the specific person who owns, uses, or otherwise interacts or engages with electronic exercise equipment. Further, for example, the particular individual may include the specific person currently using the electronic exercise equipment. Identifying the particular individual may involve a person interacting with a user interface operatively connected to the electronic exercise equipment. Additionally or alternatively, identifying the particular individual may involve detecting a person using a sensor operatively connected to the electronic exercise equipment and analyzing the data to determine which particular individual is detected by the sensor.

Figure 31A:
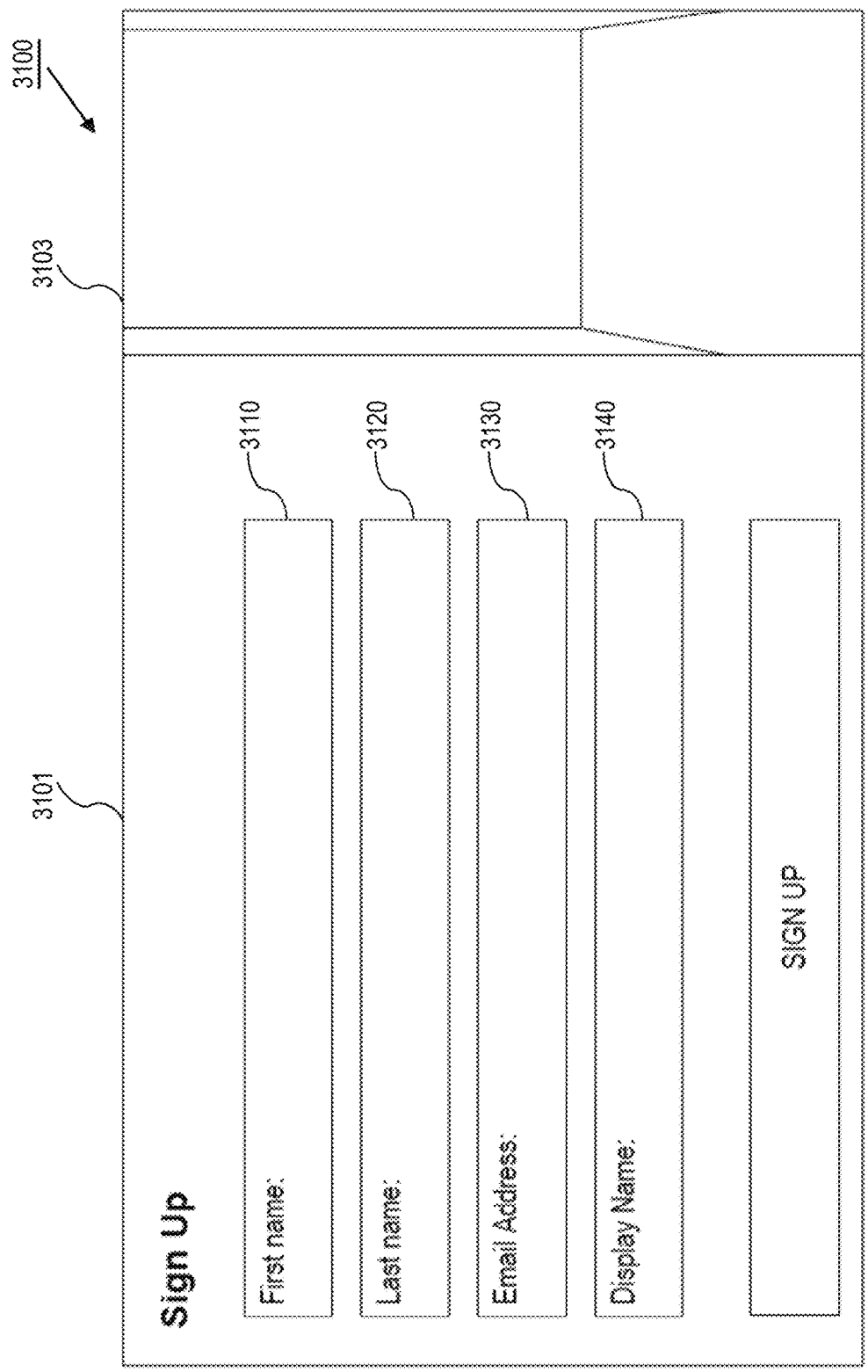

By way of a non-limiting example, FIG. 31A shows an exemplary user interface 3110, including left window 3101 and right window 3103. In some embodiments, an individual may interact with user interface 3110, such as left window 3101, and enter information, such as a first name 3110, a last name 3120, an email address 3130, a display name 3140, a username, a password, any combination of the foregoing, or any other suitable identifying information. The exemplary user interfaces depicted in FIGS. 31A-31D may be associated with input interface 2850 (FIG. 28A), a separate interactable user interface in communication with computing device 2800 (FIG. 28A), mobile communication device 224 (FIG. 3), or any other suitable device configured to display a user interface and receive user input.

Further, by way of a non-limiting example, FIGS. 3 and 28A through 29C show exemplary systems that involve electronic exercise equipment. In some embodiments, an image sensor, such as camera 2870 (FIGS. 28A, 29A, 29B) or mobile communication device 224 (FIGS. 3, 29C), may be configured to capture image data of an individual and send the image data to a processor, such as a processor part of cloud service 300 (FIG. 3). The processor may be configured to query a database, such as database 304 (FIG. 3), to determine the identity of an individual, such as individual 2895 (FIG. 28B), based on the image data and associate the individual with a particular individual and associated data, such as an exercise goal and historical exercise data.

Figure 28B:
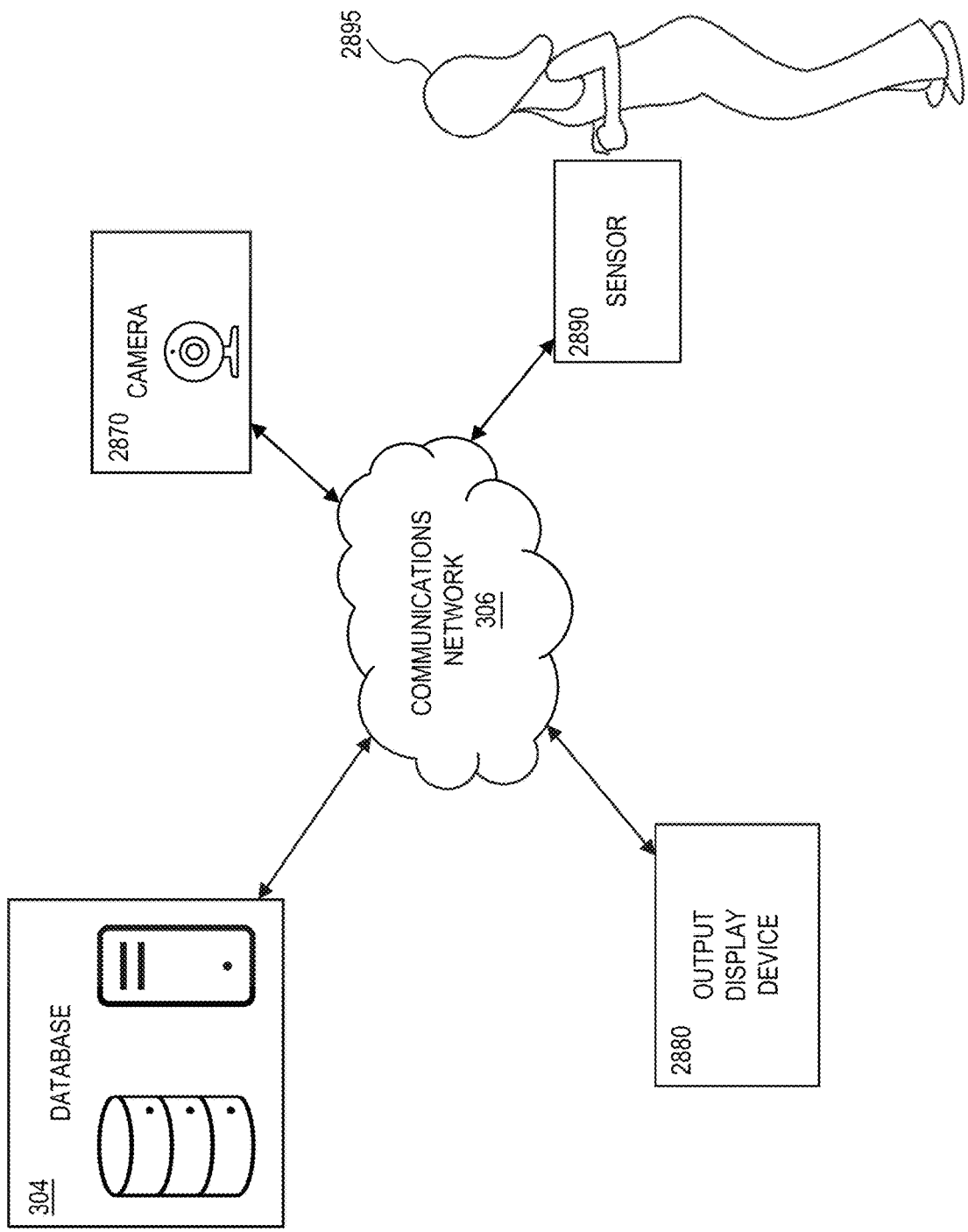
Figure 29C:
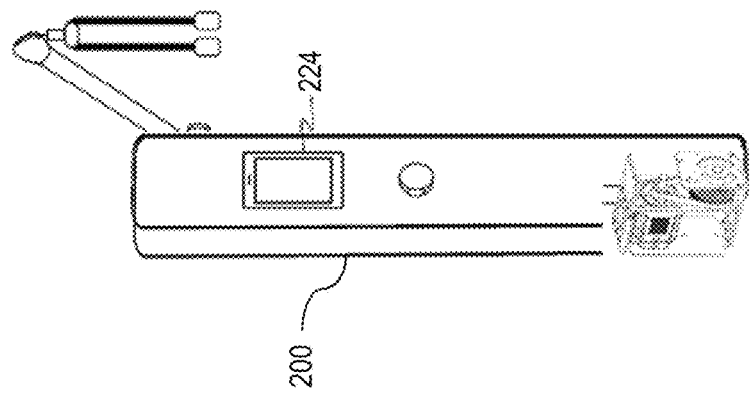
FIGS. 29A-29C are illustrations of exemplary electronic exercise equipment, consistent with disclosed embodiments.
Figure 29B:
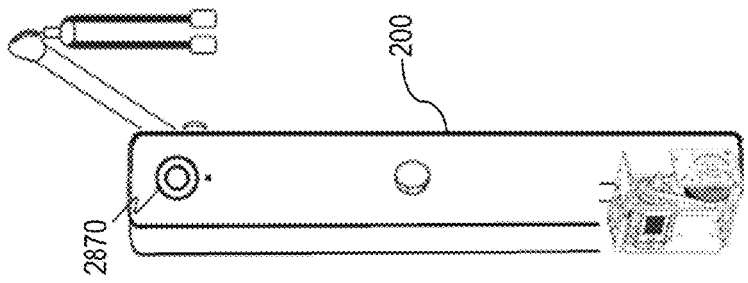
Figure 29A:
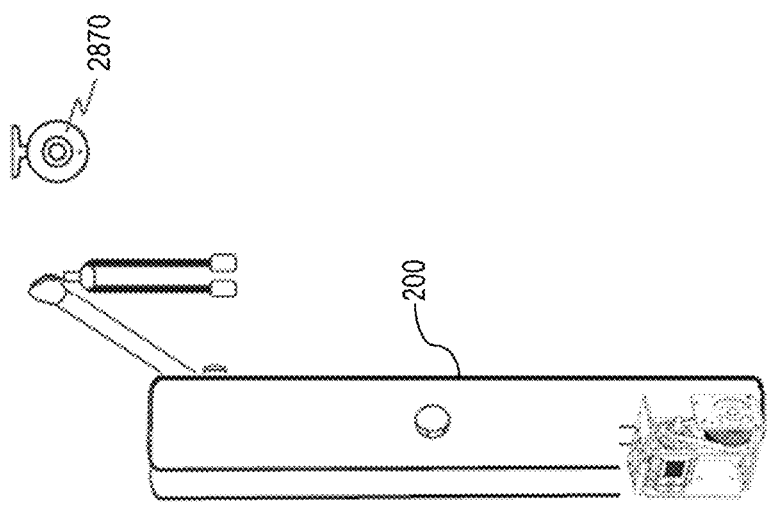

Additionally or alternatively, as illustrated, for example, in FIG. 28B, in some embodiments, a sensor, such as sensor 2890, may be configured to capture or record identifying information associated with an individual, such as individual 2895, and send the identifying information via communications network 306 to a database, such as database 304, to determine the identity of the individual and identify that individual as a particular individual and associated that individual with associated data. In general, it may be understood that sensor 2890 may comprise one or more sensors, each of which may be configured to capture or record the same type or differing types of data.

Some disclosed embodiments involve receiving from a sensor on a piece of electronic exercise equipment, exertion data. Receiving involves a process of obtaining, reading, accessing, acquiring, taking, or accepting data or information. For example, one or more processors may receive data, such as exertion data from a sensor on a piece of electronic exercise equipment or image data from an image sensor monitoring use of electronic exercise equipment. Further, for example, receiving may include a server receiving data from another processor via a network or may include a mobile communication device receiving data from another processor with which the mobile communication device is in communication. A sensor refers to a device, module, machine, subsystem, or instrument that detects and measures physical properties, environmental conditions, or changes in its surroundings. A sensor may further convert this information into signals or data that can be interpreted by humans or other systems. The sensor may send information associated with the detected event or change to another device. For example, a sensor may include an image sensor, a heartrate sensor, an accelerometer, an electromyography (EMG) sensor, other suitable sensor that may be configured to measure one or more physiological parameters or movements of an individual while exercising, and/or any combination of the foregoing.

Electronic exercise equipment may refer to an exercise machine including electronic components, as further described and exemplified elsewhere herein. For example, electronic exercise equipment may include a motor, a cable, and a single arm. A piece of electronic exercise equipment refers to either the equipment as a whole, a portion thereof, or an element or structure operatively connected to the electronic exercise equipment (e.g., a handle). Further, for example, a piece of electronic exercise equipment may include a part or device that is in communication or linked with but not necessarily physically connected the electronic exercise equipment, such as a wearable device, a smartphone, or a smart device capable of wireless communication. A sensor on a piece of electronic exercise equipment may include a sensor, as described and exemplified above, operatively connected to a piece of electronic exercise equipment. For example, a sensor on a piece of electronic exercise equipment may include a rotational sensor (e.g., a Hall Effect sensor or optical encoder), a tension sensor (e.g., a strain gauge or load cell), a direct current sensor, a voltage sensor, a torque sensor (e.g., motor current or torque relationship), motor drive feedback, or any other load sensor. In exercise equipment employing a motor for providing resistance, one or more of the previously listed sensors may detect strain, tension, and/or torque on a motor, cable spool, cable, arm, or other structural component.

Other sensor examples include a heart rate sensor physically attached to electronic exercise equipment or a heart rate sensor of a wearable device. Exertion data may be information associated with physical effort exerted by an individual. For example, exertion data may include one or more of resistance, extent of movement, acceleration, speed of movement, calories burned, energy (e.g., watts), repetitions, heart rate data, EMG data, time elapsed, data associated with one or more physiological parameters or movements of an individual while exercising, and/or any combination of two or more of the foregoing.

By way of a non-limiting example, FIG. 28B shows an exemplary system involving electronic exercise equipment and sensor 2890. In some embodiments, sensor 2890 may be a sensor that is physically attached to electronic exercise equipment, such as electronic exercise machine 200 (see FIGS. 29A to 29C). If the exercise equipment includes a motor for imposing exercise resistance, the sensor may be one of the prior listed sensors for detecting motor-related parameters reflective of exercise exertions. Additionally or alternatively, in some embodiments, sensor 2890 may be a sensor that is part of a device that is not physically attached to electronic exercise equipment and in wireless communication with electronic exercise equipment. Sensor 2890 may include a heart rate sensor, EMG sensor, or any other suitable sensor configured to capture exertion data of an individual, such as individual 2895.

Some disclosed embodiments involve receiving from at least one image sensor monitoring use of the piece of electronic exercise equipment, image data reflecting form and posture of the particular individual during an exercise set. An image sensor refers to a sensor capable of capturing monitoring, or observing visual information and converting the visual information to a signal that may be processed or stored electronically. For example, an image sensor may include a charge-coupled (CCD) device, a complementary metal-oxide-semiconductor (CMOS) device, a camera, a smartphone, or any other device configured to capture image data. Further, for example, the image sensor may be a part of a piece of electronic exercise equipment, as described and exemplified above. Monitoring may include a process of observation, surveillance, or tracking of a system, process, activity, or environment to gather information. Use may include the act of engaging or interacting with a thing, object, or system. Use of a piece of electronic exercise equipment may include the act of engaging, interacting with, or utilizing at least one part of electronic exercise equipment. For example, use of a piece of electronic exercise equipment may include an individual engaging with electronic exercise equipment to perform a workout. An image sensor monitors use when the field of view of the image sensor captures some aspect of a user performing an exercise.

Image data may include visual information captured by a sensor. For example, image data may include visual data of an individual using a piece of electronic exercise equipment. Form may include a technique and/or manner in which an individual performs a particular exercise or movement. For example, form may include body alignment, movement pattern, range of motion, and/or muscle engagement of an individual exercising. Posture may include a position and/or alignment of an individual. For example, posture may include the way an individual holds or positions their body. An exercise set may include a group of any number of repetitions (e.g., one, five, ten, or any other positive number) of the same or differing exercise by a particular individual in a particular time frame. In some disclosed embodiments, an exercise set includes a group of repetitions of a same exercise. For example, an exercise set may include performing the same exercise, such as a push-up, a bicep curl, a squat, or any other exercise, a number of times. In some disclosed embodiments, an exercise set includes a series of groups of repetitions of differing exercises. For example, an exercise set may include performing a series of a plurality of differing exercises (e.g., push-ups, sit-ups, or burpees) an equal or unequal number of times each. Form and posture of a particular individual during an exercise set may include the form and the posture of an individual as they perform an exercise set. For example, form and posture of a particular individual during an exercise set may include feet placement, spine alignment, knee position, hip hinge, or any other way in which an individual may position their body or may move during an exercise set. Image data reflecting form and posture may include visual information including one or more frames or images including an individual's body position. For example, image data reflecting form and posture may include video data of an individual during an exercise set and/or while using electronic exercise equipment.

In some disclosed embodiments, image data includes video data. Video data may include digital information including a sequence of images or frames captured over time by a sensor. For example, video data may include a number of sequential images or captures from an image sensor. In some disclosed embodiments, the at least one processor is configured to perform an analysis of the video data. Analysis of the video data may include a process of deriving analytical information from visual information. For example, at least one processor may be configured to receive video data and perform image analysis operations, such as computer vision, edge detection, image segmentation, feature extraction, object detection and recognition, image registration, any combination of the foregoing, or any other suitable image analysis operation, to derive analytical information relating to exercise performance. The term "computer vision," (e.g., "CV") may refer to technology that enables computing devices to gain a high-level of understanding from digital visual media (e.g., images, video, and optionally accompanying metadata). CV may incorporate techniques from artificial intelligence (AI), deep learning, and image processing to derive meaningful information from digital visual media. For example, CV may allow a computing device to interpret an image to determine the context and make a recommendation based on the context.

By way of a non-limiting example, FIGS. 28A-29C show an exemplary system involving electronic exercise equipment involving one or more of computing device 2800, mobile communication device 224 (FIG. 3), and camera 2870. Camera 2870 and/or mobile communication device 224 (FIG. 3) may be configured to capture image data of an individual, such as individual 2895 (FIG. 28B), and to send or provide the image data to CV engine 2810 of computing device 2800. Further and by way of a non-limiting example, FIG. 3 shows an exemplary system involving electronic exercise equipment involving T-bar 204. A T-bar may include a bracket and a shelf, as described and exemplified elsewhere herein. In some embodiments, the shelf may be configured to support a device, such as a mobile communication device. For example, the shelf may be configured to position a device such that the device and/or a display of the device is visible to an individual interacting with electronic exercise equipment. In some embodiments, a mobile communication device may be configured to display a score, image data, exertion data, feedback, any combination of the foregoing, and/or any other suitable data associated with an individual or electronic exercise equipment.

CV engine 2810 may receive the one or more images of individual 2895 (FIG. 28B) and analyze the one or more images to trace an outline of the body of individual 2895 and determine multiple key points for individual 2895, such as corresponding to the skeletal joints of individual 2895 (e.g., one or more of the feet, ankles, knees, hips, elbows, wrists, neck, shoulders, or any other point for tracking a jumping motion of individual 2895). CV engine 2810 may create a skeletal mapping for individual 2895 from the plurality of key points. The physiological indicators for individual 2895 may be stored in memory, such as memory 2820 and/or database 304. In some embodiments, camera 2870 is a 3D camera and CV engine 2810 may perform a 3D scan of individual 2895 based on the at least one image, for example to generate a 3D model of individual 2895.

In some embodiments, the CV engine may receive an image from the camera at a frequency ranging from 30 to 60 Hz. The CV engine may create a point for each image received. Each data point may include a time stamp, 2D and 3D locations on the body of the jumper for each key point, the current body distance from the surface, the last jump height, and/or the number of jumps jumped thus far by the jumper. The CV engine may provide this data to the computing device in real time. In some embodiments, the computing device may notify the CV engine when to begin and when to cease tracking the motion of the jumper. In some embodiments, the CV engine may run on a dedicated computer, on a server computer, or a single board computer.

Figure 30:
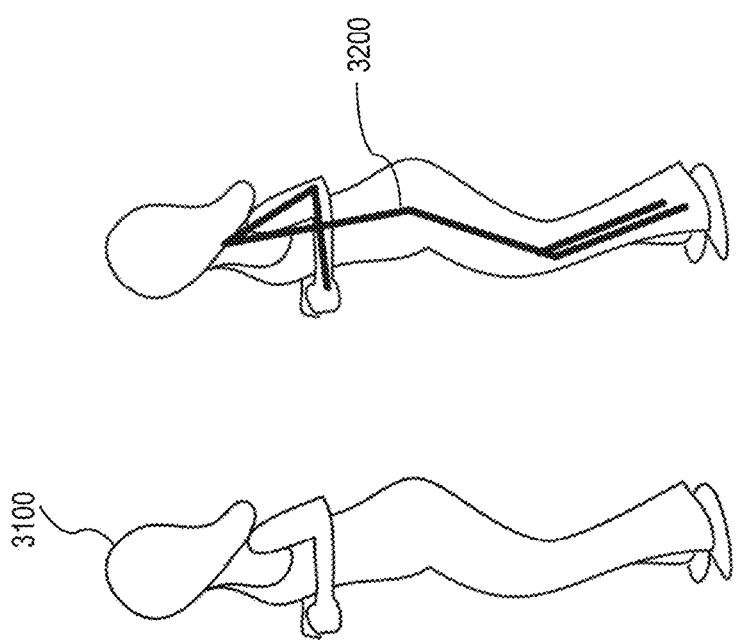
FIG. 30 is an illustration of an exemplary 3D model and an exemplary skeletal map of key points of an individual, consistent with disclosed embodiments.

Turning to FIG. 30, illustrations of an exemplary 3D model 3100 and an exemplary skeletal map 3200 of key points for individual 2895 (FIG. 28B) are shown. CV engine 2810 (FIG. 28A) may generate 3D model 3100 and skeletal map 3200 from one or more images of individual 2895 (FIG. 28B) received from camera 2870 (FIG. 28B). In some embodiments, the image is a 3D image of individual 2895. In some embodiments, CV engine 2810 (FIG. 28A) may be configured to send the generated skeletal map of individual 2895 to processor 2830 (FIG. 28A) to perform an analysis and determine a form and/or a posture of individual 2895.

Figure 31B:
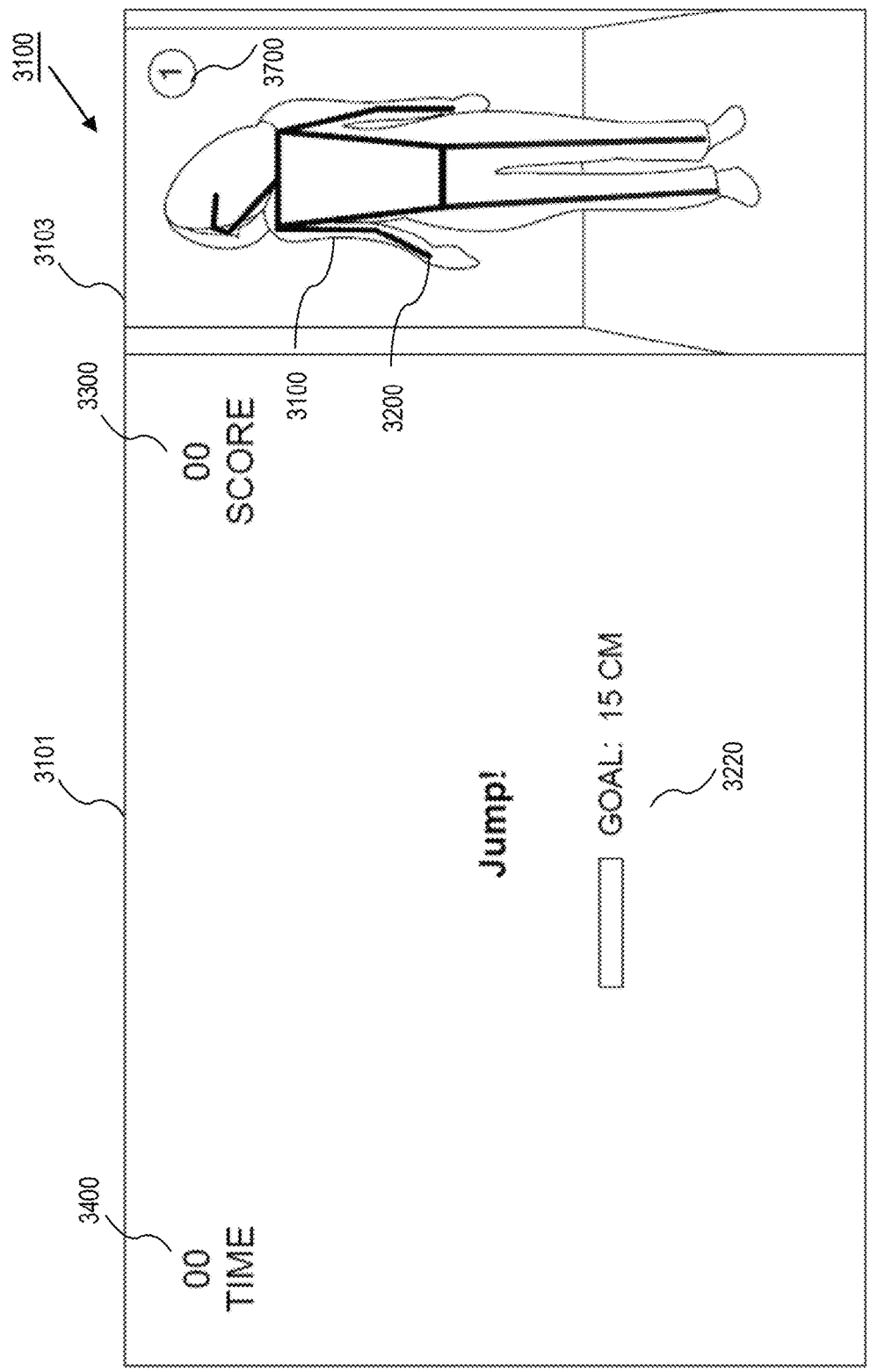
Figure 31C:
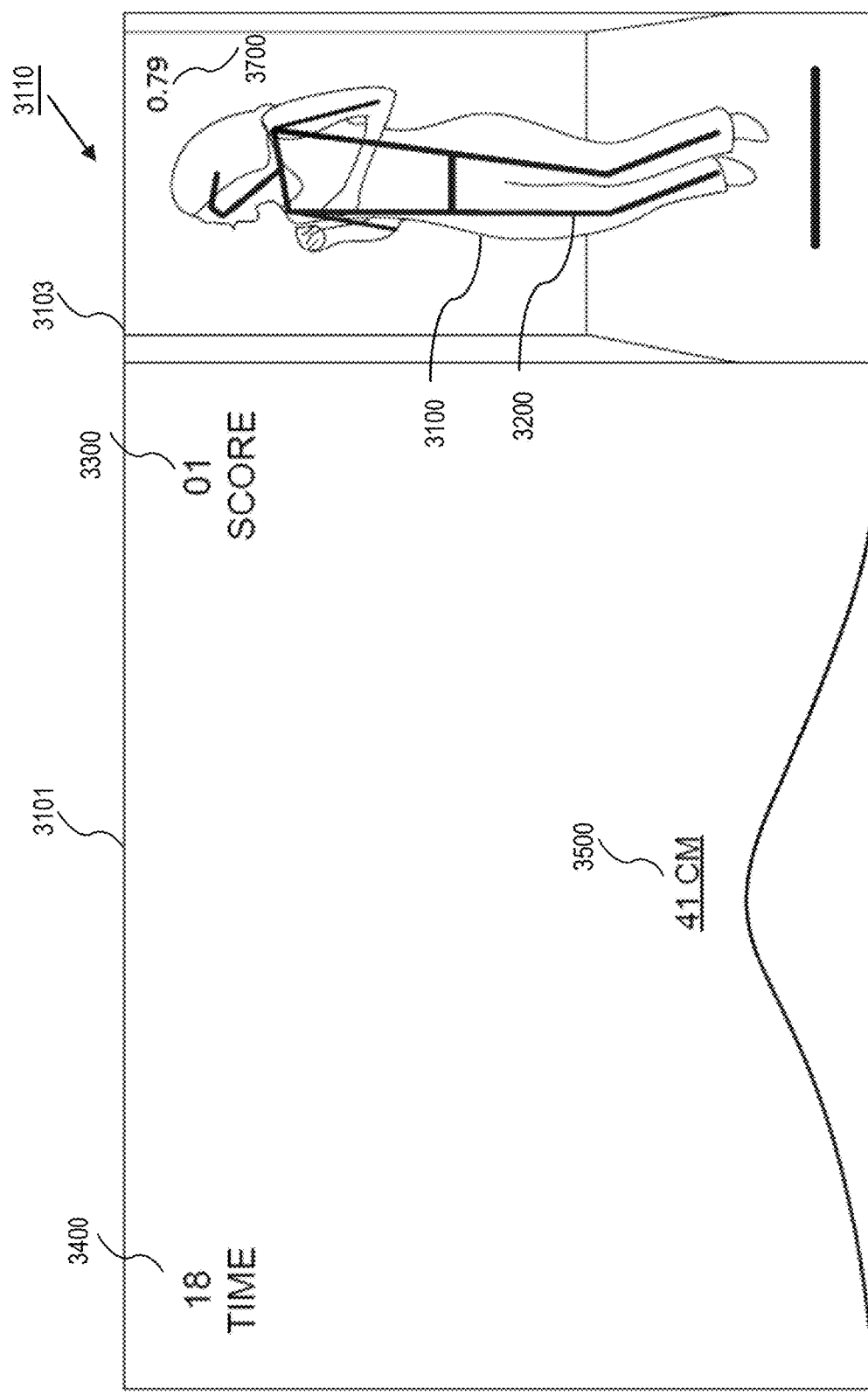

Turning to FIGS. 31B and 31C, illustrations of exemplary user interfaces 3110 displaying an exemplary 3D model 3100 and an exemplary skeletal map 3200 for individual 2895 (FIG. 28B) are shown. In some embodiments, right window 3103 may be configured to display a live or real-time 3D model 3100 and skeletal map 3200 of an individual while they are exercising.

Some disclosed embodiments involve generating a score for the exercise set by performing an aggregate analysis of the exercise goal, the exertion data, and the image data reflecting the form and posture. Generating refers to a process of creating or producing data, instructions, or outputs based on predefined rules, algorithms, or input data. For example, generating may include the process of creating text, images, code, data, or any other type of digital content. Generating a score refers to creating, via at least one processor, a score associated with a particular individual and/or a particular exercise. For example, a score may include a numeric value, an alphanumeric value, a level (e.g., low, medium, high), a percentage, any combination of the foregoing, or any other suitable measure. Further, for example, generating a score may include performing, via at least one processor, an aggregate analysis of a plurality of data points. Aggregate analysis may include a process of examining one or more inputs, such as data or information, to produce an output, such as identifying an overall trend, pattern, characteristic, and/or result. For example, aggregate analysis may include taking a number of data points (e.g., an exercise goal, exertion data, image data reflecting form and posture, any combination of the foregoing, and/or other suitable data associated with a particular individual and/or exercise set) and generating a score for the exercise set. Additionally or alternatively, aggregate analysis may include averaging, summation, grouping, visualization methods, any combination of the foregoing, and/or other suitable mathematical operations, statistical techniques, algorithms, or computational calculations that may be configured to generate an output based on one or more inputs. For example, aggregate analysis may include a weighted summation of a number of numerical data points each of which are associated with a predetermined criterion, such as an exercise goal, exertion data, and image data reflecting form and posture.

In some disclosed embodiments, the score evaluates the group of repetitions of a same exercise. Evaluating refers to assessing, judging, or forming a conclusion about the value, worth, quality, or significance. Further, for example, evaluating may include considering or including a specific set or subset of data for a calculation. A score evaluating a group of repetitions of a same exercise refers to a score, as previously defined and exemplified, that is generated by a processor based on received and/or collected data, such as exertion data and/or image data, of an exercise set consisting of repetitions of the same exercise. The score may evaluate repetitions by providing a numerical or other type of descriptive information about the repetitions. In some embodiments, a higher score may be associated with a more favorable evaluation. Additionally or alternatively, in some disclosed embodiments, a score evaluates a series of groups of repetitions of differing exercises. A score evaluating a series of groups of repetitions of differing exercises may include a score generated by a processor based on data, such as exertion data and/or image data, of an exercise set consisting of a plurality of groups of repetitions of differing exercises.

In some disclosed embodiments, a score is generated based on at least three of: detected exercise duration, intensity, form, posture, effectiveness, progress, and an exercise goal. Exercise duration refers to an amount of time an individual is exercising. For example, exercise duration may include the amount of time an individual takes to complete an exercise set. Detected refers to an indication that something is perceived or has occurred. For example, an image sensor may be configured to detect movement or a heart rate sensor may be configured to detect a change in heart rate. Detected exercise duration refers to a length of time associated with physical activity as determined via one or more sensors and at least one processor. For example, an image sensor may detect movement and send related data to a processor, which may be configured to determine whether exercise is occurring based on data indicating detected movement or lack thereof received from the image sensor. Intensity refers to a level of effort or exertion expended by an individual during physical activity. For example, intensity may involve a detected extent or aggressiveness of movement, a heart rate, one or more settings associated with an exercise machine (e.g., a resistance or weight level of the equipment, a speed of the equipment), any combination of the foregoing, or any other suitable data that may reflect a level of effort an individual is exerting while exercising. Effectiveness may include the degree to which an exercise set achieves its intended goals or produces desired outcomes. For example, effectiveness may be associated with a ratio of a number of times a repetition of an exercise is greater than or equal to an exercise goal to the total number of attempted repetitions of the same exercise. Progress may include changes made toward achieving a goal over time.

For example, progress may include advancements toward a goal, such as a target weight, target strength, or target endurance, made by an individual over time. Any data associated with detected exercise duration, intensity, form, posture, effectiveness, progress, or exercise goal may be stored in a memory, such as in a local device memory, a database, a server, or a cloud storage system.

By way of a non-limiting example, FIGS. 28A and 28B show exemplary systems involving electronic exercise equipment with computing device 2800, camera 2870, and sensor 2890. In some embodiments, a processor, such as processor 2830, may be configured to perform aggregate analysis, as described and exemplified above, based on data received from one or more sensors, such as camera 2870 and/or sensor 2890.

Some disclosed embodiments involve outputting a score. Outputting refers to producing, sending, or delivering. For example, outputting may include sending data for display on a user interface, sending data to a server, sending data to a mobile communication device, any combination of the foregoing, or sending data to any other suitable destination for storage, processing, or display. Outputting a score may include sending a score to a device for storage, processing, or display. For example, outputting a score may include a processor sending a generated score to a user interface, including a mobile communication device or display associated with electronic exercise equipment, or a server.

By way of a non-limiting example, FIGS. 3 and 28A-28B show exemplary systems involving electronic exercise equipment with cloud service 300, mobile communication device 224, and output display device 2880, any combination of which may be configured to display and/or store a score. For example, FIGS. 31B-31D show exemplary user interfaces 3110 that display a score 3300 before, during, and after an exercise set, respectively. Further, left window 3101 may be configured to display a score 3300, a time 3400, exertion data 3500, results data 3600, and/or performance data 3700. Time 3400 may include time remaining in an exercise set or detected duration of an exercise set. Exertion data may include any data associated with how an individual performs an exercise. For example, exertion data may include a height of a jump determined at least in part using image data processed by at least one processor, as depicted in FIGS. 31C and 31D. Further, exertion data may include data obtained using one or more sensors associated with electronic exercise equipment. For example, exertion data may include mechanical sensor data indicative of movement of a cable or other part of an electronic exercise equipment such as a range of motion, a speed or acceleration. In some embodiments, sensor data may be indicative of a peak force or power level exerted by the user. In some embodiments, one or more sensors may gather biometric feedback data, data indicative of the user's form or technique, and other data indicative of the user's exertion level such as audio or image data that indicates the user's breathing rate or postures associated with resting to catch a breath. Any combination of the foregoing, as well as any other suitable measure or data associated with an individual or electronic exercise equipment, may be used in conjunction with the techniques disclosed herein.

In some embodiments, data may be collected using sensors disclosed herein, such as a mechanical sensor associated with a cable of an electronic exercise machine. For example, a speed may include a speed of a cable of electronic exercise equipment at which the cable is pulled or released by an individual, and the speed may be processed by one or more processors to determine an individual's exertion level. For example, acceleration data may include an acceleration of a piece of electronic exercise equipment and may be associated with how quickly and with how much force an individual engages with the piece of electronic exercise equipment. For example, peak force measurement may include a peak force measurement of a piece of electronic exercise equipment and may be associated with a maximum force exerted by an individual when pulling a cable of electronic exercise equipment. Further, for example, peak force measurement may be associated with a direct indication of an individual's strength capabilities. In general, exertion data may be captured or recorded by one or more sensors operatively connected to electronic exercise equipment and/ or an individual.

In some embodiments, left window 3101 may be configured to display a performance datum associated with the most recently performed exercise repetitions. Results data 3500 may include one or more values, including a number of repetitions attempted, an average of the exertion data, and/or a graph displaying all or a subset of the exertion data of the exercise set. Performance data 3700 may include a value associated with how well an individual performs an exercise. For example, performance data 3700 may be associated with a ratio of detected form and posture of an individual to an expected or ideal form and posture. By displaying these data to an individual during an exercise set, the individual has access to live or real-time feedback on the quality or effectiveness of their exercise set, that can be accurately generated while the individual is exercising based on real-time data collection and evaluation. Providing such data may be able to adjust or improve said quality or effectiveness of the exercise set, or provide effective information for adjusting the exercise equipment.

In some disclosed embodiments, outputting the score includes transmitting the score to a mobile communications device associated with the particular individual. Transmitting refers to sending data from one location to another. For example, transmitting may include sending data generated from one processor, such as a processor associated with electronic exercise equipment, to another processor, such as a processor associated with a mobile communication device. A mobile communications device refers to a portable electronic device that may be configured to enable a user to communicate or access a range of information or services as described and exemplified elsewhere herein. For example, a mobile communications device may include a smartphone, a laptop, smart watch, or any other suitable device that may be configured to perform similar functions. In some embodiments, the mobile communications device may be configured to receive transmission of the score via a network such as the Internet or a cellular communication network, and provide a notification to the individual via one or more notification interfaces, or in an application running on the mobile communications device.

By way of a non-limiting example, FIGS. 3 and 28A show exemplary systems involving electronic exercise equipment with computing device 2800 and mobile communication device 224. Computing device 2800 may send, via transceiver 2860, a score generated by a processor, such as processor 2830, to mobile communication device 224 via communications network 306.

Some disclosed embodiments involve outputting in real time or near real time during an exercise set, a repetition count. Real time refers to the actual time an event occurs, or close enough to the event occurring that a delay is unnoticeable or minimal (e.g., less than a few seconds or less than a fraction of a second) . . . . For example, real time may include processing or displaying information immediately as it occurs without any noticeable delay. Outputting in real time may include outputting data without any noticeable delay. For example, outputting in real time may include sending data for display immediately after it is processed. A repetition count may include a number of times an individual performs a movement or exercise. For example, a repetition count may include a number of times an individual performs a same exercise in a single exercise set.

In some disclosed embodiments, a repetition count is derived at least in part from video data. Derived refers to being obtained, calculated, or produced through analysis, computation, and/or inference. A repetition count derived at least in part from video data refers to use of video or video-related data to determine a number of repetitions that occurred. For example, deriving a repetition count at least in part from video data may include a processor analyzing video data to determine if a repetition has occurred and generating a signal to increase a repetition count based on the determination. Further, the processor may be configured to also utilize other data, such as exertion data, or data associated with a movement or use of the exercise equipment, to determine a repetition count.

In some disclosed embodiments, a repetition count only includes repetitions that pass a threshold determined based on an analysis of video data. A threshold refers to a predetermined limit, point, or level that may serve as a boundary or criterion for making a decision or taking an action. For example, a threshold may include a data value, such a minimum amount of motion, a minimum force exerted, a target heartrate, or any other measurable exercise goal. Pass may include an indication of exceeding or surpassing something or being greater than or equal to a value. For example, passing a threshold may include a determination by a processor that a repetition is at least equal to a threshold value. An analysis of video data may include performing process of deriving information from visual information, as described and exemplified elsewhere herein. For example, an analysis of video data may include at least one processor configured to perform image analysis operations on video data of an individual exercising to determine one or more values, such as form, posture, exertion data, any combination of the foregoing, or any other suitable measure, and to determine if the determined value(s) passes a predefined threshold value. In some embodiments, analysis of video data may involve comparing one or more frames of video data to a reference image, or comparing video frames to one another. In other embodiments, analysis of video data may involve analyzing one or more attributes of the video data or analyzing attributes of one or more objects in the video.

In some disclosed embodiments, performing aggregate analysis includes only counting repetitions when a threshold exertion level is detected. Counting refers to including an item or occurrence based on one or more predefined criteria. For example, counting may include incrementing the number of repetitions based on a determination by a processor that associated exertion data is greater than a threshold exertion level. Further, only data associated with the included repetitions may be used as inputs in aggregate analysis. In some embodiments, repetitions may be counted based on a level of completeness of the moment. For example, if the exercise involves jumping, repetitions may be counted when a jump meets or exceeds a threshold height. If the exercise involves a range of motion, repetitions may be counted only when a threshold percentage of the range or movement distance is reached. In some disclosed embodiments, detecting a threshold exertion level includes an analysis of video data. For example, a processor, such as a processor part of a server, a mobile communication device, or electronic exercise equipment, may be configured to receive video data, perform an analysis of the received video data as described and exemplified elsewhere herein, detect exertion data based on at least the received video data, compare the detected exertion data against a threshold exertion level, and output a signal comprising information indicating if the detected exertion data is greater than or equal to the threshold exertion level.

By way of a non-limiting example, FIGS. 31B-31C show exemplary user interfaces associated with electronic exercise machine 200 (see FIGS. 3, and 29A-29C) that may correspond to output interface 2840 (FIG. 28A), output display device 2880 (FIG. 28B), and/or mobile communication device 224 (FIG. 3). The user interfaces display a real time status of an individual doing an exercise set, including exercise goal 3220 (FIG. 31B), score 3300, and exertion data 3400 (FIG. 31C). In some embodiments, score 300 may be associated with a repetition count and exercise goal 3220 may be associated with a threshold or threshold exertion level.

Further, by way of a non-limiting example, FIG. 3 shows an exemplary system involving electronic exercise equipment with a T-bar 204. In some embodiments, outputting a score may include outputting a performance score in real-time. A performance score may be understood to be similar to a score, as described and exemplified elsewhere herein. For example, a performance score may include a score based on workout intensity, adherence to prescribed speed or resistance levels, and/or a comparison with previous workout performances. In some embodiments, a mobile communication device may be configured to display a performance score in real-time.

Some disclosed embodiments involve generating an exercise goal. Generating an exercise goal refers to establishing or setting a goal. For example, a processor may be configured to create an exercise goal associated with a particular individual and/or a particular exercise. Further, in some disclosed embodiments, generating an exercise goal includes administering a baseline test and receiving baseline image data and baseline exertion data. Administering refers to managing, overseeing, or initiating the execution of an activity, process, or task. Baseline refers to a reference point, standard, or starting point against which data may be compared. A test refers to an evaluation of an individual's performance, ability, or skill in a particular task. A baseline test refers to an initial measurement or observation assessment for the purpose of defining or establishing a baseline. For example, a baseline test may include an exercise set. Administering a baseline test refers to conducting, initiating, or directing performance of the baseline test by an individual. For example, electronic exercise equipment may instruct an individual to perform an exercise set for the purpose of recording baseline data, such as baseline image data and/or baseline exertion data. Receiving baseline image data refers to obtaining image data from an image sensor while an individual is doing a baseline test. Receiving baseline exertion data refers to obtaining exertion data from a sensor while an individual is doing a baseline test. For example, the processor may be part of a server in communication with electronic exercise equipment via a network, a mobile communication device in communication with the electronic exercise machine, or the electronic exercise machine itself.

In some embodiments, for example, at least one processor may be configured to generate an exercise goal based on one or more rules, look up tables, formulas, algorithms, machine learning models, any combination of the foregoing, or any other suitable method of calculation that may be configured to output a goal based on inputted data. Inputted data may include baseline data, historical exercise data, data entered by a user, any combination of the foregoing, or any other suitable data.

By way of a non-limiting example, FIG. 28B shows an exemplary system involving electronic exercise equipment with output display device 2880, camera 2870, sensor 2890, and individual 2895. Output display device 2880 may display instructions for individual 2895 to perform a baseline test while one or more of camera 2870 and sensor 2890 collect baseline image data and baseline exertion data. The baseline data may be sent to database 304 or mobile communications device 224 (FIG. 3) for storage.

Some disclosed embodiments involve automatically adjusting an exercise goal as performance improvements are detected over time. Automatically refers to a performance or occurrence without direct human intervention, input, or control. For example, automatically adjusting may occur when a processor performs an action in response to a satisfaction or detection of a predefined condition. Adjusting may include making a change or modification. For example, adjusting may include increasing, decreasing, or changing a datum value stored in a memory, a server, a mobile communication device, or any other device that may be configured to store data. Performance refers to effectiveness, efficiency, or quality with which an individual accomplishes a task, activity, goal, or objective. For example, performance may include how well or poorly an individual performs an exercise. Improvements refer to something made better or more satisfactory. For example, improvements may be understood to be similar to progress, as described and exemplified elsewhere herein. Performance improvements detected over time refer to a processor configured to receive or read historical data stored in a memory and to determine or detect a trend in the historical data. For example, a processor may be configured to receive, from a memory and/or database, historical exercise data associated with a particular individual and/or an exercise set, to analyze the historical exercise data to determine a trend over time, and determine if there is an improvement or increase in the particular individual's performance. Further, for example, performance improvements detected over time may include a processor detecting a change in one or more physiological parameters of the individual associated with a higher level of physical fitness or performance. Some parameters may be inversely related to increased performance, such as a lower average heart rate, breathing rate, or blood pressure being associated with a higher level of physical fitness. In some embodiments, performance improvements may be detected based on monitored parameters indicative of exertion for the same exercise set over time, an increase in performance for the same exercise set over time, or an increase in any other data related to a particular individual and/or an exercise set. In some embodiments, performance improvements may be detected by monitoring one or more sensors of the exercise equipment, such as by monitoring a power level exerted by the individual on the exercise equipment, a speed or efficiency of performing a movement, an increase in resistance or weight level initiated by the individual, and any other measurable parameters associated with increased or improved performance. In some embodiments, one or more body measurements may be associated with an improvement in performance, such as a decrease in non-lean weight, or an increase in muscle mass of the individual.

By way of a non-limiting example, FIG. 28A shows an exemplary system involving electronic exercise equipment with computing device 2800 and database 304. Computing device 2800 may be configured to receive from a memory, such as from database 304 via transceiver 2860 or from memory 2820, historical exercise data associated with a particular individual. Then processor 2830 may be configured to analyze the received historical exercise data to detect if there is performance improvement over time. Then processor 2830 may query a memory for an exercise goal associated with the historical exercise data and automatically adjust the exercise goal based on the detected performance improvement. For example, processor 2830 may query a memory, such as database 304, for historical exercise data including heart rate data associated with a particular individual and an exercise set. Then processor 2830 may detect a change in the heart rate data over time, e.g., average heart rate across the duration of the exercise set decreases over time. Processor 2830 may automatically change an associated exercise goal based on the detected change, e.g., exercise goal increases.

By way of non-limiting example, FIG. 3 shows an exemplary system involving electronic exercise equipment with a T-bar 204. In some embodiments, outputting a score may include progress over time scoring. Progress over time scoring may be understood to be similar to performance improvements over time, as described and exemplified elsewhere herein. For example, progress over time scoring may include tracking progress across multiple sessions; score improvements in endurance, speed, and/or strength. In some embodiments one or more processors may use progress over time scoring to adjusting future workouts and to optimize training. For example, electronic exercise equipment may use scoring to evaluate whether to automatically increase a tension level on a cable, or increase another type of force applied by another type of electronic exercise equipment, when the scoring results are associated with an increase in fitness level and strength. Thus, progress over time scoring may be associated with feedback that the electronic exercise equipment collects in response to providing an automated exercise program to the user.

In some embodiments, a mobile communications device may be configured to display progress over time scoring. A processor of the mobile communications device may additionally be configured to control one or more parameters of the electronic exercise equipment, such as controlling the output and display of prompts to perform exercise movements, or automatically adjusting one or more parameters and settings of the electronic exercise equipment, such as a level of tension applied to a cable.

Figure 32:
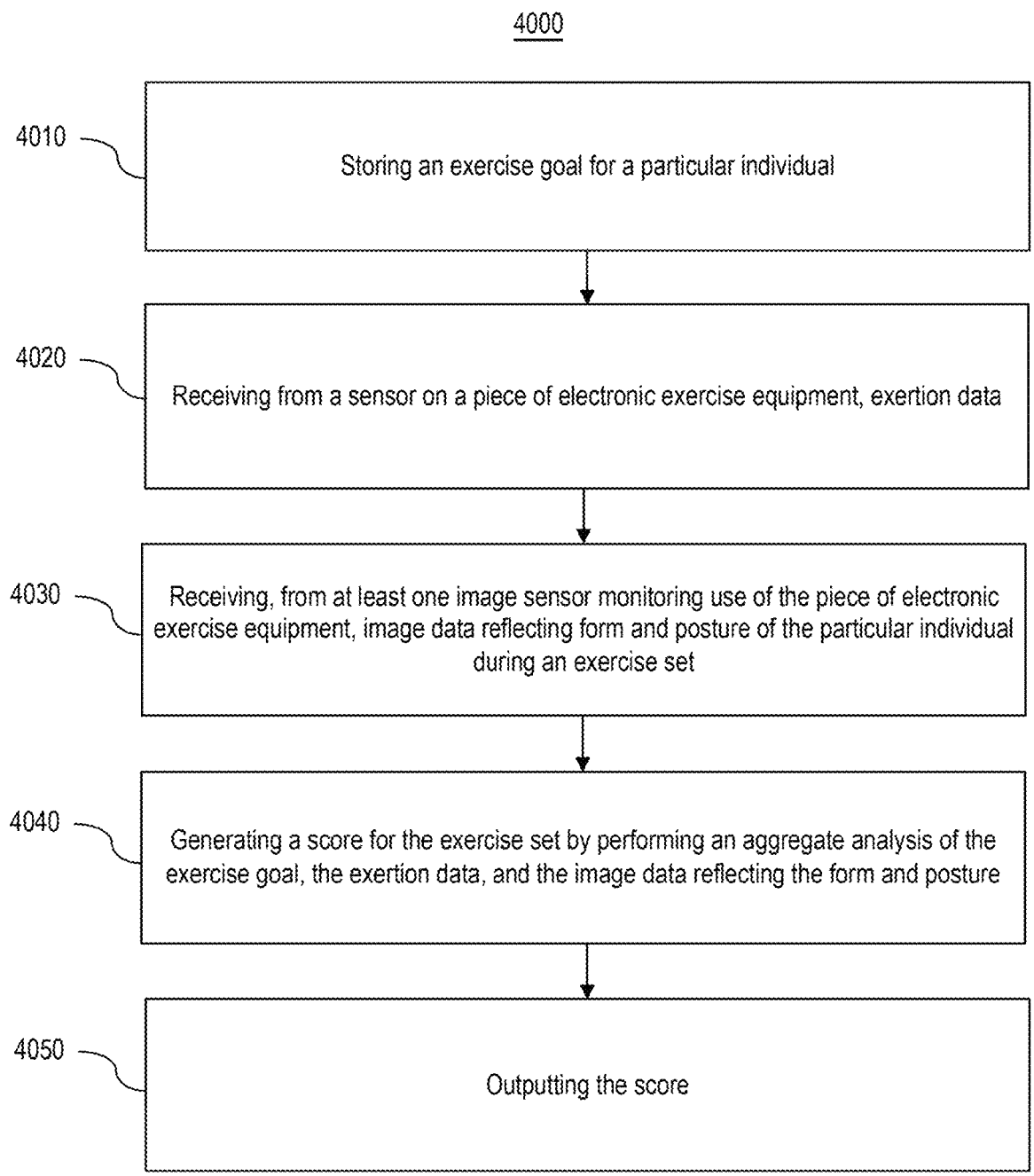
FIG. 32 is a flowchart illustrating an exemplary method for exercise scoring operations, consistent with disclosed embodiments.

Referring now to FIG. 32, which illustrates a flow diagram of an exemplary method 4000 for exercise scoring operations, consistent with some disclosed embodiments. In some embodiments, code with instructions for causing at least one processor to perform operations set forth in the steps in FIG. 32 may be stored in a non-transitory computer readable medium. Operations may be performed based on instructions executed by, for example, at least one processor such as processor 2820. It is intended that the sequence of steps shown in the figures is only for illustrative purposes and is not intended to be limited to any particular sequence of steps. As such, those skilled in the art can appreciate that these steps can be performed in a different order while implementing the same method.

In step 4010, at least one processor, such as processor 2820, may store an exercise goal, consistent with the examples discussed above. For example, as illustrated in FIGS. 3 and 28A-28B, the exercise goal may be stored in memory 2820, database 304, mobile communication device 224, or any combination of the foregoing. Further, the at least one processor may be part of computing device 2800, cloud service 300, mobile communication device 224, or any combination of the foregoing. Generally, it may be understood that any operations described and exemplified herein may be performed by a processor that is part of computing device 2800, mobile communication device 224, cloud service 300, any combination of the foregoing, or any other suitable device.

In step 4020—, at least one processor may receive from a sensor on a piece of electronic exercise equipment, exertion data, consistent with the examples discussed above.

In step 4030, at least one processor may receive, from at least one image sensor monitoring use of the piece of electronic exercise equipment, image data reflecting form and posture of the particular individual during an exercise set, consistent with the examples discussed above.

In step 4040, at least one processor may generate a score of the exercise set by performing an aggregate analysis of the exercise goal, the exertion data, and the image data reflecting the form and posture, consistent with the examples discussed above.

In step 4050, at least one processor may output a score, consistent with the examples discussed above.

Examples of inventive concepts are contained in the following clauses which are an integral part of this disclosure:

Clause 1. A non-transitory computer readable medium containing instructions that when executed by at least one processor cause the at least one processor to communicate with a plurality of remote sensors associated with disbursed exercise equipment and to simulate a virtual training experience, the operations comprising:

generating a simulated exercise environment;

presenting a first avatar in the simulated exercise environment, wherein the first avatar is associated with a first participant located in a first physical location;

presenting a second avatar in the simulated exercise environment, wherein the second avatar is associated with a second participant located in a second physical location remote from the first physical location;

receiving from at least one first sensor associated with a first piece of exercise equipment in the first physical location first signals representing first physical exertions by the first participant;

in response to the first signals, causing the first avatar to simulate, in the simulated exercise environment, the first physical exertions;

receiving from at least one second sensor associated with a second piece of exercise equipment in the second physical environment second signals representing second physical exertions by the second participant;

based on the second signals, causing the second avatar to simulate, in the simulated exercise environment, the second physical exertions;

enabling the first participant to view from the first physical location the simulations of the first physical exertions and the second physical exertions in the simulated exercise environment;

enabling the second participant to view from the second physical location the simulations of the first physical exertions and the second physical exertions in the simulated exercise environment; and enabling the first participant and the second participant to communicate with each other during a common exercise session in the simulated exercise environment.

Clause 2. The non-transitory computer readable medium of clause 1, wherein the simulated exercise environment contains a simulation of a piece of exercise equipment and wherein the first physical exertions and the second physical exertions are simulated on the simulation of the piece of exercise equipment.

Clause 3. The non-transitory computer readable medium of any of clauses 1-2, wherein the first signals are associated with tension on a first cable of the first piece of exercise equipment, and wherein the second signals are tension on a second cable of the second piece exercise equipment.

Clause 4. The non-transitory computer readable medium of any of clauses 1-3, wherein the first avatar and the second avatar mask identities of the first participant and the second participant.

Clause 5. The non-transitory computer readable medium of any of clauses 1-4, wherein the first avatar and the second avatar simulate identities of the first participant and the second participant.

Clause 6. The non-transitory computer readable medium of any of clauses 1-5, wherein the at least one first sensor and the at least one second sensor each include an image sensor, wherein the first signals and the second signals respectively reflect limb motion of the first participant and the second participant, and wherein the operations further include using the first signals and the second signals to respectively simulated via the first avatar and the second avatar the limb motion of the first participant and the second participant.

Clause 7. The non-transitory computer readable medium of any of clauses 1-6, wherein the at least one first sensor and the at least one second sensor each include an image sensor, wherein the first signals and the second signals respectively reflect posture of the first participant and the second participant, and wherein the operations further include using the first signals and the second signals to provide posture feedback to the first participant and the second participant.

Clause 8. The non-transitory computer readable medium of any of clauses 1-7, further comprising monitoring of the first signals and the second signals by a trainer, and wherein the operations further comprise enabling the trainer to provide feedback based on the first signals and the second signals.

Clause 9. The non-transitory computer readable medium of any of clauses 1-8, wherein the trainer is virtual.

Clause 10. The non-transitory computer readable medium of any of clauses 1-9, wherein the trainer is human.

Clause 11. The non-transitory computer readable medium of any of clauses 1-10, wherein the operations further comprise enabling a competition between the first participant and the second participant.

Clause 12. The non-transitory computer readable medium of any of clauses 1-11, wherein the competition involves the first participant and the second participant respectively interacting simultaneously with the first piece of exercise equipment and the second piece of exercise equipment.

Clause 13. The non-transitory computer readable medium of any of clauses 1-12, wherein the first signals and the second signals each include image data and resistance data.

Clause 14. The non-transitory computer readable medium of any of clauses 1-13, wherein the first piece of exercise equipment includes free weights, wherein the at least one first sensor includes an image sensor, and wherein the operations further include determining from the first signals repetitions occurring with the free weights.

Clause 15. The non-transitory computer readable medium of any of clauses 1-14, wherein the operations further include determining from the first signals and indication of form of the first participant.

Clause 16. The non-transitory computer readable medium of any of clauses 1-15, wherein the operations further include determining from the first signals an indication of posture of the first participant.

Clause 17. The non-transitory computer readable medium of any of clauses 1-16, wherein the operations further include determining from the first signals an indication of tempo of the first participant.

Clause 18. The non-transitory computer readable medium of any of clauses 1-17, wherein the operations further include determining from the first signals an indication of repetitions of the first participant.

Clause 19. The non-transitory computer readable medium of any of clauses 1-18, wherein the operations further include counting the repetitions only when the first physical exertions meet a threshold.

Clause 20. The non-transitory computer readable medium of any of clauses 1-19, wherein the operations further comprise outputting the simulated exercise environment and the first and second avatars in a format enabling virtual reality presentation.

Clause 21. The non-transitory computer readable medium of any of clauses 1-20, configured to cause the generated simulated exercise environment to be presented on at least one mobile computing device.

Clause 22. A non-transitory computer readable medium containing instructions that when executed by at least one processor cause the at least one processor to perform dynamic injury-related adjustments during exercise, the operations comprising:

initiating an exercise routine including a series of varied electronically controlled exercises on exercise equipment, wherein differing exercises work differing groups of muscles;

instructing a user to engage in one of the series of varied electronically controlled exercises using the exercise equipment;

receiving from the user an electronic indication of injury, wherein the electronic indication of injury includes an indication of at least one injured muscle; and in response to the received electronic indication of injury, changing the series of varied electronically controlled exercises to limit use of the injured muscle.

Clause 23. The non-transitory computer readable medium of any of clauses 1-22, wherein receiving occurs during the exercise routine.

Clause 24. The non-transitory computer readable medium of any of clauses 1-23, wherein initiating the exercise routine includes selecting the series of varied electronically controlled exercises, and wherein changing the series includes determining in the series predetermined exercises that engage the injured muscle, and substituting other exercises for the predetermined exercises that engage the injured muscle.

Clause 25. The non-transitory computer readable medium of any of clauses 1-24, wherein instructing the user to engage in one of the series of varied electronically controlled exercises includes outputting for display directions for performing at least the one exercise of the series.

Clause 26. The non-transitory computer readable medium of any of clauses 1-25, wherein instructing includes sending signals to a mobile communications device connected to the exercise equipment.

Clause 27. The non-transitory computer readable medium of any of clauses 1-26, wherein the connection is wired.

Clause 28. The non-transitory computer readable medium of any of clauses 1-27, wherein the connection is wireless.

Clause 29. The non-transitory computer readable medium of any of clauses 1-28, wherein the electronic indication includes an identification of a specific injured muscle.

Clause 30. The non-transitory computer readable medium of any of clauses 1-29, wherein the operations further comprise outputting an anatomical map, and wherein receiving an electronic indication includes a selection from the anatomical map.

Clause 31. The non-transitory computer readable medium of any of clauses 1-30, wherein the operations include determining from the anatomical map an identification of the injured muscle.

Clause 32. The non-transitory computer readable medium of any of clauses 1-31, further comprising presenting an injury button, and in response to activation of the injury button, causing a display of the anatomical map.

Clause 33. The non-transitory computer readable medium of any of clauses 1-32, wherein the operations further include changing the series of varied electronically controlled exercises to avoid the injured muscle during a subsequent exercise routine.

Clause 34. The non-transitory computer readable medium of any of clauses 1-33, wherein the operations further include, prior to initiation of a subsequent exercise routine, querying the user on the status of the injured muscle, and wherein, when a response to the query indicates improvement, reinstating exercises that engage the injured muscle.

Clause 35. The non-transitory computer readable medium of any of clauses 1-34, wherein instructing the user occurs via a mobile communications device of the user, and wherein the electronic indication of injury is received from the mobile communications device of the user.

Clause 36. A non-transitory computer readable medium containing instructions that when executed by at least one processor cause the at least one processor to perform operations for dynamically modifying automated electronic exercise equipment usage instructions, the operations comprising:
receiving a selection of a fitness a goal associated with a user of electronic exercise equipment configured for implementing an automated exercise program, wherein the fitness goal is typically associated with a series of exercises in the automated exercise program;
electronically prompting the user to identify disliked movements;
identifying alternative movements to the disliked movements, wherein the alternative movements are chosen from a group consisting of movements that work muscles typically worked by the disliked movements;
building an alternative automated exercise program including the alternative movements, wherein the alternative automated exercise program omits the disliked movements while enabling attainment of the fitness goal; and
sequentially outputting for presentation on a display prompts for performing the alternative automated exercise program;
obtaining feedback on performance of the alternative automated exercise program from at least one sensor monitoring the electronic exercise equipment.

Clause 37. The non-transitory computer readable medium of any of clauses 1-36, further comprising storing indications of the identified disliked movements, and applying the alternative automated exercise program to a subsequent exercise session based on the stored indications.

Clause 38. The non-transitory computer readable medium of any of clauses 1-37, wherein the exercise program includes exercise sequences for a series of sessions extending over a plurality of days.

Clause 39. The non-transitory computer readable medium of any of clauses 1-38, further comprising modifying the alternative automated exercise program based on the obtained feedback.

Clause 40. The non-transitory computer readable medium of any of clauses 1-39, wherein the modifying includes changing at least one of an exercise sequence in a day in the subsequent day in the series of days.

Clause 41. The non-transitory computer readable medium of any of clauses 1-40, wherein electronically prompting the user to identify disliked movements includes displaying exercise names for selection.

Clause 42. The non-transitory computer readable medium of any of clauses 1-41, wherein electronically prompting the user to identify disliked movements includes displaying graphical images for selection.

Clause 43. The non-transitory computer readable medium of any of clauses 1-42, wherein electronically prompting the user to identify disliked movements includes displaying animations for selection.

Clause 44. The non-transitory computer readable medium of any of clauses 1-43, wherein the operations further include introducing the disliked movements into the alternative automated exercise program based on the feedback.

Clause 45. The non-transitory computer readable medium of any of clauses 1-44, where the alternative automated exercise program includes instructions for altering resistance for application by the electronic exercise equipment.

Clause 46. The non-transitory computer readable medium of any of clauses 1-45, wherein the operations further comprise initiating an exercise routine including a series of varied electronically controlled exercises on exercise equipment, wherein differing exercises work differing groups of muscles.

Clause 47. The non-transitory computer readable medium of any of clauses 1-46, wherein the disliked movements correspond to an injury, wherein the operations further comprise prompting the user to report the injury, and wherein the alternative automated exercise program is configured to minimize further injury.

Clause 48. The non-transitory computer readable medium of any of clauses 1-47, wherein the operations further comprise prompting the user with an option to reinstitute disliked movements.

Clause 49. The non-transitory computer readable medium of any of clauses 1-48, wherein the operations further comprise providing a graphical user interface that presents a series of movements and permits the user to accept or reject each movement.

Clause 50. The non-transitory computer readable medium of any of clauses 1-49, wherein the series of movements includes a swipe in one direction to accept a movement, and a swipe in another direction to reject a movement.

Clause 51. The non-transitory computer readable medium of any of clauses 1-50, wherein electronically prompting the user to identify disliked movements includes sending first signals to a mobile communications device of the user, and wherein sequentially outputting for presentation on a display prompts for performing the alternative automated exercise program includes sending second signals to the mobile communications device of the user to thereby cause a presentation of the prompts on a display of the mobile communications device of the user.

Clause 52. A non-transitory computer readable medium containing instructions that when executed by at least one processor cause the at least one processor to perform operations for coordinating multi-space exertion routines, the operations comprising:
receiving from a mobile communications device during a first time period an indication of a first space in which the mobile communications device is located;
receiving from the mobile communications device first data reflective of a first exercise routine during the first time period, wherein the first exercise routine is associated with a fitness goal;
receiving from the mobile communications device at a second time different from the first time, an indication of a second space in which the mobile communications device is located;
outputting to the mobile communications device, instructions for performing a second exercise routine associated with at least one of the fitness goal or the first exercise routine;
receiving from the mobile communications device second data reflective of the second exercise routine,
wherein at least the first or the second exercise routine is preformed using at least one exercise equipment.

Clause 53. The non-transitory computer readable medium of any of clauses 1-52, wherein the at least one exercise equipment includes at least one of an electronic home gym and a non-electronic commercial gym equipment.

Clause 54. The non-transitory computer readable medium of any of clauses 1-53, wherein the first exercise routine is performed using the electronic home gym and wherein the second exercise routine is performing using the non-electronic commercial gym equipment, and wherein the instructions are configured to simulate via the commercial gym equipment, the first exercise routine.

Clause 55. The non-transitory computer readable medium of any of clauses 1-54, wherein the first exercise routine is performed using the non-electronic commercial gym equipment and wherein the second exercise routine is performing using the electronic home gym, and wherein the instructions are configured to simulate via the electronic home gym, the first exercise routine.

Clause 56. The non-transitory computer readable medium of any of clauses 1-55, wherein the first data reflects output of a resistive motor.

Clause 57. The non-transitory computer readable medium of any of clauses 1-56, wherein the first data is reflective of output from an image sensor.

Clause 58. The non-transitory computer readable medium of any of clauses 1-57, wherein the first data is reflective of output from a resistive motor and an image sensor.

Clause 59. The non-transitory computer readable medium of any of clauses 1-58, wherein the second data is obtained via manual input on the mobile communications device.

Clause 60. The non-transitory computer readable medium of any of clauses 1-59, wherein the operations further include prompting input of data recording performance of the second exercise routine.

Clause 61. The non-transitory computer readable medium of any of clauses 1-60, wherein the second data is reflective of output from an image sensor.

Clause 62. The non-transitory computer readable medium of any of clauses 1-61, wherein the first exercise equipment includes a non-electronic commercial gym equipment and wherein the second exercise equipment includes electronic home gym equipment, and wherein the instructions are configured to simulate via the electronic home gym equipment the first exercise routine.

Clause 63. The non-transitory computer readable medium of any of clauses 1-62, wherein the operations further comprise receiving input indicative of the fitness goal.

Clause 64. The non-transitory computer readable medium of any of clauses 1-63, wherein the instructions are configured to cause muscles recruited during the first exercise routine to be recruited during the second exercise routine.

Clause 65. The non-transitory computer readable medium of any of clauses 1-64, wherein at least one of the first exercise equipment and the second exercise equipment includes electronic resistance, and wherein the mobile communications device is configured to pair with the at least one of the first exercise equipment and the second exercise equipment and to send signals configured to alter the electronic resistance.

Clause 66. The non-transitory computer readable medium of any of clauses 1-65, wherein the operations further include transmitting signals to the mobile communications equipment to simulate via an avatar, at least some of the first exercise routine and at least some of the second exercise routine.

Clause 67. The non-transitory computer readable medium of any of clauses 1-66, wherein at least one of the first exercise equipment and the second exercise equipment includes free weights.

Clause 68. The non-transitory computer readable medium of any of clauses 1-67, wherein the operations further include outputting signals to the mobile communications device to present challenges.

Clause 69. The non-transitory computer readable medium of any of clauses 1-68, wherein the operations further comprise logging the first data and the second data.

Clause 70. The non-transitory computer readable medium of any of clauses 1-69, wherein the operations further comprise outputting a report reflective of the first data and the second data.

Clause 71. A method for coordinating multi-space exertion routines, the method comprising:
receiving from a mobile communications device during a first time period an indication of a first space in which the mobile communications device is located;
receiving from the mobile communications device first data reflective of a first exercise routine during the first time period, wherein the first exercise routine is associated with a fitness goal;
receiving from the mobile communications device at a second time different from the first time, an indication of a second space in which the mobile communications device is located;
outputting to the mobile communications device, instructions for performing a second exercise routine to facilitate advancement of the fitness goal; and
receiving from the mobile communications device second data reflective of the second exercise routine which conforms to the fitness goal,
wherein at least the first or the second exercise routine is performed using at least one exercise equipment.

Clause 72. A system for coordinating multi-space exertion routines, the system comprising:
at least one processor configured to:
receive from a mobile communications device during a first time period an indication of a first space in which the mobile communications device is located;
receive from the mobile communications device first data reflective of a first exercise routine during the first time period, wherein the first exercise routine is associated with a fitness goal;
receive from the mobile communications device at a second time different from the first time, an indication of a second space in which the mobile communications device is located;
output to the mobile communications device, instructions for performing a second exercise routine to facilitate advancement of the fitness goal; and
receive from the mobile communications device second data reflective of the second exercise routine which conforms to the fitness goal,
wherein at least the first or the second exercise routine is performed using at least one exercise equipment.

Clause 73. A non-transitory computer readable medium containing instruction that when executed by at least one processor cause the at least one processor to perform overlapping individualized data transfer operations, comprising:
establishing a first communications channel between a trainer application and a first piece of electronic exercise equipment associated with a first client, the first communications channel being configured to convey a first dialogue data stream and to convey a first exertion data stream from at least one first sensor associated with the first piece of electronic exercise equipment;
establishing a second communications channel between the trainer application and a second piece of electronic exercise equipment associated with a second client, the second communications channel being configured to convey a second dialogue data stream and to convey a second exertion data stream from at least a second sensor associated with the second piece of electronic exercise equipment;
enable a first selection, via the trainer application, of the first communications channel, wherein in response to the first selection, the first dialogue data stream and the first exertion data stream are open between the first client and the trainer thereby enabling the first trainer to view first exertion data while simultaneously conducting a dialogue with the first client, and wherein while the first dialogue data stream is open, at least a return path of second dialogue data stream from the trainer application to the second client is blocked, preventing dialogue from the trainer application to the second client; and
enable a second selection, via the trainer application, of the second communications channel, wherein in response to the second selection, the second dialogue data stream and the second exertion data stream are open between the first client and the trainer thereby enabling the first trainer to view first exertion data while simultaneously conducting a dialogue with the first client, and wherein while the second dialogue data stream is open, at least a return path of the first dialogue data stream from the trainer application to the first client is blocked, preventing communication from the trainer application to the first client.

Clause 74. The non-transitory computer readable medium of any of clauses 1-73, wherein the first dialogue data stream and the second dialogue data stream include video data.

Clause 75. The non-transitory computer readable medium of any of clauses 1-74, wherein when the first channel is open, the operations further include conveying audio from the second client to the trainer application, while blocking audio transmission from the trainer application to the second client.

Clause 76. The non-transitory computer readable medium of any of clauses 1-75, wherein when the first channel is open, the operations further include conveying video from the first client to the trainer application, while blocking video transmission from the trainer application to the second client.

Clause 77. The non-transitory computer readable medium of any of clauses 1-76, wherein the operations further include, when the first channel is open, logging the second exertion data stream from the second channel for later presentation on the trainer application when the second channel is open, and wherein the operations additionally include, when the second channel is open, logging the first exertion data stream from the first channel for later presentation on the trainer application when the first channel is open.

Clause 78. The non-transitory computer readable medium of any of clauses 1-77, wherein the first piece of electronic exercise equipment and the second piece of electronic exercise equipment each include a resistive motor for exerting tension on a cable, and wherein the first exertion data stream and the second exertion data stream reflect cable-applied resistive forces.

Clause 79. The non-transitory computer readable medium of any of clauses 1-78, wherein the trainer application provides a plurality of windows differentiating dialogue data from exertion data.

Clause 80. The non-transitory computer readable medium of any of clauses 1-79, wherein the first communications channel is established between a first mobile communications device associated with the first client and a trainer mobile communications device running the trainer application, and wherein the second communications channel is established between a second mobile communications device associated with the second client and the trainer mobile communications device.

Clause 81. A non-transitory computer readable medium containing instruction that when executed by at least one processor cause the at least one processor to perform exercise scoring operations, comprising:
storing an exercise goal for a particular individual;
receiving from a sensor on a piece of electronic exercise equipment, exertion data; receiving, from at least one image sensor monitoring use of the piece of electronic exercise equipment, image data reflecting form and posture of the particular individual during an exercise set;
generating a score for the exercise set by performing an aggregate analysis of the exercise goal, the exertion data, and the image data reflecting the form and posture; and outputting the score.

Clause 82. The non-transitory computer readable medium of any of clauses 1-81, wherein the exercise set includes a group of repetitions of a same exercise, and wherein the score evaluates the group of repetitions.

Clause 83. The non-transitory computer readable medium of any of clauses 1-82, wherein the exercise set includes a series of groups of repetitions of differing exercises and wherein the score evaluates the series of groups.

Clause 84. The non-transitory computer readable medium of any of clauses 1-83, wherein performance of the aggregate analysis includes only counting repetitions when a threshold exertion level is detected.

Clause 85. The non-transitory computer readable medium of any of clauses 1-84, wherein the image data is video and wherein detecting a threshold exertion level includes image analysis of the video.

Clause 86. The non-transitory computer readable medium of any of clauses 1-85, wherein the operations further include automatically adjusting the exercise goal as performance improvements are detected over time.

Clause 87. The non-transitory computer readable medium of any of clauses 1-86, wherein the operations further include generating the exercise goal.

Clause 88. The non-transitory computer readable medium of any of clauses 1-87, wherein generating the exercise goal includes administering a baseline test and receiving baseline image data and baseline exertion data.

Clause 89. The non-transitory computer readable medium of any of clauses 1-88, wherein the score is generated based on at least three of detected exercise duration, intensity, form, posture, effectiveness, progress, and the exercise goal.

Clause 90. The non-transitory computer readable medium of any of clauses 1-89, wherein the operations further include outputting in real time during the exercise set, a repetition count.

Clause 91. The non-transitory computer readable medium of any of clauses 1-90, wherein the image data includes video data and wherein the repetition count is derived at least in part from the video data.

Clause 92. The non-transitory computer readable medium of any of clauses 1-91, wherein the repetition count only includes repetitions that pass a threshold determined based on analysis of the video data.

Clause 93. The non-transitory computer readable medium of any of clauses 1-92, wherein outputting the score includes transmitting the score to a mobile communications device associated with the particular individual.

Disclosed embodiments may include any one of the following bullet-pointed features alone or in combination with one or more other bullet-pointed features, whether implemented as a system and/or method, by one or more hardware components disclosed herein, as well as by at least one processor or circuitry, and/or stored as executable instructions on non-transitory computer readable media or computer readable media.

- communicate with a plurality of remote sensors associated with disbursed exercise equipment and to simulate a virtual training experience.
- generating a simulated exercise environment.
- presenting a first avatar in the simulated exercise environment.
- the first avatar is associated with a first participant located in a first physical location.
- presenting a second avatar in the simulated exercise environment.
- the second avatar is associated with a second participant located in a second physical location remote from the first physical location.
- receiving from at least one first sensor associated with a first piece of exercise equipment in the first physical location first signals representing first physical exertions by the first participant.
- in response to the first signals, causing the first avatar to simulate, in the simulated exercise environment, the first physical exertions.
- receiving from at least one second sensor associated with a second piece of exercise equipment in the second physical environment second signals representing second physical exertions by the second participant.
- based on the second signals, causing the second avatar to simulate, in the simulated exercise environment, the second physical exertions.
- enabling the first participant to view from the first physical location the simulations of the first physical exertions and the second physical exertions in the simulated exercise environment.
- enabling the second participant to view from the second physical location the simulations of the first physical exertions and the second physical exertions in the simulated exercise environment.
- enabling the first participant and the second participant to communicate with each other during a common exercise session in the simulated exercise environment.
- the simulated exercise environment contains a simulation of a piece of exercise equipment.
- the first physical exertions and the second physical exertions are simulated on the simulation of the piece of exercise equipment.
- the first signals are associated with tension on a first cable of the first piece of exercise equipment.
- wherein the second signals are tension on a second cable of the second piece exercise equipment.
- the first avatar and the second avatar mask identities of the first participant and the second participant.
- the first avatar and the second avatar simulate identities of the first participant and the second participant.
- the at least one first sensor and the at least one second sensor each include an image sensor.
- the first signals and the second signals respectively reflect limb motion of the first participant and the second participant.
- using the first signals and the second signals to respectively simulated via the first avatar and the second avatar the limb motion of the first participant and the second participant.
- the at least one first sensor and the at least one second sensor each include an image sensor.

first signals and the second signals respectively reflect posture of the first participant and the second participant.

the operations further include using the first signals and the second signals to provide posture feedback to the first participant and the second participant.

monitoring of the first signals and the second signals by a trainer.

the operations further comprise enabling the trainer to provide feedback based on the first signals and the second signals.

the trainer is virtual.

wherein the trainer is human.

enabling a competition between the first participant and the second participant.

the competition involves the first participant and the second participant respectively interacting simultaneously with the first piece of exercise equipment and the second piece of exercise equipment.

the first signals and the second signals each include image data and resistance data.

the first piece of exercise equipment includes free weights.

the at least one first sensor includes an image sensor.

the operations further include determining from the first signals repetitions occurring with the free weights.

the operations further include determining from the first signals and indication of form of the first participant.

the operations further include determining from the first signals an indication of posture of the first participant.

the operations further include determining from the first signals an indication of tempo of the first participant.

the operations further include determining from the first signals an indication of repetitions of the first participant.

the operations further include counting the repetitions only when the first physical exertions meet a threshold.

the operations further comprise outputting the simulated exercise environment and the first and second avatars in a format enabling virtual reality presentation.

cause the generated simulated exercise environment to be presented on at least one mobile computing device.

dynamic injury-related adjustments during exercise.

initiating an exercise routine including a series of varied electronically controlled exercises on exercise equipment.

differing exercises work differing groups of muscles.

instructing a user to engage in one of the series of varied electronically controlled exercises using the exercise equipment.

receiving from the user an electronic indication of injury.

the electronic indication of injury includes an indication of at least one injured muscle.

in response to the received electronic indication of injury, changing the series of varied electronically controlled exercises to limit use of the injured muscle.

receiving occurs during the exercise routine.

initiating the exercise routine includes selecting the series of varied electronically controlled exercises.

changing the series includes determining in the series predetermined exercises that engage the injured muscle, and substituting other exercises for the predetermined exercises that engage the injured muscle.

instructing the user to engage in one of the series of varied electronically controlled exercises includes outputting for display directions for performing at least the one exercise of the series.

instructing includes sending signals to a mobile communications device connected to the exercise equipment.

the connection to the exercise equipment is wired.

the connection to the exercise equipment is wireless.

the electronic indication includes an identification of a specific injured muscle.

the operations further comprise outputting an anatomical map.

receiving an electronic indication includes a selection from the anatomical map.

the operations include determining from the anatomical map an identification of the injured muscle.

presenting an injury button, and in response to activation of the injury button, causing a display of the anatomical map.

changing the series of varied electronically controlled exercises to avoid the injured muscle during a subsequent exercise routine.

prior to initiation of a subsequent exercise routine, querying the user on the status of the injured muscle, and wherein, when a response to the query indicates improvement, reinstating exercises that engage the injured muscle.

instructing the user occurs via a mobile communications device of the user.

the electronic indication of injury is received from the mobile communications device of the user.

dynamically modifying automated electronic exercise equipment usage instructions.

receiving a selection of a fitness a goal associated with a user of electronic exercise equipment configured for implementing an automated exercise program.

the fitness goal is typically associated with a series of exercises in the automated exercise program.

electronically prompting the user to identify disliked movements.

identifying alternative movements to the disliked movements.

the alternative movements are chosen from a group consisting of movements that work muscles typically worked by the disliked movements.

building an alternative automated exercise program including the alternative movements.

the alternative automated exercise program omits the disliked movements while enabling attainment of the fitness goal.

sequentially outputting for presentation on a display prompts for performing the alternative automated exercise program.

obtaining feedback on performance of the alternative automated exercise program from at least one sensor monitoring the electronic exercise equipment.

storing indications of the identified disliked movements, and applying the alternative automated exercise program to a subsequent exercise session based on the stored indications.

the exercise program includes exercise sequences for a series of sessions extending over a plurality of days.

modifying the alternative automated exercise program based on the obtained feedback.

the modifying includes changing at least one of an exercise sequence in a day in the subsequent day in the series of days.

electronically prompting the user to identify disliked movements includes displaying exercise names for selection.

electronically prompting the user to identify disliked movements includes displaying graphical images for selection.

electronically prompting the user to identify disliked movements includes displaying animations for selection.

the operations further include introducing the disliked movements into the alternative automated exercise program based on the feedback.

the alternative automated exercise program includes instructions for altering resistance for application by the electronic exercise equipment.

initiating an exercise routine including a series of varied electronically controlled exercises on exercise equipment.

differing exercises work differing groups of muscles.

the disliked movements correspond to an injury.

the operations further comprise prompting the user to report the injury.

the alternative automated exercise program is configured to minimize further injury.

the operations further comprise prompting the user with an option to reinstitute disliked movements.

the operations further comprise providing a graphical user interface that presents a series of movements and permits the user to accept or reject each movement.

the series of movements includes a swipe in one direction to accept a movement, and a swipe in another direction to reject a movement.

electronically prompting the user to identify disliked movements includes sending first signals to a mobile communications device of the user.

sequentially outputting for presentation on a display prompts for performing the alternative automated exercise program includes sending second signals to the mobile communications device of the user to thereby cause a presentation of the prompts on a display of the mobile communications device of the user.

operations for coordinating multi-space exertion routines.

receiving from a mobile communications device during a first time period an indication of a first space in which the mobile communications device is located.

receiving from the mobile communications device first data reflective of a first exercise routine during the first time period.

the first exercise routine is associated with a fitness goal.

receiving from the mobile communications device at a second time different from the first time, an indication of a second space in which the mobile communications device is located.

outputting to the mobile communications device, instructions for performing a second exercise routine to facilitate advancement of the fitness goal receiving from the mobile communications device second data reflective of the second exercise routine which conforms to the fitness goal.

outputting to the mobile communications device, instructions for performing a second exercise routine associated with at least one of the fitness goal or the first exercise routine.

receiving from the mobile communications device second data reflective of the second exercise routine.

at least the first or the second exercise routine is preformed using at least one exercise equipment.

the at least one exercise equipment includes an electronic home gym and a non-electronic commercial gym equipment.

the first exercise routine is performed using the electronic home gym.

the second exercise routine is performing using the non-electronic commercial gym equipment.

the instructions are configured to simulate via the commercial gym equipment, the first exercise routine.

the first exercise routine is performed using the non-electronic commercial gym equipment.

the second exercise routine is performing using the electronic home gym.

the instructions are configured to simulate via the electronic home gym, the first exercise routine.

the first data reflects output of a resistive motor.

the first data is reflective of output from an image sensor.

the first data is reflective of output from a resistive motor and an image sensor.

the second data is obtained via manual input on the mobile communications device.

the operations further include prompting input of data recording performance of the second exercise routine.

the second data is reflective of output from an image sensor.

the first exercise equipment includes a non-electronic commercial gym equipment.

the second exercise equipment includes electronic home gym equipment.

the instructions are configured to simulate via the electronic home gym equipment the first exercise routine.

the operations further comprise receiving input indicative of the fitness goal.

the instructions are configured to cause muscles recruited during the first exercise routine to be recruited during the second exercise routine.

at least one of the first exercise equipment and the second exercise equipment includes electronic resistance.

the mobile communications device is configured to pair with the at least one of the first exercise equipment and the second exercise equipment and to send signals configured to alter the electronic resistance.

the operations further include transmitting signals to the mobile communications equipment to simulate via an avatar, at least some of the first exercise routine and at least some of the second exercise routine.

at least one of the first exercise equipment and the second exercise equipment includes free weights.

the operations further include outputting signals to the mobile communications device to present challenges.

the operations further comprise logging the first data and the second data.

the operations further comprise outputting a report reflective of the first data and the second data.

overlapping individualized data transfer operations.

establishing a first communications channel between a trainer application and a first piece of electronic exercise equipment associated with a first client.

the first communications channel being configured to convey a first dialogue data stream and to convey a first exertion data stream from at least one first sensor associated with the first piece of electronic exercise equipment.

establishing a second communications channel between the trainer application and a second piece of electronic exercise equipment associated with a second client.

the second communications channel being configured to convey a second dialogue data stream and to convey a second exertion data stream from at least a second sensor associated with the second piece of electronic exercise equipment.

enable a first selection, via the trainer application, of the first communications channel.

in response to the first selection, the first dialogue data stream and the first exertion data stream are open between the first client and the trainer thereby enabling the first trainer to view first exertion data while simultaneously conducting a dialogue with the first client.

while the first dialogue data stream is open, at least a return path of second dialogue data stream from the trainer application to the second client is blocked, preventing dialogue from the trainer application to the second client.

enable a second selection, via the trainer application, of the second communications channel.

in response to the second selection, the second dialogue data stream and the second exertion data stream are open between the first client and the trainer thereby enabling the first trainer to view first exertion data while simultaneously conducting a dialogue with the first client.

while the second dialogue data stream is open, at least a return path of the first dialogue data stream from the trainer application to the first client is blocked, preventing communication from the trainer application to the first client.

the first dialogue data stream and the second dialogue data stream include video data.

when the first channel is open, the operations further include conveying audio from the second client to the trainer application, while blocking audio transmission from the trainer application to the second client.

when the first channel is open, the operations further include conveying video from the first client to the trainer application, while blocking video transmission from the trainer application to the second client.

when the first channel is open, logging the second exertion data stream from the second channel for later presentation on the trainer application when the second channel is open, and wherein the operations additionally include, when the second channel is open, logging the first exertion data stream from the first channel for later presentation on the trainer application when the first channel is open.

the first piece of electronic exercise equipment and the second piece of electronic exercise equipment each include a resistive motor for exerting tension on a cable.

the first exertion data stream and the second exertion data stream reflect cable-applied resistive forces.

the trainer application provides a plurality of windows differentiating dialogue data from exertion data.

the first communications channel is established between a first mobile communications device associated with the first client and a trainer mobile communications device running the trainer application.

the second communications channel is established between a second mobile communications device associated with the second client and the trainer mobile communications device.

storing an exercise goal for a particular individual.

receiving from a sensor on a piece of electronic exercise equipment, exertion data.

receiving, from at least one image sensor monitoring use of the piece of electronic exercise equipment, image data reflecting form and posture of the particular individual during an exercise set.

generating a score for the exercise set by performing an aggregate analysis of the exercise goal, the exertion data, and the image data reflecting the form and posture.

outputting the score.

the exercise set includes a group of repetitions of a same exercise.

the score evaluates the group of repetitions.

the exercise set includes a series of groups of repetitions of differing exercises and wherein the score evaluates the series of groups.

performance of the aggregate analysis includes only counting repetitions when a threshold exertion level is detected.

the image data is video and wherein detecting a threshold exertion level includes image analysis of the video.

the operations further include automatically adjusting the exercise goal as performance improvements are detected over time.

the operations further include generating the exercise goal.

generating the exercise goal includes administering a baseline test and receiving baseline image data and baseline exertion data.

the score is generated based on at least three of detected exercise duration, intensity, form, posture, effectiveness, progress, and the exercise goal.

the operations further include outputting in real time during the exercise set, a repetition count.

the image data includes video data and the repetition count is derived at least in part from the video data.

the repetition count only includes repetitions that pass a threshold determined based on analysis of the video data.

outputting the score includes transmitting the score to a mobile communications device associated with the particular individual.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium containing instructions that when executed by at least one processor cause the at least one processor to perform exercise scoring operations, comprising:
    storing an exercise goal for a particular individual;
    receiving from a sensor on a piece of electronic exercise equipment, exertion data;
    receiving, from at least one image sensor monitoring use of the piece of electronic exercise equipment, image data reflecting form and posture of the particular individual during an exercise set;
    controlling, using control electronics associated with at least one resistance motor of the electronic exercise equipment, a resistance amount applied by the at least one resistance motor, wherein the at least one resistance motor is located inside the piece of electronic exercise equipment, and wherein the electronic exercise equipment is an electronic wall-mountable exercise machine;
    determining an intensity based on the resistance amount;
    generating a score for the exercise set by performing an aggregate analysis of the exercise goal, the exertion data, the intensity, and the image data reflecting the form and posture; and
    outputting the score.

2. The non-transitory computer readable medium of claim 1, wherein the exercise set includes a group of repetitions of a same exercise, and wherein the score evaluates the group of repetitions.

3. The non-transitory computer readable medium of claim 1, wherein the exercise set includes a series of groups of repetitions of differing exercises and wherein the score evaluates the series of groups.

4. The non-transitory computer readable medium of claim 1, wherein performing the aggregate analysis includes only counting repetitions when a threshold exertion level is detected.

5. The non-transitory computer readable medium of claim 4, wherein the image data includes video data and wherein detecting a threshold exertion level includes an analysis of the video data.

6. The non-transitory computer readable medium of claim 1, wherein the operations further include automatically adjusting the exercise goal as performance improvements are detected over time.

7. The non-transitory computer readable medium of claim 1, wherein the operations further include generating the exercise goal.

8. The non-transitory computer readable medium of claim 1, wherein generating the exercise goal includes administering a baseline test and receiving baseline image data and baseline exertion data.

9. The non-transitory computer readable medium of claim 1, wherein the score is generated based on at least three of detected exercise duration, intensity, form, posture, effectiveness, progress, and the exercise goal.

10. The non-transitory computer readable medium of claim 1, wherein the operations further include outputting in real time during the exercise set, a repetition count.

11. The non-transitory computer readable medium of claim 10, wherein the image data includes video data and wherein the repetition count is derived at least in part from the video data.

12. The non-transitory computer readable medium of claim 10, wherein the repetition count only includes repetitions that pass a threshold determined based on an analysis of the video data.

13. The non-transitory computer readable medium of claim 1, wherein outputting the score includes transmitting the score to a mobile communications device associated with the particular individual.

14. The non-transitory computer readable medium of claim 1, wherein the operations further include altering the resistance amount applied by the at least one resistance motor.

15. The non-transitory computer readable medium of claim 1, wherein the at least one resistance motor includes at least one electromagnet configured to apply a variable electromagnetic field.

16. The non-transitory computer readable medium of claim 1, wherein the resistance amount includes a digital weight.

17. The non-transitory computer readable medium of claim 1, wherein the at least one resistance motor includes a first resistance motor and a second resistance motor.

18. The non-transitory computer readable medium of claim 1, wherein the at least one resistance motor is connected to a first end of a cable.

19. The non-transitory computer readable medium of claim 1, wherein the at least one processor is configured to automatically adjust the resistance amount.

* * * * *